US011667662B2

(12) United States Patent
Debien et al.

(10) Patent No.: US 11,667,662 B2
(45) Date of Patent: *Jun. 6, 2023

(54) MODULATORS OF 5'-NUCLEOTIDASE, ECTO AND THE USE THEREOF

(71) Applicant: ARCUS BIOSCIENCES, INC., Hayward, CA (US)

(72) Inventors: Laurent Pierre Paul Debien, San Francisco, CA (US); Juan Carlos Jaen, Burlingame, CA (US); Jaroslaw Kalisiak, Mountain View, CA (US); Kenneth V. Lawson, San Francisco, CA (US); Manmohan Reddy Leleti, Dublin, CA (US); Erick Allen Lindsey, San Diego, CA (US); Dillon Harding Miles, Berkeley, CA (US); Eric Newcomb, Menlo Park, CA (US); Jay Patrick Powers, Pacifica, CA (US); Brandon Reid Rosen, San Mateo, CA (US); Ehesan Ui Sharif, Menlo Park, CA (US)

(73) Assignee: ARCUS BIOSCIENCES, INC., Hayward, CA (US)

(*) Notice: Subject to any disclaimer, the term of this patent is extended or adjusted under 35 U.S.C. 154(b) by 58 days.

This patent is subject to a terminal disclaimer.

(21) Appl. No.: 17/206,896

(22) Filed: Mar. 19, 2021

(65) Prior Publication Data

US 2021/0371449 A1 Dec. 2, 2021

Related U.S. Application Data

(63) Continuation of application No. 17/009,590, filed on Sep. 1, 2020, now Pat. No. 11,001,603, which is a continuation of application No. 16/273,843, filed on Feb. 12, 2019, now Pat. No. 10,981,944, which is a continuation of application No. 15/400,748, filed on Jan. 6, 2017, now Pat. No. 10,239,912.

(60) Provisional application No. 62/324,077, filed on Apr. 18, 2016, provisional application No. 62/276,564, filed on Jan. 8, 2016.

(51) Int. Cl.
| | |
|---|---|
| A01N 43/04 | (2006.01) |
| A61K 31/70 | (2006.01) |
| C07H 19/23 | (2006.01) |
| A61K 31/7076 | (2006.01) |
| C07H 19/16 | (2006.01) |
| C07H 19/20 | (2006.01) |
| C07H 19/207 | (2006.01) |
| C07F 9/6561 | (2006.01) |
| C07H 19/04 | (2006.01) |
| A61K 31/706 | (2006.01) |
| A61K 45/06 | (2006.01) |
| A61K 31/7052 | (2006.01) |
| A61K 31/7064 | (2006.01) |
| C07H 19/14 | (2006.01) |

(52) U.S. Cl.
CPC ............. *C07H 19/23* (2013.01); *A61K 31/70* (2013.01); *A61K 31/706* (2013.01); *A61K 31/7052* (2013.01); *A61K 31/7064* (2013.01); *A61K 31/7076* (2013.01); *A61K 45/06* (2013.01); *C07F 9/6561* (2013.01); *C07F 9/65616* (2013.01); *C07H 19/04* (2013.01); *C07H 19/14* (2013.01); *C07H 19/16* (2013.01); *C07H 19/20* (2013.01); *C07H 19/207* (2013.01)

(58) Field of Classification Search
None
See application file for complete search history.

(56) References Cited

U.S. PATENT DOCUMENTS

| | | | |
|---|---|---|---|
| 5,569,650 | A | 10/1996 | Watanabe et al. |
| 5,658,890 | A | 8/1997 | Pankiewicz et al. |
| 5,700,786 | A | 12/1997 | Watanabe et al. |
| 6,713,623 | B2 | 3/2004 | Pankiewicz et al. |
| 9,090,697 | B2 | 7/2015 | Sim |
| 10,239,912 | B2 | 3/2019 | Debien et al. |
| 10,981,944 | B2 | 4/2021 | Debien et al. |
| 11,001,603 | B2 | 5/2021 | Debien et al. |
| 2016/0000909 | A1 | 1/2016 | Eisenbach-Schwartz et al. |
| 2020/0405629 | A1 | 12/2020 | Jaen et al. |
| 2021/0395291 | A1 | 12/2021 | Pennell et al. |
| 2022/0062313 | A1 | 3/2022 | Jeffrey et al. |

FOREIGN PATENT DOCUMENTS

| | | |
|---|---|---|
| WO | 1998/015563 A1 | 4/1998 |
| WO | 2002/048165 A2 | 6/2002 |
| WO | 2012/032513 A1 | 3/2012 |
| WO | WO-2015049447 | 4/2015 |
| WO | 2015/164573 A1 | 10/2015 |
| WO | 2017/029601 A1 | 2/2017 |
| WO | 2017/118689 A1 | 7/2017 |
| WO | 2017/120422 A1 | 7/2017 |
| WO | 2017/120508 A1 | 7/2017 |

OTHER PUBLICATIONS

U.S. Appl. No. 17/193,473, filed Mar. 5, 2021, Lawson et al.
U.S. Appl. No. 17/311,945, filed Jun. 8, 2021, Jeffrey et al.
U.S. Appl. No. 17/348,833, filed Jun. 16, 2021, Pennell et al.

(Continued)

Primary Examiner — Patrick T Lewis
(74) Attorney, Agent, or Firm — Sheppard Mullin Richter & Hampton LLP

(57) ABSTRACT

Compounds that modulate the conversion of AMP to adenosine by 5'-nucleotidase, ecto, and compositions containing the compounds and methods for synthesizing the compounds, are described herein. The use of such compounds and compositions for the treatment and/or prevention of a diverse array of diseases, disorders and conditions, including cancer- and immune-related disorders, that are mediated by 5'-nucleotidase, ecto is also provided.

9 Claims, 1 Drawing Sheet

(56) References Cited

OTHER PUBLICATIONS

International Search Report and Written Opinion dated Apr. 19, 2017 corresponding to International Patent Application No. PCT/US2017/012587 filed on Jan. 6, 2017, 11 pages.
International Preliminary Report on Patentability dated Jul. 19, 2018 corresponding to International Patent Application No. PCT/US2017/012587 filed on Jan. 6, 2017, 7 pages.
Partial supplementary European Search Report dated Aug. 23, 2019 corresponding to EP Application No. 17736459.3 filed Jan. 6, 2017; 15 pages.
Extended European Search Report dated Nov. 28, 2019 corresponding to EP Application No. 17736459.3 filed Jan. 6, 2017; 11 pages.
Al-Izki, Sarah et al., "Immunosuppression with FTY720 is insufficient to prevent secondary progressive neurodegeneration in experimental autoimmune encephalomyelitis," *Multiple Sclerosis Journal* (2011; accepted Jan. 21, 2011) 17(8):939-948.
Bhattarai, Sanjay et al., "α,β-Methylene-ADP (AOPCP) Derivatives and Analogues: Development of Potent and Selective ecto-5'-Nucleotidase (CD73) Inhibitors," *J. Med. Chem.* (Jul. 6, 2015) 58:6248-6263.
Furtmann, Norbert et al., "Evaluation of molecular model-based discovery of ecto-5'-nucleotidase inhibitors on the basis of X-ray structures," *Bioorganic & Medicine Chemistry* (Aug. 17, 2013) 21(21):6616-6622.
Lesiak, Krystyna et al., Synthesis of 2'-Deoxynucleoside 5'-Methylenebis-(Phosphonates)s Using 2-(4-Nitrophenyl)Ethyl Methylene-Bis(Phosphonate) as the Phosphonylating Agent, Nucleosides & Nucleotides, 1998, 17(9-11), pp. 1857-1860.
Kulesskaya, Natalia et al., "CD73 Is a Major Regulator of Adenosinergic Signalling in Mouse Brain," *PLOS One* (Jun. 12, 2013) 8(6):e66896; 12 pages.
Maruoka, Hiroshi et al., "Pyrimidine Ribonucleotides with Enhanced Selectivity as $P2Y_6$ Receptor Agonists: Novel 4-Alkyloxyimino, (S)-Methanocarba, and 5'-Triphosphate γ-Ester Modifications," *J. Med. Chem.* (2010;Published on Web May 6, 2010) 53(11):4488-4501.
Stagg, John et al., "Anti-CD73 antibody therapy inhibits breast tumor growth and metastasis", *PNAS*, (Jan. 26, 2010) 107(4):1547-1552; *This article has supporting information online at www.pnas.org/cgi/content/full/0908801107/DCSupplemental.
Webster, Rachel M., "The immune checkpoint inhibitors: where are we now?" *Nature Reviews* (Dec. 2014; published online Oct. 27, 2014) 13:883-884.
Zhenchuk, Anna et al., "Mechanisms of anti-cancer action and pharmacology of clofarabine," *Biochemical Pharmacology* (2009; accepted Jun. 23, 2009) 78:1351-1359.

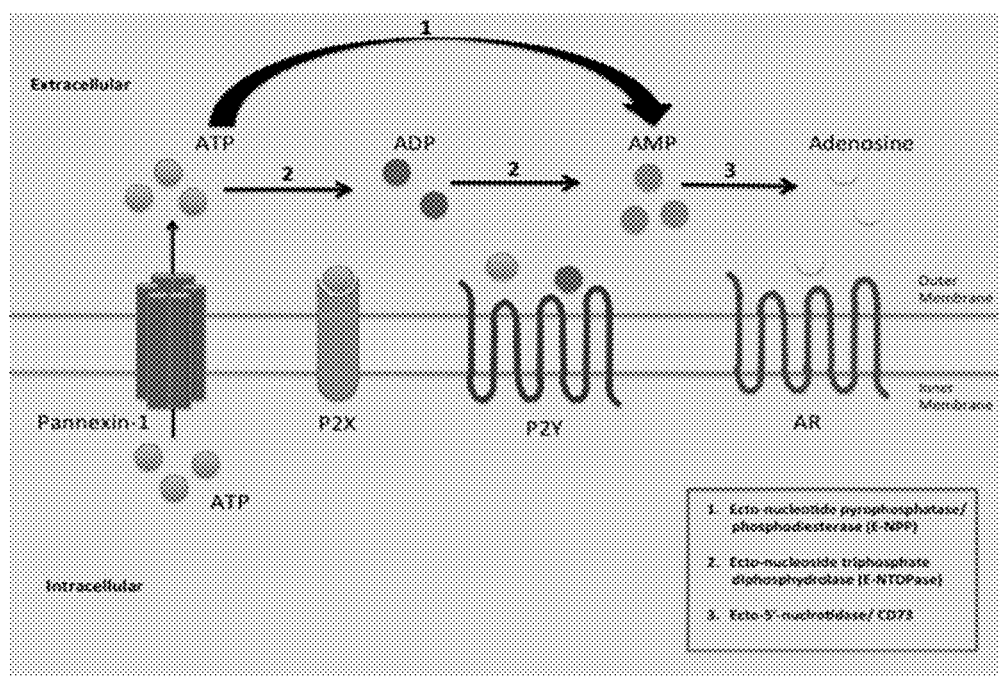

MODULATORS OF 5'-NUCLEOTIDASE, ECTO AND THE USE THEREOF

CROSS-REFERENCES TO RELATED APPLICATIONS

This application is a continuation of U.S. application Ser. No. 17/009,590, filed Sep. 1, 2020, now U.S. Pat. No. 11,001,603, which is a continuation application of U.S. application Ser. No. 16/273,843, filed Feb. 12, 2019, now U.S. Pat. No. 10,981,944, which is a continuation application of U.S. application Ser. No. 15/400,748, filed Jan. 6, 2017, now U.S. Pat. No. 10,239,912, which claims priority benefit under 35 U.S.C. § 119(e) of U.S. Provisional Application No. 62/276,564, filed Jan. 8, 2016 and U.S. Provisional Application No. 62/324,077, filed Apr. 18, 2016, all of which are herein incorporated by reference in their entireties for all purposes.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

FIELD

Provided herein are, for example, compounds and compositions for inhibition of adenosine by 5'-nucleotidase, ecto, also known as CD73, and pharmaceutical compositions comprising same. Also provided herein are, for example, methods of treating or preventing a disease, disorder or condition, or a symptom thereof, mediated by inhibition of adenosine by 5'-nucleotidase, ecto.

BACKGROUND OF THE INVENTION

Purinergic signaling, a type of extracellular signaling mediated by purine nucleotides and nucleosides such as ATP and adenosine, involves the activation of purinergic receptors in the cell and/or in nearby cells, resulting in the regulation of cellular functions. Most cells have the ability to release nucleotides, which generally occurs via regulated exocytosis (see Praetorius, H. A.; Leipziger, J. (1 Mar. 2010) *Ann Rev Physiology* 72(1): 377-393). The released nucleotides can then be hydrolyzed extracellularly by a variety of cellular membrane-bound enzymes referred to as ectonucleotidases.

Ectonucleotides catalyze the conversion of ATP to adenosine, an endogenous modulator that impacts multiple systems, including the immune system, the cardiovascular system, the central nervous system, and the respiratory system. Adenosine also promotes fibrosis in a variety of tissues. In the first step of the production of adenosine, ectonucleoside triphosphate diphosphohydrolase 1 (ENTPD1), also known as CD39 (Cluster of Differentiation 39), hydrolyzes ATP to ADP, and then ADP to AMP. In the next step, AMP is converted to adenosine by 5'-nucleotidase, ecto (NT5E or 5NT), also known as CD73 (Cluster of Differentiation 73).

The enzymatic activities of CD39 and CD73 play strategic roles in calibrating the duration, magnitude, and chemical nature of purinergic signals delivered to various cells (e.g., immune cells). Alteration of these enzymatic activities can change the course or dictate the outcome of several pathophysiological events, including cancer, autoimmune diseases, infections, atherosclerosis, and ischemia-reperfusion injury, suggesting that these ecto-enzymes represent novel therapeutic targets for managing a variety of disorders.

CD73 inhibition with monoclonal antibodies, siRNA, or small molecules delays tumor growth and metastasis (Stagg, J. (2010) PNAS U.S.A. 107:1547-52). For example, anti-CD73 antibody therapy was shown to inhibit breast tumor growth and metastasis in animal models (Stagg, J. (26 Jan. 2010) PNAS U.S.A, 107(4):1547-52). In addition, the use of antibodies that specifically bind CD73 has been evaluated for the treatment of bleeding disorders (e.g., hemophilia) (U.S. Pat. No. 9,090,697). Recently, there have been several efforts to develop therapeutically useful CD73 small molecule inhibitors. For example, Bhattarai et al. ((2015) J Med Chem 58:6248-63) have studied derivatives and analogs of α,β-Methylene-ADP (AOPCP), one of the most metabolically stable, potent and selective CD73 inhibitors known, and purine CD73 derivatives have been reported in the patent literature (WO 2015/164573). However, the development of small molecules has been hampered due to, for example, less than ideal metabolic stability.

In view of the role played by CD73 in cancer, as well as a diverse array of other diseases, disorders and conditions, and the current lack of CD73 inhibitors available to medical practitioners, new CD73 inhibitors, and compositions and methods associated therewith, are needed.

BRIEF SUMMARY OF THE INVENTION

The present invention relates to compounds that modulate the conversion of AMP to adenosine by 5'-nucleotidase, ecto (NT5E or 5NT; also known as CD73), and compositions (e.g., pharmaceutical compositions) comprising the compounds. Such compounds, including methods of their synthesis, and compositions are described in detail below.

The present invention also relates to the use of such compounds and compositions for the treatment and/or prevention of a diverse array of diseases, disorders and conditions mediated, in whole or in part, by CD73. CD73 inhibitors have been linked to the treatment of a diverse array of disorders, including cancer, fibrosis, neurological and neurodegenerative disorders (e.g., depression and Parkinson's disease), cerebral and cardiac ischemic diseases, immune-related disorders, and disorders with an inflammatory component. [See, e.g., Sorrentino et al (2013) OncoImmunol, 2:e22448, doi: 10.4161/onci.22448; and Regateiro et al. (2012) Clin. Exp. Immunol, 171:1-7]. In particular embodiments, the compounds described herein act to inhibit the immunosuppressive activity and/or the anti-inflammatory activity of CD73, and are useful as therapeutic or prophylactic therapy when such inhibition is desired. Unless otherwise indicated, when uses of the compounds of the present invention are described herein, it is to be understood that such compounds may be in the form of a composition (e.g., a pharmaceutical composition).

As used herein, the terms "CD73 inhibitor", "CD73 blocker", "adenosine by 5'-nucleotidase, ecto inhibitor", "NT5E inhibitor", "5NT inhibitor" and all other related art-accepted terms refer to a compound capable of modulating, either directly or indirectly, the CD73 receptor in an in vitro assay, an in vivo model, and/or other means indicative of therapeutic efficacy. The terms also refer to compounds that exhibit at least some therapeutic benefit in a human subject.

Although the compounds of the present invention are believed to effect their activity by inhibition of CD73, a precise understanding of the compounds' underlying mechanism of action is not required to practice the invention. For example, the compounds can also effect their activity, at least in part, through modulation (e.g., inhibition) of other components of the purinergic signaling pathway (e.g., CD39). The purinergic signaling system consists of transporters, enzymes and receptors responsible for the synthesis, release, action, and extracellular inactivation of (primarily) ATP and its extracellular breakdown product adenosine (Sperlagh, B. et al. (December 2012) Neuropsychopharmacologia Hungarica 14(4):231-38). Because inhibition of CD73 results in decreased adenosine, CD73 inhibitors can be used for the treatment of diseases or disorders mediated by adenosine and its actions on adenosine receptors, including A1, $A_{2A}$, $A_{2B}$ and A3. [see Yegutkin, G G (May 2008) Biochimica Biophysica Acta 1783(5):673-94].

For purposes of the present disclosure, the purinergic signaling process can be described as comprising the following components. The purinergic receptors (P1, P2X and P2Y), a first component, are membrane receptors that mediate various physiological functions (e.g., relaxation of gut smooth muscle) as a response to the release of ATP or adenosine; in general, all cells have the ability to release nucleotides into the extracellular environment, frequently through regulated exocytosis. The nucleoside transporters (NTs), a second component, are membrane transport proteins which transport nucleoside substrates (e.g., adenosine) across cell membranes; the extracellular concentration of adenosine can be regulated by NTs, possibly in the form of a feedback loop connecting receptor signaling with transporter function. As previously described, the ectonucleotidases (CD73 and CD39) hydrolyze nucleotides released into the extracellular environment and comprise a further component. Another component of the purinergic signaling process comprises the pannexins; in particular, the pannexin-1 channel (PANX1) is an integral component of the P2X/P2Y purinergic signaling pathway and the key contributor to pathophysiological ATP release.

In one particular aspect, the present invention provides compounds having Formula (I):

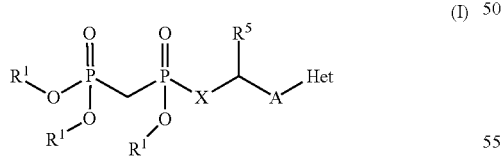

(I)

or a pharmaceutically acceptable salt, hydrate, or solvate thereof, wherein each $R^1$ is independently selected from the group consisting of hydrogen, optionally substituted $C_1$-$C_6$ alkyl, optionally substituted aryl, and —C($R^2R^2$)—O—C(O)—$OR^3$, or two $R^1$ groups are optionally combined to form a 5-to 7-membered ring; each $R^2$ is independently selected from the group consisting of H and optionally substituted $C_1$-$C_6$ alkyl; each $R^3$ is independently selected from the group consisting of H, $C_1$-$C_6$ alkyl, and optionally substituted aryl; $R^5$ is selected from the group consisting of H and optionally substituted $C_1$-$C_6$ alkyl; X is selected from the group consisting of O, $CH_2$, and S; A is selected from the group consisting of:

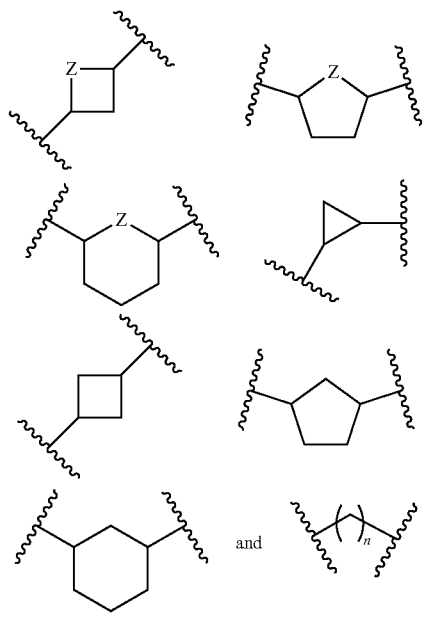

each of which is optionally substituted with from 1 to 5 $R^6$ substituents, and wherein the subscript n is an integer from 0 to 3; Z is selected from the group consisting of $CH_2$, $CHR^6$, $NR^6$, and O; each $R^6$ is independently selected from the group consisting of H, $CH_3$, OH, CN, F, optionally substituted $C_1$-$C_6$ alkyl, and OC(O)—$C_1$-$C_6$ alkyl; and optionally two $R^6$ groups on adjacent ring vertices are joined together to form a 5-to 6-membered ring having at least one heteroatom as a ring vertex; and Het is selected from the group consisting of:

a1

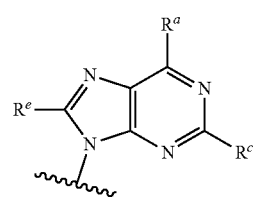

a2

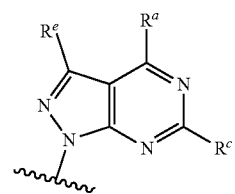

a3

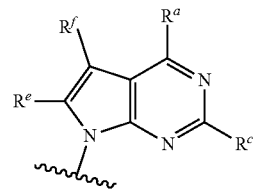

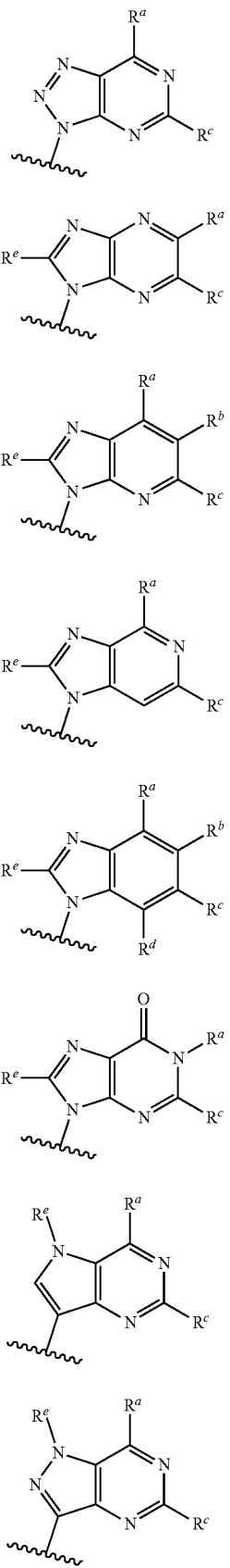
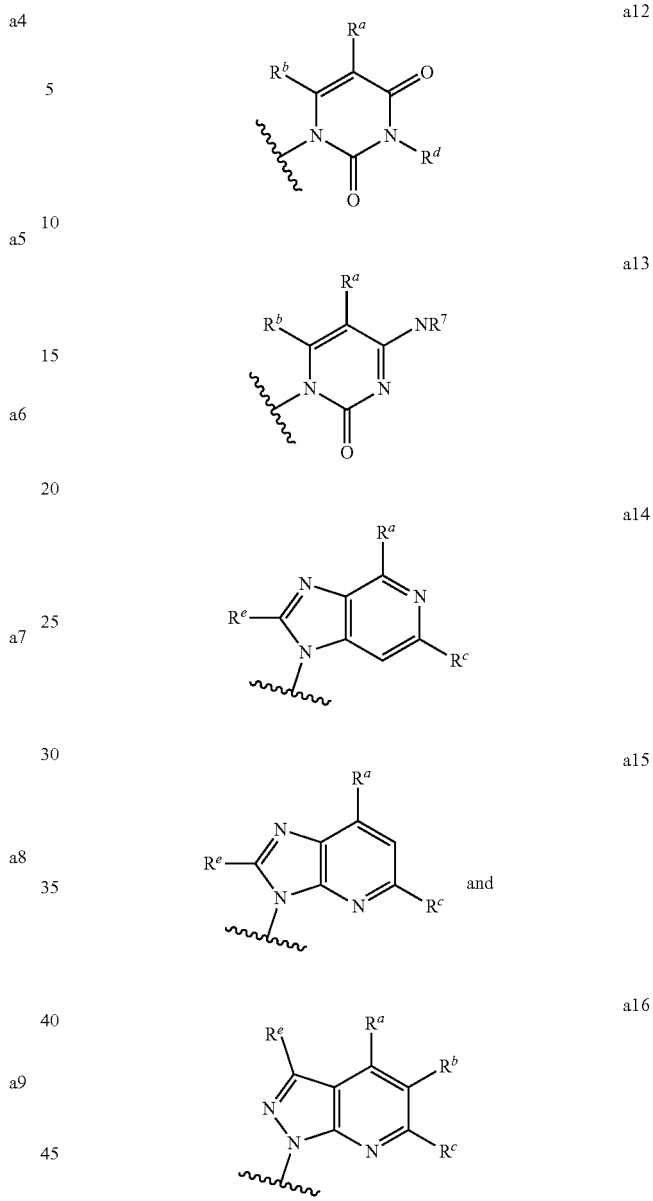

wherein the wavy line indicates the point of attachment to the remainder of the compound, and wherein $R^a$ is selected from the group consisting of H, $NH_2$, $NHR^7$, $NHC(O)R^7$, $NR^7R^7$, $R^7$, OH, $SR^7$ and $OR^7$; $R^b$ is selected from the group consisting of H, halogen, $NH_2$, $NHR^7$, $NR^7R^7$, $R^7$, OH, and $OR^7$; each $R^c$ and $R^d$ is independently selected from the group consisting of H, halogen, haloalkyl, $NH_2$, $NHR^7$, $NR^7R^7$, $R^7$, OH, and $OR^7$; each $R^e$ and $R^f$ is independently selected from the group consisting of H, halogen, and optionally substituted $C_1$-$C_6$ alkyl; and each $R^7$ is independently selected from the group consisting of optionally substituted $C_1$-$C_{10}$ alkyl, optionally substituted $C_3$-$C_7$ cycloalkyl, optionally substituted 4-7 membered cycloheteroalkyl, optionally substituted aryl, optionally substituted arylalkyl, optionally substituted heteroaryl, and optionally substituted heteroarylalkyl, and optionally, two $R^7$ groups attached to a nitrogen atom are joined together to form a 4-7 membered heterocyclic ring.

Excluded from the above are compounds wherein the combination of X, A, and Het results in

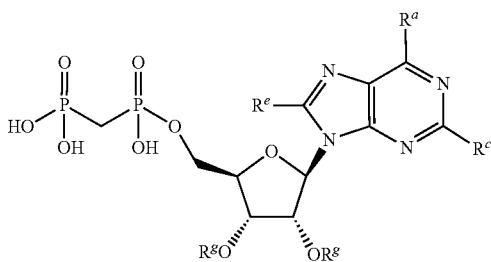

wherein $R^g$ is H or the two $R^g$ groups are combined to form an acetonide; and either
(i) $R^c$ and $R^e$ are hydrogen and $R^a$ is —OEt, —OCH$_2$Ph, —SCH$_2$Ph, —NH$_2$, methylamino, ethylamino, dimethylamino, diethylamino, N-methyl-N-ethylamino, phenylamino, benzylamino, 2-phenylethylamino, N-benzyl-N-ethylamino, dibenzylamino, 4-aminobenzylamino, 4-chlorobenzylamino, 4-nitrobenzylamino, or 4-sulfamoylbenzylamino; or
(ii) $R^c$ is hydrogen, $R^a$ is —NH$_2$, and $R^e$ is bromo, chloro, aminomethyl, or thioethyl; or
(iii) $R^c$ is hydrogen, $R^a$ is benzylamino, and $R^e$ is bromo.

In some embodiments, the present invention contemplates methods for treating or preventing cancer in a subject (e.g., a human) comprising administering to the subject a therapeutically effective amount of at least one CD73 inhibitor described herein. The present invention includes methods of treating or preventing a cancer in a subject by administering to the subject a CD73 inhibitor in an amount effective to reverse or stop the progression of CD73-mediated immunosuppression. In some embodiments, the CD73-mediated immunosuppression is mediated by an antigen-presenting cell (APC).

Examples of the cancers that can be treated using the compounds and compositions described herein include, but are not limited to: cancers of the prostate, colorectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma. In some embodiments of the present invention, the cancer is melanoma, colon cancer, pancreatic cancer, breast cancer, prostate cancer, lung cancer, leukemia, a brain tumor, lymphoma, sarcoma, ovarian cancer, or Kaposi's sarcoma. Cancers that are Candidates for treatment with the compounds and compositions of the present invention are discussed further hereafter.

The present invention contemplates methods of treating a subject receiving a bone marrow transplant or peripheral blood stem cell transplant by administering a therapeutically effective amount of an CD73 inhibitor sufficient to increase the delayed-type hypersensitivity reaction to tumor antigen, delay the time-to-relapse of post-transplant malignancy, increase relapse-free survival time post-transplant, and/or increase long-term post-transplant survival.

In certain embodiments, the present invention contemplates methods for treating or preventing an infective disorder (e.g., a viral infection) in a subject (e.g., a human) comprising administering to the subject a therapeutically effective amount of at least one CD73 inhibitor (e.g., a novel inhibitor of the instant invention). In some embodiments, the infective disorder is a viral infection (e.g., a chronic viral infection), a bacterial infection, a fungal infection, or a parasitic infection. In certain embodiments, the viral infection is human immunodeficiency virus or cytomegalovirus.

In still other embodiments, the present invention contemplates methods for treating and/or preventing immune-related diseases, disorders and conditions; diseases having an inflammatory component; as well as disorders associated with the foregoing; with at least one CD73 inhibitor of the instant invention. Examples of immune-related diseases, disorders and conditions are described hereafter.

Other diseases, disorders and conditions that can be treated or prevented, in whole or in part, by modulation of CD73 activity are Candidate indications for the CD73 inhibitor compounds of the present invention.

The present invention further contemplates the use of the CD73 inhibitors described herein in combination with one or more additional agents. The one or more additional agents may have some CD73-modulating activity and/or they may function through distinct mechanisms of action. In some embodiments, such agents comprise radiation (e.g., localized radiation therapy or total body radiation therapy) and/or other treatment modalities of a non-pharmacological nature. When combination therapy is utilized, the CD73 inhibitor(s) and the one additional agent(s) may be in the form of a single composition or multiple compositions, and the treatment modalities can be administered concurrently, sequentially, or through some other regimen. By way of example, the present invention contemplates a treatment regimen wherein a radiation phase is followed by a chemotherapeutic phase. The combination therapy can have an additive or synergistic effect. Other benefits of combination therapy are described hereafter.

In some embodiments, the present invention further comprises the use of the CD73 inhibitors described herein in combination with bone marrow transplantation, peripheral blood stem cell transplantation, or other types of transplantation therapy.

In particular embodiments, the present invention contemplates the use of the inhibitors of CD73 function described herein in combination with immune checkpoint inhibitors. The blockade of immune checkpoints, which results in the amplification of antigen-specific T cell responses, has been shown to be a promising approach in human cancer therapeutics. Examples of immune checkpoints (ligands and receptors), some of which are selectively upregulated in various types of tumor cells, that are Candidates for blockade include PD1 (programmed cell death protein 1); PDL1 (PD1 ligand); BTLA (B and T lymphocyte attenuator); CTLA4 (cytotoxic T-lymphocyte associated antigen 4); TIM3 (T-cell membrane protein 3); LAG3 (lymphocyte activation gene 3); A2aR (adenosine A2a receptor A2aR); and Killer Inhibitory Receptors. Immune checkpoint inhibitors, and combination therapy therewith, are discussed in detail elsewhere herein.

In other embodiments, the present invention provides methods for treating cancer in a subject, comprising administering to the subject a therapeutically effective amount of at least one CD73 inhibitor and at least one chemotherapeutic agent, such agents including, but not limited to alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nucleoside analogs (e.g., gemcitabine); nitroso ureas such as carmustine, lomustine, and streptozocin; topoisomerase 1 inhibitors (e.g., irinotecan); platinum complexes such as cisplatin and carboplatin; bioreductive alkylators such as mitomycin, procarbazine, dacarbazine and altretamine); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, estramustine, vinblastine, docetaxol, epothilone derivatives, and paclitaxel); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide). The present invention also contemplates the use of the CD73 inhibitors in combination with other agents known in the art (e.g., arsenic trioxide) and other chemotherapeutic agents that may be developed in the future.

In some embodiments drawn to methods of treating cancer, the administration of a therapeutically effective amount of an CD73 inhibitor in combination with at least one chemotherapeutic agent results in a cancer survival rate greater than the cancer survival rate observed by administering either agent alone. In further embodiments drawn to methods of treating cancer, the administration of a therapeutically effective amount of an CD73 inhibitor in combination with at least one chemotherapeutic agent results in a reduction of tumor size or a slowing of tumor growth greater than reduction of the tumor size or tumor growth observed by administration of either agent alone.

In further embodiments, the present invention contemplates methods for treating or preventing cancer in a subject, comprising administering to the subject a therapeutically effective amount of at least one CD73 inhibitor and at least one signal transduction inhibitor (STI). In a particular embodiment, the at least one STI is selected from the group consisting of bcr/abl kinase inhibitors, epidermal growth factor (EGF) receptor inhibitors, her-2/neu receptor inhibitors, and farnesyl transferase inhibitors (FTIs). Other Candidate STI agents are set forth elsewhere herein.

The present invention also contemplates methods of augmenting the rejection of tumor cells in a subject comprising administering an CD73 inhibitor in conjunction with at least one chemotherapeutic agent and/or radiation therapy, wherein the resulting rejection of tumor cells is greater than that obtained by administering either the CD73 inhibitor, the chemotherapeutic agent or the radiation therapy alone.

In further embodiments, the present invention provides methods for treating cancer in a subject, comprising administering to the subject a therapeutically effective amount of at least one CD73 inhibitor and at least one immunomodulator other than an CD73 inhibitor.

The present invention contemplates embodiments comprising methods for treating or preventing an infective disorder (e.g., a viral infection) in a subject (e.g., a human) comprising administering to the subject a therapeutically effective amount of at least one CD73 inhibitor and a therapeutically effective amount of an anti-infective agent(s), such as one or more antimicrobial agents.

In additional embodiments, treatment of an infective disorder is effected through the co-administration of a vaccine in combination with administration of a therapeutically effective amount of an CD73 inhibitor of the present invention. In some embodiments, the vaccine is an anti-viral vaccine, including, for example, an anti-HIV vaccine. In other embodiments, the vaccine is effective against tuberculosis or malaria. In still other embodiments, the vaccine is a tumor vaccine (e.g., a vaccine effective against melanoma); the tumor vaccine can comprise genetically modified tumor cells or a genetically modified cell line, including genetically modified tumor cells or a genetically modified cell line that has been transfected to express granulocytemacrophage stimulating factor (GM-CSF). In particular embodiments, the vaccine includes one or more immunogenic peptides and/or dendritic cells.

In certain embodiments drawn to treatment of an infection by administering an CD73 inhibitor and at least one additional therapeutic agent, a symptom of infection observed after administering both the CD73 inhibitor and the additional therapeutic agent is improved over the same symptom of infection observed after administering either alone. In some embodiments, the symptom of infection observed can be reduction in viral load, increase in $CD4^+$ T cell count, decrease in opportunistic infections, increased survival time, eradication of chronic infection, or a combination thereof.

BRIEF DESCRIPTION OF THE DRAWINGS

FIG. 1 depicts a simplified representation of extracellular purinergic signaling.

DETAILED DESCRIPTION OF THE INVENTION

Before the present invention is further described, it is to be understood that the invention is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

General

The number of subjects diagnosed with cancer and the number of deaths attributable to cancer continue to rise. Traditional treatment approaches comprising chemotherapy and radiotherapy are generally difficult for the patient to tolerate and become less effective as cancers (e.g., tumors) evolve to circumvent such treatments. Recent experimental evidence indicates that CD73 inhibitors may represent an important new treatment modality for cancer (e.g., breast cancer) treatment.

Promising data also support the role of inhibitors of CD73 function to inhibit the anti-inflammatory activity of CD73 and/or the immunosuppressive activity of CD73, and thus CD73 inhibitors may be useful to treat, for example, immunosuppressive diseases (e.g., HIV and AIDs). Inhibition of CD73 may also be an important treatment strategy for patients with neurological or neuropsychiatric diseases or disorders such as depression.

The present invention is drawn to, inter alia, small molecule compounds having CD73 inhibitory activity, as well as compositions thereof, and methods of using the compounds and compositions for the treatment and prevention of the diseases, disorders and conditions described herein.

Definitions

Unless otherwise indicated, the following terms are intended to have the meaning set forth below. Other terms are defined elsewhere throughout the specification.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like.

The term "cycloalkyl" refers to hydrocarbon rings having the indicated number of ring atoms (e.g., $C_{3-6}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc.

The term "cycloheteroalkyl" refers to a cycloalkyl ring having the indicated number of ring vertices (or members) and having from one to five heteroatoms selected from N, O, and S, which replace one to five of the carbon vertices, and wherein the nitrogen and sulfur atoms are optionally oxidized, and the nitrogen atom(s) are optionally quaternized. The cycloheteroalkyl may be a monocyclic, a bicyclic or a polycylic ring system. Non limiting examples of cycloheteroalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A cycloheteroalkyl group can be attached to the remainder of the molecule through a ring carbon or a heteroatom. When 'optionally substituted' is used to describe either of the terms "cycloheteroalkyl" or "cycloheteroalkyl-alkyl", it is meant to refer to those groups wherein the cycloheteroalkyl or alkyl portion is optionally substituted as in the definitions below that refer to the alkyl portion. For example, an optionally substituted cycloheteroalkyl-alkyl group can be optionally substituted on either or both of the cycloheteroalkyl and alkyl portions as in the definitions for alkyl substituents below.

As used herein, a wavy line, "⁓", that intersects a single, double or triple bond in any chemical structure depicted herein, represent the point attachment of the single, double, or triple bond to the remainder of the molecule. Additionally, a bond extending to the center of a ring (e.g., a phenyl ring) is meant to indicate attachment at any of the available ring vertices. One of skill in the art will understand that multiple substituents shown as being attached to a ring will occupy ring vertices that provide stable compounds and are otherwise sterically compatible. For a divalent component, a representation is meant to include either orientation (forward or reverse). For example, the group "—C(O)NH—" is meant to include a linkage in either orientation: —C(O)NH— or —NHC(O)—, and similarly, "—O—CH$_2$CH$_2$—" is meant to include both —O—CH$_2$CH$_2$— and —CH$_2$CH$_2$—O—.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as dialkylamino or —NR$^a$R$^b$ is meant to include piperidinyl, pyrrolidinyl, morpholinyl, azetidinyl and the like.

The terms "arylalkyl" and "heteroarylalkyl" are used in their conventional sense, and refer to those groups wherein an aryl group or a heteroaryl group is attached remainder of the molecule via a $C_1$-$C_4$ alkylene linker. An exemplary embodiment of "arylalkyl" is phenylmethyl (or benzyl). Similarly, an exemplary embodiment of "heteroarylalkyl" is, for example, 3-pyridylpropyl. When 'optionally substituted' is used to describe either of the terms "arylalkyl" or "heteroarylalkyl", it is meant to refer to those groups wherein the aryl or heteroaryl portion is optionally substituted as in the definitions below, and the alkyl portion is optionally substituted as in the definitions below.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. Non-limiting examples of aryl groups include phenyl, naphthyl and biphenyl.

The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for a heteroaryl ring can be selected from the group of acceptable substituents described below.

The above terms (e.g., "alkyl," "aryl" and "heteroaryl"), in some embodiments, will be optionally substituted. Selected substituents for each type of radical are provided below.

Optional substituents for the alkyl radicals (including those groups often referred to as alkylene, alkenyl, alkynyl and cycloalkyl) can be a variety of groups selected from: halogen, —OR', —NR'R", —SR', —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such radical. R', R" and R''' each independently refer to hydrogen, unsubstituted $C_{1-8}$ alkyl, unsubstituted aryl, aryl substituted with 1-3 halogens, unsubstituted $C_{1-8}$ alkyl, $C_1$-8 alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, optional substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro($C_1$-$C_4$)alkoxy, and perfluoro($C_1$-$C_4$)alkyl, in a number ranging from zero to the total number of open valences on the aromatic ring system; and where R', R" and R''' are independently selected from hydrogen, $C_{1-8}$ alkyl, $C_{1-8}$ haloalkyl, $C_{3-6}$ cycloalkyl, $C_{2-8}$ alkenyl and $C_{2-8}$ alkynyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $C_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention.

Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. When a stereochemical depiction is shown, it is meant to refer the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3H$), iodine-125 ($^{125}I$) or carbon-14 ($^{14}C$), or non-radioactive isotopes, such as deuterium ($^2H$) or carbon-13 ($^{13}C$). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, an inhibitor of CD73, a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering an inhibitor of CD73 or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering an CD73 inhibitor or a pharmaceutical composition comprising same) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. Byway of example, measurement of the serum level of an CD73 inhibitor (or, e.g., a metabolite thereof) at a particular time post-administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule may be more permeable to cells, less susceptible to degradation, and less likely to elicit an immune response than large molecules.

The term "ligand" refers to, for example, a peptide, a polypeptide, a membrane-associated or membrane-bound molecule, or a complex thereof, that can act as an agonist or antagonist of a receptor. A ligand encompasses natural and synthetic ligands, e.g., cytokines, cytokine variants, analogs, muteins, and binding compositions derived from antibodies, as well as small molecules. The term also encompasses an agent that is neither an agonist nor antagonist, but that can bind to a receptor without significantly influencing its biological properties, e.g., signaling or adhesion. Moreover, the term includes a membrane-bound ligand that has been changed by, e.g., chemical or recombinant methods, to a soluble version of the membrane-bound ligand. A ligand or receptor may be entirely intracellular, that is, it may reside in the cytosol, nucleus, or some other intracellular compartment. The complex of a ligand and receptor is termed a "ligand-receptor complex."

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of CD73, either directly or indirectly. A modulator may act alone, or it may use a cofactor, e.g., a protein, metal ion, or small molecule. Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an Activator.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

As used herein, "comparable", "comparable activity", "activity comparable to", "comparable effect", "effect comparable to", and the like are relative terms that can be viewed quantitatively and/or qualitatively. The meaning of the terms is frequently dependent on the context in which they are used. By way of example, two agents that both activate a receptor can be viewed as having a comparable effect from a qualitative perspective, but the two agents can be viewed as lacking a comparable effect from a quantitative perspective if one agent is only able to achieve 20% of the activity of the other agent as determined in an art-accepted assay (e.g., a dose-response assay) or in an art-accepted animal model. When comparing one result to another result (e.g., one result to a reference standard), "comparable" frequently (though not always) means that one result deviates from a reference standard by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one result is comparable to a reference standard if it deviates by less than 15%, by less than 10%, or by less than 5% from the reference standard. By way of example, but not limitation, the activity or effect may refer to efficacy, stability, solubility, or immunogenicity.

"Substantially pure" indicates that a component makes up greater than about 50% of the total content of the composition, and typically greater than about 60% of the total content. More typically, "substantially pure" refers to compositions in which at least 75%, at least 85%, at least 90% or more of the total composition is the component of interest. In some cases, the component of interest will make up greater than about 90%, or greater than about 95% of the total content of the composition.

The terms "specifically binds" or "selectively binds", when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two-fold greater, at least ten times greater, at least 20-times greater, or at least 100-times greater than the affinity with any other antibody, or binding composition derived therefrom. In a particular embodiment, the antibody will have an affinity that is greater than about $10^9$ liters/mol, as determined by, e.g., Scatchard analysis (Munsen, et al. 1980 Analyt. Biochem. 107:220-239).

The term "response," for example, of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence, fusion proteins with heterologous and homologous leader sequences, with or without N-terminus methionine residues; immunologically tagged proteins; and the like.

As used herein, the terms "variants" and "homologs" are used interchangeably to refer to amino acid or DNA sequences that are similar to reference amino acid or nucleic acid sequences, respectively. The term encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Thus, variants and homologs encompass naturally occurring DNA sequences and proteins encoded thereby and their isoforms, as well as splice variants of a protein or gene. The terms also encompass nucleic acid sequences that vary in one or more bases from a naturally-occurring DNA sequence but still translate into an amino acid sequence that corresponds to the naturally-occurring protein due to degeneracy of the genetic code. Non-naturally-occurring variants and homologs include polypeptides and nucleic acids that comprise a change in amino acid or nucleotide sequence, respectively, where the change in sequence is artificially introduced (e.g., muteins); for example, the change is generated in the laboratory by human intervention ("hand of man"). Therefore, non-naturally occurring variants and homologs may also refer to those that differ from the naturally-occurring sequences by one or more conservative substitutions and/or tags and/or conjugates.

The term "muteins" as used herein refers broadly to mutated recombinant proteins. These proteins usually carry single or multiple amino acid substitutions and are frequently derived from cloned genes that have been subjected to site-directed or random mutagenesis, or from completely synthetic genes.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

5'-Nucleotidase, Ecto and Inhibition Thereof

Human CD73 (also referred to as 5'-nucleotidase, ecto; NT5E; or 5NT) is a 574 amino acid residue protein (Accession No. AAH6593). Eukaryotic CD73 functions as a non-covalent homodimer with two structural domains, wherein the N- and C-terminal domains are connected by a hinge region that enables the enzyme to undergo large domain movements and switch between open and closed conformations (Knapp, K. et al. (2012) Structure 20:2161-73).

As used herein, the terms "CD73 inhibitor", "CD73 blocker", "adenosine by 5'-nucleotidase, ecto inhibitor", "NT5E inhibitor", "5NT inhibitor" and all other related art-accepted terms refer to a compound capable of modulating, either directly or indirectly, the CD73 receptor in an in vitro assay, an in vivo model, and/or other means indicative of therapeutic efficacy. The terms also refer to compounds that exhibit at least some therapeutic benefit in a human subject. An CD73 inhibitor may be a competitive, noncompetitive, or irreversible CD73 inhibitor. "A competitive CD73 inhibitor" is a compound that reversibly inhibits CD73 enzyme activity at the catalytic site; "a noncompetitive CD73 inhibitor" is a compound that reversibly inhibits CD73 enzyme activity at a non-catalytic site; and "an irreversible CD73 inhibitor" is a compound that irreversibly eliminates CD73 enzyme activity by forming a covalent bond (or other stable means of inhibiting enzyme function) with the enzyme.

CD73 inhibitors can modulate purinergic signaling, a type of extracellular signaling mediated by purine nucleotides and nucleosides such as ATP and adenosine. Purinergic signaling involves the activation of purinergic receptors in the cell and/or in nearby cells, resulting in the regulation of cellular functions. The enzymatic activity of CD73 plays a strategic role in calibrating the duration, magnitude, and chemical nature of purinergic signals delivered to various cells (e.g., immune cells). Alteration of these enzymatic activities can change the course or dictate the outcome of several pathophysiological events, including cancer, autoimmune and inflammatory diseases, infections, atherosclerosis, and ischemia-reperfusion injury, suggesting that these ecto-enzymes represent novel therapeutic targets for managing a variety of disorders.

Studies using tissues that overexpress CD73 and using CD73 knock-out mice have provided evidence that CD73 inhibitors have potential utility for melanomas, lung cancer, prostate cancer, and breast cancer (see, e.g., Sadej R. (2006) Melanoma Res 16: 213-22). Because higher expression levels of CD73 are associated with tumor neovascularization, invasiveness, resistance to chemotherapy, and metastasis, CD73 inhibitors can be used to control tumor progression and metastasis. Other potential utilities are discussed elsewhere herein.

As set forth above, although the compounds of the present invention are believed to exert their activity by inhibition of CD73, a precise understanding of the compounds' underlying mechanism of action is not required to practice the invention. For example, the compounds can also exert their activity, at least in part, through modulation (e.g., inhibition) of other components of the purinergic signaling pathway (e.g., CD39). The purinergic signaling system consists of transporters, enzymes and receptors responsible for the synthesis, release, action, and extracellular inactivation of (primarily) ATP and its extracellular breakdown product adenosine (Sperlagh, B. et al. (December 2012) Neuropsychopharmacologia Hungarica 14(4):231-38). FIG. 1 depicts a simplified representation of extracellular purinergic signaling (see, e.g., North R A (October 2002) *Physiological Reviews* 82(4):1013-67). As indicated therein, there are several potential opportunities for modulation of the signaling process. However, as will be apparent to the skilled artisan, some of these opportunities are more tractable than others.

Identification of CD73 Inhibitors Possessing Desirable Characteristics

The present invention is drawn, in part, to the identification of inhibitors of CD73 with at least one property or characteristic that is of therapeutic relevance. Candidate inhibitors may be identified by using, for example, an art-accepted assay or model, examples of which are will be apparent to the skilled artisan. The assay used to determine the CD73 inhibitory activity of the compounds described herein is set forth in the Experimental section.

After identification, Candidate inhibitors can be further evaluated by using techniques that provide data regarding characteristics of the inhibitors (e.g., pharmacokinetic parameters). Comparisons of the Candidate inhibitors to a reference standard (which may the "best-of-class" of current inhibitors) are indicative of the potential viability of such Candidates.

CD73 inhibitors that can serve as reference or benchmark compounds include α,β-Methylene-ADP (AOPCP) and its derivatives and analogs described by Bhattarai et al. ((2015) J Med Chem 58:6248-63) and the purine CD73 derivatives reported in PCT Publn. 2015/164573. Other reference compounds subsequently identified by the skilled artisan can also be used to assess the viability of Candidate CD73 inhibitors.

Compounds of the Invention

Provided herein are compounds having Formula (I):

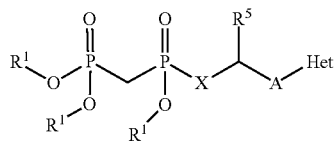

(I)

or a pharmaceutically acceptable salt, hydrate, or solvate thereof, wherein, each $R^1$ is independently selected from the group consisting of hydrogen, optionally substituted $C_1$-$C_6$ alkyl, optionally substituted aryl, and —C($R^2R^2$)—O—C(O)—O$R^3$, or two $R^1$ groups are optionally combined to form a 5-to 7-membered ring;

each $R^2$ is independently selected from the group consisting of H and optionally substituted $C_1$-$C_6$ alkyl;

each $R^3$ is independently selected from the group consisting of H, $C_1$-$C_6$ alkyl, and optionally substituted aryl;

$R^5$ is selected from the group consisting of H and optionally substituted $C_1$-$C_6$ alkyl;

X is selected from the group consisting of O, $CH_2$, and S;

A is selected from the group consisting of:

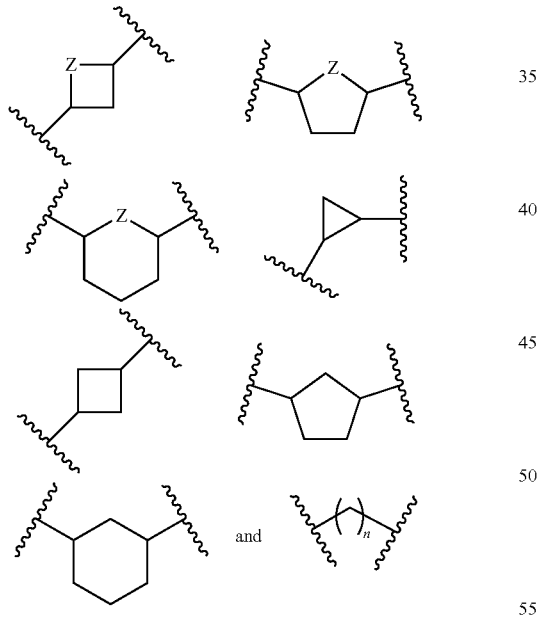

and each of which is optionally substituted with from 1 to 5 $R^6$ substituents, and wherein the subscript n is an integer from 0 to 3;

Z is selected from the group consisting of $CH_2$, $CHR^6$, $NR^6$, and O;

each $R^6$ is independently selected from the group consisting of H, $CH_3$, OH, CN, F, optionally substituted $C_1$-$C_6$ alkyl, and OC(O)—$C_1$-$C_6$ alkyl; and optionally two $R^6$ groups on adjacent ring vertices are joined together to form a 5-to 6-membered ring having at least one heteroatom as a ring vertex; and Het is selected from the group consisting of:

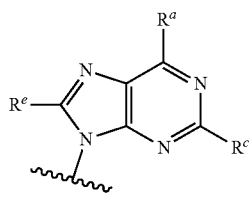

a1

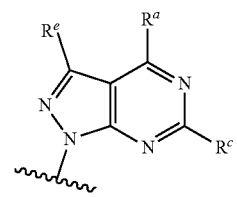

a2

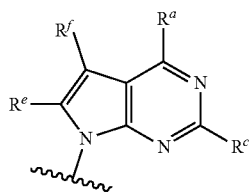

a3

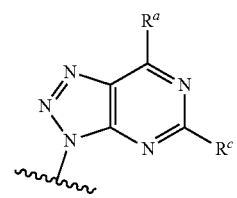

a4

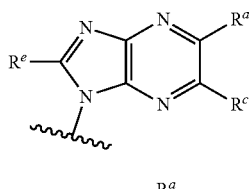

a5

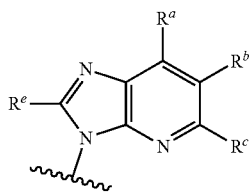

a6

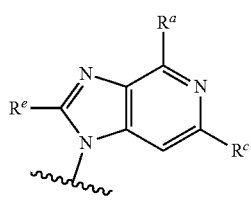

a7

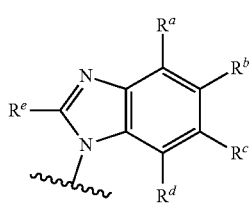

a8

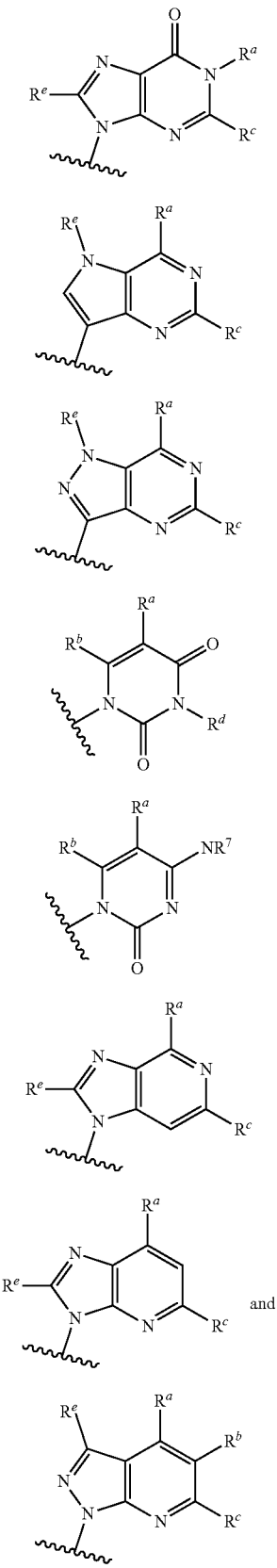

wherein the wavy line indicates the point of attachment to the remainder of the compound, and wherein:

$R^a$ is selected from the group consisting of H, NH₂, NHR⁷, NHC(O)R⁷, NR⁷R⁷, R⁷, OH, SR⁷ and OR⁷;

$R^b$ is selected from the group consisting of H, halogen, NH₂, NHR⁷, NR⁷R⁷, R⁷, OH, and OR⁷;

$R^c$ and $R^d$ are independently selected from the group consisting of H, halogen, haloalkyl, NH₂, NHR⁷, NR⁷R⁷, R⁷, OH, OR⁷, SR⁷, SO₂R⁷, —X¹—NH₂, —X¹—NHR⁷, —X¹—NR⁷R⁷, —X¹—OH, —X¹—OR⁷, —X¹—SR⁷ and —X¹—SO₂R⁷;

$R^e$ and $R^f$ are independently selected from the group consisting of H, halogen, and optionally substituted C₁-C₆ alkyl;

each X¹ is C₁-C₄alkylene; and each R⁷ is independently selected from the group consisting of optionally substituted C₁-C₁₀ alkyl, optionally substituted C₂-C₁₀ alkenyl, optionally substituted C₂-C₁₀ alkynyl, optionally substituted C₃-C₇ cycloalkyl, optionally substituted C₃-C₇ cycloalkylC₁-C₄alkyl, optionally substituted 4-7 membered cycloheteroalkyl, optionally substituted 4-7 membered cycloheteroalkylC₁-C₄alkyl, optionally substituted aryl, optionally substituted arylC₁-C₄alkyl, optionally substituted arylC₂-C₄alkenyl, optionally substituted arylC₂-C₄alkynyl, optionally substituted heteroaryl, optionally substituted heteroarylC₁-C₄alkyl, optionally substituted heteroarylC₁-C₄alkenyl, optionally substituted heteroarylC₂-C₄alkynyl, and optionally, two R⁷ groups attached to a nitrogen atom are joined together to form a 4-to 7-membered heterocyclic ring, optionally fused to an aryl ring;

with the proviso that the compounds are other than those compounds wherein the combination of X, A, and Het results in wherein R^g is H or the two R^g groups are combined to form an acetonide; and either (i) $R^c$ and $R^e$ are hydrogen and $R^a$ is —OEt, —OCH₂Ph, —SCH₂Ph, —NH₂, methylamino, ethylamino, dimethylamino, diethylamino, N-methyl-N-ethylamino, phenylamino, benzylamino, 2-phenylethylamino, N-benzyl-N-ethylamino, dibenzylamino, 4-aminobenzylamino, 4-chlorobenzylamino, 4-nitrobenzylamino, or 4-sulfamoylbenzylamino; or (ii) $R^c$ is hydrogen, $R^a$ is —NH₂, and $R^e$ is bromo, chloro, aminomethyl, or thioethyl; or (iii) $R^e$ is hydrogen, $R^a$ is benzylamino, and $R^c$ is bromo.

For the above formula, the term 'optionally substituted' is used in connection with alkyl groups, cycloalkyl groups, cycloheteroalkyl groups, aryl groups and heteroaryl groups. Within each of these groups, some selected optional substituents are as follows:

Alkyl groups: halogen, —OR', —NR'R", —SR', —SiR'R"R'", —OC(O)R', —C(O)R', —CO₂R', —CONR'R", —OC(O)NR'R", —NR"C(O)R', —NR'—C(O)NR"R'", —NR"C(O)₂R', —CN and —NO₂. R', R" and R'" each independently refer to hydrogen, unsubstituted C₁₋₄ alkyl, or $C_{1-4}$ haloalkyl. When R' and R" are attached to the same nitrogen atom, or when R" and R'" are attached to the same nitrogen, they can be combined with the nitrogen atom to form a 3-, 4-, 5-, 6-, or 7-membered ring. For example, —NR'R" is meant to include 1-pyrrolidinyl and 4-morpholinyl.

Cycloalkyl groups and cycloheteroalkyl groups: The selected substituents noted above for 'alkyl groups' are also useful with cycloalkyl and cycloheteroalkyl groups. Additionally, each of the cycloalkyl and cycloheteroalkyl groups can be optionally substituted with oxo (=O).

Aryl groups and heteroaryl groups: -halogen, —OR', —OC(O)R', —NR'R", —R', —CN, —NO$_2$, —CO$_2$R', —CONR'R", —C(O)R', —OC(O)NR'R", —NR"C(O)R', —NR"C(O)$_2$R', —NR'—C(O)NR"R'", —S(O)$_2$R', —S(O)$_2$NR'R", —NR'S(O)$_2$R", and perfluoro($C_1$-$C_4$)alkyl, where R', R" and R'" are independently selected from hydrogen, $C_{1-4}$ alkyl, $C_{1-4}$haloalkyl and $C_{3-6}$ cycloalkyl.

In one selected group of embodiments, compounds of Formula (I) are provided wherein A has the formula:

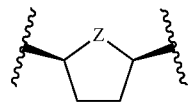

which is optionally substituted with from 1 to 5 $R^6$.

In another selected group of embodiments, compounds of Formula (I) are provided wherein A has a formula selected from the group consisting of:

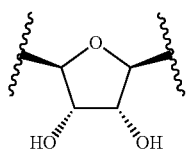
b1

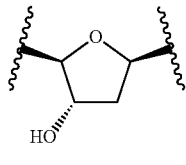
b2

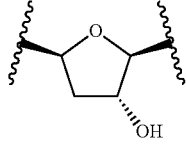
b3

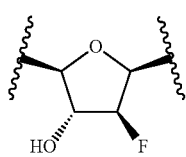
b4

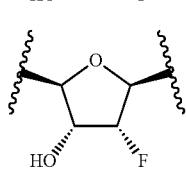
b5

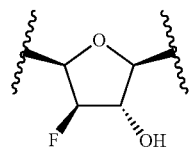
b6

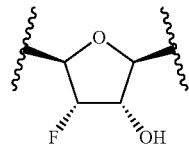
b7

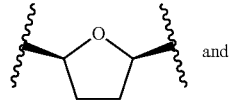
and
b8

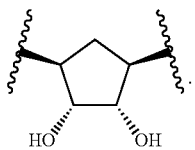
b9

In some selected embodiments, any one of a1 through a16 can be independently combined with any one of b1 through b9, to provide selected embodiments of Formula (I). For example, provided herein are compounds of Formula (I) having the following combinations of Het-A-: a1/b1; a1/b2; a1/b3; a1/b4; a1/b5; a1/b6; a1/b7; a1/b8; a1/b9; a2/b1; a2/b2; a2/b3; a2/b4; a2/b5; a2/b6; a2/b7; a2/b8; a2/b9; a3/b1; a3/b2; a3/b3; a3/b4; a3/b5; a3/b6; a3/b7; a3/b8; a3/b9; a4/b1; a4/b2; a4/b3; a4/b4; a4/b5; a4/b6; a4/b7; a4/b8; a4/b9; a5/b1; a5/b2; a5/b3; a5/b4; a5/b5; a5/b6; a5/b7; a5/b8; a5/b9; a6/b1; a6/b2; a6/b3; a6/b4; a6/b5; a6/b6; a6/b7; a6/b8; a6/b9; a7/b1; a7/b2; a7/b3; a7/b4; a7/b5; a7/b6; a7/b7; a7/b8; a7/b9; a8/b1; a8/b2; a8/b3; a8/b4; a8/b5; a8/b6; a8/b7; a8/b8; a8/b9; a9/b1; a9/b2; a9/b3; a9/b4; a9/b5; a9/b6; a9/b7; a9/b8; a9/b9; a10/b1; a10/b2; a10/b3; a10/b4; a10/b5; a10/b6; a10/b7; a10/b8; a10/b9; a11/b1; a11/b2; a11/b3; a11/b4; a11/b5; a11/b6; a11/b7; a11/b8; a1 1/b9; a12/b1; a12/b2; a12/b3; a12/b4; a12/b5; a12/b6; a12/b7; a12/b8; a12/b9; a13/b1; a13/b2; a13/b3; a13/b4; a13/b5; a13/b6; a13/b7; a13/b8; a13/b9; a14/b1; a14/b2; a14/b3; a14/b4; a14/b5; a14/b6; a14/b7; a14/b8; a14/b9; a15/b1; a15/b2; a15/b3; a15/b4; a15/b5; a15/b6; a15/b7; a15/b8; a15/b9; a16/b1; a16/b2; a16/b3; a16/b4; a16/b5; a16/b6; a16/b7; a16/b8; or a16/b9.

In still other selected embodiments, compounds of Formula (I) are provided wherein Het has the formula:

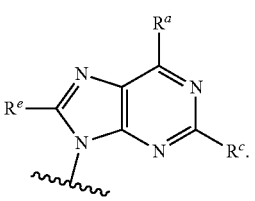
(a1)

In some selected embodiments, $R^c$ is other than H.

In yet other selected embodiments, compounds of Formula (I) are provided that are represented by one of the following subformulae:

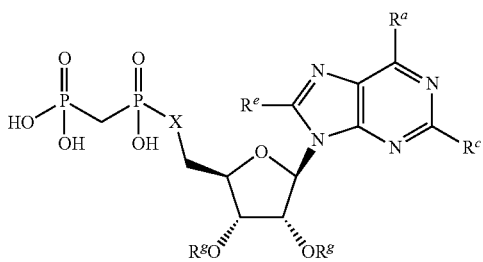
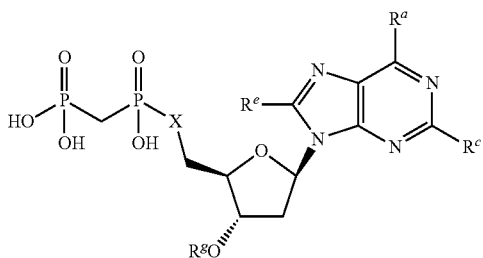
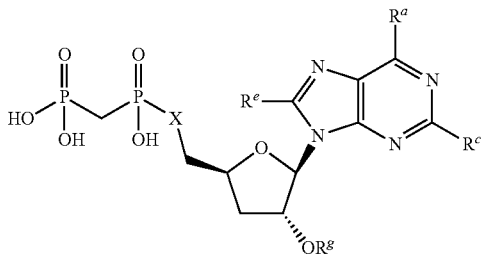
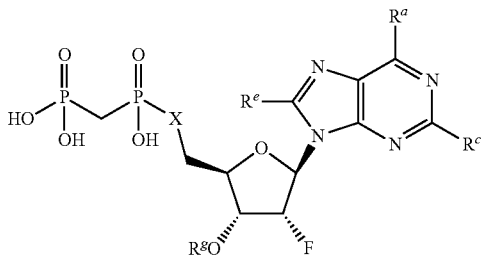
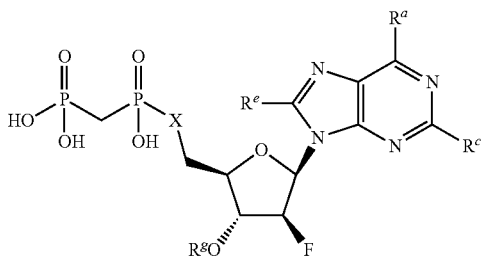
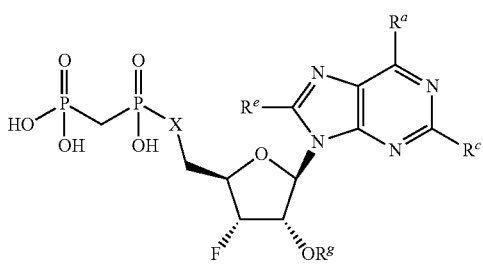

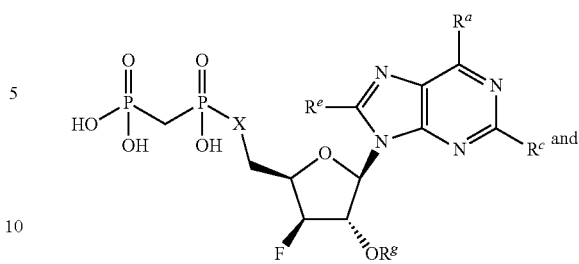
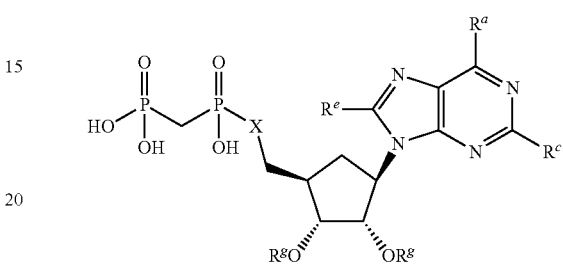

wherein each $R^E$ is independently selected from the group consisting of H and C(O)—$C_1$-$C_6$ alkyl. Still further selected embodiments of the subformulae above, are those wherein X is oxygen. In other selected embodiments of the subformulae above, X is oxygen and $R^e$ is hydrogen. In still other selected embodiments of the subformulae above, X is oxygen, $R^e$ is hydrogen, and each $R^b$ is hydrogen.

In another group of selected embodiments, compounds of Formula (I) are provided wherein Het is selected from:

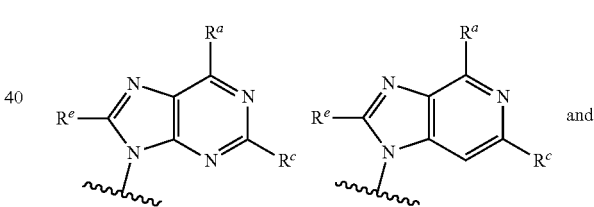

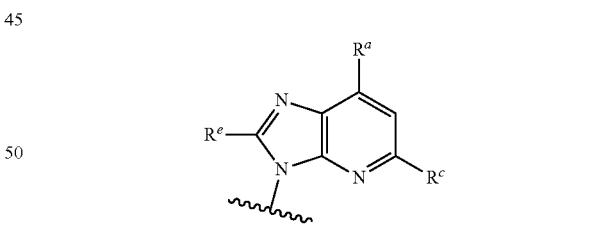

wherein $R^a$, $R^c$ and $R^e$ have the meanings provided with reference to Formula (I) above. In some further selected embodiments, $R^5$ is H, X is O, and each $R^1$ is H. In still other selected embodiments, $R^5$ is H, X is O, each $R^1$ is H, $R^c$ is H, and $R^a$ is selected from the group consisting of $NH_2$, $NHR^7$ and $N(R^7)_2$. In yet other selected embodiments, $R^5$ is H, X is O, each $R^1$ is H, $R^e$ is H, $R^c$ is other than H, and $R^a$ is $NHR^7$.

Still other selected embodiments of the Formula (I), are compounds having a subformulae selected from the following:

(IIa)

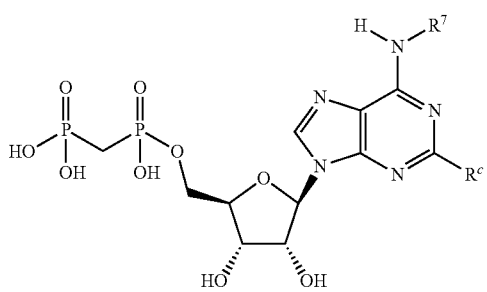

(IIIa)

(IIb)

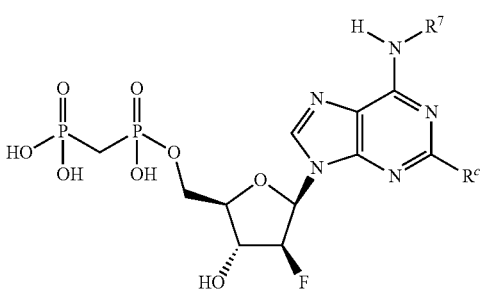

and (IIIb)

wherein $R^7$ and $R^c$ have the meanings provided with respect to Formula (I), and certain selected embodiments as described herein.

Also provided herein, in one group of embodiments, are compounds having the formula:

(IVa)

or a pharmaceutically acceptable salt, hydrate, or solvate thereof, wherein,
each $R^1$ is independently selected from the group consisting of hydrogen, optionally substituted $C_1$-$C_6$ alkyl, option-
ally substituted aryl, and —C($R^2R^2$)—O—C(O)—O$R^3$, or two $R^1$ groups are optionally combined to form a 5-to 7-membered ring;
each $R^2$ is independently selected from the group consisting of H and optionally substituted $C_1$-$C_6$ alkyl;
each $R^3$ is independently selected from the group consisting of H, $C_1$-$C_6$ alkyl, and optionally substituted aryl;
$R^5$ is selected from the group consisting of H and optionally substituted $C_1$-$C_6$ alkyl;
X is O;
A is selected from the group consisting of:

and
Het is selected from the group consisting of:

-continued

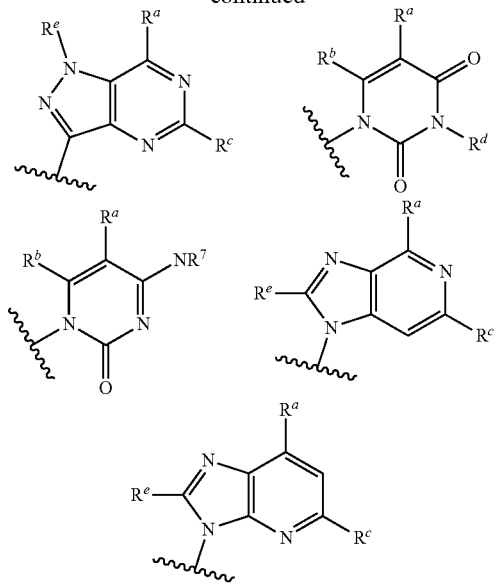

wherein the wavy line indicates the point of attachment to the remainder of the compound, and wherein:

$R^a$ is selected from the group consisting of H, $NH_2$, $NHR^7$, $NHC(O)R^7$, $NR^7R^7$, $R^7$, OH, $SR^7$ and $OR^7$;

$R^b$ is selected from the group consisting of H, halogen, $NH_2$, $NHR^7$, $NR^7R^7$, $R^7$, OH, and $OR^7$;

$R^c$ and $R^d$ are independently selected from the group consisting of H, halogen, haloalkyl, $NH_2$, $NHR^7$, $NR^7R^7$, $R^7$, OH, $OR^7$, $SR^7$, $SO_2R^7$, $—X^1—NH_2$, $—X^1—NHR^7$, $—X^1—NR^7R^7$, $—X^1—OH$, $—X^1—OR^7$, $—X^1—SR^7$ and $—X^1—SO_2R^7$;

$R^e$ and $R^f$ are independently selected from the group consisting of H, halogen, and optionally substituted $C_1$-$C_6$ alkyl;

each $X^1$ is $C_1$-$C_4$alkylene; and each $R^7$ is independently selected from the group consisting of optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_7$ cycloalkyl, optionally substituted $C_3$-$C_7$ cycloalkyl$C_1$-$C_4$alkyl, optionally substituted 4-7 membered cycloheteroalkyl, optionally substituted 4-7 membered cycloheteroalkyl$C_1$-$C_4$alkyl, optionally substituted aryl, optionally substituted aryl$C_1$-$C_4$alkyl, optionally substituted aryl$C_2$-$C_4$alkenyl, optionally substituted aryl$C_2$-$C_4$alkynyl, optionally substituted heteroaryl, optionally substituted heteroaryl$C_1$-$C_4$alkyl, optionally substituted heteroaryl$C_1$-$C_4$alkenyl, optionally substituted heteroaryl$C_2$-$C_4$alkynyl, and optionally, two $R^7$ groups attached to a nitrogen atom are joined together to form a 4-to 7-membered heterocyclic ring, optionally fused to an aryl ring.

In one selected group of embodiments, the compounds of formula (IVa) are those wherein A is

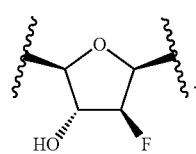 [SMILES: *[C@@H]1O[C@H](*)[C@@H](O)[C@@H]1F]

In another selected group of embodiments, the compounds of formula (IVa) are those wherein Het is selected from the group consisting of:

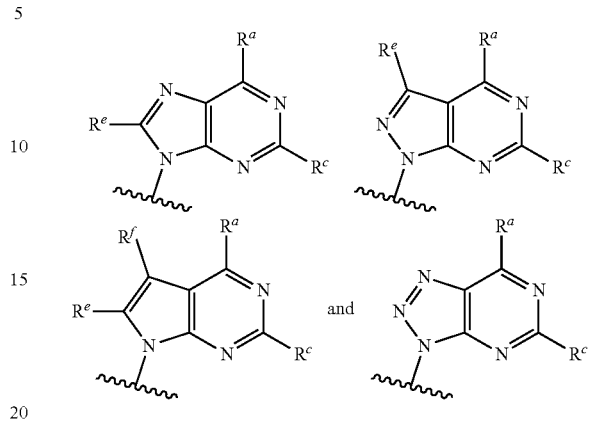

In still another selected group of embodiments, the compounds have the formula:

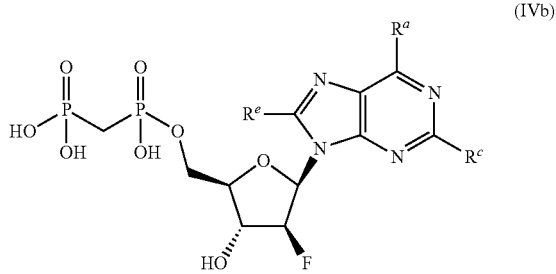

(IVb)

or a pharmaceutically acceptable salt, hydrate, or solvate thereof.

In one selected group of embodiments, the compounds of formula (IVb) are those wherein $R^a$ is selected from the group consisting of $NH_2$, $NHR^7$, $NR^7R^7$, $SR^7$ and $OR^7$. In one selected group of embodiments, the compounds of formula (Tb) are those wherein $R^c$ is selected from the group consisting of halogen, $R^7$, $OR^7$, $SR^7$, $SO_2R^7$, $—X^1—NH_2$, $—X^1—NHR^7$, $—X^1—NR^7R^7$, $—X^1—OH$, $—X^1—OR^7$, $—X^1—SR^7$ and $—X^1—SO_2R^7$.

In yet another selected group of embodiments, the compounds of formula (IVb) are those wherein $R^e$ is H.

Methods of Synthesis

In general, the compounds provided herein can be prepare by conventional methods as described in the Examples below.

Modifications to Enhance Inhibitor Characteristics

It is frequently beneficial, and sometimes imperative, to improve one of more physical properties of the treatment modalities disclosed herein and/or the manner in which they are administered. Improvements of physical properties include, for example, methods of increasing water solubility, bioavailability, serum half-life, and/or therapeutic half-life; and/or modulating biological activity.

Modifications known in the art include pegylation, Fc-fusion and albumin fusion. Although generally associated with large molecule agents (e.g., polypeptides), such modifications have recently been evaluated with particular small molecules. By way of example, Chiang, M. et al. (J. Am. Chem. Soc., 2014, 136(9):3370-73) describe a small molecule agonist of the adenosine 2a receptor conjugated to the immunoglobulin Fc domain. The small molecule-Fc conjugate retained potent Fc receptor and adenosine 2a receptor interactions and showed superior properties compared to the unconjugated small molecule. Covalent attachment of PEG molecules to small molecule therapeutics has also been described (Li, W. et al., Progress in Polymer Science, 2013 38:421-44).

Therapeutic and Prophylactic Uses

The present invention contemplates the use of the CD73 inhibitors described herein in the treatment or prevention of a broad range of diseases, disorders and/or conditions, and/or the symptoms thereof. While particular uses are described in detail hereafter, it is to be understood that the present invention is not so limited. Furthermore, although general categories of particular diseases, disorders and conditions are set forth hereafter, some of the diseases, disorders and conditions may be a member of more than one category, and others may not be a member of any of the disclosed categories.

Oncology-related Disorders. In accordance with the present invention, an CD73 inhibitor can be used to treat or prevent a proliferative condition or disorder, including a cancer, for example, cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present invention also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. The invention contemplates reducing tolerance to a tumor cell or cancer cell antigen, e.g., by modulating activity of a regulatory T-cell and/or a CD8+ T-cell (see, e.g., Ramirez-Montagut, et al. (2003) Oncogene 22:3180-87; and Sawaya, et al. (2003) New Engl. J. Med. 349:1501-09). In particular embodiments, the tumor or cancer is colon cancer, ovarian cancer, breast cancer, melanoma, lung cancer, glioblastoma, or leukemia. The use of the term(s) cancer-related diseases, disorders and conditions is meant to refer broadly to conditions that are associated, directly or indirectly, with cancer, and includes, e.g., angiogenesis and precancerous conditions such as dysplasia.

In certain embodiments, a cancer be metastatic or at risk of becoming metastatic, or may occur in a diffuse tissue, including cancers of the blood or bone marrow (e.g., leukemia). In some further embodiments, the compounds of the invention can be used to overcome T-cell tolerance.

In some embodiments, the present invention provides methods for treating a proliferative condition, cancer, tumor, or precancerous condition with an CD73 inhibitor and at least one additional therapeutic or diagnostic agent, examples of which are set forth elsewhere herein.

Immune-related Disorders and Disorders with an Inflammatory Component. As used herein, terms such as "immune disease", "immune condition", "immune disorder", "inflammatory disease", "inflammatory condition", "inflammatory disorder" and the like are meant to broadly encompass any immune-related condition (e.g., an autoimmune disease) or a disorder with an inflammatory component that can be treated by the CD73 inhibitors described herein such that some therapeutic benefit is obtained. Such conditions frequently are inextricably intertwined with other diseases, disorders and conditions. By way of example, an "immune condition" may refer to proliferative conditions, such as cancer, tumors, and angiogenesis; including infections (acute and chronic), tumors, and cancers that resist eradication by the immune system.

The CD73 inhibitors of the present invention can be used to increase or enhance an immune response; to improve immunization, including increasing vaccine efficacy; and to increase inflammation. Immune deficiencies associated with immune deficiency diseases, immunosuppressive medical treatment, acute and/or chronic infection, and aging can be treated using the compounds disclosed herein. The CD73 inhibitors can also be used to stimulate the immune system of patients suffering from iatrogenically-induced immune suppression, including those who have undergone bone marrow transplants, chemotherapy, or radiotherapy.

In particular embodiments of the present disclosure, the CD73 inhibitors are used to increase or enhance an immune response to an antigen by providing adjuvant activity. In a particular embodiment, at least one antigen or vaccine is administered to a subject in combination with at least one CD73 inhibitor of the present invention to prolong an immune response to the antigen or vaccine. Therapeutic compositions are also provided which include at least one antigenic agent or vaccine component, including, but not limited to, viruses, bacteria, and fungi, or portions thereof, proteins, peptides, tumor-specific antigens, and nucleic acid vaccines, in combination with at least one CD73 inhibitor of the present invention.

Microbial-related Disorders. By inhibiting the immunosuppressive and anti-inflammatory activity of CD73, the present invention contemplates the use of the CD73 inhibitors described herein in the treatment and/or prevention of any viral, bacterial, fungal, parasitic or other infective disease, disorder or condition for which treatment with an CD73 inhibitor may be beneficial. Examples of such diseases and disorders include HIV and AIDS, staphylococcal and streptococcal infections (e.g., *Staphylococcus aureus* and *streptococcus sanguinis*, respectively), *leishmania, toxoplasma, trichomonas*, giardia, *Candida albicans, Bacillus anthracis*, and *Pseudomonas aeruginosa*. Compounds of the invention can be used to treat sepsis, decrease or inhibit bacterial growth, and reduce or inhibit inflammatory cytokines.

CNS-related and Neurological Disorders. Inhibition of CD73 may also be an important treatment strategy for patients with neurological, neuropsychiatric, neurodegenerative or other diseases, disorders and conditions having some association with the central nervous system, including disorders associated with impairment of cognitive function and motor function. Examples include Parkinson's disease, extra pyramidal syndrome (EPS), dystonia, akathisia, tardive dyskinesia, restless leg syndrome (RLS), epilepsy, periodic limb movement in sleep (PLMS), attention deficit disorders, depression, anxiety, dementia, Alzheimer's disease, Huntington's disease, multiple sclerosis, cerebral ischemia, hemorrhagic stroke, subarachnoid hemorrhage, and traumatic brain injury.

Other Disorders. Embodiments of the present invention contemplate the administration of the CD73 inhibitors described herein to a subject for the treatment or prevention of any other disorder that may benefit from at least some level of CD73 inhibition. Such diseases, disorders and conditions include, for example, cardiovascular (e.g., cardiac ischemia), gastrointestinal (e.g., Crohn's disease), metabolic (e.g., diabetes), hepatic (e.g., hepatic fibrosis, NASH, and NAFLD), pulmonary (e.g., COPD and asthma), ophthalmologic (e.g., diabetic retinopathy), and renal (e.g., renal failure) disorders.

In some embodiments, the CD73 inhibitors of the present invention may be used to inhibit statin-induced adenosine production, or reduce or decrease increases in blood glucose caused by a statin in a subject taking a statin (e.g., lovastatin and pravastatin)

Pharmaceutical Compositions

The CD73 inhibitors of the present invention may be in the form of compositions suitable for administration to a subject. In general, such compositions are "pharmaceutical compositions" comprising an CD73 inhibitor(s) and one or more pharmaceutically acceptable or physiologically acceptable diluents, carriers or excipients. In certain embodiments, the CD73 inhibitors are present in a therapeutically acceptable amount. The pharmaceutical compositions may be used in the methods of the present invention; thus, for example, the pharmaceutical compositions can be administered ex vivo or in vivo to a subject in order to practice the therapeutic and prophylactic methods and uses described herein.

The pharmaceutical compositions of the present invention can be formulated to be compatible with the intended method or route of administration; exemplary routes of administration are set forth herein. Furthermore, the pharmaceutical compositions may be used in combination with other therapeutically active agents or compounds as described herein in order to treat or prevent the diseases, disorders and conditions as contemplated by the present invention.

The pharmaceutical compositions containing the active ingredient (e.g., an inhibitor of CD73 function) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylenevinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present invention may also be in the form of oil-in-water emulsions. The oily phase may be a vegetable oil, for example olive oil or *arachis* oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of an CD73 inhibitor contemplated by the present invention and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time delay material such as glyceryl monostearate or glyceryl stearate alone, or in combination with a wax, may be employed. Any drug delivery apparatus may be used to deliver an CD73 inhibitor, including implants (e.g., implantable pumps) and catheter systems, slow injection pumps and devices, all of which are well known to the skilled artisan.

Depot injections, which are generally administered subcutaneously or intramuscularly, may also be utilized to release the CD73 inhibitors disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The present invention contemplates the administration of the CD73 inhibitors in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The CD73 inhibitors contemplated by the present invention may be in the form of any other suitable pharmaceutical composition (e.g., sprays for nasal or inhalation use) currently known or developed in the future.

Routes of Administration

The present invention contemplates the administration of CD73 inhibitors, and compositions thereof, in any appropriate manner. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), buccal and inhalation. Depot injections, which are generally administered subcutaneously or intramuscularly, may also be utilized to release the CD73 inhibitors disclosed herein over a defined period of time.

Particular embodiments of the present invention contemplate oral administration.

Combination Therapy

The present invention contemplates the use of CD73 inhibitors in combination with one or more active therapeutic agents (e.g., chemotherapeutic agents) or other prophylactic or therapeutic modalities (e.g., radiation). In such combination therapy, the various active agents frequently have different, complementary mechanisms of action. Such combination therapy may be especially advantageous by allowing a dose reduction of one or more of the agents, thereby reducing or eliminating the adverse effects associated with one or more of the agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the CD73 inhibitors are administered or applied sequentially, e.g., where one agent is administered prior to one or more other agents. In other embodiments, the CD73 inhibitors are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present invention.

The CD73 inhibitors of the present invention may be used in combination with at least one other (active) agent in any manner appropriate under the circumstances. In one embodiment, treatment with the at least one active agent and at least one CD73 inhibitor of the present invention is maintained over a period of time. In another embodiment, treatment with the at least one active agent is reduced or discontinued (e.g., when the subject is stable), while treatment with an CD73 inhibitor of the present invention is maintained at a constant dosing regimen. In a further embodiment, treatment with the at least one active agent is reduced or discontinued (e.g., when the subject is stable), while treatment with an CD73 inhibitor of the present invention is reduced (e.g., lower dose, less frequent dosing or shorter treatment regimen). In yet another embodiment, treatment with the at least one active agent is reduced or discontinued (e.g., when the subject is stable), and treatment with the CD73 inhibitor of the present invention is increased (e.g., higher dose, more frequent dosing or longer treatment regimen). In yet another embodiment, treatment with the at least one active agent is maintained and treatment with the CD73 inhibitor of the present invention is reduced or discontinued (e.g., lower dose, less frequent dosing or shorter treatment regimen). In yet another embodiment, treatment with the at least one active agent and treatment with the CD73 inhibitor of the present invention are reduced or discontinued (e.g., lower dose, less frequent dosing or shorter treatment regimen).

Oncology-related Disorders. The present invention provides methods for treating and/or preventing a proliferative condition, cancer, tumor, or precancerous disease, disorder or condition with an CD73 inhibitor and at least one additional therapeutic or diagnostic agent.

In certain embodiments, the present invention provides methods for tumor suppression of tumor growth comprising administration of an CD73 inhibitor described herein in combination with a signal transduction inhibitor (STI) to achieve additive or synergistic suppression of tumor growth. As used herein, the term "signal transduction inhibitor" refers to an agent that selectively inhibits one or more steps in a signaling pathway. Signal transduction inhibitors (STIs) of the present invention include: (i) bcr/abl kinase inhibitors (e.g., GLEEVEC); (ii) epidermal growth factor (EGF) receptor inhibitors, including kinase inhibitors and antibodies; (iii) her-2/neu receptor inhibitors (e.g., HERCEPTIN); (iv) inhibitors of Akt family kinases or the Akt pathway (e.g., rapamycin); (v) cell cycle kinase inhibitors (e.g., flavopiridol); and (vi) phosphatidyl inositol kinase inhibitors. Agents involved in in immunomodulation can also be used in combination with the CD73 inhibitors described herein for the suppression of tumor growth in cancer patients.

Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and doxetaxel; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; and pharmaceutically acceptable salts, acids or derivatives of any of the above.

Chemotherapeutic agents also include anti-hormonal agents that act to regulate or inhibit hormonal action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above. In certain embodiments, combination therapy comprises administration of a hormone or related hormonal agent.

Additional treatment modalities that may be used in combination with an CD73 inhibitor include radiotherapy, a monoclonal antibody against a tumor antigen, a complex of a monoclonal antibody and toxin, a T-cell adjuvant, bone marrow transplant, or antigen presenting cells (e.g., dendritic cell therapy).

Immune Checkpoint Inhibitors. The present invention contemplates the use of the inhibitors of CD73 function described herein in combination with immune checkpoint inhibitors.

The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints). Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism.

Examples of immune checkpoints (ligands and receptors), some of which are selectively upregulated in various types of tumor cells, that are Candidates for blockade include PD1 (programmed cell death protein 1); PDL1 (PD1 ligand); BTLA (B and T lymphocyte attenuator); CTLA4 (cytotoxic T-lymphocyte associated antigen 4); TIM3 (T-cell membrane protein 3); LAG3 (lymphocyte activation gene 3); A2aR (adenosine A2a receptor A2aR); and Killer Inhibitory Receptors, which can be divided into two classes based on their structural features: i) killer cell immunoglobulin-like receptors (KIRs), and ii) C-type lectin receptors (members of the type II transmembrane receptor family). Other less well-defined immune checkpoints have been described in the literature, including both receptors (e.g., the 2B4 (also known as CD244) receptor) and ligands (e.g., certain B7 family inhibitory ligands such B7-H3 (also known as CD276) and B7-H4 (also known as B7-S1, B7x and VCTN1)). [See Pardoll, (April 2012) Nature Rev. Cancer 12:252-64].

The present invention contemplates the use of the inhibitors of CD73 function described herein in combination with inhibitors of the aforementioned immune-checkpoint receptors and ligands, as well as yet-to-be-described immune-checkpoint receptors and ligands. Certain modulators of immune checkpoints are currently available, whereas others are in late-stage development. To illustrate, when it was approved for the treatment of melanoma in 2011, the fully humanized CTLA4 monoclonal antibody ipilimumab (YERVOY; Bristol-Myers Squibb) became the first immune checkpoint inhibitor to receive regulatory approval in the US. Fusion proteins comprising CTLA4 and an antibody (CTLA4-Ig; abatcept (ORENCIA; Bristol-Myers Squibb)) have been used for the treatment of rheumatoid arthritis, and other fusion proteins have been shown to be effective in renal transplantation patients that are sensitized to Epstein Barr Virus. PD1 antibodies are under development (e.g., nivolumab (Bristol-Myers Squibb) and lambrolizumab (Merck)), and anti-PDL1 antibodies are also being evaluated (e.g., MPDL3280A (Roche)). Nivolumab has shown promise in patients with melanoma, lung and kidney cancer.

The present invention encompasses pharmaceutically acceptable salts, acids or derivatives of any of the above.

Metabolic and Cardiovascular Diseases. The present invention provides methods for treating and/or preventing certain cardiovascular- and/or metabolic-related diseases, disorders and conditions, as well as disorders associated therewith, with an CD73 inhibitor and at least one additional therapeutic or diagnostic agent.

Examples of therapeutic agents useful in combination therapy for the treatment of hypercholesterolemia (and atherosclerosis as well) include statins (e.g., CRESTOR, LESCOL, LIPITOR, MEVACOR, PRAVACOL, and ZOCOR), which inhibit the enzymatic synthesis of cholesterol; bile acid resins (e.g., COLESTID, LO-CHOLEST, PREVALITE, QUESTRAN, and WELCHOL), which sequester cholesterol and prevent its absorption; ezetimibe (ZETIA), which blocks cholesterol absorption; fibric acid (e.g., TRICOR), which reduces triglycerides and may modestly increase HDL; niacin (e.g., NIACOR), which modestly lowers LDL cholesterol and triglycerides; and/or a combination of the aforementioned (e.g., VYTORIN (ezetimibe with simvastatin). Alternative cholesterol treatments that may be Candidates for use in combination with the CD73 inhibitors described herein include various supplements and herbs (e.g., garlic, policosanol, and guggul).

The present invention encompasses pharmaceutically acceptable salts, acids or derivatives of any of the above.

Immune-related Disorders and Disorders Having an Inflammatory Component. The present invention provides methods for treating and/or preventing immune-related diseases, disorders and conditions; and diseases, disorders and conditions having an inflammatory component; with an CD73 inhibitor and at least one additional therapeutic or diagnostic agent.

Examples of therapeutic agents useful in combination therapy are specific to the underlying disease, disorder or condition, and are known to the skilled artisan.

Microbial Diseases. The present invention provides methods for treating and/or preventing viral, bacterial, fungal and parasitic diseases, disorders and conditions, as well as disorders associated therewith, with an CD73 inhibitor and at least one additional therapeutic or diagnostic agent (e.g., one or more other antiviral agents and/or one or more agents not associated with viral therapy).

Such combination therapy includes anti-viral agents targeting various viral life-cycle stages and having different mechanisms of action, including, but not limiting to, the following: inhibitors of viral uncoating (e.g., amantadine and rimantidine); reverse transcriptase inhibitors (e.g., acyclovir, zidovudine, and lamivudine); agents that target integrase; agents that block attachment of transcription factors to viral DNA; agents (e.g., antisense molecules) that impact translation (e.g., fomivirsen); agents that modulate translation/ribozyme function; protease inhibitors; viral assembly modulators (e.g., rifampicin); antiretrovirals such as, for example, nucleoside analogue reverse transcriptase inhibitors (e.g., azidothymidine (AZT), ddI, ddC, 3TC, d4T); non-nucleoside reverse transcriptase inhibitors (e.g., efavirenz, nevirapine); nucleotide analogue reverse transcriptase inhibitors; and agents that prevent release of viral particles (e.g., zanamivir and oseltamivir). Treatment and/or prevention of certain viral infections (e.g., HIV) frequently entail a group ("cocktail") of antiviral agents.

Other antiviral agents contemplated for use in combination with an CD73 inhibitor include, but are not limited to, the following: abacavir, adefovir, amantadine, amprenavir, ampligen, arbidol, atazanavir, atripla, boceprevirertet, cidofovir, combivir, darunavir, delavirdine, didanosine, docosanol, edoxudine, emtricitabine, enfuvirtide, entecavir, famciclovir, fosamprenavir, foscarnet, fosfonet, http://en.wikipedia.org/wiki/Fusion_inhibitor ganciclovir, ibacitabine, imunovir, idoxuridine, imiquimod, indinavir, inosine, various interferons (e.g., peginterferon alfa-2a), lopinavir, loviride, maraviroc, moroxydine, methisazone, nelfinavir, nexavir, penciclovir, peramivir, pleconaril, podophyllotoxin, raltegravir, ribavirin, ritonavir, pyramidine, saquinavir, stavudine, telaprevir, tenofovir, tipranavir, trifluridine, trizivir, tromantadine, truvada, valaciclovir, valganciclovir, vicriviroc, vidarabine, viramidine, and zalcitabine.

The present invention contemplates the use of the inhibitors of CD73 function described herein in combination with antiparasitic agents. Such agents include, but are not limited to, thiabendazole, pyrantel pamoate, mebendazole, praziquantel, niclosamide, bithionol, oxamniquine, metrifonate, ivermectin, albendazole, eflornithine, melarsoprol, pentamidine, benznidazole, nifurtimox, and nitroimidazole. The skilled artisan is aware of other agents that may find utility for the treatment of parasitic disorders.

Embodiments of the present invention contemplate the use of the CD73 inhibitors described herein in combination with agents useful in the treatment or prevention of bacterial disorders. Antibacterial agents can be classified in various manners, including based on mechanism of action, based on chemical structure, and based on spectrum of activity. Examples of antibacterial agents include those that target the bacterial cell wall (e.g., cephalosporins and penicillins) or the cell membrane (e.g., polymyxins), or interfere with essential bacterial enzymes (e.g., sulfonamides, rifamycins, and quinolines). Most antibacterial agents that target protein synthesis (e.g., tetracyclines and macrolides) are bacteriostatic, whereas agents such as the aminoglycoside are bactericidal. Another means of categorizing antibacterial agents is based on their target specificity; "narrow-spectrum" agents target specific types of bacteria (e.g., Gram-positive bacteria such as *Streptococcus*), while "broad-spectrum" agents have activity against a broader range of bacteria. The skilled artisan is aware of types of anti-bacterial agents that are appropriate for use in specific bacterial infections.

Embodiments of the present invention contemplate the use of the CD73 inhibitors described herein in combination with agents useful in the treatment or prevention of fungal disorders. Antifungal agents include polyenes (e.g., amphotericin, nystatin, and pimaricin); azoles (e.g., fluconazole, itraconazole, and ketoconazole); allylamines (e.g., naftifine, and terbinafine) and morpholines (e.g., amorolfine); and antimetabolies (e.g., 5-fluorocytosine).

The present invention encompasses pharmaceutically acceptable salts, acids or derivatives of the agents (and members of the classes of agents) set forth above.

Dosing

The CD73 inhibitors of the present invention may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the CD73 inhibitors of the present invention may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In certain embodiments, the CD73 inhibitors contemplated by the present invention may be administered (e.g., orally) at dosage levels of about 0.01 mg/kg to about 50 mg/kg, or about 1 mg/kg to about 25 mg/kg, of subject body weight per day, one or more times a day, to obtain the desired therapeutic effect.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

In certain embodiments, the dosage of the desired CD73 inhibitor is contained in a "unit dosage form". The phrase "unit dosage form" refers to physically discrete units, each unit containing a predetermined amount of the CD73 inhibitor, either alone or in combination with one or more additional agents, sufficient to produce the desired effect. It will be appreciated that the parameters of a unit dosage form will depend on the particular agent and the effect to be achieved.

Kits

The present invention also contemplates kits comprising an CD73 inhibitor, and pharmaceutical compositions thereof. The kits are generally in the form of a physical structure housing various components, as described below, and may be utilized, for example, in practicing the methods described above.

A kit can include one or more of the CD73 inhibitors disclosed herein (provided in, e.g., a sterile container), which may be in the form of a pharmaceutical composition suitable for administration to a subject. The CD73 inhibitors can be provided in a form that is ready for use (e.g., a tablet or capsule) or in a form requiring, for example, reconstitution or dilution (e.g., a powder) prior to administration. When the CD73 inhibitors are in a form that needs to be reconstituted or diluted by a user, the kit may also include diluents (e.g., sterile water), buffers, pharmaceutically acceptable excipients, and the like, packaged with or separately from the CD73 inhibitors. When combination therapy is contemplated, the kit may contain the several agents separately or they may already be combined in the kit. Each component of the kit may be enclosed within an individual container, and all of the various containers may be within a single package. A kit of the present invention may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXPERIMENTAL

The following examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: wt=wildtype; bp=base pair(s); kb=kilobase(s); nt=nucleotides(s); aa=amino acid(s); s or sec=second(s); min=minute(s); h or hr=hour(s); ng=nanogram; μg=microgram; mg=milligram; g=gram; kg=kilogram; dl or dL=deciliter; μl or μL=microliter; ml or mL=milliliter; l or L=liter; M=micromolar; mM=millimolar; M=molar; kDa=kilodalton; i.m.=intramuscular(ly); i.p.=intraperitoneal(ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; IHC=immunohistochemistry; DMEM=Dulbeco's Modification of Eagle's Medium; EDTA=ethylenediaminetetraacetic acid.

LC: Agilent 1100 series; Mass spectrometer: Agilent G6120BA, single quad
LC-MS method: Agilent Zorbax Eclipse Plus C18, 4.6×100 mm, 3.5 μM, 35° C., 1.5 mL/min flow rate, a 2.5 min gradient of 0% to 100% B with 0.5 min wash at 100% B; A=0.1% of formic acid/5% acetonitrile/94.9% water; B=0.1% of formic acid/5% water/94.9% acetonitrile
Flash column: ISCO Rf+
Reverse phase HPLC: ISCO-EZ; Column: Kinetex 5 μm EVO C18 100 A; 250×21.2 mm (Phenomenex)

Example 1

Synthesis of [({[(2R,3S,4R,5R)-5-[6-(cyclopentylamino)-2-chloro-9H-purin-9-yl]-3,4-dihydroxyoxolan-2-yl]methoxy}(hydroxy)phosphoryl)methyl] phosphonic acid

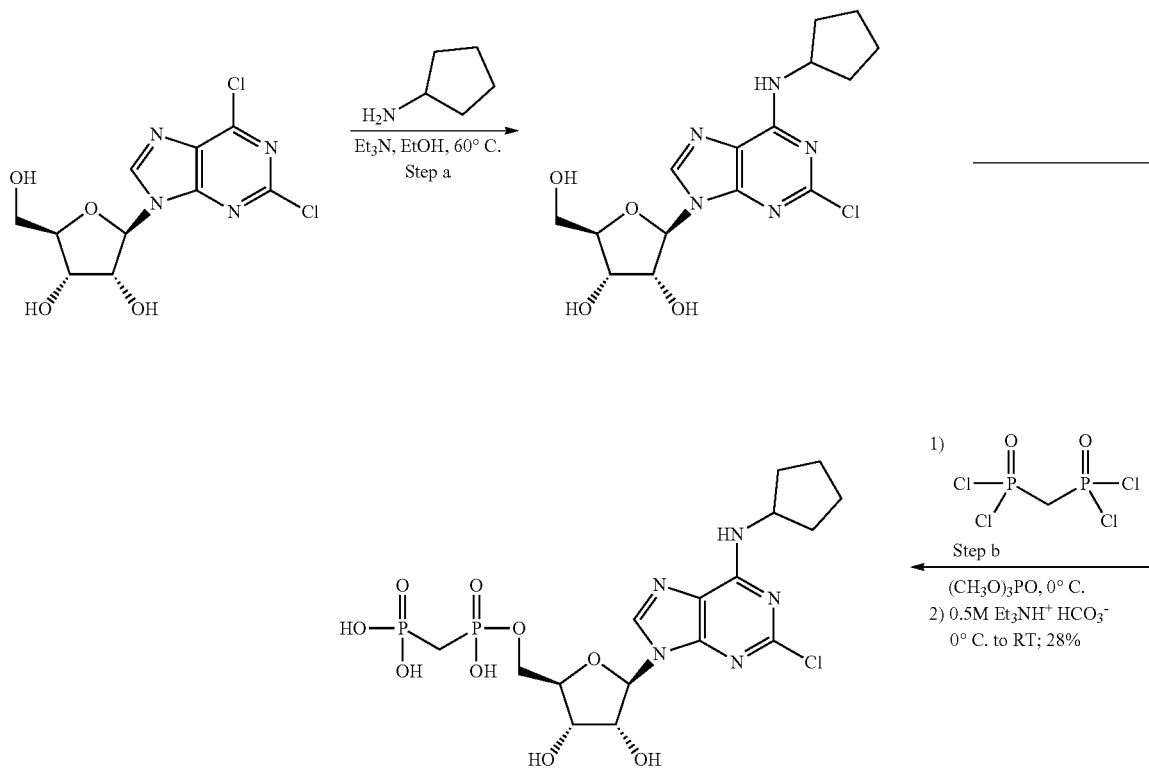

Step a: A mixture of 2,6-dichloropurine riboside (321 mg, 1 mmol), cyclopentylamine (103 μL, 1.05 mmol, 1.05 equiv.), and triethylamine (146 μL, 1.05 mmol, 1.05 equiv.) in anhydrous EtOH (3 mL) was stirred at 60° C. for overnight. Reaction mixture was evaporated and the crude product was used in the next step without purification. ESI MS [M+H]$^+$ for $C_{15}H_{21}ClN_5O_4$, calcd 370.8, found 370.2

Step b: The product from Step a (370 mg, 1 mmol) was dissolved in trimethyl phosphate (5 mL) and cooled to 0° C. (ice bath), then a cold solution of methylenebis(phosphonic dichloride) (1.25 g, 5 mmol, 5 equiv.) in trimethyl phosphate (2 mL) was added dropwise. The reaction mixture was stirred at 0° C. for 3 h, and was then carefully quenched with 0.5 M triethylammonium bicarbonate solution (7 mL) and stirred at 0° C. for 15 min, and then 2 h at room temperature. The reaction mixture was purified by reverse phase HPLC (C18 column, 0 to 30% gradient of acetonitrile and water with 0.1% TFA) to give the product as a white solid in 28% yield (181 mg): $^1$H NMR (400 MHz, DMSO) δ 8.45-8.32 (m, 2H), 5.85 (d, J=5.5 Hz, 1H), 4.55-4.36 (m, 2H), 4.23-4.07 (m, 4H), 2.26 (t, J=20.5 Hz, 2H), 2.04-1.85 (m, 2H), 1.77-1.46 (m, 6H). ESI MS [M+H]$^+$ for $C_{16}H_{25}ClN_5O_9P_2$, calcd 528.8, found 528.1.

Example 2

Synthesis of (((((2R,3S,4R,5R)-5-(6-((4-(tert-butyl)benzyl)amino)-2-chloro-9H-purin-9-yl)-3,4-dihydroxytetrahydrofuran-2-yl)methoxy)(hydroxy)phosphoryl)methyl)phosphonic acid

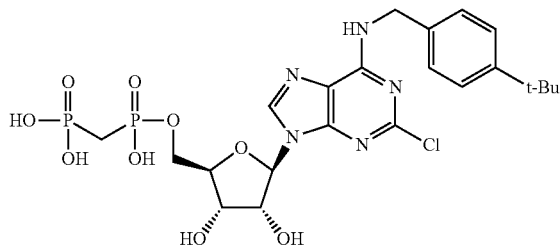 [SMILES: CC(C)(C)c1ccc(CNc2nc(Cl)nc3c2ncn3[C@@H]2O[C@H](COP(=O)(O)CP(=O)(O)O)[C@@H](O)[C@H]2O)cc1]

The title compound was synthesized in similar fashion to Example 1 using 4-tert-butylbenzylamine in place of cyclopentylamine: $^1$H NMR (400 MHz, DMSO-d$_6$) δ 8.91 (t, J=6.3 Hz, 1H), 8.43 (s, 1H), 7.33 (d, J=8.2 Hz, 2H), 7.26 (d, J=8.2 Hz, 2H), 5.86 (d, J=5.8 Hz, 1H), 4.68-4.56 (m, 2H), 4.52 (t, J=5.4 Hz, 1H), 4.23-4.03 (m, 4H), 2.26 (t, J=20.5 Hz, 2H), 1.25 (s, 9H). ESI MS [M+H]$^+$ for $C_{22}H_{31}ClN_5O_9P_2$, calcd 606.1, found 606.2.

Example 3

Synthesis of (((((2R,3S,4R,5R)-5-(2-chloro-6-(isopropylamino)-9H-purin-9-yl)-3,4 dihydroxytetrahydrofuran-2-yl)methoxy)(hydroxy)phosphoryl)methyl)phosphonic acid

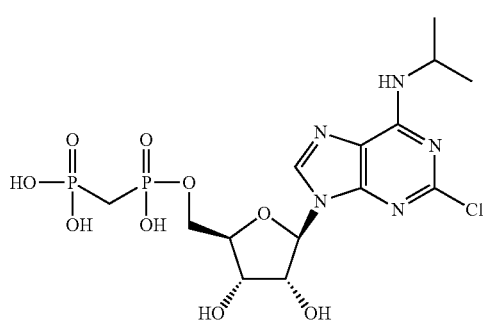 [SMILES: CC(C)Nc1nc(Cl)nc2c1ncn2[C@@H]1O[C@H](COP(=O)(O)CP(=O)(O)O)[C@@H](O)[C@H]1O]

The title compound was synthesized in similar fashion to Example 1 using isopropylamine in place of cyclopentylamine: $^1$H NMR (400 MHz, DMSO-d$_6$) δ 8.40 (s, 1H), 8.23 (d, J=8.1 Hz, 1H), 5.85 (d, J=5.9 Hz, 1H), 4.51 (t, J=5.5 Hz, 1H), 4.36 (s, 1H), 4.24-4.03 (m, 4H), 2.25 (t, J=20.5 Hz, 2H), 1.21 (dd, J=6.6, 2.0 Hz, 5H). ESI MS [M+H]$^+$ for $C_{14}H_{22}ClN_5O_9P_2$, calcd 502.1, found 502.1.

Example 4

Synthesis of (((((2R,3S,4R,5R)-5-(2-chloro-6-(cyclopropylamino)-9H-purin-9-yl)-3,4-dihydroxytetrahydrofuran-2-yl)methoxy)(hydroxy)phosphoryl)methyl)phosphonic acid

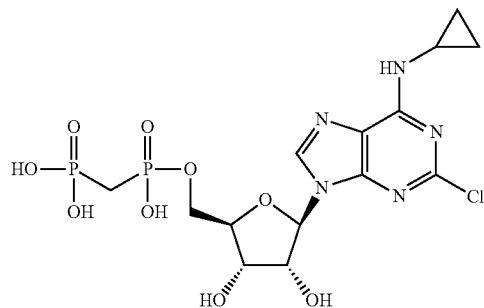 [SMILES: O=P(O)(O)CP(=O)(O)OC[C@H]1O[C@@H](n2cnc3c(NC4CC4)nc(Cl)nc32)[C@H](O)[C@@H]1O]

The title compound was synthesized in similar fashion to Example 1 using cyclopropylamine in place of cyclopentylamine: $^1$H NMR (400 MHz, DMSO-d$_6$) δ 8.54 (s, 1H), 8.42 (s, 1H), 5.86 (d, J=5.8 Hz, 1H), 4.52 (t, J=5.4 Hz, 1H), 4.28-4.03 (m, 4H), 2.97 (s, 1H), 2.25 (t, J=20.5 Hz, 2H), 0.75 (s, 2H), 0.64 (s, 3H). ESI MS [M+H]$^+$ for $C_{14}H_{20}ClN_5O_9P_2$, calcd 500.1, found 500.1.

Example 5

Synthesis of (((((2R,3S,4R,5R)-5-(2-chloro-6-(neopentylamino)-9H-purin-9-yl)-3,4-dihydroxytetrahydrofuran-2-yl)methoxy)(hydroxy)phosphoryl)methyl)phosphonic acid

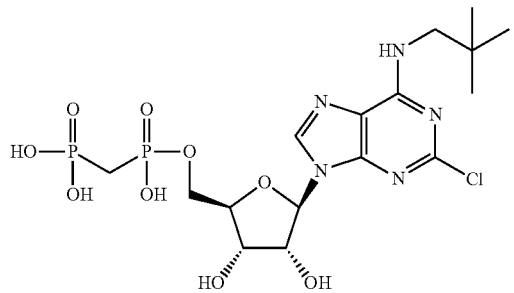 [SMILES: CC(C)(C)CNc1nc(Cl)nc2c1ncn2[C@@H]1O[C@H](COP(=O)(O)CP(=O)(O)O)[C@@H](O)[C@H]1O]

The title compound was synthesized in similar fashion to Example 1 using neopentylamine in place of cyclopentylamine: $^1$H NMR (400 MHz, DMSO-d$_6$) δ 8.42 (s, 1H), 8.32 (t, J=6.4 Hz, 1H), 5.85 (d, J=5.7 Hz, 1H), 4.52 (t, J=5.4 Hz, 1H), 4.31-4.04 (m, 4H), 3.82 (d, J=7.0 Hz, 1H), 3.42-3.17 (m, 2H), 2.26 (t, J=20.5 Hz, 2H), 0.91 (s, 9H). ESI MS [M+H]$^+$ for $C_{16}H_{26}ClN_5O_9P_2$, calcd 530.1, found 530.2.

Example 6

Synthesis of (((((2R,3S,4R,5R)-5-(2-chloro-6-(iso-propyl(methyl)amino)-9H-purin-9-yl)-3,4-dihydroxytetrahydrofuran-2-yl)methoxy)(hydroxy)phosphoryl)methyl)phosphonic acid

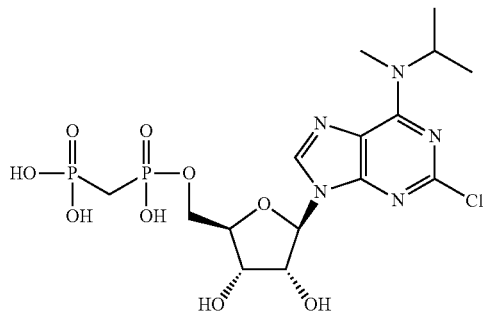 [SMILES: CC(C)N(C)c1nc(Cl)nc2c1ncn2[C@@H]1O[C@H](COP(=O)(O)CP(=O)(O)O)[C@@H](O)[C@H]1O]

The title compound was synthesized in similar fashion to Example 1 using N-methylisopropylamine in place of cyclopentylamine: $^1$H NMR (400 MHz, DMSO-$d_6$) δ 8.42 (s, 1H), 5.88 (d, J=5.9 Hz, 1H), 4.50 (t, J=5.4 Hz, 1H), 4.22-4.17 (m, 1H), 4.11 (d, J=6.4 Hz, 3H), 3.03 (s, 3H), 2.26 (t, J=20.5 Hz, 2H), 1.23 (s, 6H). ESI MS [M+H]$^+$ for $C_{15}H_{24}ClN_5O_9P_2$, calcd 516.1, found 516.1.

Example 7

Synthesis of (((((2R,3S,4R,5R)-5-(6-((3,5-bis(trifluoromethyl)benzyl)amino)-9H-purin-9-yl)-3,4-dihydroxytetrahydrofuran-2yl)methoxy)(hydroxy)phosphoryl)methyl)phosphonic acid

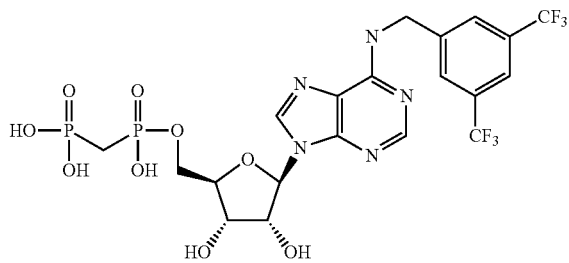 [SMILES: O=P(O)(O)CP(=O)(O)OC[C@H]1O[C@@H](n2cnc3c(NCc4cc(C(F)(F)F)cc(C(F)(F)F)c4)ncnc32)[C@H](O)[C@@H]1O]

The title compound was synthesized in similar fashion to Example 1 but using 6-chloropurine riboside and 3,5-bis(trifluoromethyl)benzylamine in step a: $^1$H NMR (400 MHz, DMSO-$d_6$) δ 8.67 (s, 1H), 8.47 (s, 1H), 8.26 (s, 1H), 8.07 (s, 2H), 7.99 (s, 1H), 5.94 (d, J=5.7 Hz, 1H), 4.88 (s, 2H), 4.61 (t, J=5.4 Hz, 1H), 4.23 (t, J=4.2 Hz, 1H), 4.20-4.04 (m, 3H), 2.25 (t, J=20.5 Hz, 2H). ESI MS [M−H]$^-$ for $C_{20}H_{20}F_6N_5O_9P_2$, calcd 650.1, found 650.2.

Example 8

Synthesis of (((((2R,3S,4R,5R)-5-(6-((4-bromobenzyl)amino)-9H-purin-9-yl)-3,4-dihydroxytetrahydrofuran-2-yl)methoxy)(hydroxy)phosphoryl)methyl)phosphonic acid

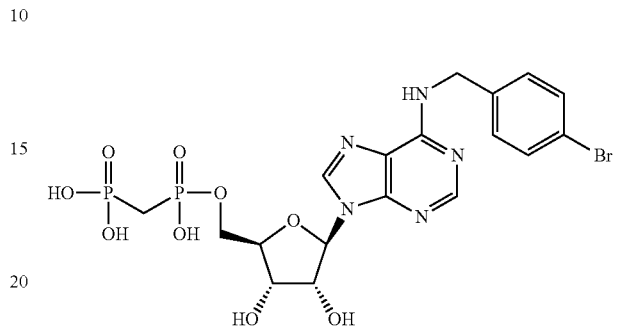

The title compound was synthesized in similar fashion to Example 1 but using 6-chloropurine riboside and corresponding amine in step a: $^1$H NMR (400 MHz, DMSO-$d_6$) δ 8.60 (s, 1H), 8.44 (s, 1H), 8.24 (s, 1H), 7.49 (d, J=8.3 Hz, 2H), 7.29 (d, J=8.3 Hz, 2H), 5.94 (d, J=5.7 Hz, 1H), 4.67 (s, 2H), 4.61 (t, J=5.3 Hz, 1H), 4.23 (t, J=4.2 Hz, 1H), 4.19-4.05 (m, 3H), 2.25 (t, J=20.5 Hz, 2H). ESI MS [M−H]$^-$ for $C_{18}H_{21}BrN_5O_9P_2$, calcd 592.0, found 592.1.

Example 9

Synthesis of (((((2R,3S,4R,5R)-5-(6-((4-(tert-butyl)benzyl)amino)-9H-purin-9-yl)-3,4-dihydroxytetrahydrofuran-2-yl)methoxy)(hydroxy)phosphoryl)methyl)phosphonic acid

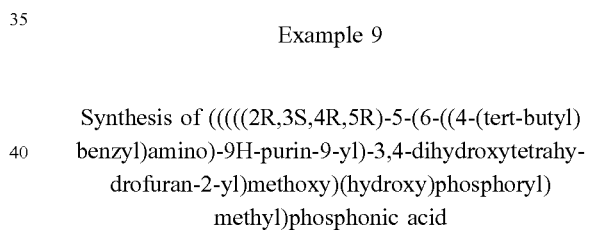

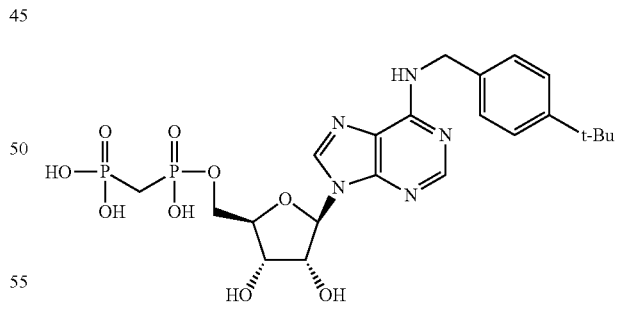

The title compound was synthesized in similar fashion to Example 1 but using 6-chloropurine riboside and corresponding amine in step a: $^1$H NMR (400 MHz, DMSO-$d_6$) δ 8.62 (s, 1H), 8.45 (s, 1H), 8.26 (s, 1H), 7.37-7.22 (m, 4H), 5.94 (d, J=5.7 Hz, 1H), 4.67 (s, 2H), 4.60 (t, J=5.4 Hz, 1H), 4.23 (t, J=4.1 Hz, 1H), 4.20-4.05 (m, 3H), 2.25 (t, J=20.5 Hz, 2H), 1.24 (s, 9H). ESI MS [M−H]$^-$ for $C_{22}H_{30}N_5O_9P_2$, calcd 570.1, found 570.3.

Example 10

Synthesis of (((((2R,3S,4R,5R)-5-(6-(([1,1'-biphenyl]-4-ylmethyl)amino)-9H-purin-9-yl)-3,4-dihydroxytetrahydrofuran-2-yl)methoxy)(hydroxy)phosphoryl)methyl)phosphonic acid

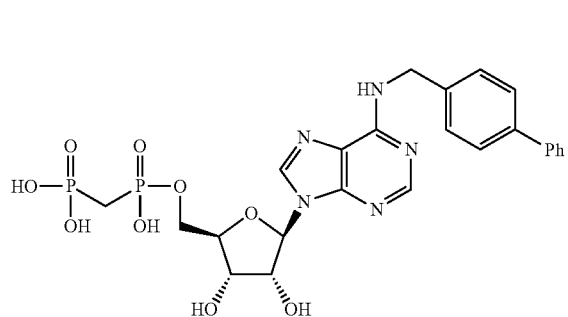

The title compound was synthesized in similar fashion to Example 1 but using 6-chloropurine riboside and corresponding amine in step a: H NMR (400 MHz, DMSO-$d_6$) δ 8.67 (s, 1H), 8.46 (s, 1H), 8.27 (s, 1H), 7.66-7.57 (m, 4H), 7.49-7.40 (m, 4H), 7.37-7.30 (m, 1H), 5.95 (d, J=5.7 Hz, 1H), 4.76 (s, 2H), 4.61 (t, J=5.3 Hz, 1H), 4.24 (t, J=4.1 Hz, 1H), 4.20-4.06 (m, 3H), 2.25 (t, J=20.5 Hz, 2H). ESI MS [M−H]$^-$ for $C_{24}H_{26}N_5O_9P_2$, calcd 590.1, found 590.2.

Example 11

Synthesis of (((((2R,3S,4R,5R)-3,4-dihydroxy-5-(6-((4-(trifluoromethyl)benzyl)amino)-9H-purin-9-yl)tetrahydrofuran-2-yl)methoxy)(hydroxy)phosphoryl)methyl)phosphonic acid

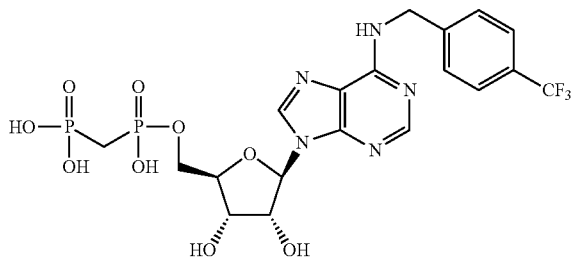 [SMILES: O=P(O)(O)CP(=O)(O)OC[C@H]1O[C@@H](n2cnc3c(NCc4ccc(C(F)(F)F)cc4)ncnc32)[C@H](O)[C@@H]1O]

The title compound was synthesized in similar fashion to Example 1 but using 6-chloropurine riboside and corresponding amine in step a: $^1$H NMR (400 MHz, DMSO-$d_6$) δ 8.68 (s, 1H), 8.46 (s, 1H), 8.25 (s, 1H), 7.67 (d, J=8.1 Hz, 2H), 7.54 (d, J=8.1 Hz, 2H), 5.95 (d, J=5.8 Hz, 1H), 4.79 (s, 2H), 4.61 (t, J=5.3 Hz, 1H), 4.24 (t, J=4.1 Hz, 1H), 4.20-4.06 (m, 3H), 2.25 (t, J=20.5 Hz, 2H). ESI MS [M−H]$^-$ for $C_{19}H_{21}F_3N_5O_9P_2$, calcd 582.1, found 582.2.

Example 12

Synthesis of (((((2R,3S,4R,5R)-3,4-dihydroxy-5-(6-((4-methylbenzyl)amino)-9H-purin-9-yl)tetrahydrofuran-2-yl)methoxy)(hydroxy)phosphoryl)methyl) phosphonic acid

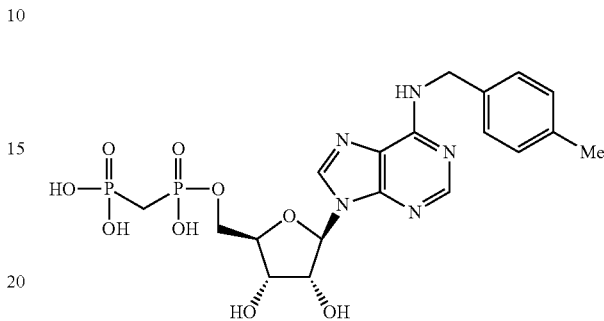

The title compound was synthesized in similar fashion to Example 1 but using 6-chloropurine riboside and corresponding amine in step a: $^1$H NMR (400 MHz, DMSO-$d_6$) δ 8.61 (s, 1H), 8.45 (s, 1H), 8.26 (s, 1H), 7.22 (d, J=7.8 Hz, 2H), 7.10 (d, J=7.8 Hz, 2H), 5.94 (d, J=5.7 Hz, 1H), 4.67 (s, 2H), 4.60 (t, J=5.4 Hz, 1H), 4.23 (t, J=4.2 Hz, 1H), 4.19-4.04 (m, 3H), 2.31-2.18 (m, 5H). ESI MS [M−H]$^-$ for $C_{19}H_{24}N_5O_9P_2$, calcd 528.1, found 528.2.

Example 13

Synthesis of (((((2R,3S,4R,5R)-5-(6-((3,5-dichlorobenzyl)amino)-9H-purin-9-yl)-3,4-dihydroxytetrahydrofuran-2-yl)methoxy)(hydroxy)phosphoryl)methyl)phosphonic acid

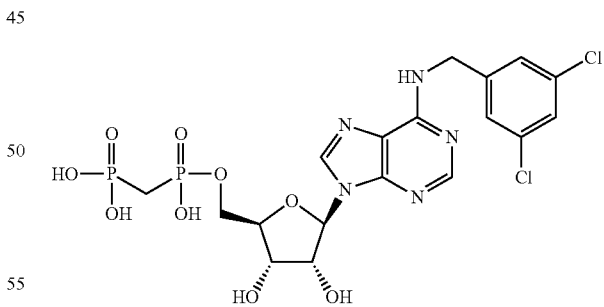

The title compound was synthesized in similar fashion to example 1 but using 6-chloropurine riboside and corresponding amine in step a: $^1$H NMR (400 MHz, DMSO-$d_6$) δ 8.61 (s, 1H), 8.46 (s, 1H), 8.26 (s, 1H), 7.48 (t, J=2.0 Hz, 1H), 7.39 (s, 2H), 5.95 (d, J=5.7 Hz, 1H), 4.70 (s, 2H), 4.61 (t, J=5.4 Hz, 1H), 4.24 (t, J=4.2 Hz, 1H), 4.20-4.05 (m, 3H), 2.26 (t, J=20.5 Hz, 2H). ESI MS [M−H]$^-$ for $C_{18}H_{20}Cl_2N_5O_9P_2$, calcd 582.1, found 582.2.

Example 14

Synthesis of (((((2R,3S,4R,5R)-5-(6-(benzylamino)-2-methyl-9H-purin-9-yl)-3,4-dihydroxytetrahydrofuran-2-yl)methoxy)(hydroxy)phosphoryl)methyl)phosphonic acid

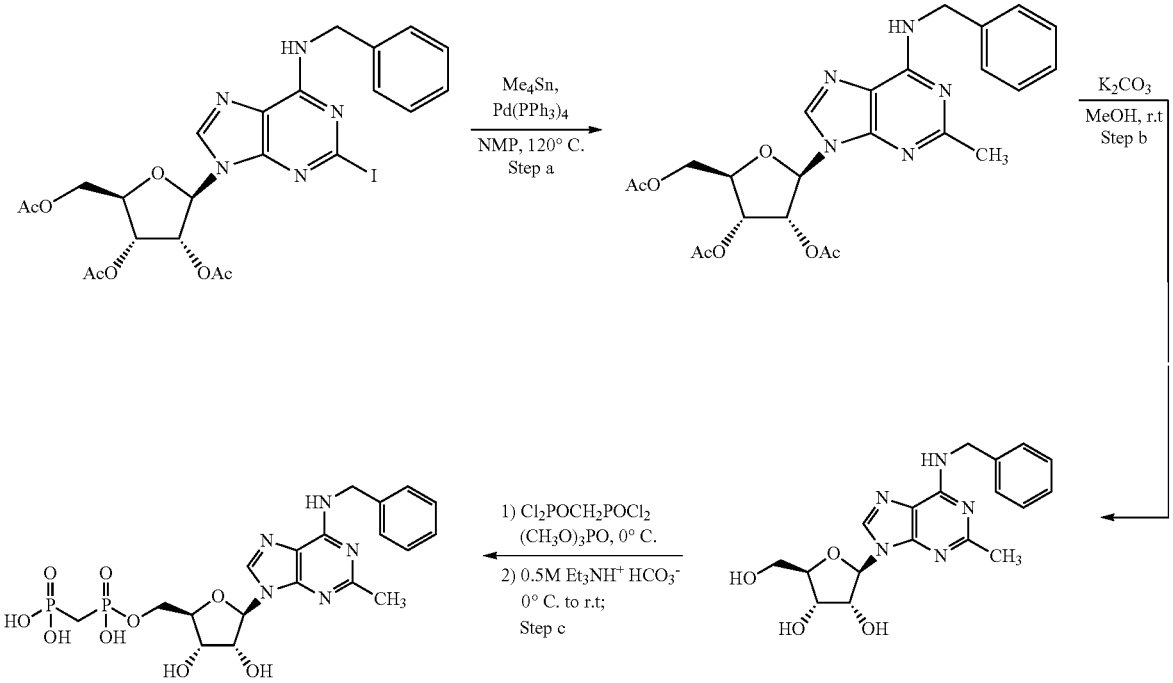

Step a: To a nitrogen purged reaction mixture of the iodo derivative (1.03 g, 1.7 mmol) and tetramethyltin (470 µL, 3.34 mmol) in NMP (10 mL) was added Pd(PPh$_3$)$_4$ (196 mg, 0.17 mmol, 10 mol %) and the reaction mixture was heated at 120° C. for overnight. LCMS indicated product formation. It was cooled to room temperature, diluted with water, extracted with ethyl acetate, dried (MgSO$_4$), filtered and concentrated. The residue was purified by flash column to get the product (1 g). ESI MS [M+H]$^+$ for C$_{24}$H$_{27}$N$_5$O$_7$, calcd 498.2, found 498.3

Step b: To a solution of the acetate derivative from Step a (1 g, 2.01 mmo) in methanol (5 mL) was added K$_2$CO$_3$ (276 mg, 2 mmol) and the reaction mixture was stirred at r.t for 1 h. Then, it was diluted with dichloromethane, filtered through a pad of silica. The filtrate was concentrated and purified by flash column (ISCO, 40 g column, 0 to 20% methanol in dichloromethane, 20 min) to get the compound as off white solid (450 mg, 60%) ESI MS [M+H]$^+$ for C$_{18}$H$_{21}$N$_5$O$_4$, calcd 372.2, found 372.2

Step c: The product from Step b (150 mg, 0.4 mmol) was dissolved in trimethyl phosphate (3 mL) and cooled to 0° C. (ice bath), then an ice cold solution of methylenebis(phosphonic dichloride) (504 mg, 2 mmol, 5 equiv.) in trimethyl phosphate (1 mL) was added dropwise. The reaction mixture was stirred at 0° C. for 3 h, and was then carefully quenched with 0.5 M triethylammonium bicarbonate solution (8 mL) and stirred at 0° C. for 15 min, and then 2 h at room temperature. The reaction mixture was purified by reverse phase HPLC (C18 column, 0 to 30% gradient of acetonitrile and water with 0.1% TFA) to give the product as a white solid: $^1$H NMR (400 MHz, DMSO-d$_6$) δ 8.48-8.32 (m, 2H), 7.38-7.18 (m, 5H), 5.92 (d, J=6.0 Hz, 1H), 4.71 (s, 2H), 4.55 (t, J=5.5 Hz, 1H), 4.19-3.98 (m, 4H), 2.44 (s, 3H), 2.23 (t, J=20.5 Hz, 2H). ESI MS [M−H]$^-$ for C$_{19}$H$_{25}$N$_5$O$_9$P$_2$, calcd 528.1, found 528.2.

Example 15

Synthesis of (((((2R,3S,4R,5R)-5-(6-(benzylamino)-2-vinyl-9H-purin-9-yl)-3,4-dihydroxytetrahydrofuran-2-yl)methoxy)(hydroxy)phosphoryl)methyl)phosphonic acid

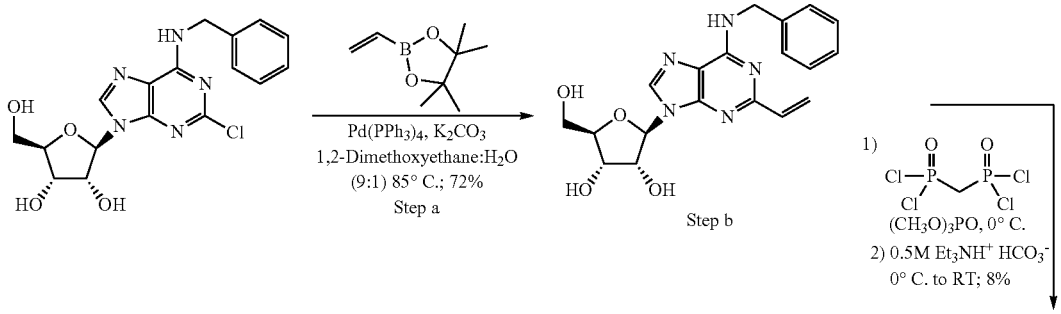

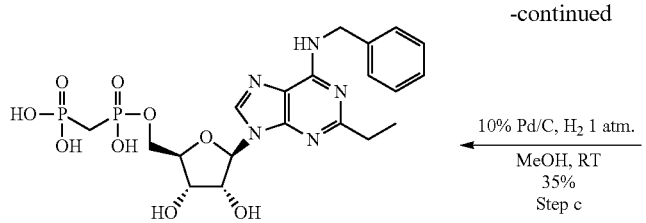
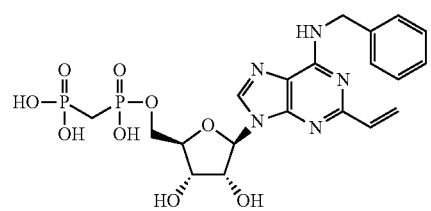

Step a: A mixture of N⁶-benzyl-2-chloropurine riboside (783 mg, 2 mmol), vinylboronic acid pinacol ester (462 mg, 3 mmol, 1.5 equiv.), $K_2CO_3$ (828 mg, 6 mmol, 3 equiv.) and $Pd(PPh_3)_4$ in 1,2-dimethoxyethane:$H_2O$ (9:1, 10 mL) was stirred under $N_2$ at 85° C. for 1 day. Reaction mixture was cooled down to room temperature, diluted with EtOAc (100 mL) and washed with $H_2O$ (50 mL). Organic layer was separated, dried over $MgSO_4$, filtered and evaporated to give yellow solid. Crude product was washed with MTBE (50 mL) and used directed in the next step (550 mg, 72%).

Step b: The title compound was synthesized in similar fashion to example 1. ¹H NMR (400 MHz, DMSO-$d_6$) δ 8.39 (s, 1H), 7.38 (d, J=7.0 Hz, 2H), 7.29 (t, J=7.6 Hz, 2H), 7.25-7.15 (m, 1H), 6.64 (dd, J=17.2, 10.4 Hz, 1H), 6.39 (dd, J=17.2, 2.4 Hz, 1H), 5.94 (d, J=6.0 Hz, 1H), 5.55 (d, J=10.5 Hz, 1H), 4.73 (s, 2H), 4.63 (t, J=5.5 Hz, 1H), 4.28-4.00 (m, 4H), 2.25 (t, J=20.4 Hz, 2H). ESI MS [M+H]⁺ for $C_{20}H_{26}N_5O_9P_2$, calcd 542.1, found 542.2.

Step c: Product from step b (40 mg, 0.06 mmol) was dissolved in MeOH (10 mL), purged with $N_2$ and 10% Pd/C (50% wet, 30 mg) was added. Reaction mixture was vigorously stirred under $H_2$ (balloon) for 2 h and after filtration the product was purified by RP18 HPLC ($H_2O$+0.1% TFA/acetonitrile+0.1% TFA) to give white solid (14 mg, 35%): ¹H NMR (400 MHz, DMSO-$d_6$) δ 8.52-8.18 (m, 2H), 7.33-7.27 (m, 2H), 7.27-7.18 (m, 2H), 7.15 (t, J=7.2 Hz, 1H), 5.86 (d, J=6.0 Hz, 1H), 4.64 (s, 2H), 4.55 (t, J=5.5 Hz, 1H), 4.19-3.98 (m, 4H), 2.70-2.61 (m, 2H), 2.16 (t, J=20.5 Hz, 2H), 1.16 (t, J=7.6 Hz, 3H). ESI MS [M+H]⁺ for $C_{20}H_{27}N_5O_9P_2$, calcd 544.1, found 544.2.

Example 16

Synthesis of (((((2R,3S,4R,5R)-5-(2-allyl-6-(benzylamino)-9H-purin-9-yl)-3,4-dihydroxytetrahydrofuran-2-yl)methoxy)(hydroxy)phosphoryl)methyl)phosphonic acid

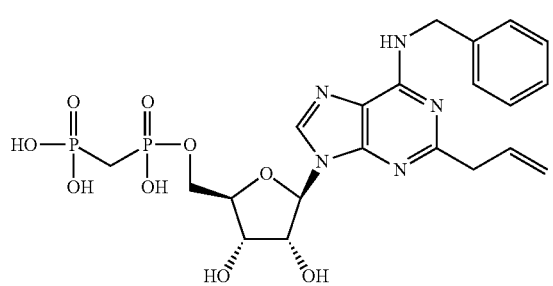 [SMILES: C=CCc1nc(NCc2ccccc2)c2ncn([C@@H]3O[C@H](COP(=O)(O)CP(=O)(O)O)[C@@H](O)[C@H]3O)c2n1]

The title compound was synthesized in similar fashion to Example 15: ¹H NMR (400 MHz, DMSO-$d_6$) δ 8.46 (s, 1H), 8.37 (s, 1H), 7.41-7.34 (m, 2H), 7.30 (t, J=7.5 Hz, 2H), 7.25-7.18 (m, 1H), 6.17-6.03 (m, 1H), 5.92 (d, J=6.0 Hz, 1H), 5.28-5.00 (m, 2H), 4.70 (s, 2H), 4.60 (t, J=5.6 Hz, 1H), 4.27-4.02 (m, 4H), 3.49 (d, J=6.8 Hz, 2H), 2.24 (t, J=20.5 Hz, 2H). ESI MS [M+H]⁺ for $C_{21}H_{28}N_5O_9P_2$, calcd 556.1, found 556.3.

Example 17

Synthesis of (((((2R,3S,4R,5R)-5-(6-(benzylamino)-2-propyl-9H-purin-9-yl)-3,4-dihydroxytetrahydrofuran-2-yl)methoxy)(hydroxy)phosphoryl)methyl)phosphonic acid

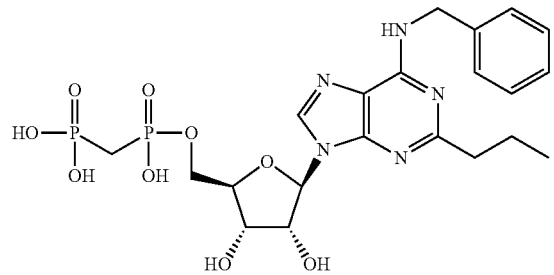 [SMILES: CCCc1nc(NCc2ccccc2)c2ncn([C@@H]3O[C@H](COP(=O)(O)CP(=O)(O)O)[C@@H](O)[C@H]3O)c2n1]

The title compound was synthesized in similar fashion to step c of Example 15: ¹H NMR (400 MHz, DMSO-$d_6$) δ 8.40 (s, 2H), 8.29 (s, 1H), 7.29 (d, J=7.6 Hz, 2H), 7.23 (t, J=7.5 Hz, 2H), 7.15 (t, J=7.2 Hz, 1H), 5.86 (d, J=6.0 Hz, 1H), 4.64 (s, 2H), 4.54 (t, J=5.5 Hz, 1H), 4.19-3.94 (m, 4H), 2.71-2.55 (m, 2H), 2.17 (t, J=20.5 Hz, 2H), 1.66 (q, J=7.4 Hz, 2H), 0.93-0.70 (m, 3H). ESI MS [M+H]⁺ for $C_{21}H_{30}N_5O_9P_2$, calcd 558.1, found 558.2.

Example 18

Synthesis of [({[(2R,3S,4R,5R)-5-[6-(benzylamino)-2-methoxy-9H-purin-9-yl]-3,4-dihydroxyoxolan-2-yl]methoxy}(hydroxy)phosphoryl)methyl]phosphonic acid

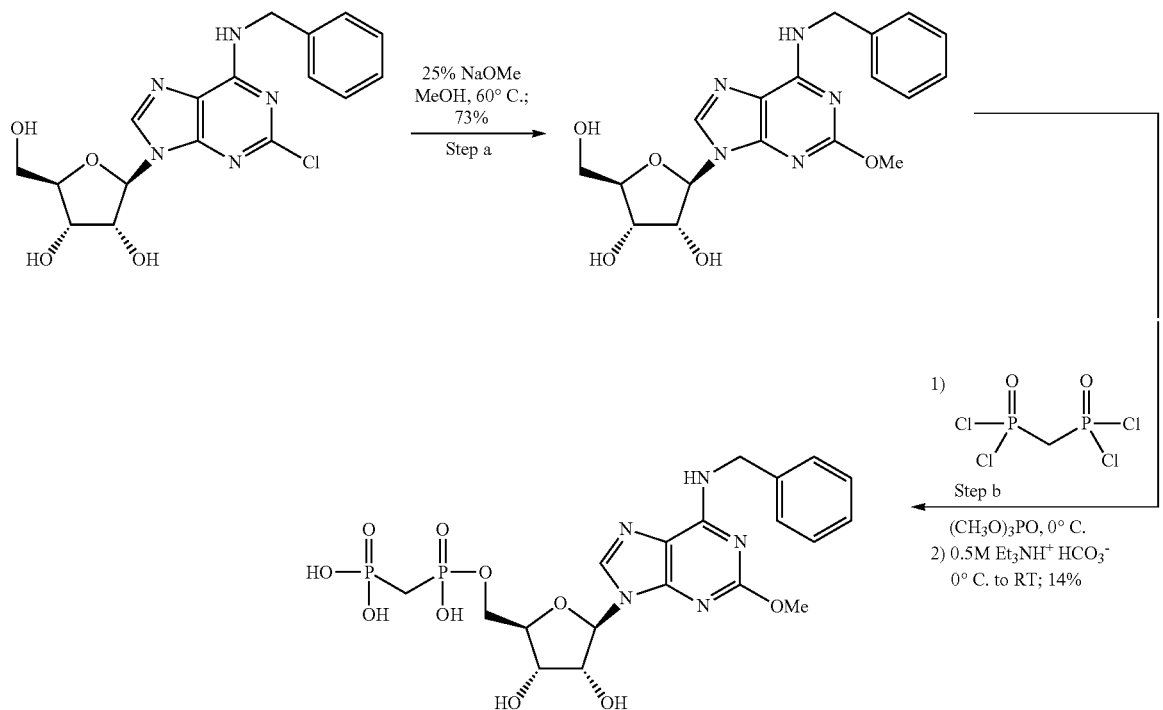 [SMILES: OC[C@H]1O[C@@H](n2cnc3c(NCc4ccccc4)nc(Cl)nc32)[C@H](O)[C@@H]1O ; COc1nc(NCc2ccccc2)c2ncn([C@@H]3O[C@H](CO)[C@@H](O)[C@H]3O)c2n1 ; COc1nc(NCc2ccccc2)c2ncn([C@@H]3O[C@H](COP(=O)(O)CP(=O)(O)O)[C@@H](O)[C@H]3O)c2n1 ; O=P(Cl)(Cl)CP(=O)(Cl)Cl]

Step a: The known riboside (250 mg, 0.64 mmol) was dissolved in 25% NaOMe in MeOH solution (2 mL) and stirred at 60° C. for overnight. The reaction mixture was concentrated under reduced pressure and the residue was then diluted with H$_2$O (15 mL) and acetic acid until neutral pH. The product was collected by filtration (white solid, 180 mg, 73%). ESI MS [M+H]$^+$ for C$_{18}$H$_{22}$N$_5$O$_5$, calcd 388.4, found 388.1.

Step b: The title compound was obtained using a similar procedure as for example 1 to give a white solid (37 mg, 14%): $^1$H NMR (400 MHz, DMSO) δ 8.48 (s, 1H), 8.20 (s, 1H), 7.37-7.17 (m, 5H), 5.82 (d, J=5.9 Hz, 1H), 4.64 (d, J=5.0 Hz, 3H), 4.28-4.00 (m, 4H), 3.80 (s, 3H), 2.23 (t, J=20.5 Hz, 2H). ESI MS [M+H]$^+$ for C$_{19}$H$_{26}$N$_5$O$_{10}$P$_2$, calcd 546.4, found 546.1.

Example 19

Synthesis of [({[(2R,3S,4R,5R)-5-[6-(benzylamino)-2-(methylamino)-9H-purin-9-yl]-3,4-dihydroxyoxolan-2-yl]methoxy}(hydroxy)phosphoryl)methyl] phosphonic acid

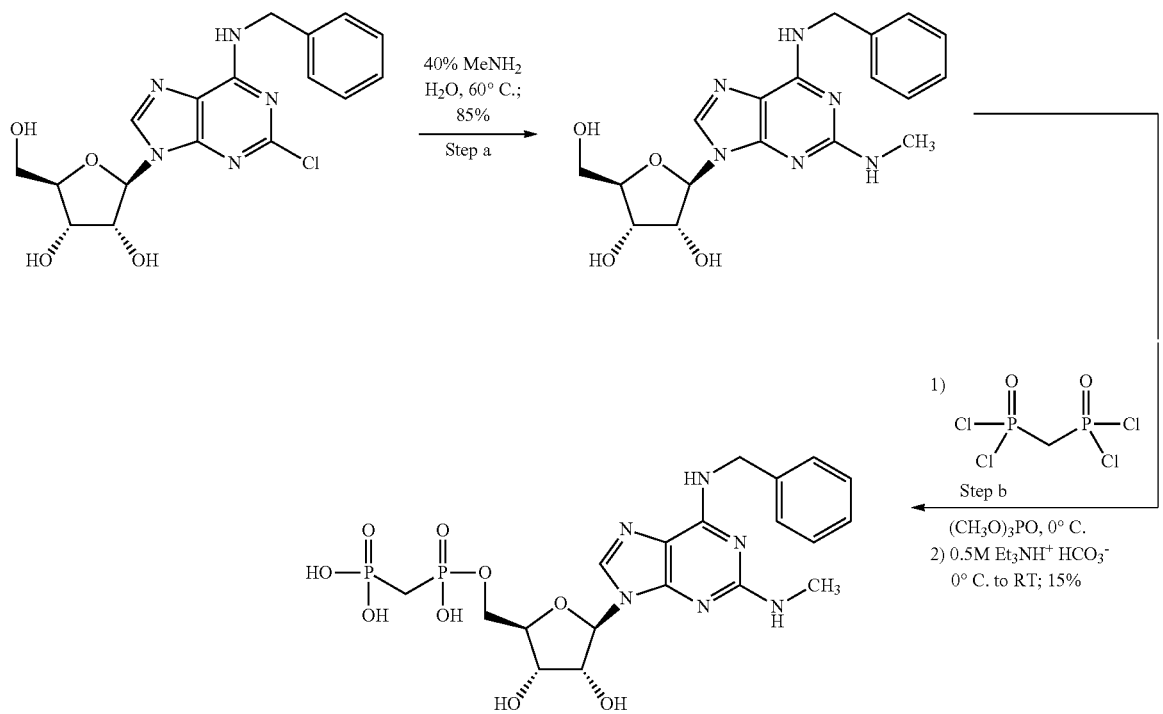 [SMILES: OC[C@H]1O[C@@H](n2cnc3c(NCc4ccccc4)nc(Cl)nc32)[C@H](O)[C@@H]1O ; CNc1nc(NCc2ccccc2)c2ncn([C@@H]3O[C@H](CO)[C@@H](O)[C@H]3O)c2n1 ; CNc1nc(NCc2ccccc2)c2ncn([C@@H]3O[C@H](COP(=O)(O)CP(=O)(O)O)[C@@H](O)[C@H]3O)c2n1 ; O=P(Cl)(Cl)CP(=O)(Cl)Cl]

Step a: The known riboside (250 mg, 0.64 mmol) was dissolved in 40% MeNH$_2$ in H$_2$O solution (2 mL) and stirred at 60° C. for overnight. The reaction mixture was then concentrated under reduced pressure and the residue was diluted with H$_2$O (15 mL). The product was collected by filtration (white solid, 210 mg, 85%). ESI MS [M+H]$^+$ for C$_{18}$H$_{23}$N$_6$O$_4$, calcd 387.4, found 387.3.

Step b: The title compound was obtained using a similar procedure as for Example 1 to give white solid (38 mg, 15%): $^1$H NMR (400 MHz, DMSO) δ 8.08 (s, 1H), 7.42-7.19 (m, 5H), 5.79 (d, J=6.1 Hz, 1H), 4.75-4.45 (m, 3H), 4.24-4.02 (m, 4H), 2.81 (s, 3H), 2.22 (t, J=20.4 Hz, 2H). ESI MS [M−H]$^-$ for C$_{19}$H$_{26}$N$_6$O$_9$P$_2$, calcd 543.4, found 543.2.

Example 20

Synthesis of (((((2R,3S,4R,5R)-5-(6-(benzylamino)-2-(dimethylamino)-9H-purin-9-yl)-3,4-dihydroxytetrahydrofuran-2-yl)methoxy)(hydroxy)phosphoryl)methyl)phosphonic acid

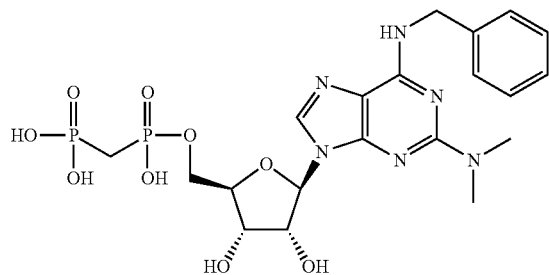 [SMILES: CN(C)c1nc(NCc2ccccc2)c2ncn([C@@H]3O[C@H](COP(=O)(O)CP(=O)(O)O)[C@@H](O)[C@H]3O)c2n1]

The title compound was synthesized in similar fashion to Example 19 but using dimethylamine in step a: $^1$H NMR (400 MHz, DMSO-d$_6$) δ 8.15 (s, 1H), 8.09 (s, 1H), 7.36 (d, J=7.2 Hz, 2H), 7.29 (t, J=7.5 Hz, 2H), 7.21 (t, J=7.2 Hz, 1H), 5.81 (d, J=5.5 Hz, 1H), 4.68-4.57 (m, 3H), 4.26-4.20 (m, 1H), 4.20-4.00 (m, 3H), 3.06 (s, 6H), 2.24 (t, J=20.4 Hz, 2H). ESI MS [M+H]$^+$ for C$_{20}$H$_{29}$N$_6$O$_9$P$_2$, calcd 559.1, found 559.2.

Example 21

Synthesis of (((((2R,3S,4R,5R)-5-(6-(benzylamino)-2-(pyrrolidin-1-yl)-9H-purin-9-yl)-3,4-dihydroxytetrahydrofuran-2-yl)methoxy)(hydroxy)phosphoryl)methyl)phosphonic acid

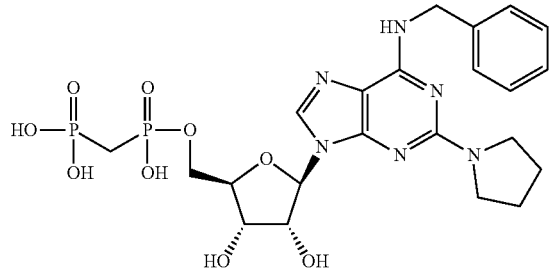 [SMILES: O=P(O)(O)CP(=O)(O)OC[C@H]1O[C@@H](n2cnc3c(NCc4ccccc4)nc(N4CCCC4)nc32)[C@H](O)[C@@H]1O]

The title compound was synthesized in similar fashion to Example 19 but using pyrrolidine in step a: $^1$H NMR (400 MHz, DMSO-d$_6$) δ 8.15 (s, 2H), 7.42-7.14 (m, 5H), 5.82 (d, J=5.5 Hz, 1H), 4.71-4.51 (m, 3H), 4.26 (t, J=4.3 Hz, 1H), 4.21-4.00 (m, 3H), 3.46 (s, 4H), 2.23 (t, J=20.4 Hz, 2H), 1.89 (s, 4H). ESI MS [M+H]$^+$ for C$_{22}$H$_{31}$N$_6$O$_9$P$_2$, calcd 585.1, found 585.2.

Example 22

Synthesis of (((((2R,3S,4R,5R)-5-(6-(benzylamino)-2-(piperidin-1-yl)-9H-purin-9-yl)-3,4-dihydroxytetrahydrofuran-2-yl)methoxy)(hydroxy)phosphoryl)methyl)phosphonic acid

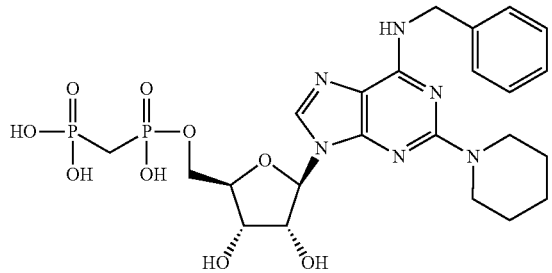 [SMILES: O=P(O)(O)CP(=O)(O)OC[C@H]1O[C@@H](n2cnc3c(NCc4ccccc4)nc(N4CCCCC4)nc32)[C@H](O)[C@@H]1O]

The title compound was synthesized in similar fashion to Example 19 but using piperidine in step a: $^1$H NMR (400 MHz, DMSO-d$_6$) δ 8.20 (s, 1H), 8.10 (s, 1H), 7.38-7.33 (m, 2H), 7.33-7.25 (m, 2H), 7.25-7.16 (m, 1H), 5.81 (d, J=5.6 Hz, 1H), 4.66-4.52 (m, 3H), 4.20 (t, J=4.3 Hz, 1H), 4.17-4.00 (m, 3H), 3.74-3.62 (m, 4H), 2.24 (t, J=20.5 Hz, 2H), 1.64-1.38 (m, 6H). ESI MS [M−H]$^-$ for C$_{23}$H$_{31}$N$_6$O$_9$P$_2$, calcd 597.2, found 597.3.

Example 23

Synthesis of (((((2R,3S,4R,5R)-5-(6-(benzylamino)-2-morpholino-9H-purin-9-yl)-3,4-dihydroxytetrahydrofuran-2-yl)methoxy)(hydroxy)phosphoryl)methyl)phosphonic acid

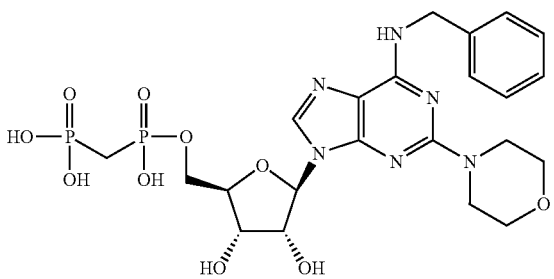 [SMILES: O=P(O)(O)CP(=O)(O)OC[C@H]1O[C@@H](n2cnc3c(NCc4ccccc4)nc(N4CCOCC4)nc32)[C@H](O)[C@@H]1O]

The title compound was synthesized in similar fashion to Example 19 but using morpholine in step a: $^1$H NMR (400 MHz, DMSO-d$_6$) δ 8.24-8.02 (m, 2H), 7.37-7.17 (m, 5H), 5.79 (d, J=5.9 Hz, 1H), 4.72-4.51 (m, 3H), 4.23-3.99 (m, 4H), 3.61 (s, 8H), 2.23 (t, J=20.5 Hz, 2H). ESI MS [M−H]$^-$ for C$_{22}$H$_{29}$N$_6$O$_{10}$P$_2$, calcd 599.2, found 599.3.

Example 24

Synthesis of (((((2R,3S,4R,5R)-5-(6-(benzylamino)-2-(isopropylthio)-9H-purin-9-yl)-3,4-dihydroxytetrahydrofuran-2-yl)methoxy)(hydroxy)phosphoryl)methyl)phosphonic acid

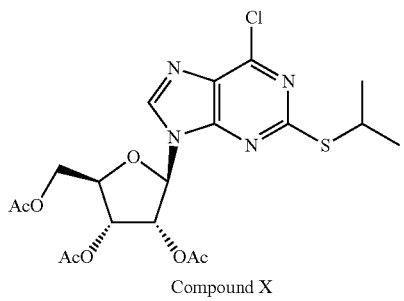

Compound X

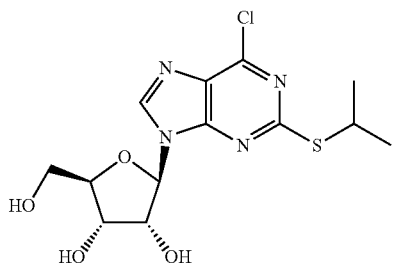

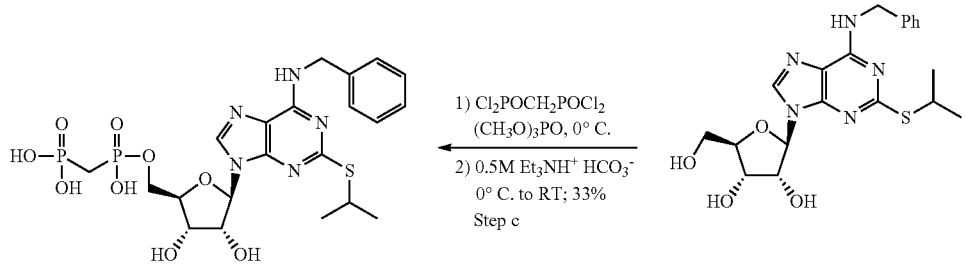

Step a: A solution of compound X (5 g, 10.2 mmol) in MeOH (60 ml) was treated with ammonia gas for 10 mins at −20° C. The mixture was then warmed to room temperature and stirred until the reaction was complete. Nitrogen was then bubbled through the reaction to remove excess ammonia gas. The mixture was concentrated and purified by prep-HPLC to give the desired product (750 mg, 20%).

Step b: The product from Step a (0.36 g, 1 mmol), benzyl amine (0.115 mL, 1.05 mmol, 1.05 equiv.), and Et$_3$N (0.15 mL, 1.1 mmol, 1.1 equiv.) in anhydrous EtOH (3.3 mL) was stirred at 70° C. for 4 hours. The reaction mixture was then cooled to room temperature, concentrated and used without further purification.

Step c: The product from Step b was dissolved in trimethyl phosphate (5 mL) and cooled to 0° C. (ice bath), then a cold solution of methylenebis(phosphonic dichloride) (1.2 g, 15 mmol, 5 equiv.) in trimethyl phosphate (3 mL) was added dropwise. The reaction mixture was stirred at 0° C. for 3 h, and was then carefully quenched with 0.5 M triethylammonium bicarbonate solution (6 mL) and stirred at 0° C. for 15 min, and then 2 h at room temperature. The reaction mixture was purified by reverse phase HPLC (C18 column, 0 to 40% gradient of acetonitrile and water with 0.1% TFA) to give the product as a white solid in 6% yield (38 mg): $^1$H NMR (400 MHz, DMSO-d$_6$) δ 8.53 (s, 1H), 8.27 (s, 1H), 7.37-7.17 (m, 5H), 5.84 (d, J=5.8 Hz, 1H), 4.65 (s, 2H), 4.56 (t, J=5.5 Hz, 1H), 4.24-4.17 (m, 1H), 4.17-4.01 (m, 3H), 3.82-3.71 (m, 1H), 2.24 (t, J=20.5 Hz, 2H), 1.28 (d, J=6.8 Hz, 6H). ESI MS [M+H]$^+$ for C$_{21}$H$_{29}$N$_5$O$_9$P$_2$S, calcd 590.1, found 590.2.

Example 25

Synthesis of (((((2R,3S,4R,5R)-5-(6-(benzylamino)-2-(isopropylsulfonyl)-9H-purin-9-yl)-3,4-dihydroxytetrahydrofuran-2-yl)methoxy)(hydroxy)phosphoryl)methyl)phosphonic acid

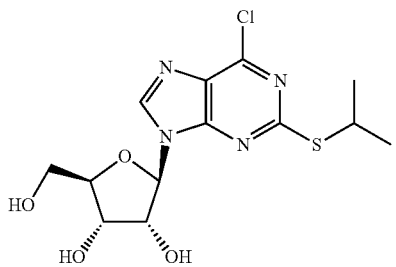

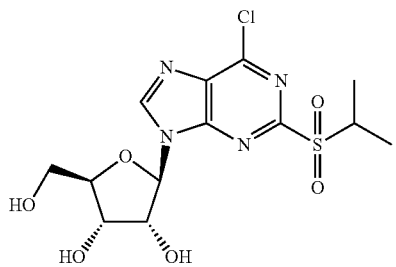

-continued

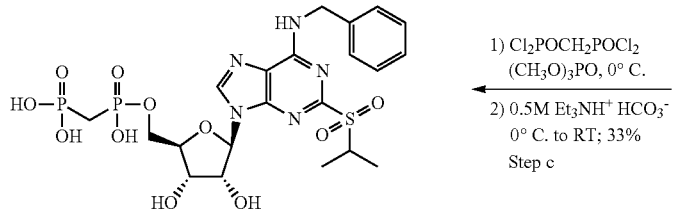 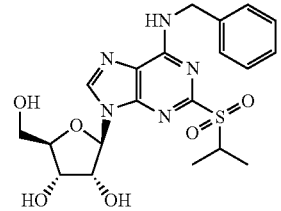

Step a: The product from Step a of Example 24 (4.5 g, 12.5 mmol) in methylene chloride (50 mL) was treated with m-CPBA (2.2 g, 38.2 mmol) portion-wise. The reaction was stirred at room temperature until complete. The mixture was diluted with methylene chloride (200 mL), washed with aqueous NaHSO$_3$ twice, dried over Na$_2$SO$_4$, and concentrated. The residue was purified by prep-HPLC to give the desired product as a white solid (780 mg, 16%).

Step b: The product from Step a (0.393 g, 1 mmol), benzyl amine (0.115 mL, 1.05 mmol, 1.05 equiv.), and Et$_3$N (0.15 mL, 1.1 mmol, 1.1 equiv.) in anhydrous EtOH (3.3 mL) was stirred at 70° C. for 4 hours. The reaction mixture was then cooled to room temperature, concentrated and used without further purification.

Step c: The product from Step b was dissolved in trimethyl phosphate (4 mL) and cooled to 0° C. (ice bath), then a cold solution of methylenebis(phosphonic dichloride) (1.2 g, 5 mmol, 5 equiv.) in trimethyl phosphate (2 mL) was added dropwise. The reaction mixture was stirred at 0° C. for 3 h, and was then carefully quenched with 0.5 M triethylammonium bicarbonate solution (6 mL) and stirred at 0° C. for 15 min, and then 2 h at room temperature. The reaction mixture was purified by reverse phase HPLC (C18 column, 0 to 40% gradient of acetonitrile and water with 0.1% TFA) to give the product as a white solid in 22% yield (50 mg): $^1$H NMR (400 MHz, DMSO-d$_6$) δ 9.21 (t, J=6.2 Hz, 1H), 8.66 (s, 1H), 7.42-7.15 (m, 5H), 5.97 (d, J=6.1 Hz, 1H), 4.74-4.66 (m, 2H), 4.60 (dd, J=6.1, 5.0 Hz, 1H), 4.26-4.22 (m, 1H), 4.19-4.07 (m, 4H), 3.78 (p, J=6.8 Hz, 1H), 2.26 (t, J=20.5 Hz, 2H), 1.12 (dd, J=6.8, 2.4 Hz, 6H). ESI MS [M+H]$^+$ for C$_{21}$H$_{29}$N$_5$O$_{11}$P$_2$S, calcd 622.1, found 622.2.

Example 26

Synthesis of (((((2R,3S,4S,5R)-5-(6-amino-2-fluoro-9H-purin-9-yl)-3,4-dihydroxytetrahydrofuran-2-yl)methoxy)(hydroxy)phosphoryl)methyl)phosphonic acid

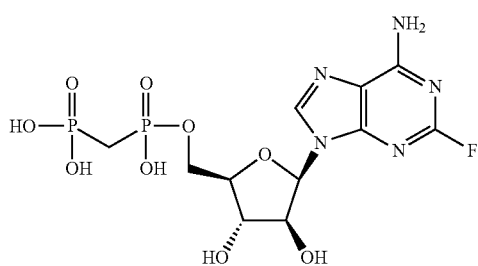 [SMILES: Nc1nc(F)nc2c1ncn2[C@@H]1O[C@H](COP(=O)(O)CP(=O)(O)O)[C@@H](O)[C@@H]1O]

The title compound was synthesized in similar fashion to step b of Example 1 using corresponding alcohol: $^1$H NMR (400 MHz, DMSO-d$_6$) δ 8.17 (s, 1H), 8.02-7.72 (m, 2H), 6.15 (d, J=4.3 Hz, 1H), 4.30-4.09 (m, 4H), 4.00-3.88 (m, 1H), 2.24 (t, J=20.5 Hz, 2H). ESI MS [M+H]$^+$ for C$_{11}$H$_{17}$FN$_5$O$_9$P$_2$, calcd 444.0, found 444.1.

Example 27

Synthesis of (((((2R,3R,4R,5R)-5-(6-amino-9H-purin-9-yl)-4-fluoro-3-hydroxytetrahydrofuran-2-yl)methoxy)(hydroxy)phosphoryl)methyl)phosphonic acid

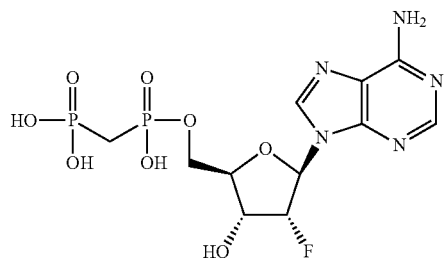 [SMILES: Nc1ncnc2c1ncn2[C@@H]1O[C@H](COP(=O)(O)CP(=O)(O)O)[C@@H](O)[C@H]1F]

The title compound was synthesized in similar fashion to step b of Example 1 using corresponding alcohol: $^1$H NMR (400 MHz, DMSO-d$_6$) δ 8.45 (s, 1H), 8.26 (s, 1H), 7.92 (s, 2H), 6.27 (dd, J=17.2, 2.8 Hz, 1H), 5.50 (ddd, J=52.5, 4.5, 2.8 Hz, 1H), 4.64-4.52 (m, 1H), 4.29-4.08 (m, 3H), 2.25 (t, J=20.4 Hz, 2H). ESI MS [M+H]$^+$ for C$_{11}$H$_{16}$FN$_5$O$_8$P$_2$, calcd 428.1, found 428.1.

Example 28

Synthesis [({[(2R,3R,4S,5R)-5-(6-amino-2-chloro-9H-purin-9-yl)-4-fluoro-3-hydroxyoxolan-2-yl]methoxy}(hydroxy)phosphoryl)methyl]phosphonic acid

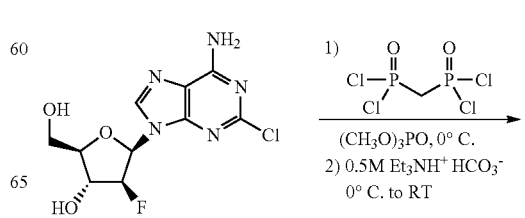

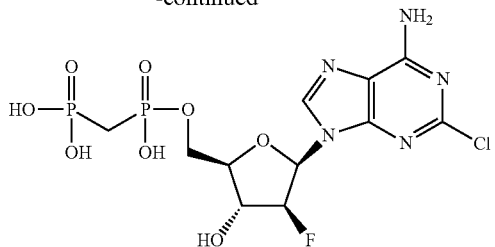

The title compound was synthesized in similar fashion to Example 1 using commercially available alcohol. $^1$H NMR (400 MHz, DMSO-$d_6$) δ 8.28 (d, J=2.2 Hz, 1H), 7.92 (s, 2H), 6.36 (dd, J=14.3, 4.6 Hz, 1H), 5.26 (dt, J=52.5, 4.3 Hz, 1H), 4.51 (dt, J=18.6, 4.7 Hz, 1H), 4.19 (t, J=6.0 Hz, 2H), 4.04 (t, J=5.0 Hz, 1H), 2.26 (t, J=20.5 Hz, 2H); MS: (ES) m/z calculated for $C_{11}H_{15}ClFN_5O_8P_2$ [M–H]$^-$ 460.1, found 460.1.

Example 29

Synthesis of (((((2R,3R,4S,5R)-5-(6-(benzylamino)-2-chloro-9H-purin-9-yl)-4-fluoro-3-hydroxytetrahydrofuran-2-yl)methoxy)(hydroxy)phosphoryl)methyl)phosphonic acid (7.72 g). $^1$H NMR (400 MHz, Chloroform-d) δ 8.39 (d, J=3.0 Hz, 1H), 8.10 (ddt, J=8.5, 3.1, 0.9 Hz, 4H), 7.74-7.36 (m, 6H), 6.64 (dd, J=21.8, 2.8 Hz, 1H), 5.83-5.69 (m, 1H), 5.40 (ddd, J=49.9, 2.8, 0.8 Hz, 1H), 4.89-4.77 (m, 2H), 4.62 (q, J=4.0 Hz, 1H). ESI MS [M+H]$^+$ for $C_{24}H_{17}C_{12}FN_4O_5$, calcd 531.1, found 531.1.

Step b: The product from Step a (9.0 g, 17 mmol), benzyl amine (3 mL, 26 mmol, 1.5 equiv.), and Et$_3$N (5 mL, 34 mmol, 2.0 equiv.) in anhydrous EtOH (60 mL) was stirred at 70° C. for 4 hours. The reaction mixture was then cooled to room temperature and the product was collected by filtration and used without further purification (white solid, 8.9 g, 87%). ESI MS [M+H]$^+$ for $C_{31}H_{25}ClFN_5O_5$, calcd 602.2, found 602.0.

The above product (10.2 g, 17 mmol) and K$_2$CO$_3$ (7 g, 51 mmol, 3 equiv) were dissolved in 170 mL of methanol and stirred at room temperature for 4 hours. The reaction mixture was then filtered and concentrated on a pad of silica gel. The reaction mixture was purified using column chromatography (methylene chloride/methanol) to provide the product was a white solid in 80% yield (5.3 g): $^1$H NMR (400 MHz, DMSO-$d_6$) δ 8.97 (t, J=6.3 Hz, 1H), 8.31 (d, J=2.0 Hz, 1H), 7.36-7.18 (m, 5H), 6.34 (dd, J=13.6, 4.7 Hz, 1H), 5.23 (dt, J=52.6, 4.3 Hz, 1H), 4.66 (q, J=7.3, 5.7 Hz, 2H), 4.43 (dt, J=19.0, 4.8 Hz, 1H), 3.84 (q, J=4.9 Hz, 1H), 3.65 (tq, J=12.0, 6.2, 5.2 Hz, 2H).) ESI MS [M+H]$^+$ for $C_{17}H_{18}ClFN_5O_3$, calcd 394.1, found 394.1.

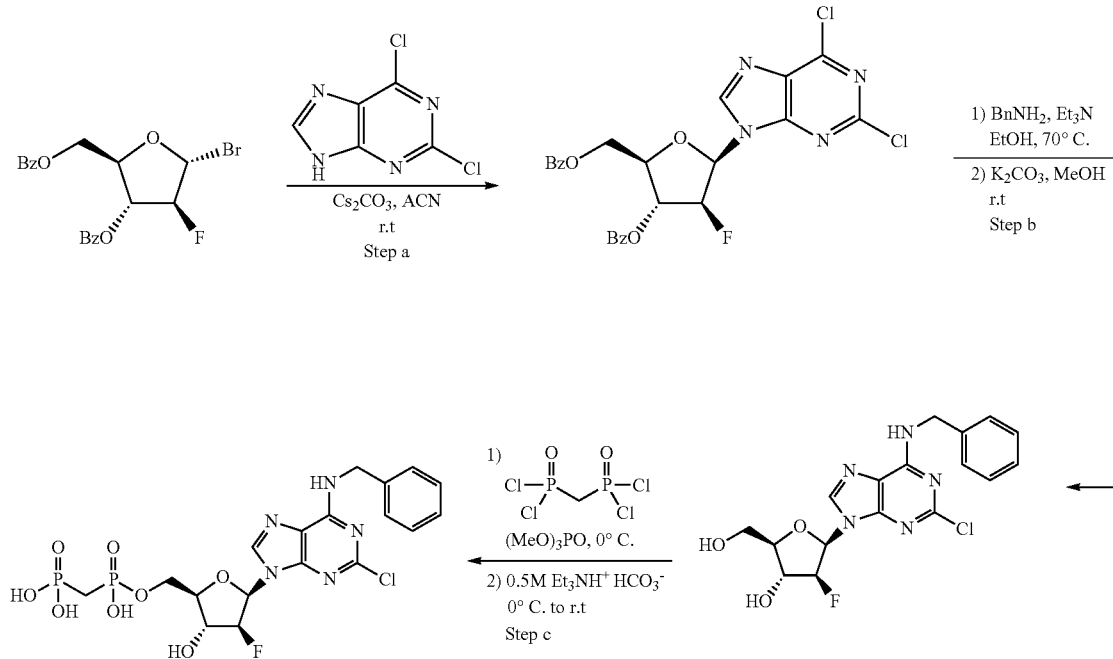

Step a: 2,6-dichloropurine (3.6 g, 18.8 mmol) was dissolved in 90 mL of acetonitrile and treated with Cs$_2$CO$_3$ (7.5 g, 23 mmol, 1.2 equiv.). The mixture was stirred at room temperature for 30 min. The known bromo derivative (8.75 g, 21 mmol, 1.1 equiv.) was dissolved in 100 mL of acetonitrile and added to the mixture dropwise via an addition funnel. The mixture was allowed to stir overnight at room temperature. The mixture was filtered on a pad of silica gel and concentrated. The residue was adsorbed on silica and purified using column chromatography (hexanes/ethyl acetate) to provide the product as a white solid in 77% yield Step c: The product from Step b (800 mg, 2 mmol) was dissolved in trimethyl phosphate (15 mL) and cooled to 0° C. (ice bath), then a cold solution of methylenebis(phosphonic dichloride) (2.5 g, 10 mmol, 5 equiv.) in trimethyl phosphate (5 mL) was added dropwise. The reaction mixture was stirred at 0° C. for 3 h, and was then carefully quenched with 0.5 M triethylammonium bicarbonate solution (15 mL) and stirred at 0° C. for 15 min, and then 2 h at room temperature. The reaction mixture was purified by reverse phase HPLC (C18 column, 0 to 40% gradient of acetonitrile and water with 0.1% TFA) to give the product as a white solid in 22% yield (290 mg): $^1$H NMR (400 MHz, DMSO-d$_6$) δ 8.99 (t, J=6.3 Hz, 1H), 8.30 (d, J=2.2 Hz, 1H), 7.40-7.18 (m, 5H), 6.38 (dd, J=14.3, 4.6 Hz, 1H), 5.45-5.04 (m, 1H), 4.65 (t, J=5.5 Hz, 2H), 4.54-4.42 (m, 1H), 4.19 (t, J=6.1 Hz, 2H), 4.04 (t, J=5.1 Hz, 1H), 2.26 (t, J=20.5 Hz, 2H). ESI MS [M−H]$^-$ for C$_{18}$H$_{21}$ClFN$_5$O$_8$P$_2$, calcd 550.8, found 550.2.

Example 30

Synthesis of (((((2R,3R,4S,5R)-5-(6-(benzyl(methyl)amino)-2-chloro-9H-purin-9-yl)-4-fluoro-3-hydroxytetrahydrofuran-2-yl)methoxy)(hydroxy)phosphoryl)methyl)phosphonic acid

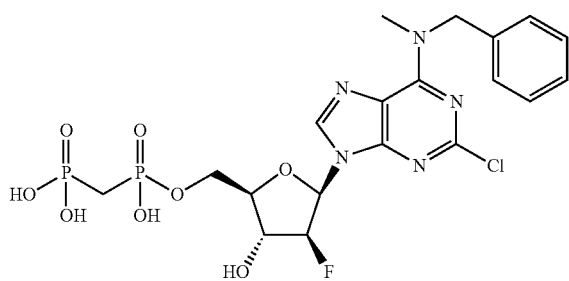

The title compound was synthesized in similar fashion to Example 29 using step a product of example 29 and corresponding amine: $^1$H NMR (400 MHz, DMSO-d$_6$) as a mixture of rotamers δ 8.32 (d, J=2.1 Hz, 1H), 7.40-7.19 (m, 5H), 6.42 (dd, J=14.5, 4.6 Hz, 1H), 5.55 (s, 1H), 5.27 (dt, J=52.4, 4.2 Hz, 1H), 4.95 (s, 1H), 4.50 (dt, J=18.4, 4.5 Hz, 1H), 4.19 (t, J=6.1 Hz, 2H), 4.05 (q, J=5.0 Hz, 1H), 3.65 (s, 1H), 3.11 (s, 2H), 2.26 (t, J=20.5 Hz, 2H). ESI MS [M+H]$^+$ for C$_{19}$H$_{23}$ClFN$_5$O$_8$P$_2$, calcd 566.1, found 566.2.

Example 31a

Synthesis of ((((((2R,3R,4S,5R)-5-(2-chloro-6-(methylamino)-9H-purin-9-yl)-4-fluoro-3-hydroxytetrahydrofuran-2-yl)methoxy)(hydroxy)phosphoryl)methyl)phosphonic acid

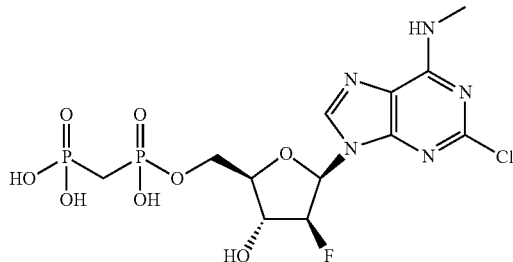 [SMILES: CNc1nc(Cl)nc2c1ncn2[C@@H]1O[C@H](COP(=O)(O)CP(=O)(O)O)[C@@H](O)[C@@H]1F]

The title compound was synthesized in similar fashion to Example 29 using step a product of example 29 and corresponding amine: $^1$H NMR (400 MHz, DMSO-d$_6$) δ 8.36 (q, J=4.6 Hz, 1H), 8.27 (s, 1H), 6.45 (brs, 2H), 6.37 (dd, J=14.3, 4.6 Hz, 1H), 5.25 (dt, J=52.4, 4.3 Hz, 1H), 4.50 (dt, J=18.6, 4.6 Hz, 1H), 4.19 (t, J=5.9 Hz, 2H), 4.04 (q, J=5.2 Hz, 1H), 3.33 (brs, 1H), 2.93 (d, J=4.5 Hz, 3H), 2.26 (t, J=20.4 Hz, 2H). ESI MS [M−H]$^-$ for C$_{12}$H$_{17}$ClFN$_5$O$_8$P$_2$, calcd 474.7, found 474.1.

Example 31b

Synthesis of (((((2R,3R,4S,5R)-5-(2-chloro-6-(ethylamino)-9H-purin-9-yl)-4-fluoro-3-hydroxytetrahydrofuran-2-yl)methoxy)(hydroxy)phosphoryl)methyl)phosphonic acid

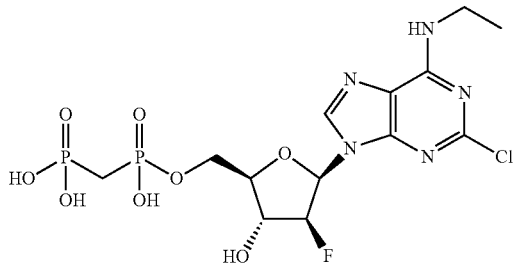 [SMILES: CCNc1nc(Cl)nc2c1ncn2[C@@H]1O[C@H](COP(=O)(O)CP(=O)(O)O)[C@@H](O)[C@@H]1F]

The title compound was synthesized in similar fashion to Example 29 using step a product of example 29 and corresponding amine: $^1$H NMR (400 MHz, DMSO-d$_6$) δ 8.43 (t, J=5.7 Hz, 1H), 8.26 (s, 1H), 7.28 (brs, 2H), 6.37 (dd, J=14.3, 4.6 Hz, 1H), 5.25 (dt, J=52.4, 4.3 Hz, 1H), 4.50 (dt, J=18.5, 4.6 Hz, 1H), 4.19 (t, J=6.1 Hz, 2H), 4.03 (q, J=5.1 Hz, 1H), 3.87 (brs, 1H), 3.45 (m, 1H), 2.27 (t, J=20.5 Hz, 2H), 1.17 (t, J=7.2 Hz, 3H). ESI MS [M+H]$^+$ for C$_{13}$H$_{19}$ClFN$_5$O$_8$P$_2$, calcd 490.7, found 490.1.

Example 32

Synthesis of (((((2R,3R,4S,5R)-5-(2-chloro-6-(isopropylamino)-9H-purin-9-yl)-4-fluoro-3-hydroxytetrahydrofuran-2-yl)methoxy)(hydroxy)phosphoryl)methyl)phosphonic acid

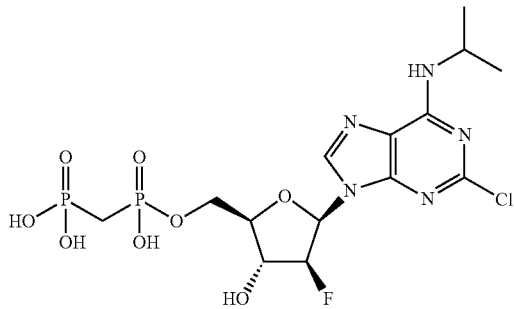 [SMILES: CC(C)Nc1nc(Cl)nc2c1ncn2[C@@H]1O[C@H](COP(=O)(O)CP(=O)(O)O)[C@@H](O)[C@@H]1F]

The title compound was synthesized in similar fashion to Example 29 using step a product of example 29 and corresponding amine: $^1$H NMR (400 MHz, DMSO-d$_6$) δ 8.27 (m, 2H), 6.37 (d, J=13.9 Hz, 1H), 5.28 (brs, 2H), 5.25 (d, J=52.1 Hz, 1H), 4.98 (brs, 1H), 4.51 (d, J=18.3 Hz, 1H), 4.35 (sept, J=7.9 Hz, 1H), 4.19 (m, 2H), 4.04 (m, 1H), 2.26 (t, J=20 Hz, 2H), 1.21 (dd, J=6.6, 2.1 Hz, 6H). ESI MS [M−H]$^-$ for C$_{14}$H$_{21}$ClFN$_5$O$_8$P$_2$, calcd 502.7, found 502.2.

Example 33

(((((2R,3R,4S,5R)-5-(2-chloro-6-(cyclopropylamino)-9H-purin-9-yl)-4-fluoro-3-hydroxytetrahydrofuran-2-yl)methoxy)(hydroxy)phosphoryl)methyl)phosphonic acid

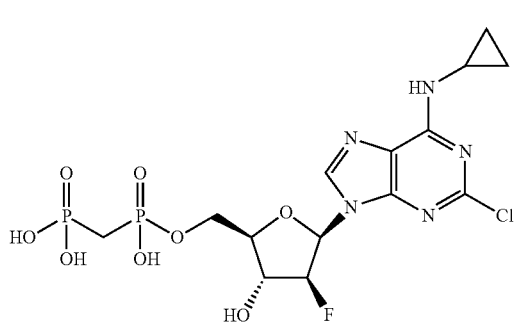 [SMILES: O=P(O)(O)CP(=O)(O)OC[C@H]1O[C@@H](n2cnc3c(NC4CC4)nc(Cl)nc32)[C@@H](F)[C@@H]1O]

The title compound was synthesized in similar fashion to Example 29 using step a product of example 29 and corresponding amine: $^1$H NMR (400 MHz, DMSO-d$_6$) δ 8.59 (s, 1H), 8.28 (d, J=2.1 Hz, 1H), 6.38 (dd, J=14.2, 4.6 Hz, 1H), 5.26 (ddd, J=52.5, 4.3, 4.3 Hz, 1H), 4.51 (dt, J=18.5, 4.5 Hz, 11H), 4.19 (t, J=6.1 Hz, 2H), 4.03 (q, J=5.0 Hz, 11H), 2.98 (s, 1H), 2.36-2.15 (m, 2H), 0.82-0.48 (m, 4H). ESI MS [M−H]$^-$ for C$_{14}$H$_{18}$ClFN$_5$O$_8$P$_2$, calcd 500.03, found 500.0.

Example 34

Synthesis of (((((2R,3R,4S,5R)-5-(2-chloro-6-((cyclopropylmethyl)amino)-9H-purin-9-yl)-4-fluoro-3-hydroxytetrahydrofuran-2-yl)methoxy)(hydroxy)phosphoryl)methyl)phosphonic acid

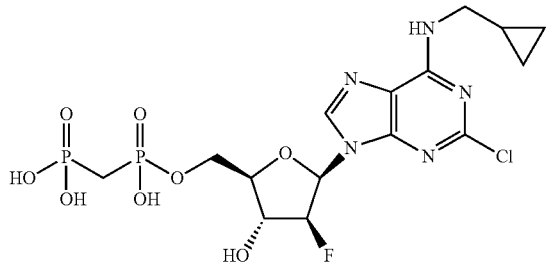 [SMILES: O=P(O)(O)CP(=O)(O)OC[C@H]1O[C@@H](n2cnc3c(NCC4CC4)nc(Cl)nc32)[C@@H](F)[C@@H]1O]

The title compound was synthesized in similar fashion to Example 29 using step a product of example 29 and corresponding amine: $^1$H NMR (400 MHz, DMSO-d$_6$) δ 8.54 (s, 1H), 8.28 (s, 1H), 6.37 (dd, J=14.2, 4.6 Hz, 1H), 5.25 (ddd, J=52.5, 4.3, 4.3 Hz, 1H), 4.54-4.47 (m, 1H), 4.19 (t, J=6.3 Hz, 2H), 4.05-4.01 (m, 1H), 3.81-3.74 (m, 1H), 3.30-3.27 (m, 1H), 2.26 (dd, J=20.5, 20.5 Hz, 2H), 1.1-1.3 (m, 1H), 0.48-0.37 (m, 2H), 0.28-0.26 (m, 2H). ESI MS [M−H]$^-$ for C$_{15}$H$_{20}$ClFN$_5$O$_8$P$_2$, calcd 514.1, found 514.0.

Example 35

Synthesis of (((((2R,3R,4S,5R)-5-(2-chloro-6-(cyclopentylamino)-9H-purin-9-yl)-4-fluoro-3-hydroxytetrahydrofuran-2-yl)methoxy)(hydroxy)phosphoryl)methyl)phosphonic acid

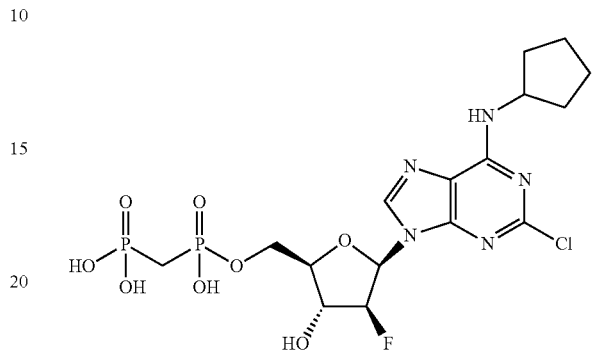

The title compound was synthesized in similar fashion to Example 29 using step a product of example 29 and corresponding amine: $^1$H NMR (400 MHz, DMSO-d$_6$) δ 8.41 (d, J=7.8 Hz, 1H), 8.27 (s, 1H), 6.37 (dd, J=14.4, 4.6 Hz, 1H), 5.25 (dt, J=52.4, 4.3 Hz, 1H), 4.55-4.37 (m, 2H), 4.19 (t, J=6.1 Hz, 2H), 4.03 (q, J=5.1 Hz, 1H), 2.26 (t, J=20.5 Hz, 2H), 1.93 (s, 2H), 1.64 (d, J=62.5 Hz, 6H). ESI MS [M+H]$^+$ for C$_{16}$H$_{23}$ClFN$_5$O$_8$P$_2$, calcd 530.1, found 530.2.

Example 36

Synthesis of (((((2R,3R,4S,5R)-5-(2-chloro-6-(((S)-tetrahydrofuran-3-yl)amino)-9H-purin-9-yl)-4-fluoro-3-hydroxytetrahydrofuran-2-yl)methoxy)(hydroxy)phosphoryl)methyl)phosphonic acid

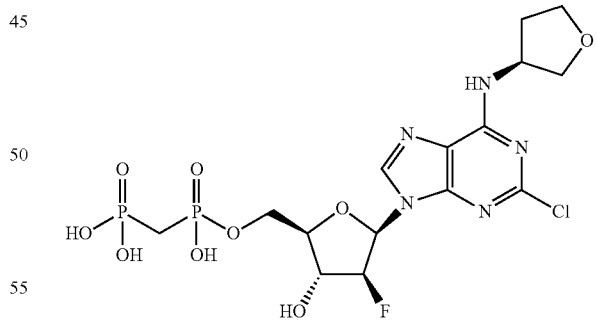

The title compound was synthesized in similar fashion to Example 29 using step a product of example 29 and corresponding amine: $^1$H NMR (400 MHz, DMSO-d$_6$) δ 8.66 (d, J=6.2 Hz, 1H), 8.31 (s, 1H), 6.38 (dd, J=14.3, 4.6 Hz, 1H), 5.26 (ddd, J=52.4, 4.2, 2.4 Hz, 1H), 4.61-4.67 (m, 1H), 4.57-4.45 (m, 1H), 4.19 (t, J=6.1 Hz, 2H), 4.04 (q, J=5.0 Hz, 1H), 3.89 (dt, J=15.3, 7.8 Hz, 2H), 3.73 (q, J=7.8 Hz, 1H), 3.61 (dd, J=8.9, 4.4 Hz, 1H), 2.36-1.99 (m, 4H). ESI MS [M−H]$^-$ for C$_{15}$H$_{20}$ClFN$_5$O$_9$P$_2$, calcd 530.04, found 530.1.

Example 37

Synthesis of (((((2R,3R,4S,5R)-5-(2-chloro-6-(((R)-tetrahydrofuran-3-yl)amino)-9H-purin-9-yl)-4-fluoro-3-hydroxytetrahydrofuran-2-yl)methoxy)(hydroxy)phosphoryl)methyl)phosphonic acid

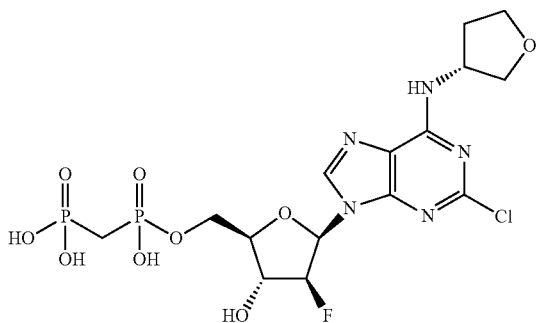 [SMILES: O=P(O)(O)CP(=O)(O)OC[C@H]1O[C@@H](n2cnc3c(N[C@@H]4CCOC4)nc(Cl)nc32)[C@@H](F)[C@@H]1O]

The title compound was synthesized in similar fashion to Example 29 using step a product of example 29 and corresponding amine: $^1$H NMR (400 MHz, DMSO-d$_6$) δ 8.65 (d, J=6.8 Hz, 1H), 8.31 (s, 1H), 6.39 (dd, J=14.2, 4.6 Hz, 1H), 5.26 (ddd, J=52.4, 4.3, 4.3 Hz, 1H), 4.69-4.56 (m, 1H), 4.51 (dt, J=18.6, 4.6 Hz, 1H), 4.20 (t, J=6.1 Hz, 2H), 4.04 (q, J=5.0 Hz, 1H), 3.89 (dt, J=18.6, 7.9 Hz, 2H), 3.74 (q, J=7.8 Hz, 1H), 3.67-3.54 (m, 1H), 2.35-1.90 (m, 4H). ESI MS [M–H]$^-$ for C$_{15}$H$_{20}$ClFN$_5$O$_9$P$_2$, calcd 530.04, found 530.1.

Example 38

Synthesis of (((((2R,3R,4S,5R)-5-(2-chloro-6-((tetrahydro-2H-pyran-4-yl)amino)-9H-purin-9-yl)-4-fluoro-3-hydroxytetrahydrofuran-2-yl)methoxy)(hydroxy)phosphoryl)methyl)phosphonic acid

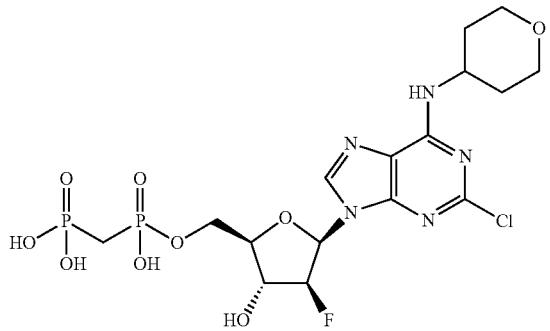 [SMILES: O=P(O)(O)CP(=O)(O)OC[C@H]1O[C@@H](n2cnc3c(NC4CCOCC4)nc(Cl)nc32)[C@@H](F)[C@@H]1O]

The title compound was synthesized in similar fashion to Example 29 using step a product of example 29 and corresponding amine: $^1$H NMR (400 MHz, DMSO-d$_6$) δ 8.47-8.34 (m, 1H), 8.30 (s, 1H), 6.37 (dd, J=14.1, 4.8 Hz, 1H), 5.25 (ddd, J=52.4, 4.3, 4.3 Hz, 1H), 4.92-4.65 (m, 1H), 4.59-4.39 (m, 1H), 4.19 (t, J=6.2 Hz, 2H), 4.03 (q, J=5.1 Hz, 1H), 3.89 (d, J=11.3 Hz, 2H), 3.41 (t, J=11.4 Hz, 2H), 2.26 (dd, J=20.5 Hz, 2H), 1.92-1.45 (m, 4H). ESI MS [M–H]$^-$ for C$_{16}$H$_{22}$ClFN$_5$O$_9$P$_2$, calcd 544.06, found 544.1.

Example 39

Synthesis of (((((2R,3R,4S,5R)-5-(2-chloro-6-(pyrrolidin-1-yl)-9H-purin-9-yl)-4-fluoro-3-hydroxytetrahydrofuran-2-yl)methoxy)(hydroxy)phosphoryl)methyl)phosphonic acid

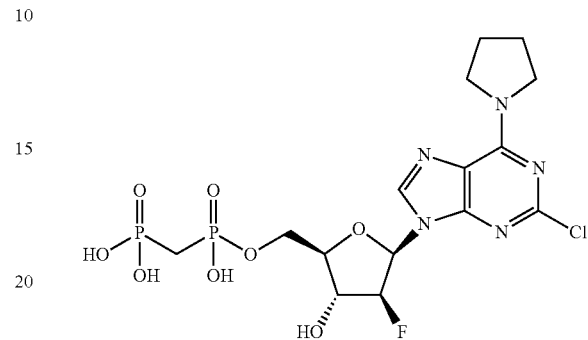

The title compound was synthesized in similar fashion to Example 29 using step a product of example 29 and corresponding amine: $^1$H NMR (400 MHz, DMSO-d$_6$) δ 8.27 (d, J=2.1 Hz, 1H), 6.39 (dd, J=14.1, 4.7 Hz, 1H), 5.26 (dt, J=52.5, 4.3 Hz, 1H), 4.50 (dt, J=18.5, 4.6 Hz, 1H), 4.19 (t, J=5.9 Hz, 2H), 4.05 (q, J=5.3, 4.1 Hz, 3H), 3.60 (t, J=6.8 Hz, 2H), 2.27 (t, J=20.5 Hz, 2H), 2.01 (p, J=6.7 Hz, 2H), 1.92 (q, J=6.7 Hz, 2H). ESI MS [M+H]$^+$ for C$_{15}$H$_{21}$ClFN$_5$O$_8$P$_2$, calcd 516.1, found 516.1.

Example 40

Synthesis of ((((2R,3R,4S,5R)-5-(2-chloro-6-(piperidin-1-yl)-9H-purin-9-yl)-4-fluoro-3-hydroxytetrahydrofuran-2-yl)methoxy)(hydroxy)phosphoryl)methyl)phosphonic acid

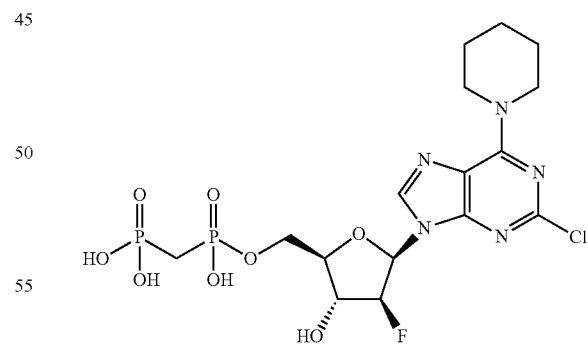

The title compound was synthesized in similar fashion to Example 29 using step a product of example 29 and corresponding amine: $^1$H NMR (400 MHz, DMSO-d$_6$) δ 8.30 (d, J=2.2 Hz, 1H), 6.39 (dd, J=14.3, 4.6 Hz, 1H), 5.26 (dt, J=52.4, 4.3 Hz, 1H), 4.50 (dt, J=18.4, 4.6 Hz, 1H), 4.19 (t, J=6.0 Hz, 2H), 4.04 (q, J=5.0 Hz, 11H), 3.88 (m, 2H), 2.27 (t, J=20.5 Hz, 2H), 1.64 (d, J=31.0 Hz, 8H). ESI MS [M+H]$^+$ for C$_{16}$H$_{23}$ClFN$_5$O$_8$P$_2$, calcd 530.1, found 530.2.

Example 41

Synthesis of (((((2R,3R,4S,5R)-5-(2-chloro-6-morpholino-9H-purin-9-yl)-4-fluoro-3-hydroxytetrahydrofuran-2-yl)methoxy)(hydroxy)phosphoryl)methyl)phosphonic acid

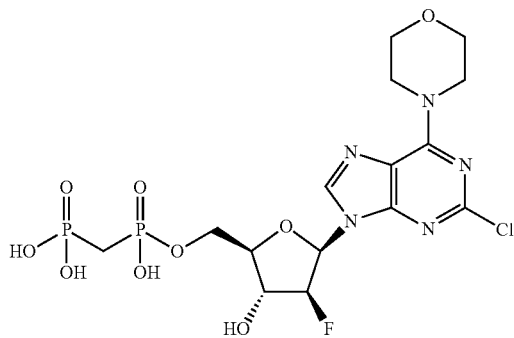 [SMILES: O=P(O)(O)CP(=O)(O)OC[C@H]1O[C@@H](n2cnc3c(N4CCOCC4)nc(Cl)nc32)[C@@H](F)[C@@H]1O]

The title compound was synthesized in similar fashion to Example 29 using step a product of example 29 and corresponding amine: ¹H NMR (400 MHz, DMSO-d₆) δ 8.34 (d, J=2.1 Hz, 1H), 6.41 (dd, J=13.9, 4.6 Hz, 1H), 5.27 (dt, J=52.5, 4.3 Hz, 1H), 4.51 (dt, J=18.5, 4.6 Hz, 1H), 4.19 (t, J=5.8 Hz, 2H), 4.04 (q, J=5.1 Hz, 1H), 3.79-3.67 (m, 5H), 2.26 (t, J=20.5 Hz, 2H). ESI MS [M+H]⁺ for $C_{15}H_{21}ClFN_5O_9P_2$, calcd 532.1, found 532.1.

Example 42

Synthesis of (((((2R,3R,4S,5R)-5-(2-chloro-6-(isoindolin-2-yl)-9H-purin-9-yl)-4-fluoro-3-hydroxytetrahydrofuran-2-yl)methoxy)(hydroxy)phosphoryl)methyl)phosphonic acid

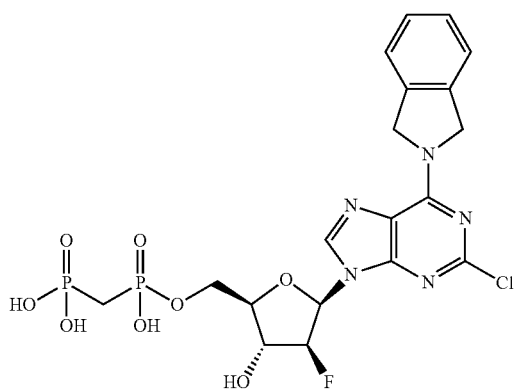 [SMILES: O=P(O)(O)CP(=O)(O)OC[C@H]1O[C@@H](n2cnc3c(N4Cc5ccccc5C4)nc(Cl)nc32)[C@@H](F)[C@@H]1O]

The title compound was synthesized in similar fashion to Example 29 using step a product of example 29 and corresponding amine: ¹H NMR (400 MHz, DMSO-d₆) δ 8.37 (d, J=2.1 Hz, 1H), 7.48 (dt, J=9.9, 4.7 Hz, 2H), 7.43-7.28 (m, 2H), 6.44 (dd, J=13.8, 4.7 Hz, 1H), 5.41 (s, 2H), 5.29 (dt, J=52.6, 4.4 Hz, 1H), 4.98 (s, 2H), 4.54 (dt, J=18.7, 4.7 Hz, 1H), 4.21 (t, J=5.9 Hz, 2H), 4.05 (q, J=4.9 Hz, 1H), 2.27 (t, J=20.5 Hz, 2H). ESI MS [M+H]⁺ for $C_{19}H_{21}ClFN_5O_8P_2$, calcd 564.1, found 564.1.

Example 43

Synthesis of (((((2R,3R,4S,5R)-5-(2-chloro-6-((4-chlorobenzyl)amino)-9H-purin-9-yl)-4-fluoro-3-hydroxytetrahydrofuran-2-yl)methoxy)(hydroxy)phosphoryl)methyl)phosphonic acid

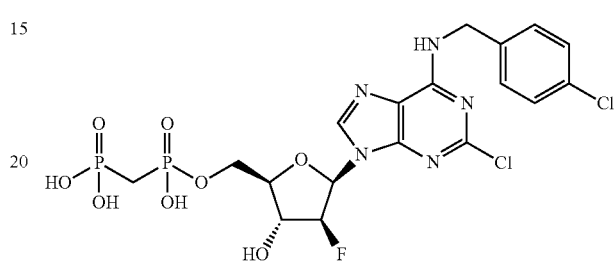

The title compound was obtained using identical procedure as for Example 29 using step a product of example 29 and corresponding amine: ¹H NMR (400 MHz, DMSO-d₆) δ 9.01 (t, J=6.2 Hz, 1H), 8.32 (d, J=2.1 Hz, 1H), 7.64-7.08 (m, 4H), 6.38 (dd, J=14.3, 4.6 Hz, 1H), 5.26 (dt, J=52.5, 4.3 Hz, 1H), 4.64 (q, J=7.3, 5.4 Hz, 2H), 4.51 (dt, J=18.7, 4.6 Hz, 1H), 4.28-4.11 (m, 2H), 4.04 (q, J=5.1 Hz, 1H), 2.27 (t, J=20.5 Hz, 2H). ESI MS [M−H]⁻ for $C_{18}H_{20}Cl_2FN_5O_8P_2$, calcd 584.0, found 584.1.

Example 44

Synthesis of (((((2R,3R,4S,5R)-5-(2-chloro-6-((4-fluorobenzyl)amino)-9H-purin-9-yl)-4-fluoro-3-hydroxytetrahydrofuran-2-yl)methoxy)(hydroxy)phosphoryl)methyl)phosphonic

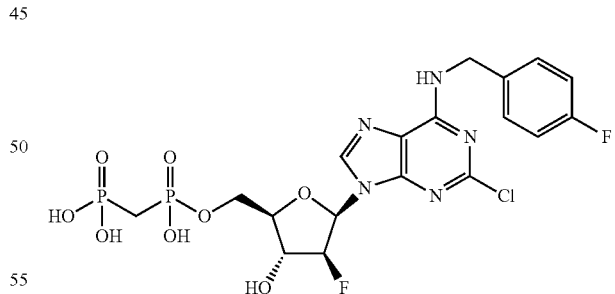

The title compound was obtained using identical procedure as for Example 29 using step a product of example 29 and corresponding amine: ¹H NMR (400 MHz, DMSO-d₆) δ 9.00 (t, J=6.3 Hz, 1H), 8.31 (d, J=2.2 Hz, 1H), 7.52-7.24 (m, 3H), 7.23-7.01 (m, 2H), 6.38 (dd, J=14.3, 4.6 Hz, 1H), 5.26 (dt, J=52.4, 4.3 Hz, 1H), 4.72-4.55 (m, 2H), 4.20 (t, J=6.0 Hz, 3H), 4.04 (q, J=5.1 Hz, 1H), 2.27 (t, J=20.5 Hz, 2H). ESI MS [M−H]⁻ for $C_{18}H_{20}ClF_2N_5O_8P_2$, calcd 568.0, found 568.2.

Example 45

Synthesis of (((((2R,3R,4S,5R)-5-(2-chloro-6-((3-methylbenzyl)amino)-9H-purin-9-yl)-4-fluoro-3-hydroxytetrahydrofuran-2-yl)methoxy)(hydroxy)phosphoryl)methyl)phosphonic acid

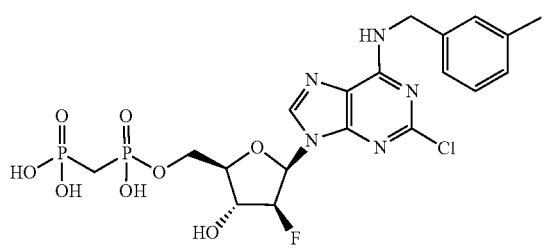 [SMILES: Cc1cccc(CNc2nc(Cl)nc3c2ncn3[C@@H]2O[C@H](COP(=O)(O)CP(=O)(O)O)[C@@H](O)[C@@H]2F)c1]

The title compound was synthesized as a white solid (87.1 mg; 310%) in similar fashion to Example 29 using step a product of example 29 and corresponding amine: $^1$H NMR (400 MHz, DMSO-d$_6$) δ 8.96 (t, J=6.3 Hz, 1H), 8.30 (d, J=2.2 Hz, 1H), 7.20 (t, J=7.5 Hz, 1H), 7.17-7.10 (m, 2H), 7.04 (d, J=7.4 Hz, 1H), 6.38 (dd, J=14.3, 4.6 Hz, 1H), 5.25 (dt, J=52.4, 4.3 Hz, 1H), 4.68-4.56 (m, 2H), 4.51 (dt, J=18.4, 4.6 Hz, 1H), 4.19 (t, J=6.0 Hz, 2H), 4.03 (q, J=5.1 Hz, 1H), 2.35-2.17 (m, 2H). ESI MS [M−H]$^-$ for $C_{19}H_{22}ClFN_5O_8P_2$, calcd 564.1, found 564.2.

Example 46

Synthesis of (((((2R,3R,4S,5R)-5-(2-chloro-6-((3-fluorobenzyl)amino)-9H-purin-9-yl)-4-fluoro-3-hydroxytetrahydrofuran-2-yl)methoxy)(hydroxy)phosphoryl)methyl)phosphonic acid

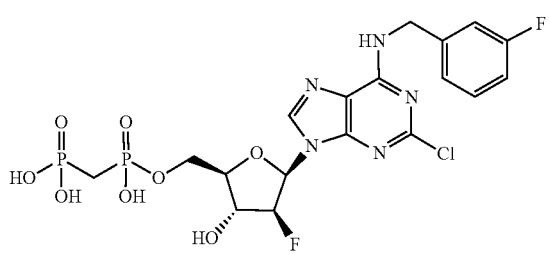 [SMILES: O=P(O)(O)CP(=O)(O)OC[C@H]1O[C@@H](n2cnc3c(NCc4cccc(F)c4)nc(Cl)nc32)[C@@H](F)[C@@H]1O]

The title compound was synthesized as a white solid (65.1 mg; 23%) in similar fashion to Example 29 using step a product of example 29 and corresponding amine: $^1$H NMR (400 MHz, DMSO-d$_6$) δ 9.02 (t, J=6.3 Hz, 1H), 8.32 (d, J=2.2 Hz, 1H), 7.42-7.32 (m, 1H), 7.17 (t, J=9.2 Hz, 2H), 7.07 (td, J=8.4, 2.2 Hz, 1H), 6.39 (dd, J=14.4, 4.6 Hz, 1H), 5.26 (dt, J=52.5, 4.3 Hz, 1H), 4.74-4.60 (m, 2H), 4.51 (dt, J=18.5, 4.7 Hz, 1H), 4.26-4.13 (m, 2H), 4.04 (q, J=5.0 Hz, 1H), 2.27 (t, J=20.5 Hz, 2H). ESI MS [M−H]$^-$ for $C_{18}H_{19}ClF_2N_5O_8P_2$, calcd 568.0, found 568.2.

Example 47

Synthesis of (((((2R,3R,4S,5R)-5-(2-chloro-6-((3-chlorobenzyl)amino)-9H-purin-9-yl)-4-fluoro-3-hydroxytetrahydrofuran-2-yl)methoxy)(hydroxy)phosphoryl)methyl)phosphonic acid

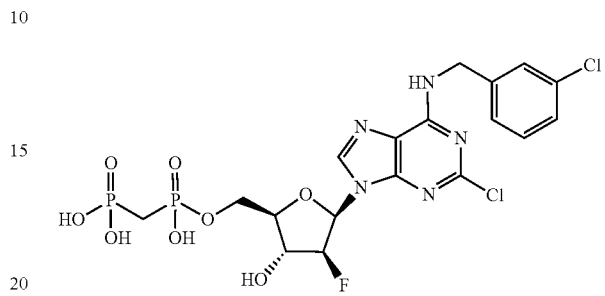

The title compound was synthesized as a white solid (70.6 mg; 24%) in similar fashion to Example 29 using step a product of example 29 and corresponding amine: $^1$H NMR (400 MHz, DMSO-d$_6$) δ 9.03 (t, J=6.2 Hz, 1H), 8.33 (d, J=2.2 Hz, 1H), 7.45-7.27 (m, 4H), 6.39 (dd, J=14.4, 4.6 Hz, 1H), 5.26 (dt, J=52.4, 4.2 Hz, 1H), 4.74-4.58 (m, 2H), 4.51 (dt, J=18.5, 4.6 Hz, 1H), 4.20 (t, J=6.1 Hz, 2H), 4.04 (q, J=5.1 Hz, 1H), 2.27 (t, J=20.5 Hz, 2H). ESI MS [M−H]$^-$ for $C_{18}H_{19}Cl_2FN_5O_8P_2$, calcd 584.0, found 584.0.

Example 48

Synthesis of (((((2R,3R,4S,5R)-5-(2-chloro-6-((2-chlorobenzyl)amino)-9H-purin-9-yl)-4-fluoro-3-hydroxytetrahydrofuran-2-yl)methoxy)(hydroxy)phosphoryl)methyl)phosphonic acid

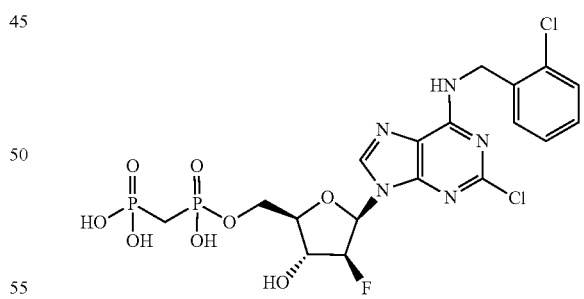

The title compound was synthesized in similar fashion to Example 29 using step a product of example 29 and corresponding amine: $^1$H NMR (400 MHz, DMSO-d$_6$) δ 8.99 (t, J=6.1 Hz, 1H), 8.35 (s, 1H), 7.47 (dd, J=6.0, 3.3 Hz, 1H), 7.35-7.22 (m, 3H), 6.40 (dd, J=14.2, 4.6 Hz, 1H), 5.27 (dt, J=52.4, 4.3 Hz, 1H), 4.73 (d, J=5.2 Hz, 2H), 4.52 (d, J=18.5 Hz, 1H), 4.20 (t, J=6.2 Hz, 2H), 4.05 (q, J=5.1 Hz, 1H), 2.27 (t, J=20.5 Hz, 2H). ESI MS [M+H]$^+$ for $C_{18}H_{20}C_{12}FN_5O_8P_2$, calcd 586.0, found 586.1.

Example 49

Synthesis of (((((2R,3R,4S,5R)-5-(2-chloro-6-((2-chlorobenzyl)(methyl)amino)-9H-purin-9-yl)-4-fluoro-3-hydroxytetrahydrofuran-2-yl)methoxy)(hydroxy)phosphoryl)methyl)phosphonic acid

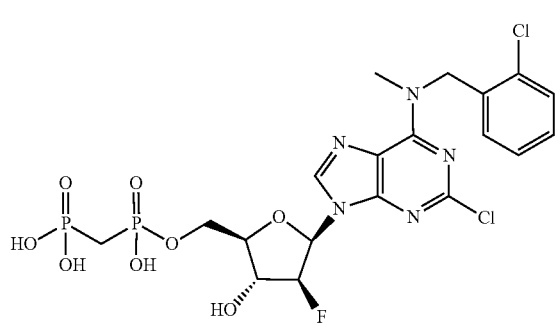 [SMILES: CN(Cc1ccccc1Cl)c1nc(Cl)nc2c1ncn2[C@@H]1O[C@H](COP(=O)(O)CP(=O)(O)O)[C@@H](O)[C@@H]1F]

The title compound was synthesized in similar fashion to Example 29 using step a product of example 29 and corresponding amine: $^1$H NMR (400 MHz, DMSO-$d_6$) δ 8.32 (d, J=37.7 Hz, 1H), 7.55-7.46 (m, 1H), 7.31 (bs, 2H), 7.15 (bs, 1H), 6.41 (d, J=14.4 Hz, 1H), 5.61 (bs, 1H), 5.26 (d, J=52.6 Hz, 1H), 5.00 (b, 1H), 4.49 (bs, 1H), 4.17 (bs, 2H), 4.03 (bs, 1H), 3.70 (bs, 1H), 3.18 (bs, 2H), 2.25 (t, J=20.4 Hz, 2H). ESI MS [M+H]$^+$ for $C_{19}H_{24}Cl_2N_5O_9P_2$, calcd 600.0, found 600.1.

Example 50

Synthesis of (((((2R,3R,4S,5R)-5-(2-chloro-6-((pyridin-4-ylmethyl)amino)-9H-purin-9-yl)-4-fluoro-3-hydroxytetrahydrofuran-2-yl)methoxy)(hydroxy)phosphoryl)methyl)phosphonic acid

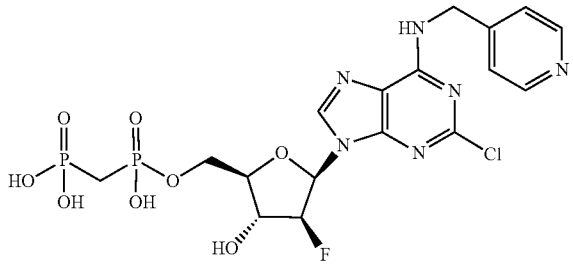 [SMILES: O=P(O)(O)CP(=O)(O)OC[C@H]1O[C@@H](n2cnc3c(NCc4ccncc4)nc(Cl)nc32)[C@@H](F)[C@@H]1O]

The title compound was synthesized in similar fashion to Example 29 using step a product of example 29 and corresponding amine: $^1$H NMR (400 MHz, DMSO-$d_6$) δ 9.13 (s, 1H), 8.66 (d, J=5.7 Hz, 2H), 8.37 (s, 1H), 7.65 (d, J=5.6 Hz, 2H), 6.40 (dd, J=14.0, 4.6 Hz, 1H), 5.40-5.08 (m, 1H), 4.80 (d, J=6.1 Hz, 2H), 4.53 (d, J=18.3 Hz, 1H), 4.19 (s, 2H), 4.04 (d, J=5.2 Hz, 1H), 2.25 (t, J=20.4 Hz, 2H). ESI MS [M+H]$^+$ for $C_{17}H_{20}ClFN_6O_8P_2$, calcd 553.1, found 553.2.

Example 51

Synthesis of (((((2R,3R,4S,5R)-5-(2-chloro-6-(phenethylamino)-9H-purin-9-yl)-4-fluoro-3-hydroxytetrahydrofuran-2-yl)methoxy)(hydroxy)phosphoryl)methyl)phosphonic acid

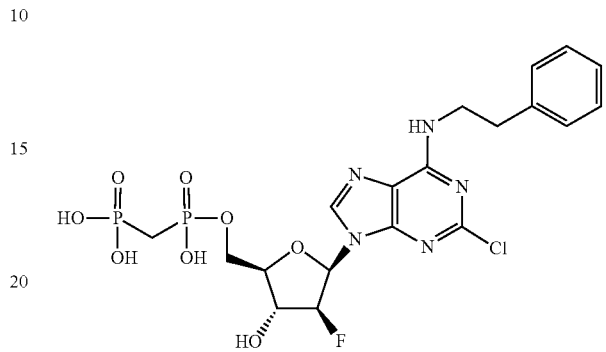

The title compound was synthesized in similar fashion to Example 29 using step a product of example 29 and corresponding amine: $^1$H NMR (400 MHz, DMSO-$d_6$) δ 8.50 (t, J=5.7 Hz, 1H), 8.27 (s, 1H), 7.38-7.13 (m, 5H), 6.37 (dd, J=14.4, 4.7 Hz, 1H), 5.25 (dt, J=52.4, 4.2 Hz, 1H), 4.51 (dt, J=18.5, 4.6 Hz, 1H), 4.19 (t, J=6.1 Hz, 2H), 4.04 (t, J=5.1 Hz, 1H), 3.66 (d, J=7.2 Hz, 2H), 2.92 (t, J=7.5 Hz, 2H), 2.26 (t, J=20.5 Hz, 2H). ESI MS [M+H]$^+$ for $C_{19}H_{23}ClFN_5O_8P_2$, calcd 566.1, found 566.1.

Example 52

Synthesis of (((((2R,3R,4S,5R)-5-(6-(benzylamino)-2-methyl-9H-purin-9-yl)-4-fluoro-3-hydroxytetrahydrofuran-2-yl)methoxy)(hydroxy)phosphoryl)methyl)phosphonic acid

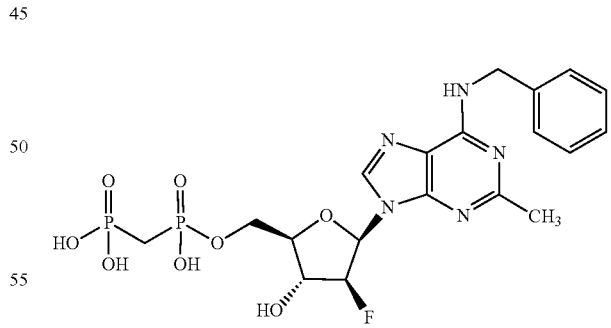

The title compound was synthesized in similar fashion to Example 29 using 6-chloro-2-methylpurine in place of 2,6-dichloropurine: $^1$H NMR (400 MHz, DMSO-$d_6$) δ 8.51 (s, 1H), 8.23 (s, 1H), 7.44-7.19 (m, 5H), 6.44 (dd, J=15.0, 4.6 Hz, 1H), 5.41-5.13 (m, 1H), 4.72 (s, 2H), 4.53 (dd, J=18.4, 4.7 Hz, 1H), 4.19 (t, J=6.1 Hz, 2H), 4.04 (t, J=5.1 Hz, 1H), 2.46 (s, 3H), 2.26 (t, J=20.5 Hz, 2H). ESI MS [M+H]$^+$ for $C_{19}H_{24}FN_5O_8P_2$, calcd 532.1, found 532.2.

Example 53

Synthesis of (((((2R,3R,4S,5R)-5-(6-(cyclopentylamino)-2-methyl-9H-purin-9-yl)-4-fluoro-3-hydroxytetrahydrofuran-2-yl)methoxy)(hydroxy)phosphoryl)methyl)phosphonic acid

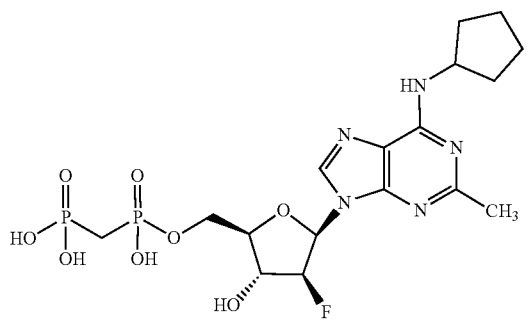 [SMILES: Cc1nc(NC2CCCC2)c2ncn([C@@H]3O[C@H](COP(=O)(O)CP(=O)(O)O)[C@@H](O)[C@@H]3F)c2n1]

The title compound was synthesized in similar fashion to Example 29 using 6-chloro-2-methylpurine in place of 2,6-dichloropurine and cyclopentylamine in place of benzylamine: $^1$H NMR (400 MHz, DMSO-$d_6$) δ 8.56 (s, 1H), 8.30 (s, 1H), 6.45 (dd, J=14.4, 4.6 Hz, 1H), 5.25 (dt, J=52.5, 4.3 Hz, 1H), 4.53 (dt, J=18.3, 4.5 Hz, 1H), 4.20 (t, J=6.1 Hz, 2H), 4.04 (q, J=5.0 Hz, 1H), 2.26 (t, J=20.5 Hz, 2H), 1.98 (s, 2H), 1.82-1.46 (m, 6H). ESI MS [M+H]$^+$ for $C_{17}H_{26}FN_5O_8P_2$, calcd 510.1, found 510.2.

Example 54

Synthesis of (((((2R,3R,4S,5R)-5-(6-(benzylamino)-2-(trifluoromethyl)-9H-purin-9-yl)-4-fluoro-3-hydroxytetrahydrofuran-2-yl)methoxy)(hydroxy)phosphoryl)methyl)phosphonic acid

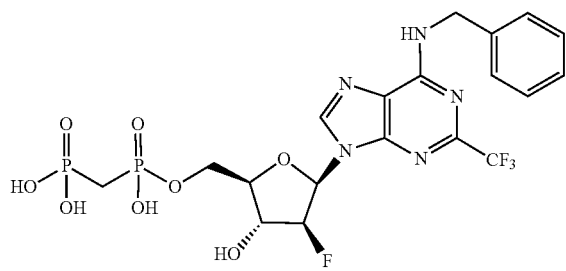 [SMILES: O=P(O)(O)CP(=O)(O)OC[C@H]1O[C@@H](n2cnc3c(NCc4ccccc4)nc(C(F)(F)F)nc32)[C@@H](F)[C@@H]1O]

The title compound was synthesized in similar fashion to Example 29 using 6-chloro-2-trifluoromethylpurine in place of 2,6-dichloropurine: $^1$H NMR (400 MHz, DMSO-$d_6$) δ 9.11 (d, J=6.3 Hz, 1H), 8.49 (d, J=2.1 Hz, 1H), 7.39-7.35 (m, 2H), 7.34-7.27 (m, 2H), 7.25-7.20 (m, 1H), 6.48 (dd, J=14.0, 4.7 Hz, 1H), 5.30 (dt, J=52.4, 4.3 Hz, 1H), 5.20 (bs, 1H), 4.70 (t, J=5.7 Hz, 1H), 4.56 (dt, J=18.6, 4.7 Hz, 1H), 4.21 (t, J=6.2 Hz, 2H), 4.06 (q, J=5.1 Hz, 1H), 2.26 (t, J=20.5 Hz, 2H). ESI MS [M+H]$^+$ for $C_{19}H_{21}F_4N_5O_8P_2$, calcd 586.1, found 586.2.

Example 55

Synthesis of (((((2R,3R,4S,5R)-5-(6-(cyclopentylamino)-2-(trifluoromethyl)-9H-purin-9-yl)-4-fluoro-3-hydroxytetrahydrofuran-2-yl)methoxy)(hydroxy)phosphoryl)methyl)phosphonic acid

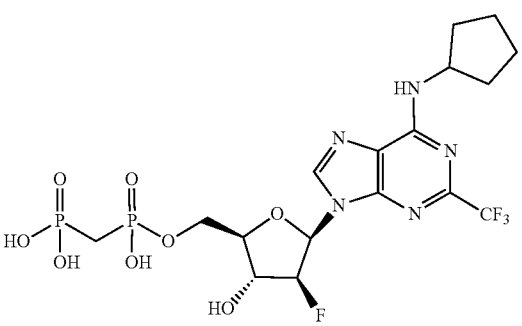

The title compound was synthesized in similar fashion to Example 29 using 6-chloro-2-trifluoromethylpurine in place of 2,6-dichloropurine and cyclopentylamine in place of benzylamine: $^1$H NMR (400 MHz, DMSO-$d_6$) δ 8.59-8.40 (m, 2H), 6.47 (dd, J=13.9, 4.7 Hz, 1H), 5.30 (dt, J=52.4, 4.3 Hz, 1H), 5.11 (bs, 1H), 4.52 (dd, J=28.1, 14.1 Hz, 2H), 4.21 (t, J=6.0 Hz, 2H), 4.06 (q, J=5.2 Hz, 1H), 2.26 (t, J=20.4 Hz, 2H), 2.08-1.90 (m, 2H), 1.80-1.50 (m, 6H). ESI MS [M+H]$^+$ for $C_{17}H_{23}F_4N_5O_8P_2$, calcd 564.2, found 564.1.

Example 56

Synthesis of (((((2R,3R,4S,5R)-5-(6-(benzylamino)-2-phenyl-9H-purin-9-yl)-4-fluoro-3-hydroxytetrahydrofuran-2-yl)methoxy)(hydroxy)phosphoryl)methyl)phosphonic acid

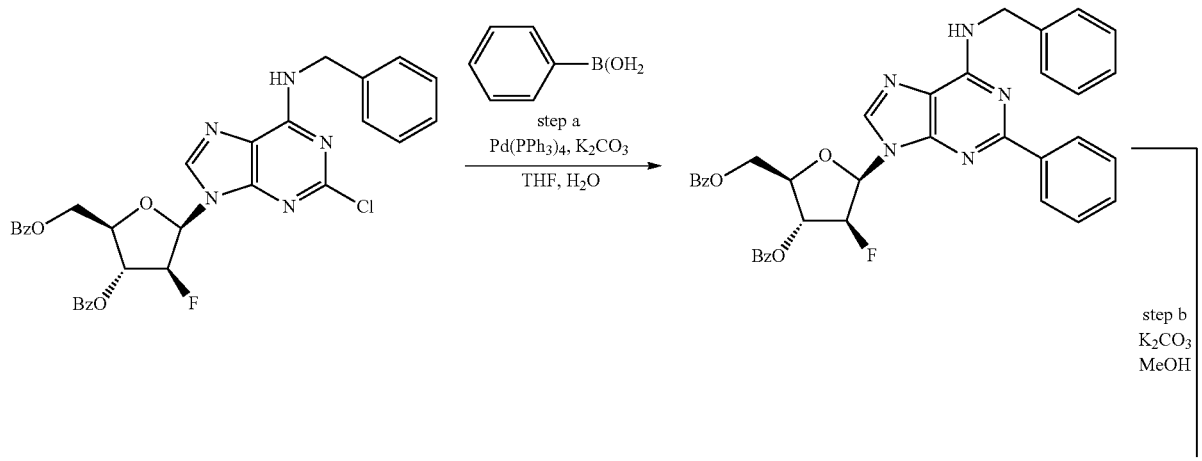

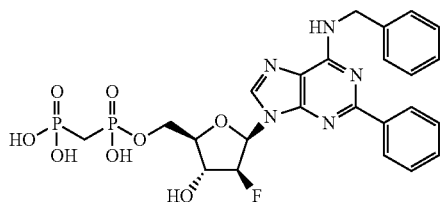
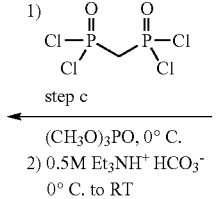
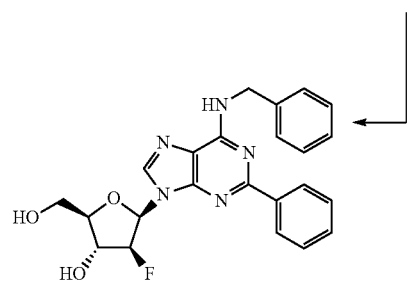

Step a: Product of step b (1) from Example 29 (750 mg, 1.25 mmol), phenylboronic acid (229 mg, 1.88 mmol), and potassium carbonate (518 mg, 3.75 mmol) were suspended in 3:1 THF:H$_2$O (10.3 mL). This mixture was degassed by N$_2$ sparge for 10 minutes. Subsequently Pd(PPh$_3$)$_4$ (144 mg, 0.13 mmol) was added and the resulting mixture was degassed for an additional 5 minutes then sealed and heated to 80° C. overnight. After cooling to room temperature the reaction was diluted with EtOAc and washed with water and brine. The organics were dried over MgSO$_4$, filtered and concentrated under reduced pressure. The crude material was comprised of a mixture mono- and di-debenzoylated products which was used directly in step b.

Step b: The product from step a was dissolved in methanol (12.5 mL) and potassium carbonate (518 mg, 3.75 mmol) was added. The resulting suspension was stirred overnight at room temperature then portioned between EtOAc and water. The organics were washed with brine then dried (MgSO$_4$) and concentrated under reduced pressure. The desired product was obtained following column chromatography (SiO$_2$, 0 to 10% gradient of MeOH and CH$_2$C$_{12}$) as a white solid (41 mg, 8% two-steps). ESI MS [M+H]$^+$ for C$_{23}$H$_{22}$FN$_5$O$_3$, calcd 436.2, found 436.3.

Step c: The title compound was obtained using identical procedure as for Example 1 to give white solid: $^1$H NMR (400 MHz, DMSO-d$_6$) δ 8.58 (s, 1H), 8.44-8.32 (m, 2H), 8.29 (d, J=2.4 Hz, 1H), 7.40-7.50 (m, 5H), 7.31 (dd, J=8.3, 6.9 Hz, 2H), 7.24-7.15 (m, 1H), 6.59 (dd, J=15.4, 4.6 Hz, 1H), 5.30 (dt, J=52.4, 4.1 Hz, 1H), 4.82 (s, 2H), 4.69-4.48 (m, 1H), 4.22 (d, J=6.6 Hz, 2H), 4.08 (q, J=5.1 Hz, 1H), 2.27 (t, J=20.5 Hz, 2H). ESI MS [M−H]$^-$ for C$_{24}$H$_{26}$FN$_5$O$_8$P$_2$, calcd 592.1, found 592.2.

Example 57

Synthesis of (((((2R,3R,4S,5R)-5-(2-benzyl-6-(benzylamino)-9H-purin-9-yl)-4-fluoro-3-hydroxytetrahydrofuran-2-yl)methoxy)(hydroxy)phosphoryl)methyl)phosphonic acid

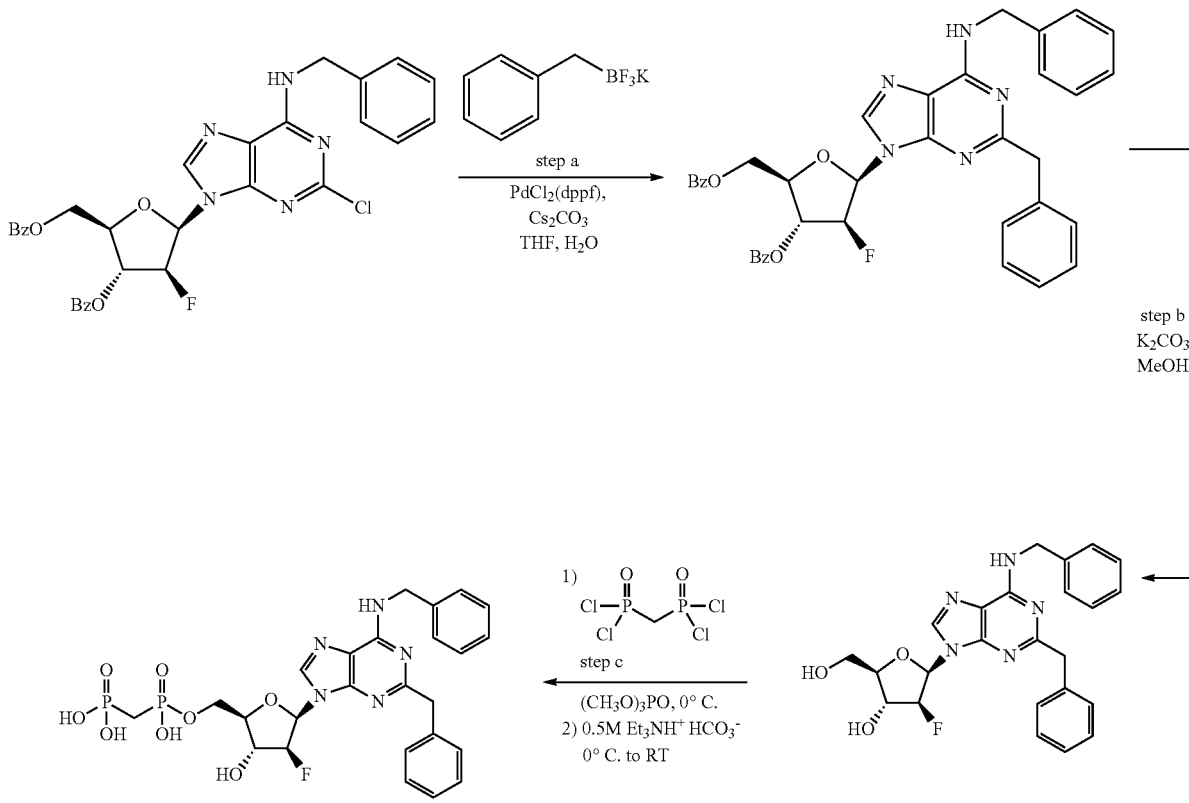

Step a: Product of step b (1) from Example 29 (391 mg, 0.659 mmol), potassium benzyltrifluoroborate (391 mg, 1.98 mmol), and cesium carbonate (1.07 g, 3.30 mmol) were suspended in 20:1 THF:$H_2O$ (6.5 mL). This mixture was degassed by $N_2$ sparge for 10 minutes. Subsequently $Pd(PPh_3)_2Cl_2$ (96 mg, 0.132 mmol) was added and the resulting mixture was degassed for an additional 5 minutes then sealed and heated to 80° C. for 48 hours. After cooling to room temperature the reaction was diluted with EtOAc and washed with water and brine. The organics were dried over $MgSO_4$, filtered and concentrated under reduced pressure. The desired product was obtained following column chromatography ($SiO_2$, EtOAc/Hexane) as a beige solid (174 mg, 40%).

Step b: The product from step a (174 mg, 0.265 mmol) was dissolved in methanol (2.65 mL) and potassium carbonate (110 mg, 3.75 mmol) was added. The resulting suspension was stirred at room temperature for 1.5 hours then partioned between EtOAc and water. The organics were washed with brine then dried ($MgSO_4$) and concentrated under reduced pressure. The desired product was obtained following column chromatography ($SiO_2$, 0 to 10% gradient of MeOH and $CH_2Cl_2$) as a white solid (102 mg, 86%). ESI MS $[M+H]^+$ for $C_{24}H_{24}FN_5O_3$, calcd 450.2, found 450.3.

Step c: The title compound was obtained using identical procedure as for Example 1 to give white solid: $^1$H NMR (400 MHz, DMSO-$d_6$) δ 8.54 (s, 1H), 8.22 (s, 1H), 7.61-6.94 (m, 10H), 6.44 (dd, J=15.1, 4.6 Hz, 1H), 5.23 (dt, J=52.4, 4.1 Hz, 1H), 4.82-4.40 (m, 3H), 4.18 (t, J=6.5 Hz, 2H), 4.03 (dd, J=10.9, 5.9 Hz, 3H), 2.26 (t, J=20.5 Hz, 2H). ESI MS $[M-H]^-$ for $C_{25}H_{28}FN_5O_8P_2$, calcd 606.1, found 606.3.

Example 58

Synthesis of (((((2R,3R,4S,5R)-5-(6-(cyclopentylamino)-2-(piperidin-1-ylmethyl)-9H-purin-9-yl)-4-fluoro-3-hydroxytetrahydrofuran-2-yl)methoxy)(hydroxy)phosphoryl)methyl)phosphonic acid

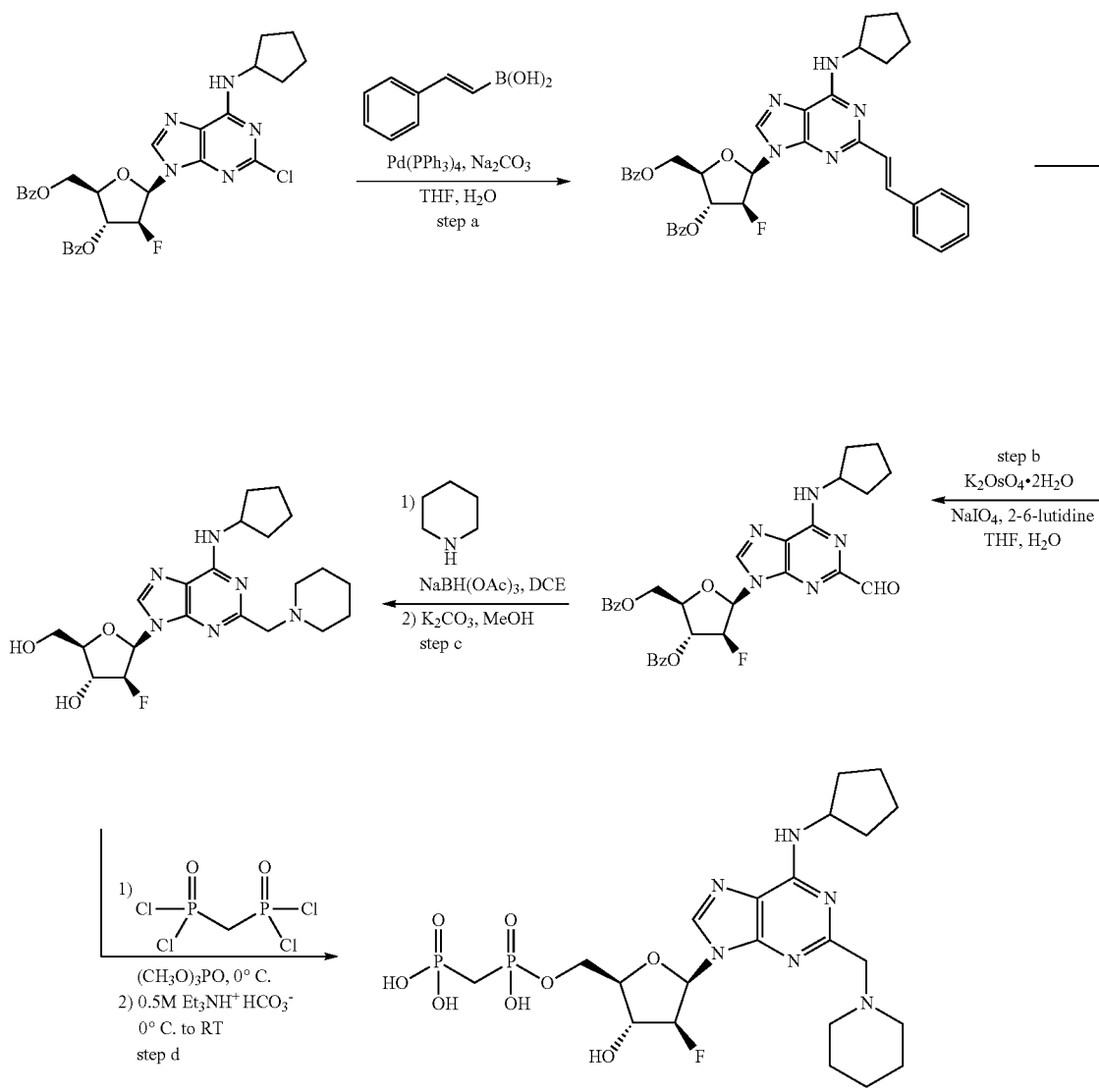

Step a: Product of step a from Example 35 (10.0 g, 17.24 mmol), phenylvinylboronic acid (3.83 g, 25.86 mmol), and sodium carbonate (5.44 mg, 51.72 mmol) were suspended in 3:1 THF:H$_2$O (100 mL). This mixture was degassed by N$_2$ sparge for 10 minutes. Subsequently Pd(PPh$_3$)$_4$ (1.99 g, 1.72 mmol) was added and the resulting mixture was degassed for an additional 5 minutes then heated to reflux overnight. After cooling to room temperature the reaction was diluted with EtOAc and washed with water and brine. The organics were dried over MgSO$_4$, filtered and concentrated under reduced pressure. The desired product was obtained following column chromatography (SiO$_2$, 5% to 50% EtOAc/Hexane) as a colorless solid (8.06 g, 72%).

Step b: To a suspension of the product from step a (8.06 g, 12.04 mmol), sodium periodate (15.5 g, 72.4 mmol), and 2,6-lutidine (2.80 mL, 24.1 mmol) in 2:1 THF:H$_2$O (127.5 mL) was added potassium osmate dihydrate (100 mg, 0.30 mmol). The resulting thick suspension was stirred overnight at room temperature then partitioned between EtOAc and water. The organics were washed sequentially with water and brine, dried over MgSO$_4$ and concentrated under reduced pressure. The title compounds was obtained following column chromatography (SiO$_2$, EtOAc/Hexane) as an off-white oil (6.74 g, 97%). ESI MS [M+H]$^+$ for C$_{30}$H$_{28}$FN$_5$O$_6$, calcd 574.2, found 574.4.

Step c: 1) To a solution of the product of step b (500 mg, 0.87 mmol) in dichloroethane (4.5 mL) was added piperidine (104 uL, 1.05 mmol) followed sodium triacetoxyborohydride (223 mg, 1.05 mmol) in a single portion. The reaction was stirred at room temperature overnight then partitioned between EtOAc and water. The organics were washed with brine, dried over MgSO$_4$ and concentrated under reduced pressure to afford the title compound which was used without further purification. ESI MS [M+H]$^+$ for C$_{35}$H$_{39}$FN$_6$O$_5$, calcd 643.3, found 643.3.

Step c: 2) The above crude product was dissolved in methanol (8.7 mL) and potassium carbonate (362 mg, 2.62 mmol) was added. The resulting suspension was stirred at room temperature overnight then partitioned between EtOAc and water. The organics were washed with brine then dried (MgSO$_4$) and concentrated under reduced pressure. The desired product was obtained following column chromatography (SiO$_2$, 0 to 100% gradient of MeOH and CH$_2$Cl$_2$) as a white solid (151 mg, 40% two-steps). ESI MS [M+H]$^+$ for C$_{21}$H$_{31}$FN$_6$O$_3$, calcd 435.2, found 435.3.

Step d: The title compound was obtained using identical procedure as for Example 1 to give white solid: $^1$H NMR (400 MHz, DMSO-d$_6$) δ 9.40 (s, 1H), 8.58-8.03 (m, 2H), 6.45 (dd, J=14.1, 4.8 Hz, 1H), 5.25 (dt, J=52.5, 4.3 Hz, 1H), 4.59 (d, J=16.3 Hz, 2H), 4.40 (s, 1H), 4.20 (t, J=6.1 Hz, 2H), 4.04 (q, J=5.1 Hz, 1H), 3.61 (s, 1H), 3.08 (s, 2H), 2.24 (t, J=20.4 Hz, 2H), 2.06-1.35 (m, 10H). ESI MS [M−H]$^−$ for C$_{22}$H$_{35}$FN$_6$O$_8$P$_2$, calcd 591.2, found 591.3.

Example 59

Synthesis of (((((2R,3R,4S,5R)-5-(6-(cyclopentylamino)-2-(methoxymethyl)-9H-purin-9-yl)-4-fluoro-3-hydroxytetrahydrofuran-2-yl)methoxy)(hydroxy)phosphoryl)methyl)phosphonic acid

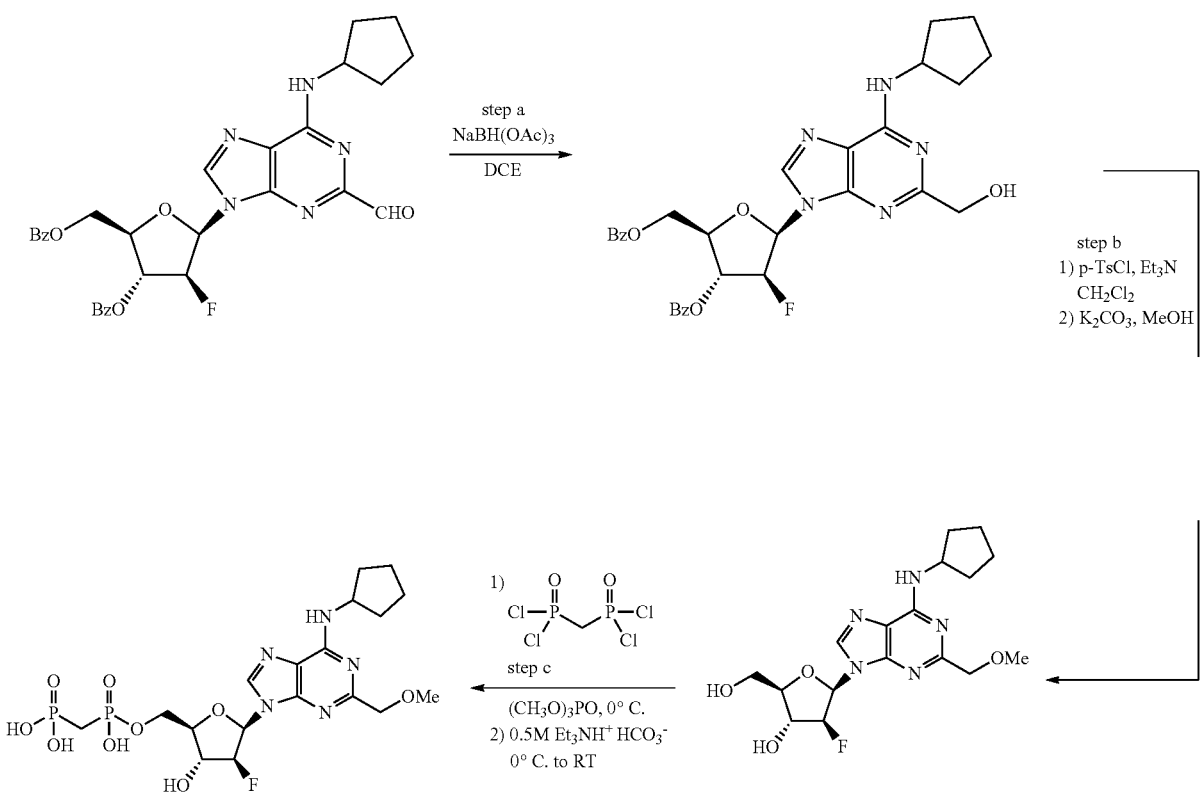

Step a: To a solution of the product of step b from Example 58 (1.0 g, 1.74 mmol) in dichloroethane (20 mL) was added sodium triacetoxyborohydride (443 mg, 2.09 mmol) in a single portion. The reaction was stirred at room temperature overnight then partitioned between EtOAc and water. The organics were washed with brine, dried over MgSO$_4$ and concentrated under reduced pressure to afford the title compound which was used without further purification. ESI MS [M+H]$^+$ for $C_{30}H_{30}FN_5O_6$, calcd 576.2, found 576.3.

Step b: 1) To a solution of the product of step a in dichloromethane (10 mL) at 0° C. were added TsCl (436 mg, 2.29 mmol) and triethylamine (400 uL, 2.87 mmol). The reaction was allowed to warm to room temperature and stir overnight. The reaction was diluted with EtOAc and washed with sat. NaHCO$_3$, 10% citric acid, water and brine. The organics were dried over MgSO$_4$ and concentrated under reduced pressure to afford the crude title compound (1.20 g, 94% two-steps) which was used directly in the next step.

Step b: 2) To a flask charged with crude tosylate (700 mg, 0.959 mmol) and potassium carbonate (662 mg, 4.8 mmol) was added methanol (10 ml). The resulting suspension was stirred overnight then diluted with EtOAc and washed with water and brine. The organics were dried over MgSO$_4$ and concentrated under reduced pressure. The title compound (85 mg, 23%) was obtained following column chromatography (SiO$_2$, 0 to 15% gradient of MeOH and CH$_2$Cl$_2$). ESI MS [M+H]$^+$ for $C_{17}H_{24}FN_5O_4$, calcd 382.2, found 382.3.

Step c: The title compound was obtained using identical procedure as for Example 1 to give white solid: $^1$H NMR (400 MHz, DMSO-d$_6$) δ 8.24 (s, 1H), 6.46 (dd, J=14.9, 4.6 Hz, 2H), 5.24 (dt, J=52.5, 4.2 Hz, 1H), 4.54 (dt, J=18.3, 4.4 Hz, 2H), 4.40 (s, 2H), 4.20 (t, J=6.1 Hz, 3H), 4.04 (t, J=5.0 Hz, 1H), 3.37 (s, 5H), 2.26 (t, J=20.5 Hz, 2H), 1.96 (s, 3H), 1.81-1.41 (m, 10H). ESI MS [M–H]$^-$ for $C_{18}H_{28}FN_5O_9P_2$, calcd 538.1, found 538.2.

Example 60

Synthesis of (((((2R,3R,4S,5R)-5-(6-(cyclopentylamino)-2-(hydroxy(phenyl)methyl)-9H-purin-9-yl)-4-fluoro-3-hydroxytetrahydrofuran-2-yl)methoxy)(hydroxy)phosphoryl)methyl)phosphonic acid

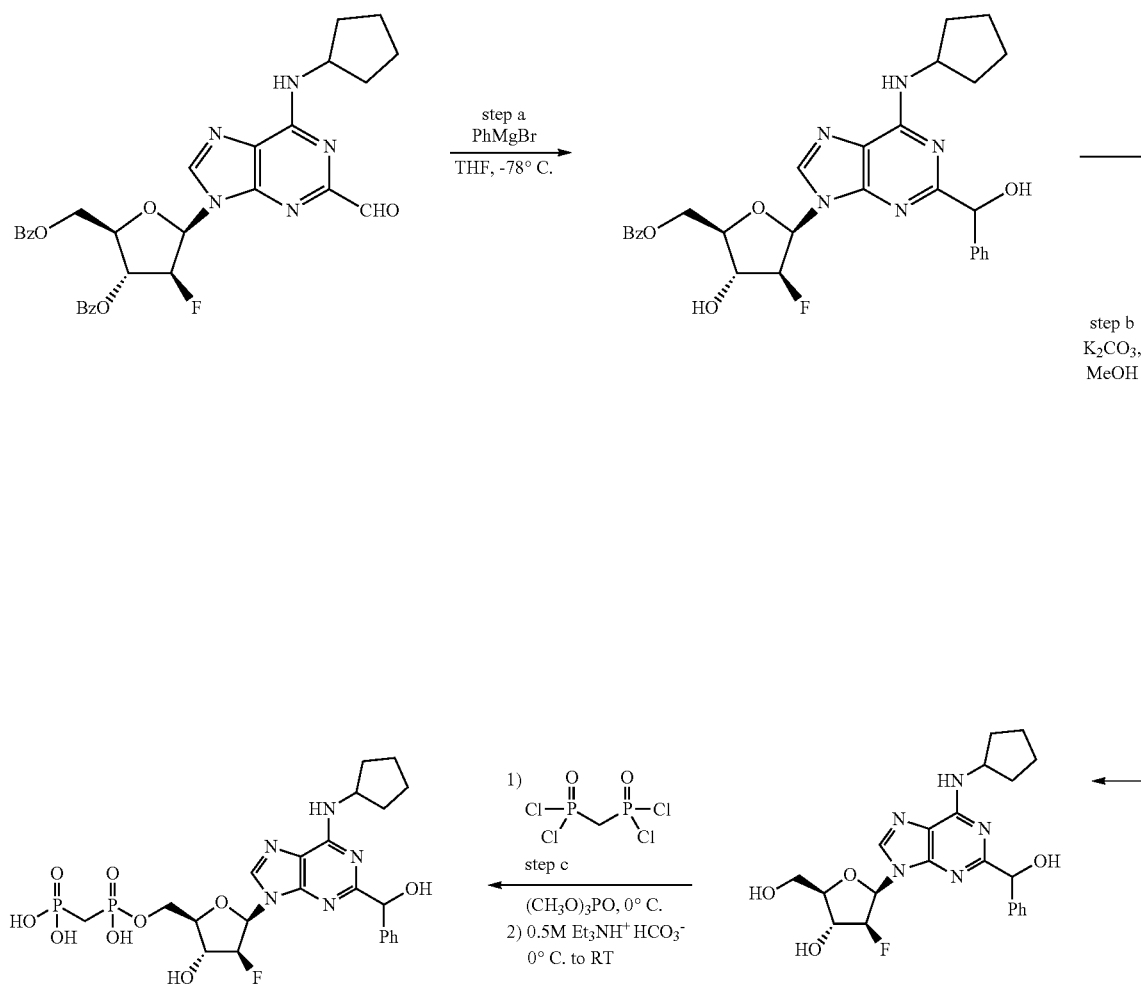

Step a: To a solution of the product of step b from Example 58 (330 mg, 0.58 mmol) in THF (6 mL) at −78° C. was added phenylmagnesium bromide (3.0 M/Et$_2$O, 0.86 mL). The reaction was stirred at this temperature for 1 hour then quenched with sat. NaHCO$_3$. The crude reaction mixture was partitioned between EtOAc and water. The organics were washed with water and brine, dried over MgSO$_4$ and concentrated under reduced pressure. The crude material was comprised of an isomeric mono-debenzoylated products which was used directly in step b. ESI MS [M+H]$^+$ for C$_{29}$H$_{30}$FN$_5$O$_5$, calcd 548.2, found 548.3.

Step b: The product from step a was dissolved in methanol (5.8 mL) and potassium carbonate (240 mg, 1.74 mmol) was added. The resulting suspension was stirred at room temperature overnight then partioned between EtOAc and water. The organics were washed with brine then dried (MgSO$_4$) and concentrated under reduced pressure. The desired product was obtained following column chromatography (SiO$_2$, 0 to 10% gradient of MeOH and CH$_2$C$_{12}$) as a white solid (118 mg, 46% two-steps). ESI MS [M+H]$^+$ for C$_{22}$H$_{26}$FN$_5$O$_4$, calcd 444.2, found 444.3.

Step c: The title compound was obtained using identical procedure as for Example 1 to give white solid (1:1 mixture of diastereomers): $^1$H NMR (400 MHz, DMSO-d$_6$) δ 8.78-7.85 (m, 4H), 7.49 (s, 4H), 7.41-7.08 (m, 8H), 6.47 (dd, J=14.8, 4.6 Hz, 2H), 5.98-5.39 (m, 2H), 5.24 (dt, J=52.4, 4.2 Hz, 1H), 5.07 (s, 1H), 4.54 (d, J=14.1 Hz, 0H), 4.39-3.86 (m, 6H), 2.26 (t, J=20.5 Hz, 3H), 1.99 (d, J=34.0 Hz, 5H), 1.65 (d, J=52.4 Hz, 13H). ESI MS [M−H]$^-$ for C$_{23}$H$_{30}$FN$_5$O$_9$P$_2$, calcd 600.2, found 600.3.

Step a: Product of step b (1) from Example 29 (750 mg, 1.24 mmol) was suspended in in DMF (8.3 mL) and Et$_3$N (260 uL) was added followed by phenyl acetylene (205 uL). This mixture was degassed by N$_2$ sparge for 10 minutes. Subsequently CuI (24 mg) and Pd(PPh$_3$)$_2$Cl$_2$ (44 mg) were added and the resulting mixture heated to 80° C. overnight. After cooling to room temperature, the reaction was diluted with EtOAc and washed with 10% citric acid (aqueous), water and brine. The organics were dried over MgSO$_4$, filtered and concentrated under reduced pressure. The desired product was obtained following column chromatography (SiO$_2$, EtOAc/Hexane) as a tan oil (762 mg, 92%).

Step b: The product from step a (762 mg, 1.14 mmol) was dissolved in methanol (11.4 mL) and potassium carbonate (473 mg, 3.42 mmol) was added. The resulting suspension was stirred overnight at room temperature then portioned between EtOAc and water. The organics were washed with brine the brine then dried (Na2SO4) and concentrated under reduced pressure. The desired product was obtained following column chromatography (SiO$_2$, 0 to 10% gradient of MeOH and CH$_2$Cl$_2$) as a colorless oil. ESI MS [M+H]$^+$ for C$_{25}$H$_{22}$FN$_5$O$_3$, calcd 460.2, found 460.2.

Step c: The title compound was obtained using identical procedure as for Example 1 to give white solid: $^1$H NMR (400 MHz, DMSO-d$_6$) δ 8.65 (s, 1H), 8.37 (d, J=2.3 Hz, 1H), 7.67-7.57 (m, 1H), 7.47 (td, J=5.2, 2.1 Hz, 2H), 7.39-7.29 (m, 4H), 7.28-7.16 (m, 1H), 6.50 (dd, J=15.2, 4.4 Hz, 1H), 5.28 (dt, J=52.4, 4.1 Hz, 1H), 4.75 (s, 2H), 4.52 (d, J=18.1 Hz, 1H), 4.20 (d, J=6.4 Hz, 2H), 4.06 (q, J=5.0 Hz, 1H), 2.28 (t, J=20.5 Hz, 2H). ESI MS [M−H]$^-$ for C$_{26}$H$_{26}$FN$_5$O$_8$P$_2$, calcd 616.1, found 616.3.

Example 61

Synthesis of (((((2R,3R,4S,5R)-5-(6-(benzylamino)-2-(phenylethynyl)-9H-purin-9-yl)-4-fluoro-3-hydroxytetrahydrofuran-2-yl)methoxy)(hydroxy)phosphoryl)methyl)phosphonic acid Example 62

Synthesis of (((((2R,3R,4S,5R)-5-(6-(benzylamino)-2-phenethyl-9H-purin-9-yl)-4-fluoro-3-hydroxytetrahydrofuran-2-yl)methoxy)(hydroxy)phosphoryl)methyl)phosphonic acid

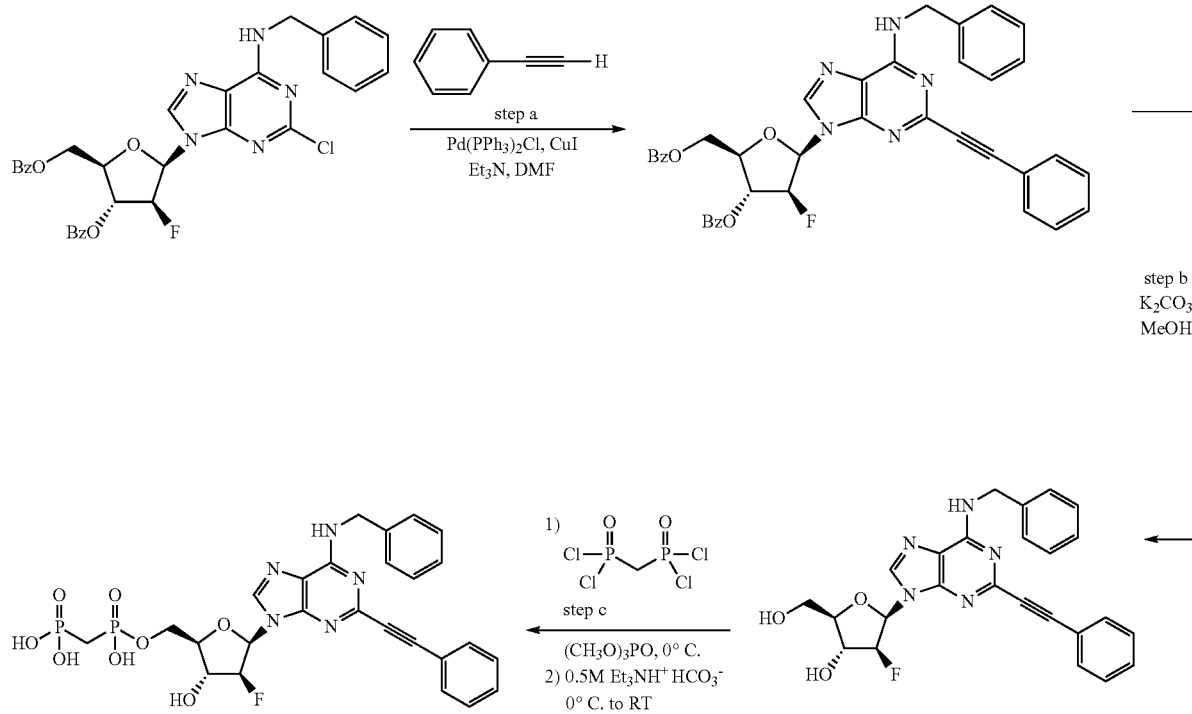

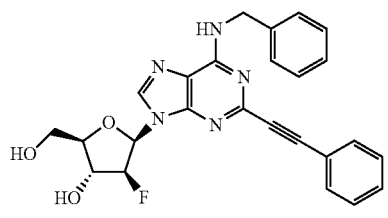
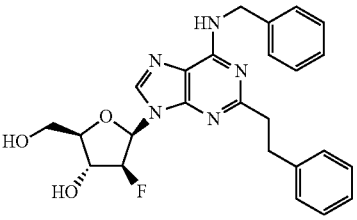
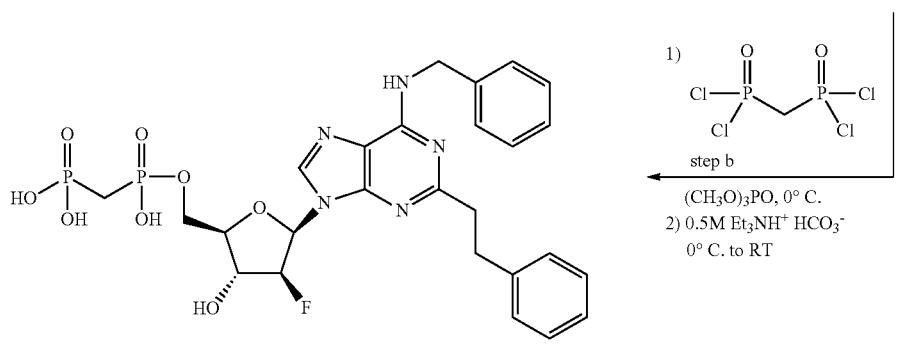

Step a: To a solution of the product of step b from Example 61 (203 mg, 0.44 mmol) in ethanol (4.4 mL) under a nitrogen atmosphere was added palladium on carbon (10 wt % wet, 20 mg). The nitrogen atmosphere was displaced with hydrogen and the stirred at room temperature. After stirring overnight the reaction was diluted with EtOAc and filtered through celite. The filtrate was concentrated under reduced pressure to afford the title compound (161 mg, 79%) which was used without further purification. ESI MS [M+H]$^+$ for $C_{25}H_{26}FN_5O_3$, calcd 464.2, found 464.4.

Step b: The title compound was obtained using identical procedure as for Example 1 to give white solid: $^1$H NMR (400 MHz, DMSO-d$_6$) δ 8.60-8.14 (m, 2H), 7.58-6.91 (m, 11H), 6.44 (d, J=15.0 Hz, 1H), 5.22 (d, J=52.4 Hz, 1H), 4.71 (s, 2H), 4.54 (dt, J=18.4, 4.4 Hz, 1H), 4.19 (t, J=6.2 Hz, 2H), 4.11-3.96 (m, 1H), 3.23-2.83 (m, 5H), 2.26 (t, J=20.5 Hz, 2H). ESI MS [M−H]$^-$ for $C_{26}H_{30}FN_5O_8P_2$, calcd 620.2, found 620.2.

Example 63

Synthesis of (((((2R,3R,4S,5R)-5-(6-(benzylamino)-2-ethynyl-9H-purin-9-yl)-4-fluoro-3-hydroxytetrahydrofuran-2-yl)methoxy)(hydroxy)phosphoryl)methyl)phosphonic acid

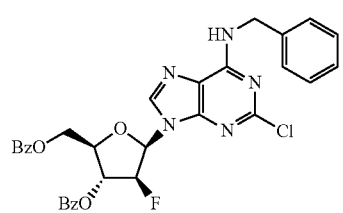
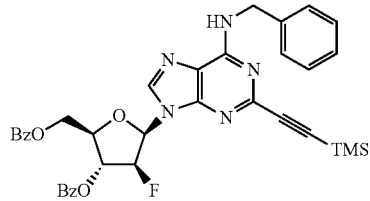

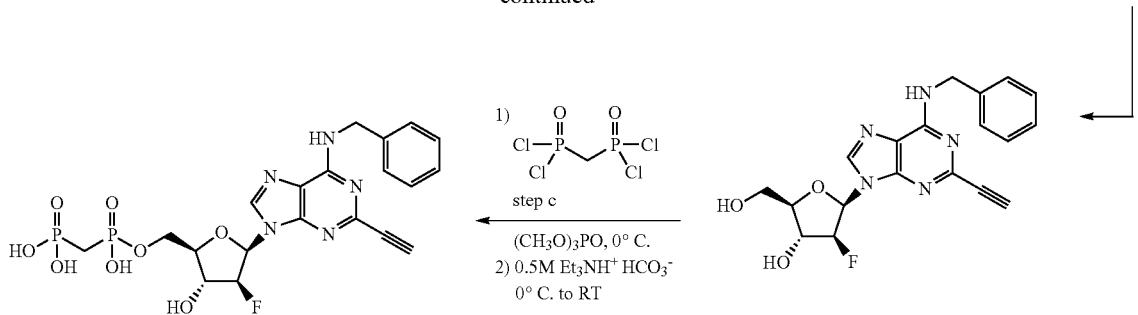

Step a: Product of step b (1) from Example 29 (2.0 g, 3.32 mmol) was suspended in in DMF (7.4 mL) and diisopropylamine (2.3 mL) was added followed by trimethylsilylacetylene (703 uL, 4.98). This mixture was degassed by $N_2$ sparge for 10 minutes. Subsequently CuI (125 mg, 0.66 mmol) and Pd(PPh$_3$)$_2$Cl$_2$ (233 mg, 0.0.33 mmol) was added and the resulting mixture was degassed for an additional 5 minutes then sealed and heated to 80° C. for 36 hours. After cooling to room temperature the reaction was diluted with EtOAc and washed with sat. NH$_4$Cl (aqueous), water and brine. The organics were dried over MgSO$_4$, filtered and concentrated under reduced pressure. The desired product was obtained following column chromatography (SiO$_2$, 5% to 70% EtOAc/Hexane) as a beige solid (950 mg, 43%).

Step b: The product from step a (950 mg, 1.43 mmol) was dissolved in methanol (14 mL) and potassium carbonate (592 mg, 4.29 mmol) was added. The resulting suspension was stirred overnight at room temperature then partioned between EtOAc and water. The organics were washed with brine then dried (Na$_2$SO$_4$) and concentrated under reduced pressure. The desired product was obtained following column chromatography (SiO$_2$, 0 to 10% gradient of MeOH and CH$_2$Cl$_2$) to afford the title compounds as a white solid (230 mg, 42%). ESI MS [M+H]$^+$ for C$_{19}$H$_{18}$FN$_5$O$_3$, calcd 384.1, found 384.2.

Step c: The title compound was obtained using identical procedure as for Example 1 to give white solid: $^1$H NMR (400 MHz, DMSO-d$_6$) δ 8.65 (s, 1H), 8.36 (d, J=2.2 Hz, 1H), 7.39-7.26 (m, 5H), 7.28-7.17 (m, 1H), 6.44 (dd, J=14.8, 4.5 Hz, 1H), 5.25 (dt, J=52.5, 4.1 Hz, 1H), 4.69 (s, 2H), 4.51 (d, J=18.1 Hz, 1H), 4.19 (d, J=7.1 Hz, 2H), 2.27 (t, J=20.5 Hz, 2H). ESI MS [M−H]$^-$ for C$_{20}$H$_{22}$FN$_5$O$_8$P$_2$, calcd 540.1, found 540.2.

Example 64

Synthesis of [({[(2R,3S,4S,5R)-5-[6-(benzyloxy)-2-chloro-9H-purin-9-yl]-4-fluoro-3-hydroxyoxolan-2-yl]methoxy}(hydroxy)phosphoryl)methyl]phosphonic acid

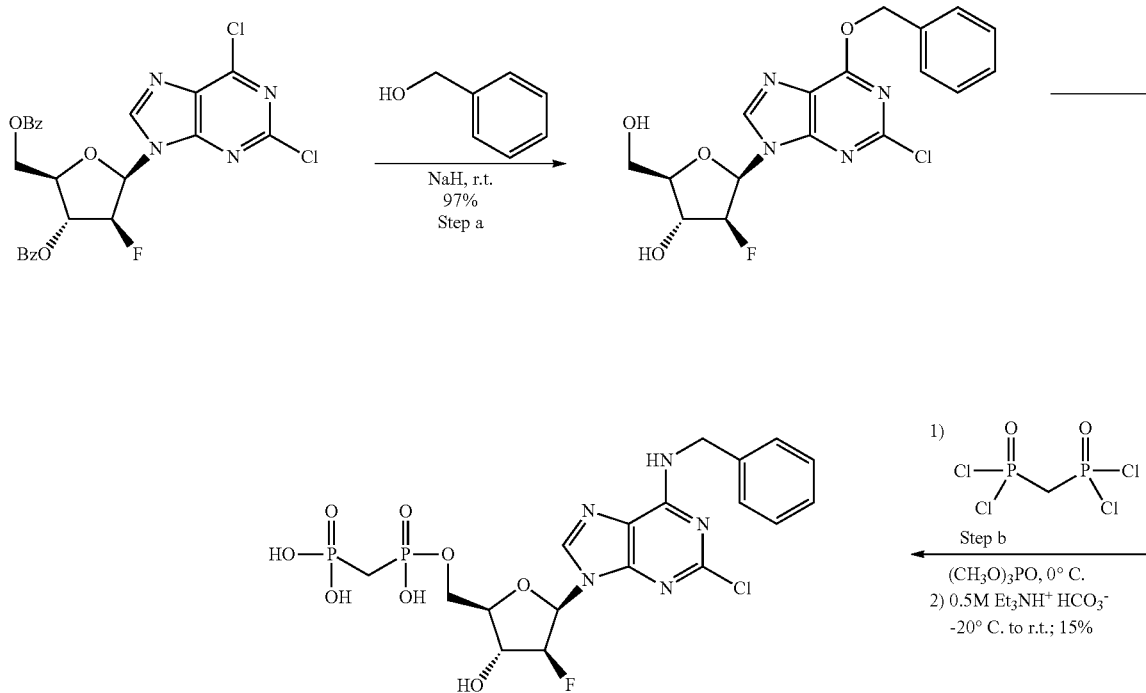

Step a: Under a nitrogen atmosphere, sodium hydride (90 mg, 2.26 mmol, 1.2 equiv., 60% in oil) and benzyl alcohol (10 mL) were stirred at r.t. for 15 min. Product of step b (1) from Example 29 (1.00 g, 1.88 mmol) was added and the mixture stirred at r.t. for 2 h. The reaction mixture was purified directly by column chromatography (0-10% MeOH in dichloromethane) to afford the desired product as a white solid (721 mg, 97%). ESI MS [M+H]$^+$ for $C_{17}H_{17}ClFN_4O_4$, calcd 395.1, found 395.1.

Step b: The product from Step a (197 mg, 0.5 mmol) was dissolved in trimethyl phosphate (2.5 mL) and cooled to 0° C. A solution of methylenebis(phosphonic dichloride) (624 mg, 2.5 mmol, 5 equiv.) in trimethyl phosphate (1.5 mL) was added dropwise. The reaction mixture was stirred at 0° C. for 3 h and then carefully quenched at −20° C. with 0.5 M triethylammonium bicarbonate solution (3.6 mL). The mixture was stirred at −20° C. for 15 min, then stirred at 0° C. for 15 min, then stirred at r.t. for 15 min. The mixture was washed with ethyl acetate (10 mL) three times. The aqueous layer was purified directly by reverse phase HPLC (C18 column, 0 to 50% gradient of acetonitrile and water with 0.1% TFA) to afford the desired product as a white solid (40.2 mg, 15%): $^1$H NMR (400 MHz, DMSO-d$_6$) δ 8.55 (d, J=2.1 Hz, 1H), 7.57-7.51 (m, 2H), 7.46-7.35 (m, 3H), 6.49 (dd, J=13.6, 4.7 Hz, 1H), 5.61 (s, 2H), 5.30 (dt, J=52.4, 4.4 Hz, 1H), 4.53 (dt, J=18.6, 4.7 Hz, 1H), 4.21 (t, J=6.0 Hz, 2H), 4.06 (q, J=5.0 Hz, 1H), 2.27 (t, J=20.6 Hz, 2H). ESI MS [M−H]$^-$ for $C_{18}H_{19}ClFN_4O_9P_2$, calcd 551.0, found 551.2.

Example 65

Synthesis of (((((2R,3R,4S,5R)-5-(6-(benzylamino)-2-chloro-9H-purin-9-yl)-4-fluoro-3-hydroxytetrahydrofuran-2-yl)methoxy)(hydroxy)phosphoryl)methyl)phosphonic acid oxy-2-fluoro-α-D-arabinofuranosyl bromide 3, 5-dibenzoate (787 mg, 1.86 mmol, 1 equiv.) was dissolved in 10 mL of acetonitrile and added to the mixture dropwise via an addition funnel. The mixture was allowed to stir overnight at room temperature. The mixture was filtered on a pad of silica gel and concentrated. The residue was adsorbed on silica, purified using column chromatography (hexanes/ethyl acetate) to provide the product as a white solid in 49% yield (480 mg).

Step b: A mixture of the product from Step a (480 mg, 0.9 mmol), benzyl amine (97 mg, 0.9 mmol), and Et$_3$N (91 mg, 0.9 mmol,) in anhydrous EtOH (4 mL) was stirred at 65° C. for 6 hours. Excess solvent removed in vacuo. The residue was dried under high vacuum for 30 min. Methanol (4 mL) and K$_2$CO$_3$ (249 mg, 1.8 mmol) were added and stirred for 1 h. at room temperature. LCMS indicated completion of the reaction. It was filtered and the filtrate was concentrated. The residue was purified by flash column to get the product in quantitative yield Step c: The product from Step b (360 mg, 0.91 mmol) was dissolved in trimethyl phosphate (4 mL) and cooled to 0° C. (ice bath), then a cold solution of methylenebis(phosphonic dichloride) (801 g, 3.2 mmol, 3.5 equiv.) in trimethyl phosphate (2 mL) was added dropwise. The reaction mixture was stirred at 0° C. for 1 h, and was then carefully quenched with an ice-cold 0.5 M triethylammonium bicarbonate solution (11 mL) and stirred at 0° C. for 15 min, and then 1 h at room temperature. The reaction mixture was purified by reverse phase HPLC (C18 column, 0 to 40% gradient of acetonitrile and water with 0.1% TFA) to give the product as a white solid: $^1$H NMR (400 MHz, DMSO-d$_6$) δ 8.60 (t, J=6.0 Hz, 1H), 7.59-7.13 (m, 6H), 6.72 (s, 1H), 6.49 (dd,

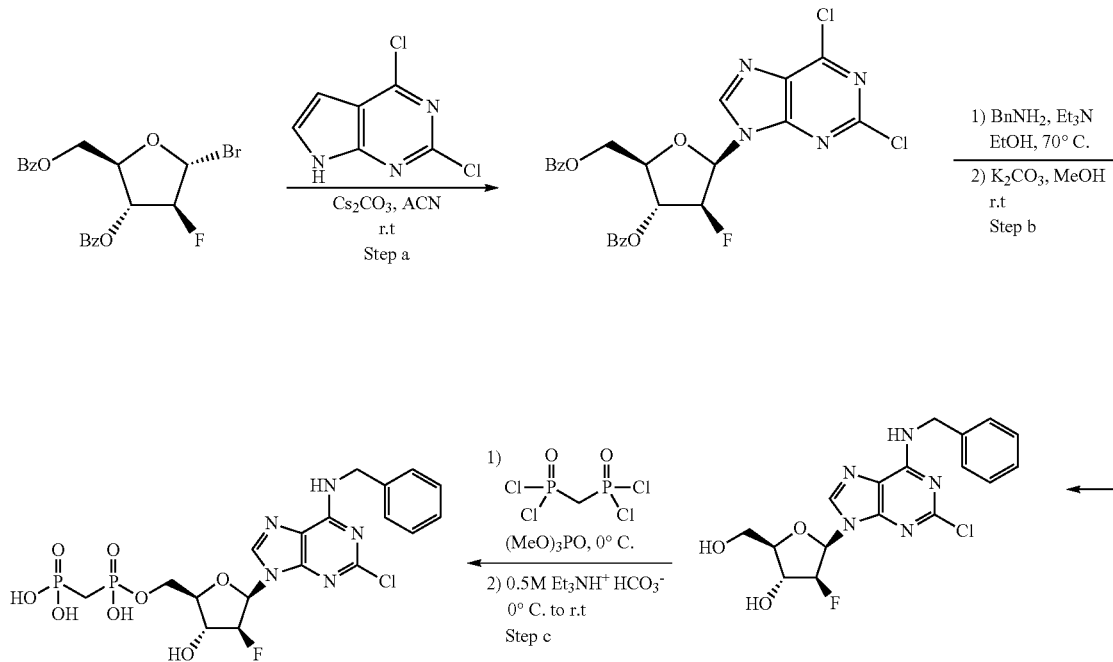

Step a: 2,4-Dichloro-7H-pyrrolo[2,3-d]pyrimidine (350 mg, 1.86 mmol) was dissolved in 15 mL of acetonitrile and treated with Cs$_2$CO$_3$ (788 mg, 2.42 mmol, 1.3 equiv.). The mixture was stirred at room temperature for 60 min. 2-De- J=15.7, 4.5 Hz, 1H), 5.45-5.04 (m, 1H), 4.80-4.57 (m, 2H), 4.42 (dt, J=18.6, 4.4 Hz, 1H), 4.19-4.15 (m, 2H), 3.98 (q, J=5.0 Hz, 1H), 2.26 (t, J=20.5 Hz, 2H). ESI MS [M−H]$^-$ for $C_{18}H_{22}ClFN_4O_8P_2$, calcd 549.1, found 549.2.

Example 66

Synthesis of (((((2R,3R,4S,5R)-5-(2-chloro-6-(cyclopentylamino)-9H-purin-9-yl)-4-fluoro-3-hydroxytetrahydrofuran-2-yl)methoxy)(hydroxy)phosphoryl)methyl)phosphonic acid

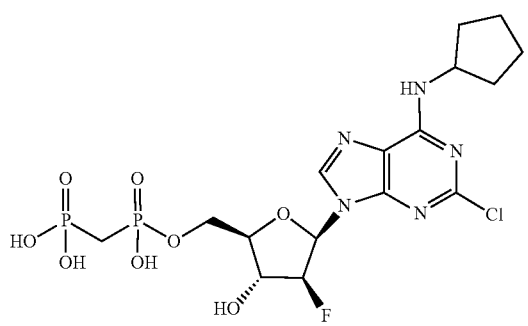 [SMILES: O=P(O)(O)CP(=O)(O)OC[C@H]1O[C@@H](n2cnc3c(NC4CCCC4)nc(Cl)nc32)[C@@H](F)[C@@H]1O]

The title compound was synthesized in similar fashion to Example 65 using cyclopentylamine in place of benzylamine: $^1$H NMR (400 MHz, DMSO-$d_6$) δ 7.90 (d, J=7.2 Hz, 1H), 7.24 (s, 1H), 6.72 (d, J=3.6 Hz, 1H), 6.47 (dd, J=15.9, 4.4 Hz, 1H), 5.15 (dt, J=52.6, 4.1 Hz, 1H), 4.52-4.35 (m, 2H), 4.15 (q, J=6.3, 5.3 Hz, 2H), 3.97 (q, J=5.1 Hz, 1H), 2.23 (d, J=20.5 Hz, 1H), 1.98 (d, J=10.6 Hz, 2H), 1.72 (s, 2H), 1.67-1.45 (m, 5H). ESI MS [M−H]$^−$ for $C_{17}H_{24}ClFN_4O_8P_2$, calcd 527.1, found 527.2.

Example 67

Synthesis of ((((1-(6-(benzylamino)-9H-purin-9-yl)propan-2-yl)oxy)(hydroxy)phosphoryl)-methyl)phosphonic acid

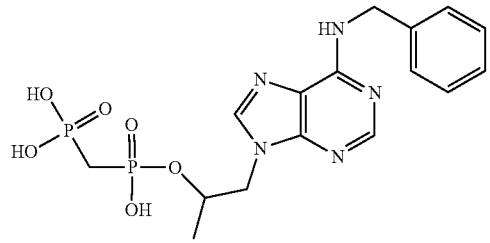 [SMILES: CC(Cn1cnc2c(NCc3ccccc3)ncnc21)OP(=O)(O)CP(=O)(O)O]

The title compound was synthesized in similar fashion to step b of Example 1 using corresponding alcohol: $^1$H NMR (400 MHz, DMSO-$d_6$) δ 8.79 (s, 1H), 8.31 (d, J=15.8 Hz, 2H), 7.46-7.13 (m, 5H), 4.92-4.62 (m, 2H), 4.49-4.25 (m, 2H), 2.17 (td, J=20.4, 4.8 Hz, 2H), 1.14 (d, J=6.3 Hz, 3H). ESI MS [M+H]$^+$ for $C_{16}H_{22}N_5O_6P_2$, calcd 442.1, found 442.1.

Example 68

Synthesis of (((2-(6-(benzylamino)-9H-purin-9-yl)propoxy)(hydroxy)phosphoryl)-methyl)phosphonic acid

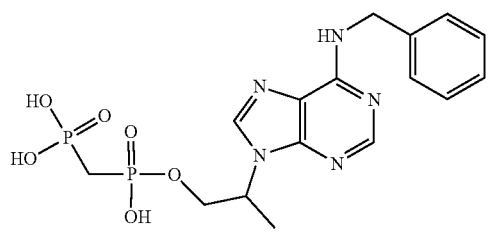 [SMILES: CC(COP(=O)(O)CP(=O)(O)O)n1cnc2c(NCc3ccccc3)ncnc21]

The title compound was synthesized in similar fashion to step b of Example 1 using corresponding alcohol: $^1$H NMR (400 MHz, DMSO-$d_6$) δ 8.73 (s, 1H), 8.35 (s, 1H), 8.27 (s, 1H), 7.41-7.18 (m, 5H), 4.96-4.82 (m, 1H), 4.72 (s, 2H), 4.39-4.19 (m, 2H), 2.18 (t, J=20.5, 1.6 Hz, 2H), 1.55 (d, J=7.0 Hz, 3H). ESI MS [M+H]$^+$ for $C_{16}H_{22}N_5O_6P_2$, calcd 442.0, found 442.1.

Example 69

Synthesis of (((((((2R,3R,4S,5R)-5-(2-chloro-6-(cyclopentylamino)-9H-purin-9-yl)-4-fluoro-3-hydroxytetrahydrofuran-2-yl)methoxy)(hydroxy)phosphoryl)methyl)-phosphoryl)bis(oxy)) bis(methylene) diisopropyl bis(carbonate)

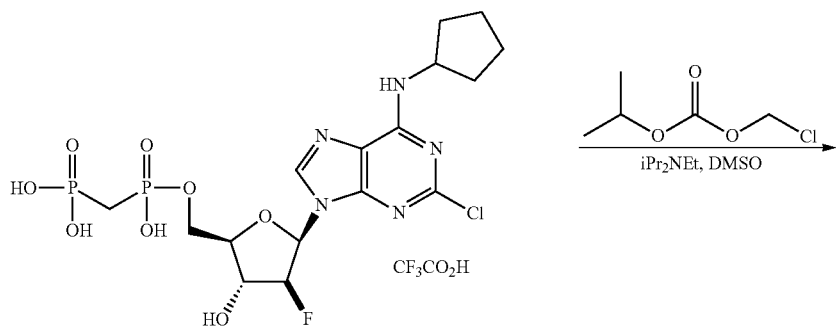

-continued

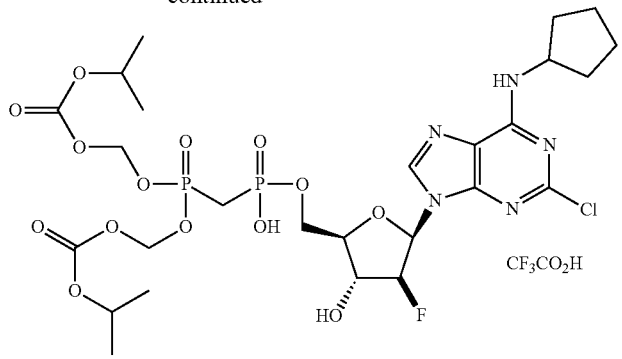

The methylene bisphosphonic acid (20 mg, 0.03 mmol, trifluoroacetate salt of Example 66) was dissolved in 0.5 mL of DMSO. Hunig's base (0.18 mL, 1 mmol, 30 eq) was added followed by chloromethyl isopropyl carbonate (0.13 mL, 1 mmol, 30 eq). The reaction mixture was allowed to stir at room temperature for 5 days. The reaction mixture was purified by reverse phase HPLC (C18 column, 0 to 40% gradient of acetonitrile and water with 0.1% TFA) to give the product as a white solid in 14% yield (3.6 mg). $^1$H NMR (400 MHz, DMSO-$d_6$) δ 8.42 (d, J=7.7 Hz, 1H), 8.25 (s, 1H), 6.37 (dd, J=15.2, 4.4 Hz, 1H), 5.67-5.43 (m, 4H), 5.24 (ddt, J=52.1, 7.7, 4.1 Hz, 1H), 4.79 (pd, J=6.2, 3.8 Hz, 2H), 4.57-4.38 (m, 1H), 4.37-4.19 (m, 2H), 4.06 (q, J=5.1 Hz, 1H), 2.68 (t, J=21.2 Hz, 2H), 1.92 (s, 2H), 1.80-1.47 (m, 6H), 1.28-1.15 (m, 12H).) ESI MS [M−H]$^-$ for $C_{26}H_{39}ClFN_5O_4P_2$, calcd 760.2, found 760.3.

Example 70

Synthesis of [({[(2S,3S,4R,5R)-5-{2-chloro-6-[cyclopentyl(methyl)amino]-9H-purin-9-yl}-3,4-dihydroxyoxolan-2-yl]methoxy}(hydroxy)phosphoryl)methyl]phosphonic acid

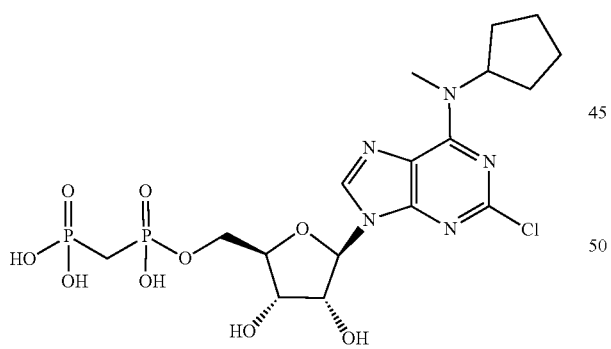

The title compound was synthesized in similar fashion to Example 1. $^1$H NMR (400 MHz, DMSO-$d_6$) δ 8.42 (s, 1H), 5.88 (d, J=5.9 Hz, 1H), 4.53-4.46 (m, 1H), 4.19 (dd, J=5.0, 3.1 Hz, 1H), 4.15-4.06 (m, 3H), 3.17 (brs, 3H), 2.26 (t, J=20.5 Hz, 2H), 1.94-1.53 (m, 9H). ESI MS [M+H]$^+$ for $C_{17}H_{27}ClN_5O_9P_2$, calcd 542.1, found 542.2.

Example 71

Synthesis of [({1-[(2S,3S,4R,5R)-5-[6-(benzylamino)-2-chloro-9H-purin-9-yl]-3,4-dihydroxyoxolan-2-yl]ethoxy}(hydroxy)phosphoryl)methyl]phosphonic acid

101          102

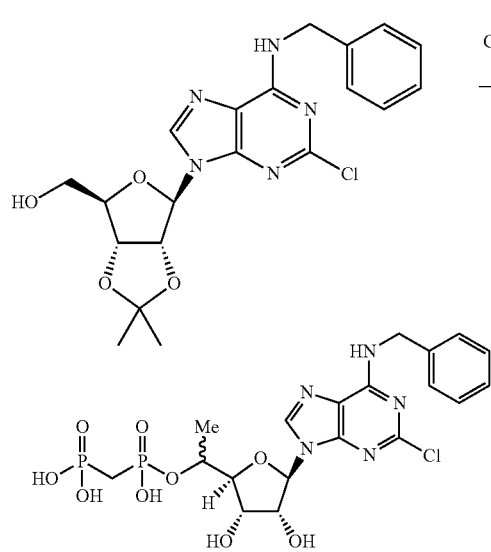
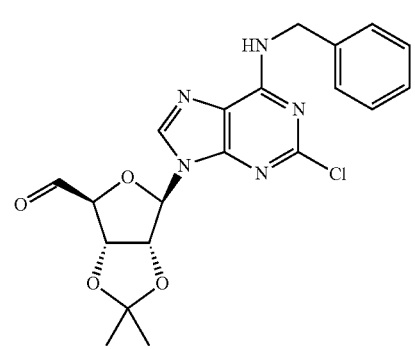

Step a: The alcohol (4.8 g, 11.1 mmol) was dissolved in anhydrous $CH_2Cl_2$ (100 mL) and Dess-Martin periodinane (5.6 g, 13.3 mmol, 1.2 equiv.) was added. Reaction mixture was stirred at room temperature for 3 h, then quenched with 10% $Na_2S_2O_3$ (20 mL) and saturated $NaHCO_3$ (50 mL). Organic layer was separated, dried over $MgSO_4$, filtered and evaporated. Crude aldehyde was purified by column chromatography ($SiO_2$, $CH_2Cl_2 \rightarrow CH_2Cl_2$:MeOH, 9:1) to give yellow solid (4.8 g, quant.). ESI MS $[M+H]^+$ for $C_{20}H_{21}ClN_5O_4$, calcd 430.1, found 430.2

Step b: Product from Step a (860 mg, 2.0 mmol) was dissolved in anhydrous THF (20 mL) and cooled to −78° C. 3M MeMgBr solution in $Et_2O$ (2 mL, 6 mmol, 3 equiv.) was added dropwise and reaction mixture was stirred at −78° C. for 10 min then slowly warmed up to room temperature and stirred at rt for 2 h. Quenched with saturated $NH_4Cl$ (10 mL), organic layer was separated, dried over $MgSO_4$, filtered and evaporated. Crude product was used without further purification. ESI MS $[M+H]^+$ for $C_{21}H_{25}ClN_5O_4$, calcd 446.2, found 446.3.

Step c: The phosphonylation step was performed in similar fashion to Example 1. $^1H$ NMR (400 MHz, DMSO-$d_6$) δ 9.00-8.88 (m, 1H), 8.51 (s, 1H), 7.37-7.17 (m, 5H), 5.81 (d, J=7.0 Hz, 1H), 4.70-4.51 (m, 4H), 4.32-4.25 (m, 1H), 3.83 (dd, J=5.3, 2.6 Hz, 1H), 2.22 (t, J=20.5 Hz, 2H), 1.26 (d, J=6.4 Hz, 3H). ESI MS $[M+H]^+$ for $C_{19}H_{25}ClN_5O_9P_2$, calcd 564.1, found 564.1.

Example 72

Synthesis of [({1-[(2S,3S,4R,5R)-5-[6-(benzylamino)-2-chloro-9H-purin-9-yl]-3,4-dihydroxyoxolan-2-yl]propoxy}(hydroxy)phosphoryl)methyl] phosphonic acid

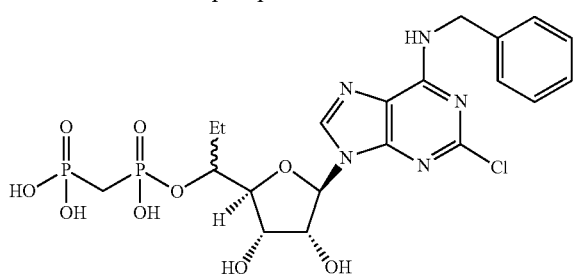

The title compound was synthesized in similar fashion to Example 71. H NMR (400 MHz, DMSO-$d_6$) δ 8.97-8.91 (m, 1H), 8.53 (s, 1H), 7.38-7.20 (m, 5H), 5.79 (d, J=7.4 Hz, 1H), 4.65 (d, J=6.3 Hz, 2H), 4.62-4.56 (m, 1H), 4.54-4.46 (m, 1H), 4.34 (d, J=5.5 Hz, 1H), 3.89 (dd, J=6.1, 2.2 Hz, 1H), 2.22 (t, J=20.5 Hz, 2H), 1.69 (s, 1H), 1.58 (q, J=7.1 Hz, 1H), 0.90 (t, J=7.4 Hz, 3H). ESI MS $[M+H]^+$ for $C_{20}H_{27}ClN_5O_9P_2$, calcd 578.1, found 578.2.

Example 73

Synthesis of [({[(2R,3R,4R,5R)-5-[2-chloro-6-(cyclopentylamino)-9H-purin-9-yl]-3,4-dihydroxy-4-methyloxolan-2-yl]methoxy}(hydroxy)phosphoryl) methyl]phosphonic acid

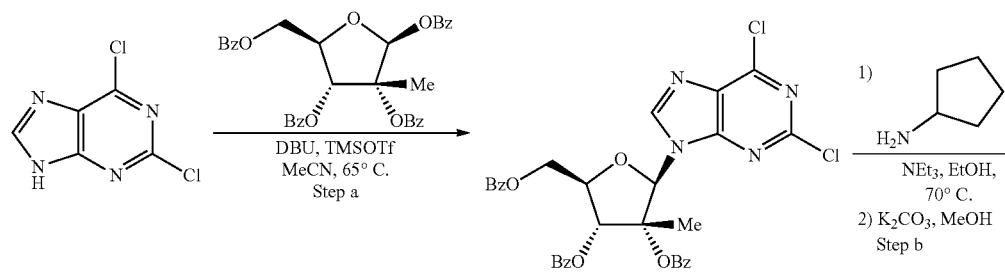

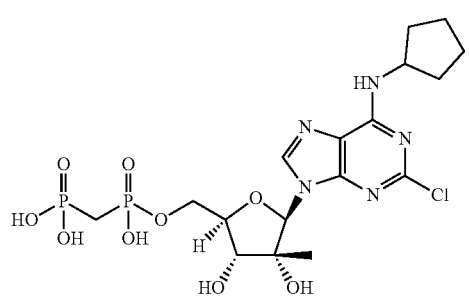
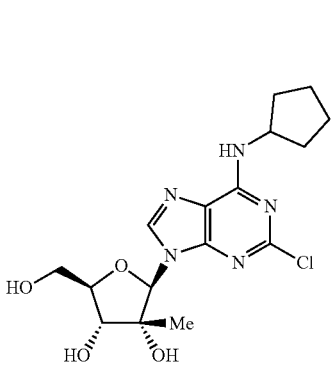

Step a: To β-D-ribofuranose, 2-C-methyl-, 1,2,3,5-tetrabenzoate (4.0 g, 6.89 mmol, 1 equiv.) and 2,6-dichloropurine (1.43 g, 7.58 mmol, 1.1 equiv.) in acetonitrile (23 mL) at 0° C. was added 1,8-Diazabicyclo[5.4.0]undec-7-ene (2.58 mL, 17.23 mmol, 2.5 equiv.) followed by trimethylsilyl trifluoromethanesulfonate (5.11 mL, 28.25 mmol, 4.1 equiv.) dropwise over 5 minutes. The reaction mixture was stirred at 0° C. for 15 minutes and heated at 65° C. for 5 hours. After cooling to room temperature the reaction was diluted with dichloromethane, washed with sat. aq. sodium bicarbonate (×2), and brine (×1). The organics were dried over MgSO$_4$, filtered and concentrated under reduced pressure. The desired product was obtained following column chromatography (SiO$_2$, 25% to 66% EtOAc/Hexane) as a white solid (1.30 g, 97%).

Step b: 1) A product from Step a (1.3 g, 2.01 mmol), cyclopentylamine (297 μL, 3.01 mmol, 1.5 equiv.), and triethylamine (560 μL, 4.02 mmol, 2.0 equiv.) were suspended in anhydrous EtOH (6.7 mL). The mixture was stirred at 70° C. for 4 hours. After cooling to room temperature the mixture was concentrated under reduced pressure and the material obtained used without further purification.

2) The above product was dissolved methanol (20 mL) and potassium carbonate (1.06 g, 7.63 mmol, 3.8 equiv.) was added. After stirring at ambient temperature for 2 hours the residue was adsorbed on celite and purified using column chromatography (SiO$_2$, 0% to 10% DCM/MeOH) as a colorless oil (612 mg, 79%, two steps).

Step c: The title compound was synthesized in similar fashion to Example 1. $^1$H NMR (400 MHz, DMSO-d$_6$) δ 8.38 (dd, J=18.2, 8.1 Hz, 1H), 8.26 (d, J=10.0 Hz, 1H), 5.86 (s, 1H), 4.42 (q, J=7.2 Hz, 1H), 4.27 (h, J=10.6, 10.0 Hz, 2H), 4.06 (s, 3H), 2.28 (t, J=20.4 Hz, 2H), 1.93 (d, J=16.3 Hz, 2H), 1.78–1.43 (m, 6H). ESI MS [M–H]$^-$ for C$_{17}$H$_{25}$ClN$_5$O$_9$P$_2$, calcd 540.1, found 540.2.

Example 74

Synthesis of ((2R,3S,4R,5R)-5-(2-chloro-6-(cyclopentylamino)-9H-purin-9-yl)-3,4-dihydroxytetrahydrofuran-2-yl)methyl hydrogen ((hydroxy(methoxy)phosphoryl) methyl)phosphonate

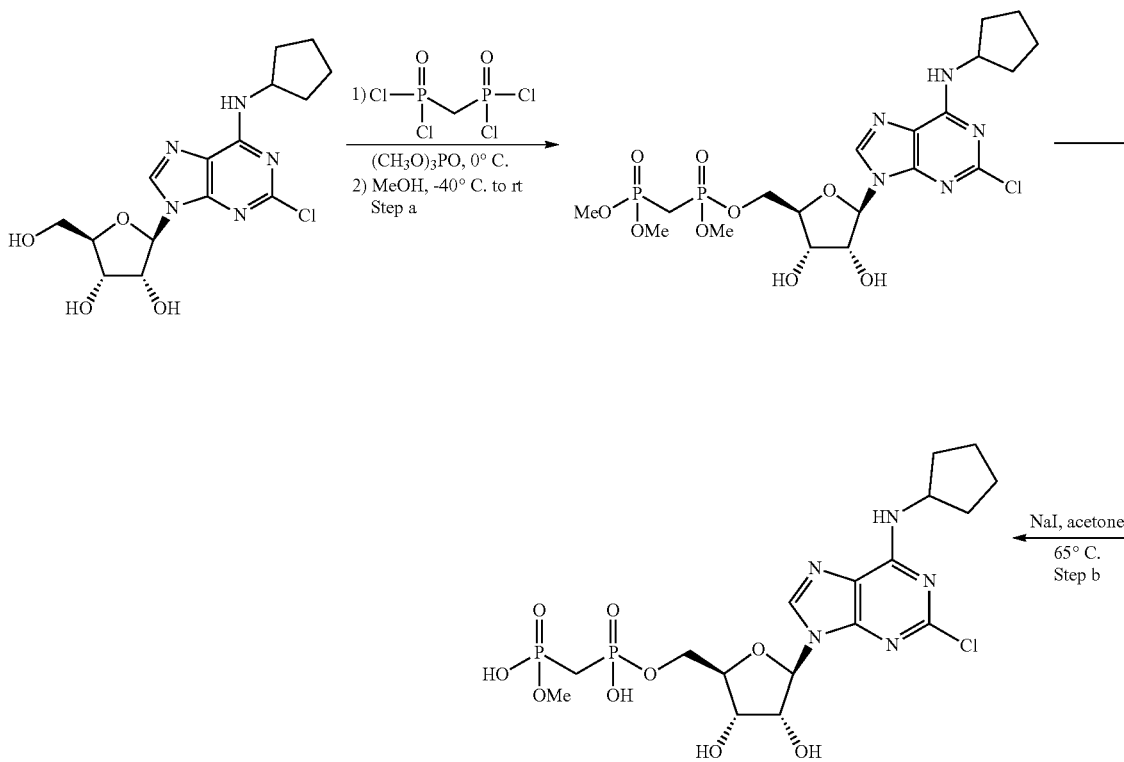

Step a: The nucleoside (2.0 g, 5.4 mmol) was dissolved in trimethyl phosphate (30 mL) and cooled to 0° C. (ice bath), then cold solution of methylenebis(phosphonic dichloride) (4.0 g, 16.2 mmol, 3 equiv.) in trimethyl phosphate (15 mL) was added dropwise. Reaction mixture was stirred at 0° C. for 2 h, then cooled to approx. −40° C. and anhydrous MeOH (30 mL) was added and slowly warmed up to room temperature. The reaction mixture was neutralized with saturated NaHCO$_3$ (80 mL) and diluted with water (150 mL) and EtOAc (150 mL). The organic layer was separated, dried over MgSO$_4$, filtered and evaporated. The product was purified first by column chromatography (SiO$_2$, EtOAc→EtOAc:MeOH, 8:2) and then by RP18 HPLC (H$_2$O+0.10% TFA/acetonitrile+0.1% TFA) to give the desired product as a white solid in 11% yield (405 mg). ESI MS [M+H]f for C$_{19}$H$_{31}$ClN$_5$O$_9$P$_2$, calcd 570.1, found 570.2.

Step b: To a solution of the product from step a (75 mg, 0.13 mmol) in acetone (1 mL), was added sodium iodide (50 mg, 0.33 mmol). This solution was heated to 65° C. for 6 h. The solvent was evaporated; the residue was dissolved in water and purified by reverse phase HPLC (C18 column, 0 to 40% gradient of acetonitrile and water with 0.1% TFA) to give the product as a white solid in 62% yield (51 mg). $^1$H NMR (400 MHz, DMSO-d$_6$) δ 8.41 (d, J=2.0 Hz, 1H), 8.36 (d, J=7.8 Hz, 1H), 5.85 (d, J=5.6 Hz, 1H), 5.04 (brs, 1H), 4.53 (t, J=5.5 Hz, 1H), 4.47-4.34 (m, 1H), 4.24-3.95 (m, 4H), 3.58 (d, J=11.3 Hz, 2H), 2.37 (dd, J=20.5, 20.5 Hz, 2H), 2.07-1.36 (m, 8H). ESI MS [M+H]$^+$ for C$_{17}$H$_{26}$ClN$_5$O$_9$P$_2$, calcd 542.8, found 542.2.

Example 75

Synthesis of [(2R,3S,4R,5R)-5-{2-chloro-6-[cyclopentyl(methyl)amino]-9H-purin-9-yl}-3,4-dihydroxyoxolan-2-yl]methyl phenyl [(diphenoxyphosphoryl)methyl]phosphonate

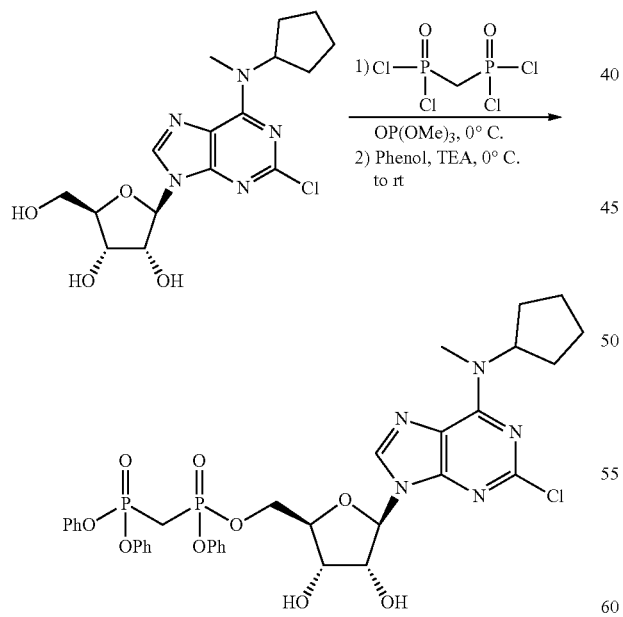

The alcohol (380 mg, 1 mmol) was dissolved in trimethyl phosphate (5 mL) and cooled to 0° C. (ice bath), then cold solution of methylenebis(phosphonic dichloride) (375 mg, 1.5 mmol, 1.5 equiv.) in trimethyl phosphate (3 mL) was added dropwise and reaction mixture was stirred at 0° C. for 3 h. Solid phenol (470 mg, 5 mmol, 5 equiv.) was added and once dissolved TEA (835 μL, 6 mmol, 6 equiv.) was added dropwise. The mixture was stirred at 0° C. for 15 min then at room temperature for overnight. Diluted with H$_2$O (15 mL) and the product was extracted with MTBE (2×10 mL). Combined organics were dried over MgSO$_4$, filtered and evaporated. Crude product was purified by column chromatography (SiO$_2$, Hex→100% EtOAc) to give white solid (80 mg, 10%). $^1$H NMR (400 MHz, DMSO-d$_6$) δ 8.38 (d, J=4.3 Hz, 1H), 7.41-7.33 (m, 4H), 7.32-7.25 (m, 2H), 7.25-7.11 (m, 9H), 5.89 (dd, J=5.3, 3.2 Hz, 1H), 5.63 (dd, J=6.0, 4.4 Hz, 1H), 5.47-5.41 (m, 1H), 4.62-4.54 (m, 1H), 4.49-4.32 (m, 2H), 4.28-4.08 (m, 1H), 3.67-3.47 (m, 2H), 3.35 (s, 3H), 1.90-1.52 (m, 8H). ESI MS [M+H]$^+$ for C$_{35}$H$_{39}$ClN$_5$O$_9$P$_2$, calcd 770.2, found 770.3.

Example 76

Synthesis of bis (3-chlorophenyl) [({[(2R,3S,4R,5R)-5-{2-chloro-6-[cyclopentyl(methyl)-amino]-9H-purin-9-yl}-3,4-dihydroxyoxolan-2-yl]methoxy}(3-chlorophenoxy)phosphoryl)-methyl]phosphonate

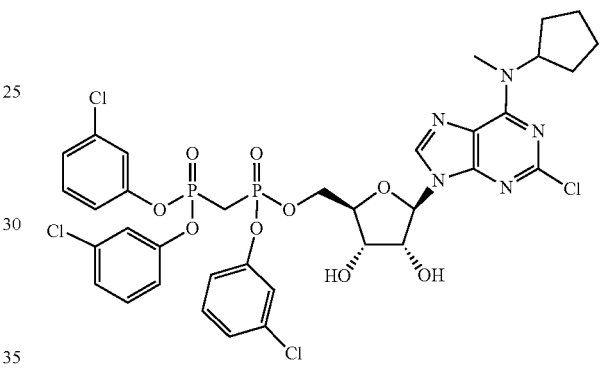

The title compound was synthesized in similar fashion to Example 75. $^1$H NMR (400 MHz, DMSO-d$_6$) δ 8.32 (s, 1H), 7.43-7.34 (m, 2H), 7.34-7.05 (m, 10H), 5.88 (t, J=4.7 Hz, 1H), 5.62 (s, 1H), 5.43 (s, 1H), 4.59-4.36 (m, 3H), 4.26-4.10 (m, 2H), 3.86-3.70 (m, 2H), 3.04 (s, 3H), 1.90-1.46 (m, 8H). ESI MS [M+H]$^+$ for C$_{35}$H$_{36}$C$_{14}$N$_5$O$_9$P$_2$, calcd 872.1, found 872.2.

Example 77

Synthesis of bis (3,4-dichlorophenyl) [({[(2R,3S,4R,5R)-5-{2-chloro-6-[cyclopentyl(methyl)amino]-9H-purin-9-yl}-3,4-dihydroxyoxolan-2-yl]methoxy}(3,4-dichlorophenoxy)phosphoryl)methyl]phosphonate

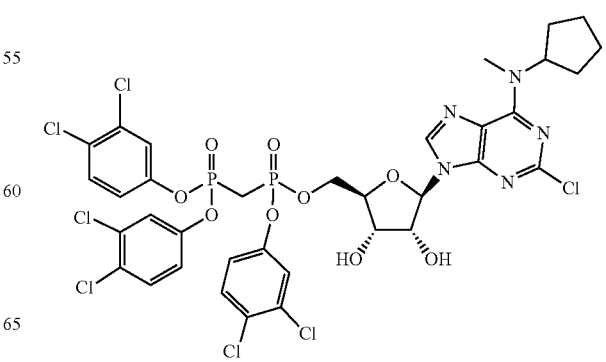

The title compound was synthesized in similar fashion to Example 75. ¹H NMR (400 MHz, DMSO-d₆) δ 8.27 (s, 1H), 7.65-7.57 (m, 2H), 7.52-7.40 (m, 3H), 7.32-7.04 (m, 4H), 5.87 (t, J=5.0 Hz, 1H), 5.63 (t, J=6.1 Hz, 1H), 5.43 (dd, J=5.6, 3.7 Hz, 1H), 4.59-4.35 (m, 3H), 4.30-4.08 (m, 2H), 3.85 (t, J=22.0 Hz, 2H), 3.32 (s, 3H), 1.89-1.45 (m, 8H). ESI MS [M+H]⁺ for $C_{35}H_{33}Cl_7N_5O_9P_2$, calcd 974.0, found 974.2.

Example 78

Synthesis of methyl 2-({[({[(2R,3S,4R,5R)-5-{2-chloro-6-[cyclopentyl(methyl)amino]-9H-purin-9-yl}-3,4-dihydroxyoxolan-2-yl]methoxy}[2-(methoxycarbonyl)phenoxy]phosphoryl)-methyl][2-(methoxycarbonyl)phenoxy]phosphoryl}oxy)benzoate

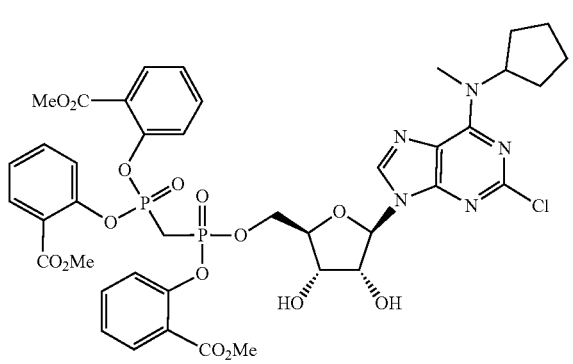 [SMILES: COC(=O)c1ccccc1OP(=O)(CP(=O)(Oc1ccccc1C(=O)OC)Oc1ccccc1C(=O)OC)OC[C@H]1O[C@@H](n2cnc3c(N(C)C4CCCC4)nc(Cl)nc32)[C@H](O)[C@@H]1O]

The title compound was synthesized in similar fashion to Example 75. H NMR (400 MHz, DMSO-d₆) δ 8.31-8.27 (m, 1H), 7.82-7.74 (m, 3H), 7.57-7.49 (m, 2H), 7.46-7.39 (m, 1H), 7.36-7.17 (m, 6H), 5.83 (t, J=5.9 Hz, 1H), 5.60-5.52 (m, 1H), 5.37 (s, 1H), 4.55-4.29 (m, 3H), 4.15-4.04 (m, 2H), 3.81-3.74 (m, 2H), 3.72-3.65 (m, 3H), 3.32 (s, 9H), 1.88-1.47 (m, 8H). ESI MS [M+H]⁺ for $C_{41}H_{45}ClN_5O_{15}P_2$, calcd 944.2, found 944.3.

Example 79

Synthesis of [({[(2R,3R,4S,5R)-5-(2-chloro-6-{[(1S)-1-(4-fluorophenyl)ethyl]amino}-9H-purin-9-yl)-4-fluoro-3-hydroxyoxolan-2-yl]methoxy}(hydroxy)phosphoryl)methyl]-phosphonic acid

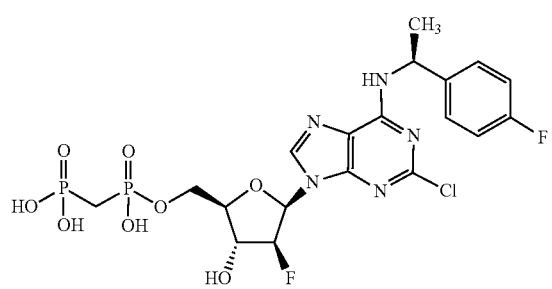 [SMILES: C[C@H](Nc1nc(Cl)nc2c1ncn2[C@@H]1O[C@H](COP(=O)(O)CP(=O)(O)O)[C@@H](O)[C@@H]1F)c1ccc(F)cc1]

The title compound was synthesized in similar fashion to Example 29. ¹H NMR (400 MHz, DMSO-d₆) δ 8.92 (d, J=8.3 Hz, 1H), 8.28 (s, 1H), 7.45 (bs, 2H), 7.11 (td, J=9.1, 1.4 Hz, 2H), 6.34 (dd, J=14.3, 4.6 Hz, 1H), 5.39 (bs, 1H), 5.31-5.12 (m, 1H), 5.14 (bs, 1H), 4.48 (dt, J=18.5, 4.5 Hz, 1H), 4.17 (s, 3H), 4.01 (d, J=5.2 Hz, 2H), 2.24 (t, J=20.4 Hz, 3H), 1.51 (d, J=7.0 Hz, 3H). ESI MS [M+H]⁺ for $C_{19}H_{23}ClF_2N_5O_8P_2$, calcd 584.1, found 584.2.

Example 80

Synthesis of [({[(2R,3R,4S,5R)-5-(2-chloro-6-{[(1R)-1-phenylethyl]amino}-9H-purin-9-yl)-4-fluoro-3-hydroxyoxolan-2-yl]methoxy}(hydroxy)phosphoryl)methyl]phosphonic acid

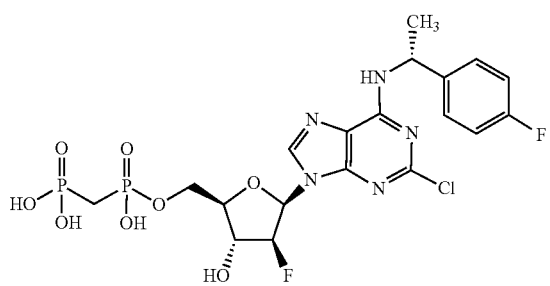 [SMILES: C[C@@H](Nc1nc(Cl)nc2c1ncn2[C@@H]1O[C@H](COP(=O)(O)CP(=O)(O)O)[C@@H](O)[C@@H]1F)c1ccc(F)cc1]

The title compound was synthesized in similar fashion to Example 29. ¹H NMR (400 MHz, DMSO-d₆) δ 8.90 (d, J=8.3 Hz, 1H), 8.28 (s, 1H), 7.42 (d, J=7.6 Hz, 2H), 7.29 (t, J=7.5 Hz, 2H), 7.19 (bs, 1H), 6.34 (dd, J=14.8, 4.4 Hz, 1H), 5.39 (bs, 1H), 5.23 (d, J=52.6 Hz, 1H), 4.49 (d, J=19.2 Hz, 2H), 4.17 (bs, 2H), 4.01 (d, J=5.1 Hz, 1H), 2.24 (t, J=20.6 Hz, 2H), 1.52 (d, J=7.0 Hz, 3H). ESI MS [M+H]⁺ for $C_{19}H_{24}ClFN_5O_8P_2$, calcd 566.1, found 566.1.

Example 81

Synthesis of [({[(2R,3R,4S,5R)-5-(2-chloro-6-{[(1S)-1-phenylethyl]amino}-9H-purin-9-yl)-4-fluoro-3-hydroxyoxolan-2-yl]methoxy}(hydroxy)phosphoryl)methyl]phosphonic acid

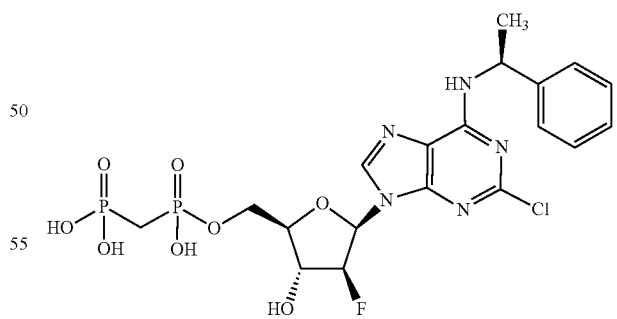

The title compound was synthesized in similar fashion to Example 29. ¹H NMR (400 MHz, DMSO-d₆) δ 8.91 (d, J=8.3 Hz, 1H), 8.28 (s, 1H), 7.41 (d, J=7.5 Hz, 2H), 7.29 (t, J=7.6 Hz, 2H), 7.20 (d, J=7.6 Hz, 1H), 6.34 (d, J=14.1 Hz, 1H), 5.39 (bs, 1H), 5.21 (d, J=52.5 Hz, 1H), 4.47 (d, J=18.3 Hz, 2H), 4.17 (s, 2H), 4.01 (s, 1H), 2.24 (t, J=20.6 Hz, 2H), 1.52 (d, J=7.1 Hz, 3H). ESI MS [M+H]⁺ for $C_{19}H_{24}ClFN_5O_8P2$, calcd 566.1, found 566.1.

Example 82

Synthesis of [({[(2R,3R,4S,5R)-5-[6-(cyclopentylamino)-2-[hydroxy(oxan-4-yl)methyl]-9H-purin-9-yl]-4-fluoro-3-hydroxyoxolan-2-yl]methoxy}(hydroxy)phosphoryl)methyl]-phosphonic acid

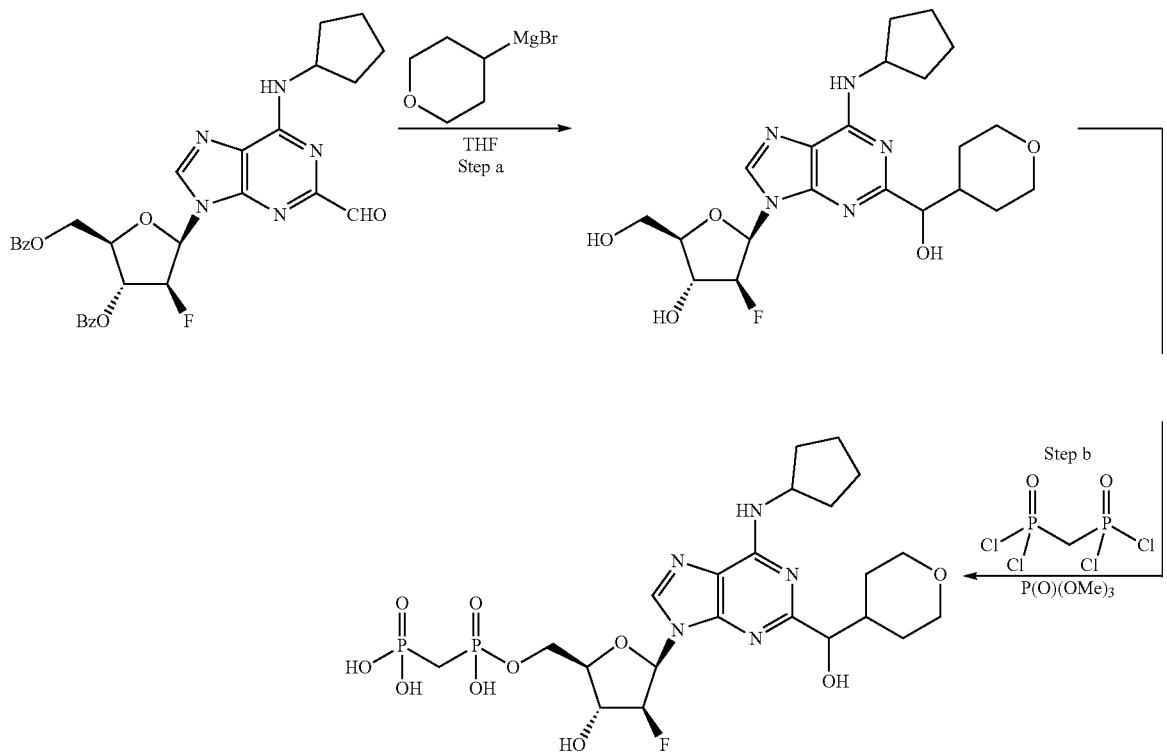

Step a: The product of step b from Example 58 (1.00 g, 1.75 mmol) was dissolved in THF (9 mL) and cooled to −78° C. 4-tetrahydropyranylmagnesium bromide (9 mL, 8.75 mmol, 0.2 M in THF) was added dropwise. The reaction mixture was allowed to warm to r.t. and stirred at r.t. for 3 h. The reaction mixture was cooled to 0° C., methanol (50 mL) was added, and the mixture stirred at r.t. for 14 h. The reaction mixture was dry loaded onto silica gel and purified by silica gel chromatography (0-10% MeOH in DCM) to afford the desired product as a white solid (273 mg, 35%).

Step b: The title compound was synthesized as a white solid (44 mg; 29%) in similar fashion Example 29. $^1$H NMR (400 MHz, DMSO-$d_6$) δ 6.60-6.40 (m, 1H), 5.26 (d, J=53.3 Hz, 1H), 4.63-4.39 (m, 2H), 4.30-4.13 (m, 2H), 4.13-3.97 (m, 1H), 3.94-3.75 (m, 2H), 3.38-3.13 (m, 2H), 2.26 (t, J=20.4 Hz, 2H), 2.17-1.85 (m, 3H), 1.85-1.22 (m, 12H). ESI MS [M−H]⁻ for $C_{23}H_{35}FN_5O_9P_2$, calcd 606.2, found 606.3.

Example 83

Synthesis of (((((2R,3R,4S,5R)-5-(2-chloro-6-(cyclopentyl(methyl)amino)-9H-purin-9-yl)-4-fluoro-3-hydroxytetrahydrofuran-2-yl)methoxy)(hydroxy)phosphoryl)methyl)phosphonic acid

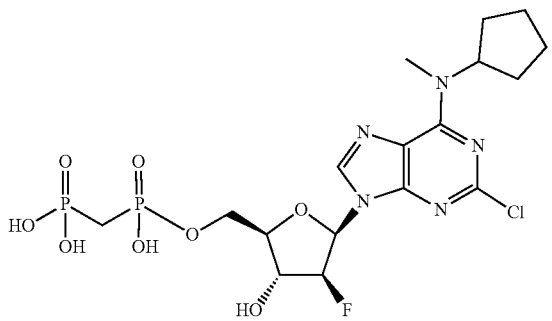 [SMILES: CN(c1nc(Cl)nc2c1ncn2[C@@H]1O[C@H](COP(=O)(O)CP(=O)(O)O)[C@@H](O)[C@@H]1F)C1CCCC1]

This compound was obtained similar fashion to Example 29. $^1$H NMR (400 MHz, DMSO-$d_6$) δ 8.7 (brs, 2H), 8.30 (d, J=2.1 Hz, 1H), 6.40 (dd, J=14.3, 4.6 Hz, 1H), 6.09 (brs, 1H), 5.25 (dt, J=52.5, 4.3 Hz, 1H), 4.53-4.43 (m, 1H), 4.23-4.14 (m, 2H), 4.09-3.98 (m, 1H), 2.28 (dd, J=20.5 Hz, J=20.5 Hz, 2H), 2.5 (s, 3H), 1.96-1.44 (m, 9H). ESI MS [M+H]⁺ for $C_{17}H_{25}ClFN_5O_8P_2$, calcd 544.8, found: 544.2.

Example 84

Synthesis of ((2R,3R,4S,5R)-5-(2-chloro-6-(cyclopentyl(methyl)amino)-9H-purin-9-yl)-4-fluoro-3-hydroxytetrahydrofuran-2-yl)methyl hydrogen((hydroxy(methoxy)phosphoryl) methyl)phosphonate

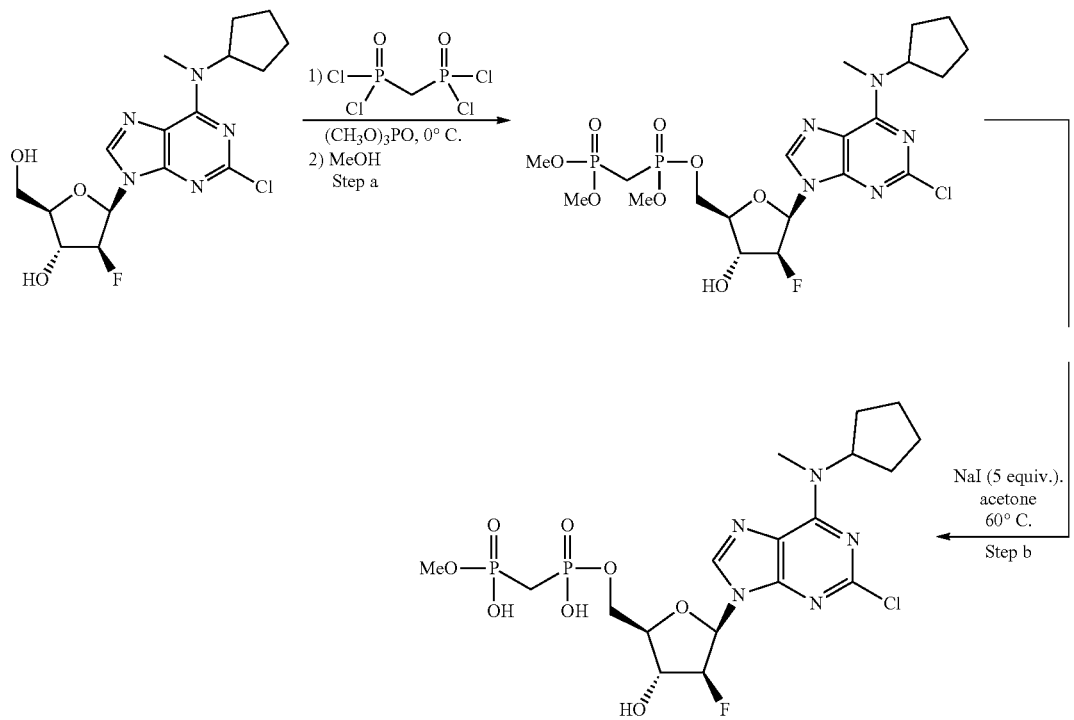

Step a: 2-chloropurine fluororiboside (579 mg, 1.5 mmol) was dissolved in trimethyl phosphate (7.5 mL) and cooled to 0° C. (ice bath), then a cold solution of methylenebis (phosphonic dichloride) (1.87 g, 7.5 mmol, 5 equiv.) in trimethyl phosphate (4.5 mL) was added dropwise. The reaction mixture was stirred at 0° C. for 3 h, and was then carefully quenched with methanol (7 mL) and stirred at 0° C. for 30 min, then 1 h at room temperature and then 3 h at 40° C. The reaction mixture was concentrated under vacuum and dissolved in ethyl acetate (20 mL). The organic layer was washed with saturated aqueous NaHCO$_3$, dried over sodium sulfate and evaporated to dryness. The residue was purified by column chromatography (gradient of methanol in dichloromethane 0 to 10%) to afford the desired product as a pale yellow solid (701 mg, 80%). $^1$H NMR (400 MHz, DMSO-d$_6$) δ 8.32 (dd, J=12.0, 2.3 Hz, 1H), 6.42 (dd, J=15.5, 4.4 Hz, 1H), 6.15 (t, J=4.8 Hz, 1H), 5.43-5.07 (m, 1H), 4.60-4.39 (m, 1H), 4.27 (q, J=7.3, 5.7 Hz, 2H), 4.12-4.03 (dq, J=9.6, 5.3 Hz, 1H), 3.69-3.59 (m, 9H), 2.96-2.74 (m, 2H), 2.50 (s, 3H), 2.04-1.42 (m, 9H). ESI MS [M+H]$^+$ for C$_{20}$H$_{31}$ClFN$_5$O$_8$P$_2$, calcd 586.9, found 586.2.

Step b: To a solution of the product from step a (58 mg, 0.1 mmol) in acetone (1 mL), was added sodium iodide (75 mg, 0.5 mmol). This solution was heated to 60° C. for 24 h. The solvent was evaporated, the residue was dissolved in water and purified by reverse phase HPLC (C18 column, 0 to 30% gradient of acetonitrile and water with 0.1% TFA) to give the product as a white solid in 65% yield (42 mg). $^1$H NMR (400 MHz, DMSO-d$_6$) δ 8.31 (d, J=2.2 Hz, 1H), 6.40 (dd, J=14.6, 4.6 Hz, 1H), 5.25 (dt, J=52.4, 4.2 Hz, 1H), 4.48 (dt, J=18.3, 4.4 Hz, 1H), 4.18 (t, J=6.1 Hz, 2H), 4.04 (m, 2H), 3.58 (d, J=11.2 Hz, 3H), 2.5 (s, 3H). 2.39 (dd, J=20.4 Hz, J=20.4 Hz, 2H), 2.00-1.42 (m, 9H). ESI MS [M+H]$^+$ for C$_{18}$H$_{27}$ClFN$_5$O$_8$P$_2$, calcd 558.8, found 558.2.

Example 85

Synthesis of ((2R,3R,4S,5R)-5-(2-chloro-6-(cyclopentyl(methyl)amino)-9H-purin-9-yl)-4-fluoro-3-hydroxytetrahydrofuran-2-yl)methyl hydrogen ((dimethoxyphosphoryl)methyl) phosphonate and Synthesis of methyl hydrogen (((((2R,3R,4S,5R)-5-(2-chloro-6-(cyclopentyl(methyl)amino)-9H-purin-9-yl)-4-fluoro-3-hydroxytetrahydrofuran-2-yl)methoxy)(methoxy)phosphoryl) methyl)phosphonate

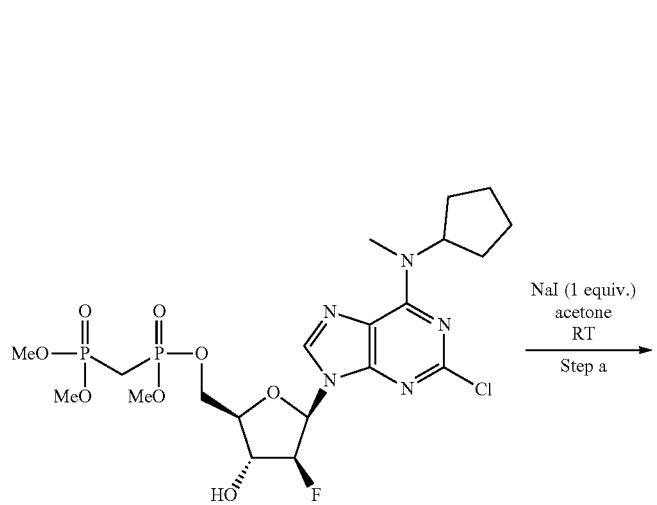

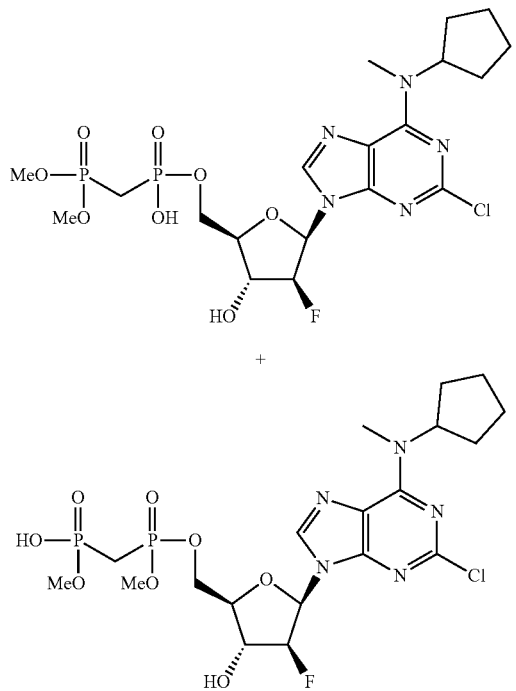

Step a: To a solution of the product from example 83, step a (150 mg, 0.26 mmol) in acetone (3 mL), was added sodium iodide (40 mg, 0.26 mmol). This solution was stirred at room temperature for 24 h. The solvent was evaporated, the residue was dissolved in water and purified by reverse phase HPLC (C18 column, 0 to 30% gradient of acetonitrile and water with 0.1% TFA) to give ((2R,3R,4S,5R)-5-(2-chloro-6-(cyclopentyl(methyl)amino)-9H-purin-9-yl)-4-fluoro-3-hydroxy-tetrahydrofuran-2-yl)methyl hydrogen ((dimethoxyphosphoryl)methyl)-phosphonate as a white solid in 20% yield (35 mg). $^1$H NMR (400 MHz, DMSO-d$_6$) δ 8.31 (d, J=2.2 Hz, 1H), 6.41 (dd, J=14.9, 4.5 Hz, 1H), 5.25 (dt, J=52.3, 4.1 Hz, 1H), 4.53-4.43 (m, 1H), 4.24-4.12 (m, 2H), 4.08-4.02 (m, 1H), 3.66 (d, J=2.0 Hz, 3H), 3.63 (d, J=2.0 Hz, 3H), 2.60 (dd, J=20.8 Hz, J=20.8 Hz, 2H), 2.50 (s, 3H), 2.01-1.55 (m, 9H). ESI MS [M+H]$^+$ for $C_{19}H_{29}ClFN_5O_8P_2$, calcd 572.9, found 572.3.

Methyl hydrogen (((((2R,3R,4S,5R)-5-(2-chloro-6-(cyclopentyl(methyl)amino)-9H-purin-9-yl)-4-fluoro-3-hydroxytetrahydrofuran-2-yl)methoxy)(methoxy)phosphoryl) methyl)-phosphonate as a white solid as 1:1 mixture of diastereoisomers in 30% yield (52 mg). $^1$H NMR (400 MHz, DMSO-d$_6$) δ 8.34 (d, J=2.3 Hz, 0.5H, 1$^{st}$ dia), 8.30 (d, J=2.3 Hz, 0.5H, 2$^{nd}$ dia), 6.54-6.32 (m, 1H), 5.38-5.11 (m, 1H), 4.59-4.39 (m, 1H), 4.26 (m, 2H), 4.07 (m, 1H), 3.64 (d, J=11.3 Hz, 3H), 3.59 (d, J=11.2, 1.5H, 1$^{st}$ dia), 3.59 (d, J=11.2, 1.5H, 1$^{st}$ dia), 2.69-2.53 (m, 2H), 2.5 (s, 3H), 1.97-1.52 (m, 9H). ESI MS [M+H]$^+$ for $C_{19}H_{29}ClFN_5O_8P_2$, calcd 572.9, found 572.2.

Example 86

Synthesis of (((((2R,3R,4S,5R)-5-(2-chloro-6-(cyclopentyl(methyl)amino)-9H-purin-9-yl)-4-fluoro-3-hydroxytetrahydrofuran-2-yl)methoxy)(methoxy) phosphoryl)methyl)phosphonic acid

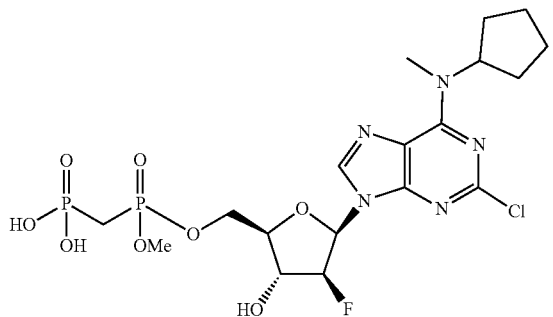 [SMILES: COP(=O)(CP(=O)(O)O)OC[C@H]1O[C@@H](n2cnc3c(N(C)C4CCCC4)nc(Cl)nc32)[C@@H](F)[C@@H]1O]

This compound was obtained as a 1:1 mixture of diastereoisomers in a manner similar to Example 84. $^1$H NMR (400 MHz, DMSO-d$_6$) δ 8.34 (d, J=2.3 Hz, 0.5H, 1$^{st}$ dia), 8.29 (d, J=2.3 Hz, 0.5H, 2$^{nd}$ dia), 6.52-6.32 (m, 1H), 6.07 (brs, 1H), 5.34-5.14 (m, 1H), 4.56-4.43 (m, 1H), 4.30-4.21 (m, 2H), 4.11-4.03 (m, 1H), 3.63 (d, J=11.2 Hz, 1.5H, 1$^{st}$ dia), 3.63 (d, J=11.2 Hz, 1.5H, 2$^{nd}$ dia), 2.50 (s, 3H), 2.48-2.34 (m, 2H), 1.92-1.53 (m, 9H). ESI MS [M+H]$^+$ for $C_{18}H_{27}ClFN_5O_8P_2$, calcd 558.3, found 558.2.

Example 87

Synthesis of [({[(2R,3S,4R,5R)-5-[6-chloro-4-(cyclopentylamino)-1H-pyrazolo[3,4-d]pyrimidin-1-yl]-3,4-dihydroxyoxolan-2-yl]methoxy}(hydroxy)phosphoryl)methyl]phosphonic acid

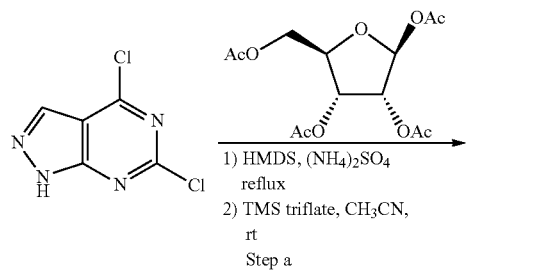

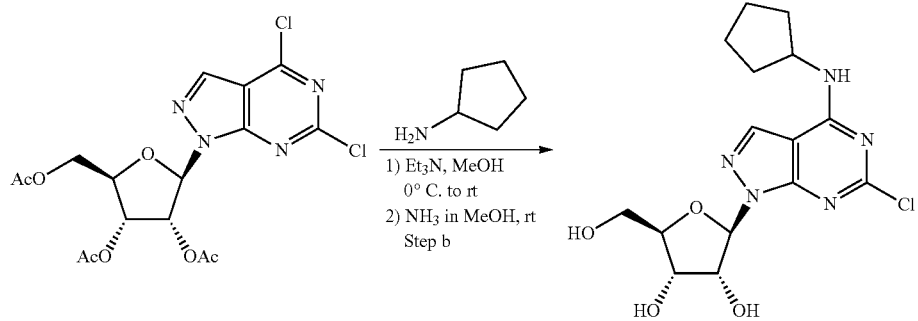

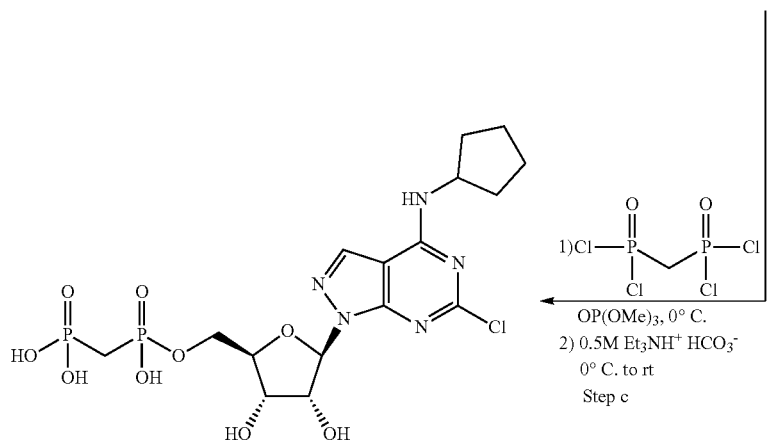

Step a: 4,6-Dichloro-1H-pyrazolo[3,4-d]pyrimidine (25 g, 132 mmol) and Ammonium Sulfate (0.20 g, 1.5 mmol) were dissolved in 150 mL of hexamethyldisilziane. The mixture was then warmed to reflux and stirred for 3 hrs. The mixture was then concentrated to dryness. The solid residue was then taken up in 300 mL of acetonitrile, and the protected ribose (50.6 g, 159 mmol) was added. This mixture was cooled 0° C. and TMSOTf (27 mL, 145 mmol) was added dropwise. The mixture was then warmed to room temperature and allowed to stir overnight. The mixture was then concentrated and taken up in ethyl acetate. The organics were washed with saturated NaHCO$_3$ and brine. The organics were dried with MgSO$_4$, filtered and concentrated. The crude residue was purified using column chromatography (Hexanes/Ethyl Acetate) to provide the desired compound (48 g, 108 mmol) in 82% overall yield. $^1$H NMR (400 MHz, DMSO-d$_6$) δ 8.75 (s, 1H), 6.47 (d, J=3.2 Hz, 1H), 5.82 (dd, J=5.3, 3.2 Hz, 1H), 5.63 (t, J=5.8 Hz, 1H), 4.47-4.40 (m, 1H), 4.37-4.30 (m, 1H), 4.12-4.02 (m, 1H), 2.09 (s, 3H), 2.06 (s, 3H), 1.97 (s, 3H). ESI MS [M+Na]$^+$ for C$_{16}$H$_{16}$Cl$_2$N$_4$NaO$_7$, calcd 469.0, found 469.0.

Step b: Product from Step a (22 g, 49.3 mmol) was dissolved in MeOH (100 mL) and cooled to 0° C. Cyclopentylamine (5.1 g, 51.8 mmol, 1.05 equiv.), and triethylamine (7.2 mL, 51.8 mmol, 1.05 equiv.) were added and reaction mixture was stirred at 0° C. for 15 min then at rt for 4 h. 7 M NH$_3$ in MeOH (60 mL) was added and reaction was stirred at rt for 1 day. Reaction mixture was evaporated and the crude product was used in the next step without purification. ESI MS [M+H]$^+$ for C$_{15}$H$_{21}$ClN$_5$O$_4$, calcd 370.1, found 370.2.

Step c: The phosphonylation step was carried out in similar fashion to example 1. $^1$H NMR (400 MHz, DMSO-d$_6$) δ 8.68 (d, J=7.2 Hz, 1H), 8.24 (s, 1H), 6.00 (d, J=4.2 Hz, 1H), 4.49 (t, J=4.7 Hz, 1H), 4.41 (q, J=6.7 Hz, 1H), 4.26 (t, J=4.7 Hz, 1H), 4.15-4.00 (m, 2H), 3.94-3.84 (m, 1H), 2.16 (t, J=20.5 Hz, 2H), 2.04-1.91 (m, 2H), 1.79-1.45 (m, 6H). ESI MS [M+H]$^+$ for C$_{16}$H$_{25}$ClN$_5$O$_9$P$_2$, calcd 528.1, found 528.2.

Example 88

Synthesis of [({[(2R,3S,4R,5R)-5-[4-(benzylamino)-6-chloro-1H-pyrazolo[3,4-d]pyrimidin-1-yl]-3,4-dihydroxyoxolan-2-yl]methoxy}(hydroxy)phosphoryl)methyl]phosphonic acid

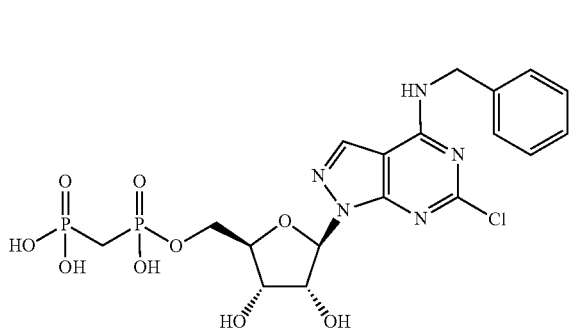 [SMILES: O=P(O)(O)CP(=O)(O)OC[C@H]1O[C@@H](n2ncc3c(NCc4ccccc4)nc(Cl)nc32)[C@H](O)[C@@H]1O]

The title compound was synthesized in similar fashion to Example 87. $^1$H NMR (400 MHz, DMSO-d$_6$) δ 9.38-9.18 (m, 1H), 8.35-8.16 (m, 1H), 7.39-7.19 (m, 5H), 6.07-5.94 (m, 1H), 4.69 (d, J=5.4 Hz, 2H), 4.58-4.44 (m, 1H), 4.30-4.20 (m, 1H), 4.15-4.01 (m, 2H), 3.96-3.80 (m, 1H), 2.17 (t, J=20.9 Hz, 2H). ESI MS [M−H]$^−$ for C$_{18}$H$_{22}$ClN$_5$O$_9$P$_2$, calcd 548.1, found 548.1.

Example 89

Synthesis of [({[(2R,3S,4R,5R)-5-(6-chloro-4-{[(1S)-1-phenylethyl]amino}-1H-pyrazolo[3,4-d]pyrimidin-1-yl)-3,4-dihydroxyoxolan-2-yl]methoxy}(hydroxy)phosphoryl)methyl]phosphonic acid

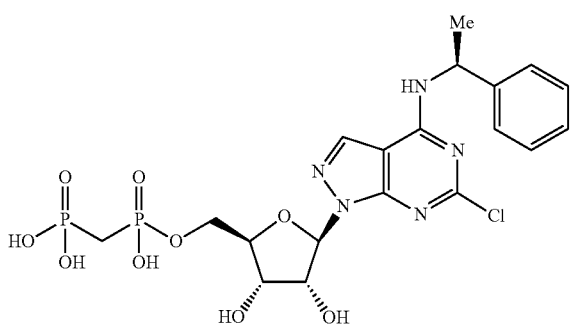 [SMILES: C[C@H](Nc1nc(Cl)nc2c1cnn2[C@@H]1O[C@H](COP(=O)(O)CP(=O)(O)O)[C@@H](O)[C@H]1O)c1ccccc1]

The title compound was synthesized in similar fashion to Example 87. H NMR (400 MHz, DMSO-d$_6$) δ 9.26-8.95 (m, 1H), 8.35-8.17 (m, 1H), 7.48-7.28 (m, 4H), 7.28-7.09 (m, 1H), 6.09-5.87 (m, 1H), 5.42 (q, J=6.9 Hz, 1H), 4.60-4.33 (m, 1H), 4.33-4.16 (m, 1H), 4.13-3.96 (m, 2H), 3.97-3.80 (m, 1H), 2.35-1.95 (m, 2H), 1.62-1.36 (m, 3H). ESI MS [M−H]$^−$ for C$_{19}$H$_{24}$ClN$_5$O$_9$P2, calcd 562.1, found 562.2.

Example 90

Synthesis of [({[(2R,3S,4R,5R)-5-(6-chloro-4-{[(1R)-1-phenylethyl]amino}-1H-pyrazolo[3,4-d]pyrimidin-1-yl)-3,4-dihydroxyoxolan-2-yl]methoxy}(hydroxy)phosphoryl)methyl]phosphonic acid

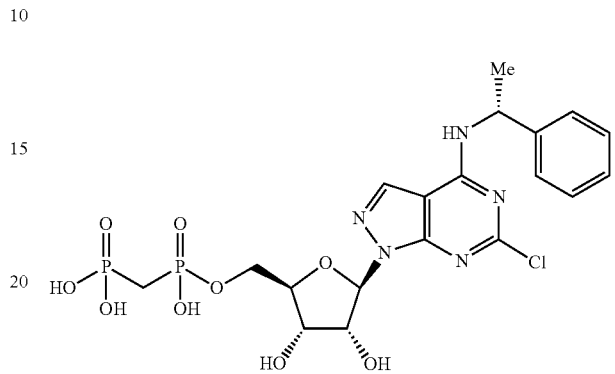

The title compound was synthesized in similar fashion to Example 87. $^1$H NMR (400 MHz, DMSO-d$_6$) δ 9.16 (d, J=8.4 Hz, 1H), 8.32 (s, 1H), 7.48-7.30 (m, 4H), 7.28-7.15 (m, 1H), 6.09-5.79 (m, 1H), 5.47-5.36 (m, 1H), 4.58-4.42 (m, 1H), 4.32-4.19 (m, 1H), 4.17-3.95 (m, 2H), 3.95-3.79 (m, 1H), 2.18 (t, J=20.8 Hz, 2H), 1.71-1.37 (m, 4H). ESI MS [M−H]$^−$ for C$_{19}$H$_{24}$ClN$_5$O$_9$P2, calcd 562.1, found 562.2.

Example 91

Synthesis of [({[(2R,3S,4R,5R)-5-(6-chloro-4-{[(4-chlorophenyl)methyl]amino}-1H-pyrazolo[3,4-d]pyrimidin-1-yl)-3,4-dihydroxyoxolan-2-yl]methoxy}(hydroxy)phosphoryl)methyl]phosphonic acid

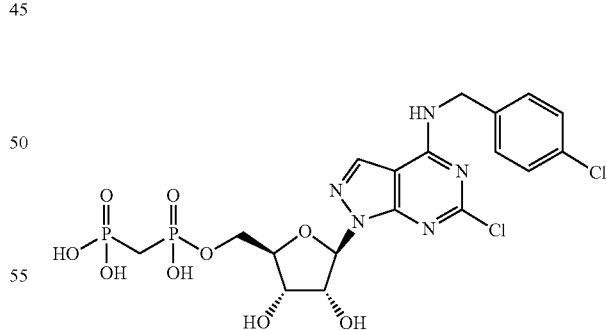

The title compound was synthesized in similar fashion to Example 87. $^1$H NMR (400 MHz, DMSO-d$_6$) δ 9.41-9.19 (m, 1H), 8.32-8.17 (m, 1H), 7.43-7.30 (m, 4H), 6.02 (d, J=2.9 Hz, 1H), 4.68 (d, J=4.4 Hz, 2H), 4.56-4.45 (m, 1H), 4.33-4.18 (m, 1H), 4.13-3.80 (m, 2H), 3.62-3.44 (m, 1H), 2.17 (t, J=20.4 Hz, 1H). ESI MS [M−H]$^−$ for C$_{18}$H$_{21}$C$_{12}$N$_5$O$_9$P$_2$, calcd 582.0, found 582.0.

Example 92

Synthesis of [({[(2R,3S,4R,5R)-5-(6-chloro-4-{[(1S)-1-(2-fluorophenyl)ethyl]amino}-1H-pyrazolo[3,4-d]pyrimidin-1-yl)-3,4-dihydroxyoxolan-2-yl]methoxy}(hydroxy)phosphoryl)-methyl]phosphonic acid

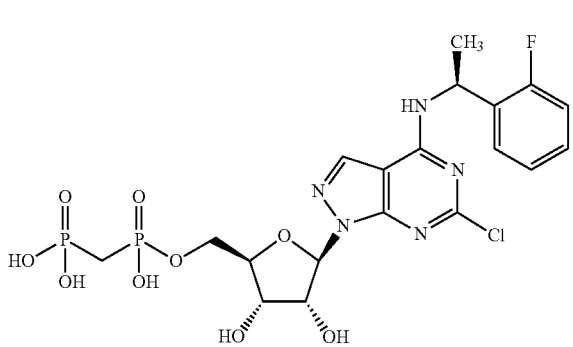 [SMILES: C[C@H](Nc1nc(Cl)nc2c1cnn2[C@@H]1O[C@H](COP(=O)(O)CP(=O)(O)O)[C@@H](O)[C@H]1O)c1ccccc1F]

The title compound was synthesized in similar fashion to Example 87. $^1$H NMR (400 MHz, DMSO-d$_6$) δ 9.28-9.15 (m, 1H), 8.33 (dd, J=1.5, 0.7 Hz, 1H), 7.43 (t, J=7.8 Hz, 1H), 7.29 (dd, J=7.8, 5.6 Hz, 1H), 7.23-7.08 (m, 2H), 6.00 (d, J=4.2 Hz, 1H), 5.65-5.51 (m, 1H), 4.48 (t, J=4.9 Hz, 1H), 4.26 (t, J=4.5 Hz, 1H), 4.05 (dq, J=10.1, 5.9, 5.2 Hz, 2H), 3.88 (dt, J=11.3, 6.0 Hz, 1H), 2.29-2.08 (t, J=20.4 Hz, 2H), 1.53 (d, J=6.8 Hz, 3H). ESI MS [M+H]$^+$ for C$_{19}$H$_{24}$ClFN$_5$O$_9$P$_2$, calcd 582.1, found 582.1.

Example 93

Synthesis of [({[(2R,3S,4R,5R)-5-(6-chloro-4-{[(1R)-1-(2-fluorophenyl)ethyl]amino}-1H-pyrazolo[3,4-d]pyrimidin-1-yl)-3,4-dihydroxyoxolan-2-yl]methoxy}(hydroxy)phosphoryl)-methyl] phosphonic acid

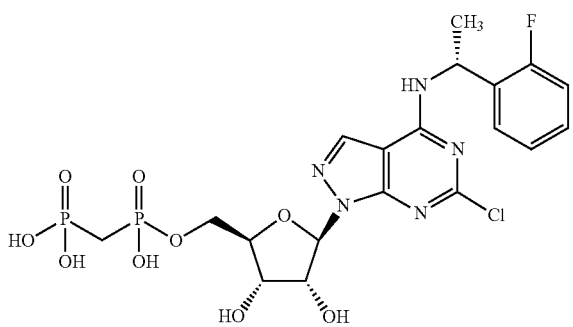 [SMILES: C[C@@H](Nc1nc(Cl)nc2c1cnn2[C@@H]1O[C@H](COP(=O)(O)CP(=O)(O)O)[C@@H](O)[C@H]1O)c1ccccc1F]

The title compound was synthesized in similar fashion to Example 87. $^1$H NMR (400 MHz, DMSO-d$_6$) δ 9.23 (d, J=7.6 Hz, 1H), 8.34 (s, 1H), 7.44 (t, J=7.8 Hz, 1H), 7.30 (q, J=7.0 Hz, 1H), 7.18 (dt, J=9.4, 6.4 Hz, 2H), 6.00 (d, J=4.3 Hz, 1H), 5.60 (q, J=7.1 Hz, 1H), 4.51 (t, J=4.6 Hz, 1H), 4.26 (t, J=4.6 Hz, 1H), 4.05 (tt, J=10.1, 5.8 Hz, 2H), 3.88 (dd, J=11.0, 6.2 Hz, 1H), 2.17 (t, J=20.4 Hz, 2H), 1.53 (d, J=6.7 Hz, 3H). ESI MS [M+H]$^+$ for C$_{19}$H$_{24}$ClFN$_5$O$_9$P$_2$, calcd 582.1, found 582.1.

Example 94

Synthesis of [({[(2R,3S,4R,5R)-5-(6-chloro-4-{[(1S)-1-(3-fluorophenyl)ethyl]amino}-1H-pyrazolo[3,4-d]pyrimidin-1-yl)-3,4-dihydroxyoxolan-2-yl]methoxy}(hydroxy)-phosphoryl)methyl]phosphonic acid

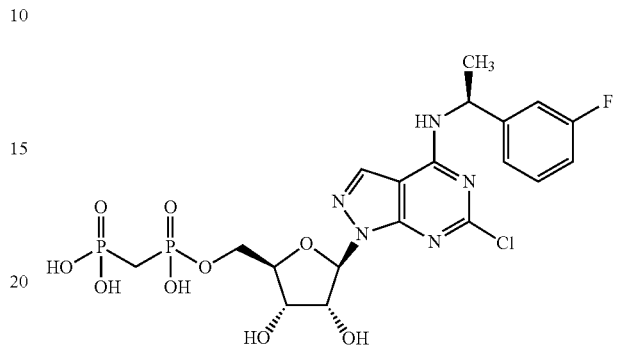

The title compound was synthesized in similar fashion to Example 87. $^1$H NMR (400 MHz, DMSO-d$_6$) δ 9.17 (d, J=7.9 Hz, 1H), 8.31 (s, 1H), 7.50-7.30 (m, 1H), 7.22 (d, J=8.2 Hz, 2H), 7.06 (td, J=8.7, 2.5 Hz, 1H), 6.00 (d, J=4.2 Hz, 1H), 5.41 (t, J=7.3 Hz, 1H), 4.48 (t, J=4.7 Hz, 1H), 4.26 (t, J=4.8 Hz, 1H), 4.05 (dq, J=11.7, 6.5 Hz, 2H), 3.88 (dt, J=11.2, 6.2 Hz, 1H), 2.17 (t, J=20.5 Hz, 2H), 1.53 (d, J=7.0 Hz, 3H). ESI MS [M+H]$^+$ for C$_{19}$H$_{24}$ClFN$_5$O$_9$P$_2$, calcd 582.1, found 582.1.

Example 95

Synthesis of [({[(2R,3S,4R,5R)-5-(6-chloro-4-{[(1R)-1-(3-fluorophenyl)ethyl]amino}-1H-pyrazolo[3,4-d]pyrimidin-1-yl)-3,4-dihydroxyoxolan-2-yl]methoxy}(hydroxy)phosphoryl)-methyl]phosphonic acid

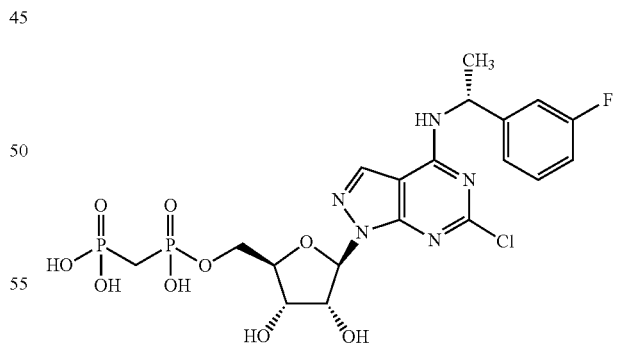

The title compound was synthesized in similar fashion to Example 87. $^1$H NMR (400 MHz, DMSO-d$_6$) δ 9.18 (d, J=7.9 Hz, 1H), 8.31 (t, J=0.9 Hz, 1H), 7.43-7.32 (m, 1H), 7.23 (d, J=8.8 Hz, 2H), 7.07 (t, J=8.6 Hz, 1H), 6.00 (d, J=4.3 Hz, 1H), 5.42 (t, J=7.3 Hz, 1H), 4.51 (t, J=4.5 Hz, 1H), 4.26 (t, J=4.7 Hz, 1H), 4.11-3.98 (m, 2H), 3.88 (t, J=8.6 Hz, 1H), 2.17 (t, J=20.5 Hz, 2H), 1.52 (d, J=7.0 Hz, 3H). ESI MS [M+H]$^+$ for C$_{19}$H$_{24}$ClFN$_5$O$_9$P$_2$, calcd 582.1, found 582.1.

Example 96

Synthesis of [({[(2R,3S,4R,5R)-5-(6-chloro-4-{[(1S)-1-(4-fluorophenyl)ethyl]amino}-1H-pyrazolo[3,4-d]pyrimidin-1-yl)-3,4-dihydroxyoxolan-2-yl]methoxy}(hydroxy)phosphoryl)-methyl]phosphonic acid

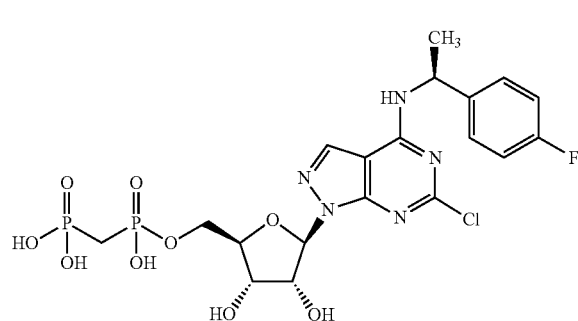 [SMILES: C[C@H](Nc1nc(Cl)nc2c1cnn2[C@@H]1O[C@H](COP(=O)(O)CP(=O)(O)O)[C@@H](O)[C@H]1O)c1ccc(F)cc1]

The title compound was synthesized in similar fashion to Example 87. $^1$H NMR (400 MHz, DMSO-$d_6$) δ 9.16 (d, J=7.9 Hz, 1H), 8.30 (d, J=1.2 Hz, 1H), 7.42 (dd, J=8.4, 5.4 Hz, 2H), 7.15 (td, J=8.9, 1.2 Hz, 2H), 6.00 (d, J=4.2 Hz, 1H), 5.40 (t, J=7.3 Hz, 1H), 4.48 (t, J=4.8 Hz, 1H), 4.25 (t, J=4.5 Hz, 1H), 4.18-3.95 (m, 2H), 3.95-3.82 (m, 1H), 2.16 (t, J=20.4 Hz, 2H), 1.52 (d, J=7.2 Hz, 3H). ESI MS [M+H]$^+$ for $C_{19}H_{24}ClFN_5O_9P_2$, calcd 582.1, found 582.1.

Example 97

Synthesis of [({[(2R,3S,4R,5R)-5-(6-chloro-4-{[(1R)-1-(4-fluorophenyl)ethyl]amino}-1H-pyrazolo[3,4-d]pyrimidin-1-yl)-3,4-dihydroxyoxolan-2-yl]methoxy}(hydroxy)-phosphoryl)methyl]phosphonic acid

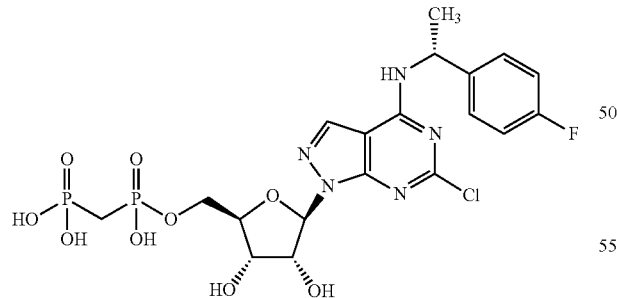

The title compound was synthesized in similar fashion to Example 87. $^1$H NMR (400 MHz, DMSO-$d_6$) δ 9.16 (d, J=7.9 Hz, 1H), 8.30 (t, J=0.9 Hz, 1H), 7.42 (dt, J=6.1, 3.2 Hz, 2H), 7.23-7.08 (m, 2H), 6.00 (d, J=4.3 Hz, 1H), 5.40 (t, J=7.2 Hz, 1H), 4.50 (t, J=4.5 Hz, 1H), 4.26 (t, J=4.7 Hz, 1H), 4.15-3.98 (m, 2H), 3.87 (q, J=8.1, 5.5 Hz, 1H), 2.16 (t, J=20.4 Hz, 2H), 1.52 (d, J=6.9 Hz, 3H). ESI MS [M+H]$^+$ for $C_{19}H_{24}ClFN_5O_9P_2$, calcd 582.1, found 582.1.

Example 98

Synthesis of [({[(2R,3S,4R,5R)-5-(6-chloro-4-{[(2-chlorophenyl)methyl]amino}-1H-pyrazolo[3,4-d]pyrimidin-1-yl)-3,4-dihydroxyoxolan-2-yl]methoxy}(hydroxy)-phosphoryl)methyl]phosphonic acid

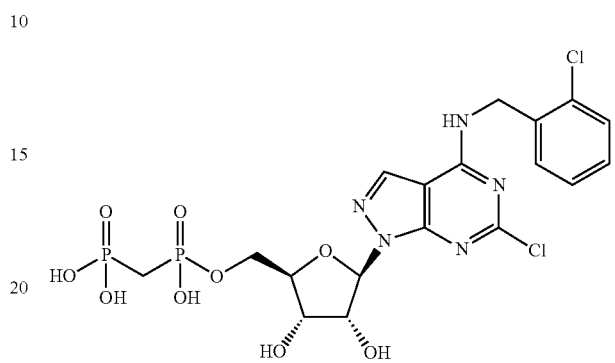

The title compound was synthesized in similar fashion to Example 87. $^1$H NMR (400 MHz, DMSO-$d_6$) δ 9.29 (s, 1H), 8.29 (d, J=1.9 Hz, 1H), 7.48 (dd, J=5.9, 3.1 Hz, 1H), 7.43 (d, J=5.9 Hz, 1H), 7.32 (dt, J=6.6, 2.5 Hz, 2H), 6.07-6.00 (m, 1H), 4.84-4.69 (m, 2H), 4.51 (d, J=5.0 Hz, 1H), 4.27 (s, 1H), 4.06 (s, 2H), 3.89 (s, 1H), 2.16 (t, J=20.6 Hz, 2H). ESI MS [M+H]$^+$ for $C_{18}H_{22}Cl_2N_5O_9P_2$, calcd 584.0, found 584.1.

Example 99

Synthesis of [({[(2R,3S,4R,5R)-5-(6-chloro-4-{[(2-chlorophenyl)methyl](methyl)amino}-1H-pyrazolo[3,4-d]pyrimidin-1-yl)-3,4-dihydroxyoxolan-2-yl]methoxy}(hydroxy)phosphoryl)methyl]phosphonic acid

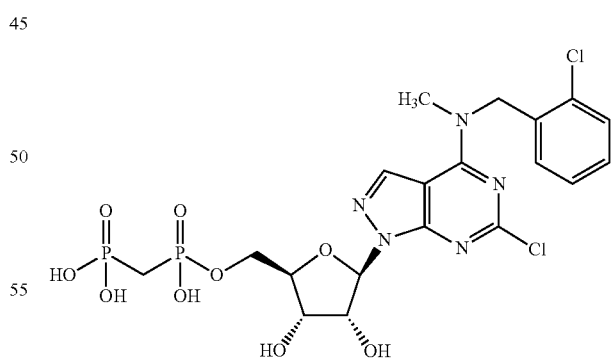

The title compound was synthesized in similar fashion to Example 87. $^1$H NMR (400 MHz, DMSO-$d_6$) δ 8.41 (s, 1H), 7.49 (d, J=7.4 Hz, 1H), 7.38-7.24 (m, 2H), 7.16 (d, J=7.6 Hz, 1H), 6.08 (bs, 1H), 5.04 (bs, 2H), 4.50 (d, J=30.8 Hz, 1H), 4.24 (d, J=39.5 Hz, 1H), 4.06 (s, 2H), 3.89 (s, 1H), 3.37 (d, J=54.8 Hz, 3H), 2.15 (t, J=20.8 Hz, 2H). ESI MS [M+H]$^+$ for $C_{19}H_{24}Cl_2N_5O_9P_2$, calcd 598.0, found 598.1.

Example 100

Synthesis of [({[(2R,3S,4R,5R)-5-(6-chloro-4-{[2-(2-chlorophenyl)ethyl]amino}-1H-pyrazolo[3,4-d]pyrimidin-1-yl)-3,4-dihydroxyoxolan-2-yl]methoxy}(hydroxy)-phosphoryl)methyl]phosphonic acid

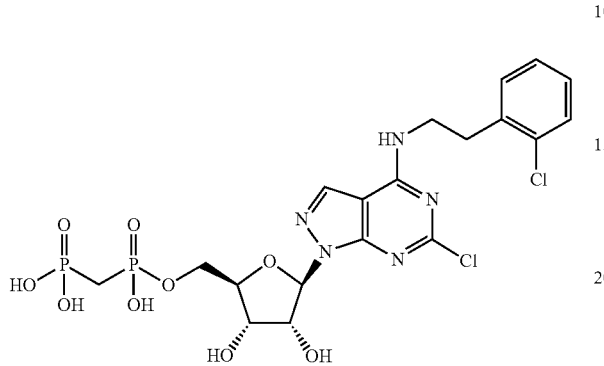

The title compound was synthesized in similar fashion to Example 87. $^1$H NMR (400 MHz, DMSO-d$_6$) δ 8.95 (t, J=5.6 Hz, 1H), 8.28-8.10 (m, 1H), 7.48-7.39 (m, 1H), 7.33 (d, J=6.4 Hz, 1H), 7.29-7.18 (m, 2H), 6.00 (d, J=4.0 Hz, 1H), 4.50 (t, J=4.5 Hz, 1H), 4.25 (t, J=4.5 Hz, 1H), 4.06 (d, J=14.9 Hz, 2H), 3.87 (t, J=5.8 Hz, 1H), 3.69 (q, J=6.8 Hz, 2H), 3.10-3.00 (m, 2H), 2.15 (t, J=20.4 Hz, 2H). ESI MS [M+H]$^+$ for C$_{19}$H$_{24}$Cl$_2$N$_5$O$_9$P$_2$, calcd 598.0, found 598.2.

Example 101

Synthesis of [({[(2R,3S,4R,5R)-5-{4-[benzyl(methyl)amino]-6-chloro-1H-pyrazolo[3,4-d]pyrimidin-1-yl}-3,4-dihydroxyoxolan-2-yl]methoxy}(hydroxy)phosphoryl)methyl]phosphonic acid

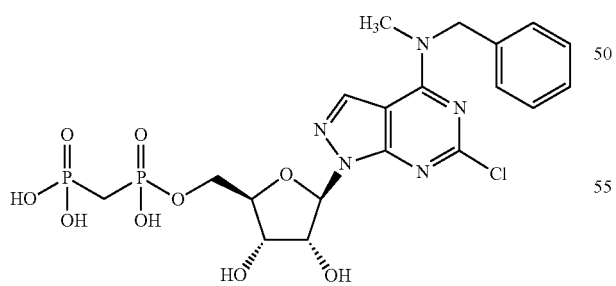

The title compound was synthesized in similar fashion to Example 87. $^1$H NMR (400 MHz, DMSO-d$_6$) δ 8.35 (s, 1H), 7.30 (dd, J=20.4, 7.5 Hz, 5H), 6.07 (bs, 1H), 4.99 (bs, 1H), 4.53 (bs, 1H), 4.28 (bs, 1H), 4.05 (s, 3H), 3.88 (s, 1H), 3.37-3.24 (m, 3H), 2.14 (t, J=20.9 Hz, 3H). ESI MS [M+H]$^+$ for C$_{19}$H$_{25}$ClN$_5$O$_9$P$_2$, calcd 564.1, found 564.1.

Example 102

Synthesis of [({[(2R,3S,4R,5R)-5-{6-chloro-4-[cyclopentyl(methyl)amino]-1H-pyrazolo[3,4-d]pyrimidin-1-yl}-3,4-dihydroxyoxolan-2-yl]methoxy}(hydroxy)phosphoryl)methyl]phosphonic acid

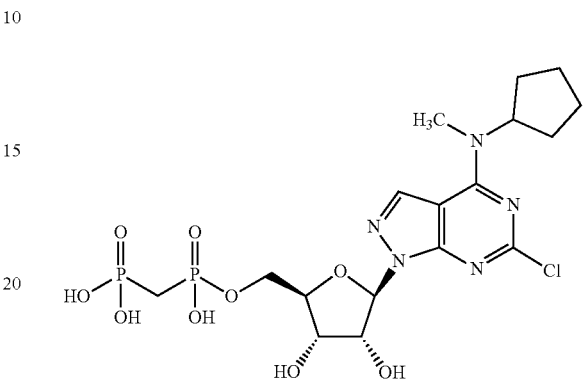

The title compound was synthesized in similar fashion to Example 87. $^1$H NMR (400 MHz, DMSO-d$_6$) δ 8.31 (s, 1H), 6.06 (s, 1H), 4.51 (d, J=4.7 Hz, 1H), 4.28 (d, J=5.1 Hz, 1H), 4.14-3.96 (m, 2H), 3.88 (s, 1H), 3.21 (s, 3H), 2.14 (t, J=19.9 Hz, 2H), 1.67 (bs, 8H). ESI MS [M+H]$^+$ for C$_{17}$H$_{27}$ClN$_5$O$_9$P$_2$, calcd 542.1, found 542.2.

Example 103

Synthesis of [({[(2R,3S,4R,5R)-5-[6-chloro-4-(methylamino)-1H-pyrazolo[3,4-d]pyrimidin-1-yl]-3,4-dihydroxyoxolan-2-yl]methoxy}(hydroxy)phosphoryl)methyl]phosphonic acid

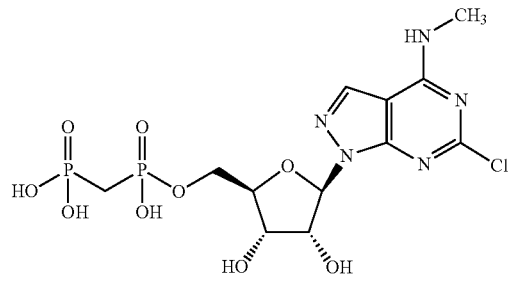 [SMILES: CNc1nc(Cl)nc2c1cnn2[C@@H]1O[C@H](COP(=O)(O)CP(=O)(O)O)[C@@H](O)[C@H]1O]

The title compound was synthesized in similar fashion to Example 87. $^1$H NMR (400 MHz, DMSO-d$_6$) δ 8.82 (s, 1H), 8.16 (s, 1H), 6.01 (bs, 1H), 4.50 (d, J=5.9 Hz, 1H), 4.26 (bs, 1H), 4.05 (bs, 2H), 3.88 (bs, 1H), 2.95 (d, J=4.6 Hz, 3H), 2.15 (t, J=20.4 Hz, 2H). ESI MS [M+H]$^+$ for C$_{12}$H$_{19}$ClN$_5$O$_9$P$_2$, calcd 474.0, found 474.2.

Example 104

Synthesis of [({[(2R,3S,4R,5R)-5-(6-chloro-4-{[(1R)-2,2,2-trifluoro-1-phenylethyl]amino}-1H-pyrazolo[3,4-d]pyrimidin-1-yl)-3,4-dihydroxyoxolan-2-yl]methoxy}(hydroxy)phosphoryl)methyl]phosphonic acid

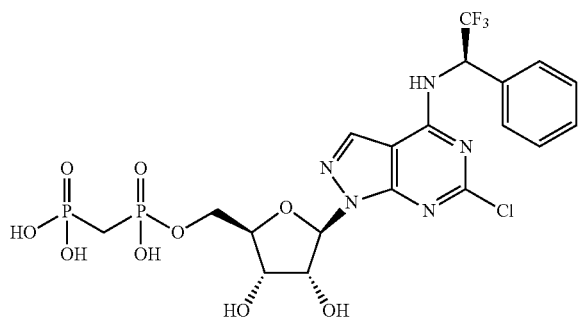 [SMILES: O=P(O)(O)CP(=O)(O)OC[C@H]1O[C@@H](n2ncc3c(N[C@H](c4ccccc4)C(F)(F)F)nc(Cl)nc32)[C@H](O)[C@@H]1O]

The title compound was synthesized in similar fashion to Example 87. $^1$H NMR (400 MHz, DMSO-$d_6$) δ 9.82 (d, J=9.3 Hz, 1H), 8.51 (s, 1H), 7.65 (d, J=7.2 Hz, 2H), 7.56-7.31 (m, 3H), 6.33 (p, J=8.8 Hz, 1H), 6.04 (d, J=4.2 Hz, 1H), 4.50 (t, J=4.4 Hz, 1H), 4.26 (t, J=4.6 Hz, 1H), 4.16-4.00 (m, 2H), 3.90 (dd, J=10.6, 5.8 Hz, 1H), 2.18 (t, J=20.5 Hz, 2H). ESI MS [M−H]$^-$ for $C_{19}H_{21}ClF_3N_5O_9P_2$, calcd 616.1, found 616.2.

Example 105

Synthesis of [({[(2R,3S,4R,5R)-5-(6-chloro-4-{[(3S)-oxolan-3-yl]amino}-1H-pyrazolo[3,4-d]pyrimidin-1-yl)-3,4-dihydroxyoxolan-2-yl]methoxy}(hydroxy)phosphoryl)methyl]phosphonic acid

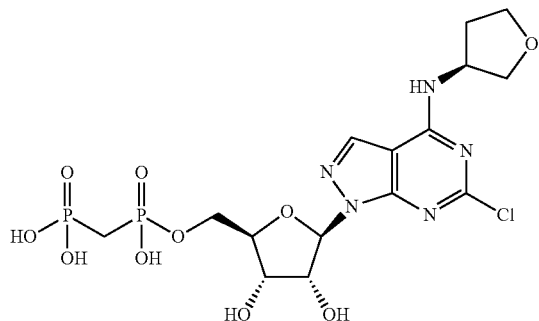 [SMILES: O=P(O)(O)CP(=O)(O)OC[C@H]1O[C@@H](n2ncc3c(N[C@H]4CCOC4)nc(Cl)nc32)[C@H](O)[C@@H]1O]

The title compound was synthesized in similar fashion to Example 87. $^1$H NMR (400 MHz, DMSO-$d_6$) δ 8.95 (d, J=6.4 Hz, 1H), 8.26 (s, 1H), 6.01 (d, J=4.2 Hz, 1H), 4.69-4.59 (m, 1H), 4.50 (t, J=4.2 Hz, 1H), 4.26 (t, J=4.5 Hz, 1H), 4.15-3.99 (m, 2H), 3.95-3.81 (m, 3H), 3.74 (d, J=7.9 Hz, 1H), 3.67-3.58 (m, 1H), 2.35-2.06 (m, 3H), 1.98-1.80 (m, 1H). ESI MS [M−H]$^-$ for $C_{15}H_{22}ClN_5O_{10}P_2$, calcd 528.1, found 528.2.

Example 106

Synthesis of [({[(2R,3S,4R,5R)-5-[6-chloro-4-(cyclopentylamino)-1H-pyrazolo[3,4-d]pyrimidin-1-yl]-3,4-dihydroxyoxolan-2-yl]methoxy}({[(propan-2-yloxy)carbonyl]oxy}methoxy)phosphoryl)methyl]({[(propan-2-yloxy)carbonyl]oxy}methoxy)phosphinic acid

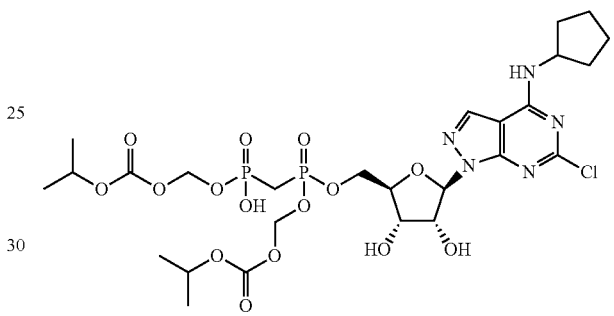

The title compound was synthesized in similar fashion to Example 69. $^1$H NMR (400 MHz, DMSO-$d_6$) δ 8.71-8.60 (m, 1H), 8.26-8.15 (m, 1H), 6.02-5.96 (m, 1H), 5.60-5.38 (m, 5H), 4.87-4.68 (m, 2H), 4.51-4.37 (m, 2H), 4.33-3.79 (m, 5H), 2.74-2.53 (m, 2H), 2.07-1.89 (m, 2H), 1.79-1.42 (m, 7H), 1.27-1.12 (m, 12H). ESI MS [M−H]$^-$ for $C_{26}H_{40}ClN_5O_{15}P_2$, calcd 758.2, found 758.3.

Example 107

Synthesis of [({[(2R,3S,4R,5R)-5-(6-chloro-4-{[(1S)-1-phenylethyl]amino}-1H-pyrazolo[3,4-d]pyrimidin-1-yl)-3,4-dihydroxyoxolan-2-yl]methoxy}({[(propan-2-yloxy)carbonyl]oxy}-methoxy)phosphoryl)methyl]({[(propan-2-yloxy)carbonyl]oxy}methoxy)phosphinic acid

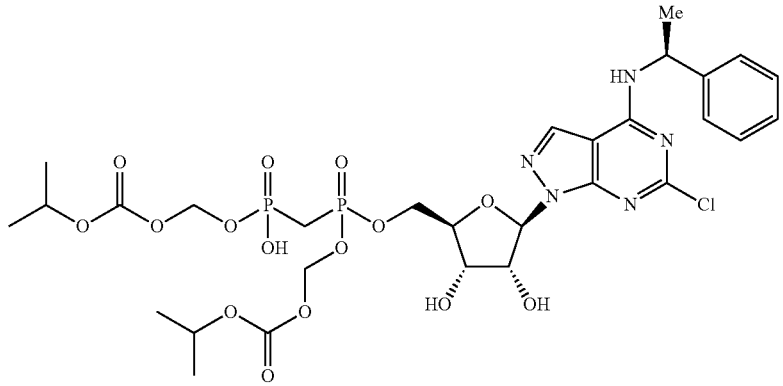 [SMILES: CC(C)OC(=O)OCOP(=O)(O)CP(=O)(OCOC(=O)OC(C)C)OC[C@H]1O[C@@H](n2ncc3c(N[C@@H](C)c4ccccc4)nc(Cl)nc32)[C@H](O)[C@@H]1O]

The title compound was synthesized in similar fashion to Example 69. $^1$H NMR (400 MHz, DMSO-$d_6$) δ 9.17 (d, J=7.9 Hz, 1H), 8.32-8.27 (m, 1H), 7.42-7.28 (m, 4H), 7.26-7.20 (m, 1H), 6.01 (d, J=3.7 Hz, 1H), 5.58-5.32 (m, 6H), 4.84-4.69 (m, 2H), 4.49-4.37 (m, 1H), 4.37-3.81 (m, 5H), 2.72-2.52 (m, 1H), 1.53 (d, J=6.9 Hz, 3H), 1.28-1.17 (m, 12H). ESI MS [M−H]$^−$ for $C_{29}H_{40}ClN_5O_5P_2$, calcd 794.2, found 794.2.

Example 108

Synthesis of [({[(2R,3R,4S,5R)-5-[4-(benzylamino)-6-chloro-1H-pyrazolo[3,4-d]pyrimidin-1-yl]-4-fluoro-3-hydroxyoxolan-2-yl]methoxy}(hydroxy)phosphoryl)methyl]phosphonic acid

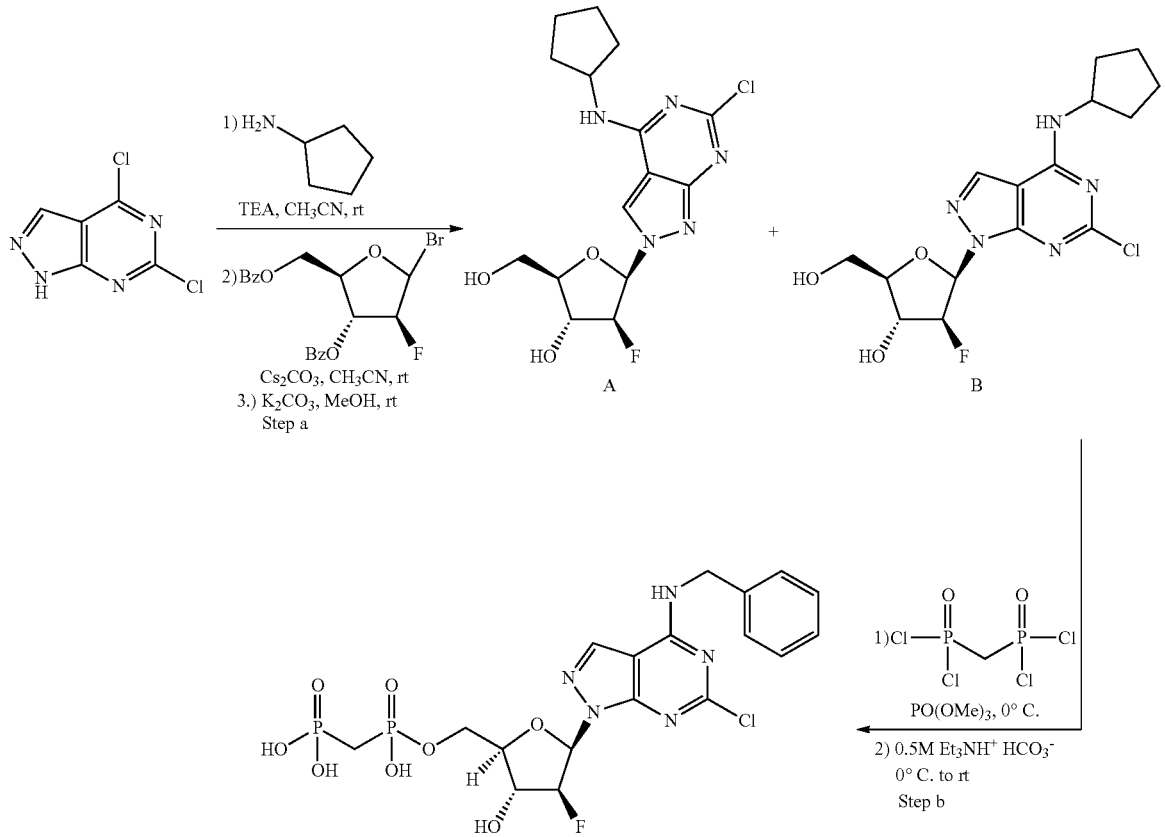

Step a: 4,6-Dichloro-1H-pyrazolo[3,4-d]pyrimidine (1.0 g, 5.3 mmol) was dissolved in anhydrous CH$_3$CN (10 mL) and cyclopentylamine (478 mg, 5.6 mmol, 1.05 equiv.) was added followed by TEA (779 µL, 5.6 mmol, 1.05 equiv.). The mixture was stirred at room temperature for overnight, then anhydrous Cs$_2$CO$_3$ (3.4 g, 10.6 mmol, 2 equiv.) and the bromide (2.2 g, 5.3 mmol) were added. Reaction mixture was stirred at room temperature for overnight then evaporated. Crude residue was dissolved in MeOH (20 mL) and anhydrous K$_2$CO$_3$ (2.2 g, 15.9 mmol, 3 equiv.) was added. The mixture was stirred at room temperature for overnight, evaporated with silica gel and purified by column chromatography (SiO$_2$, Hex→100% EtOAc) to give product B first (800 mg, 41%) and then product A (600 mg, 30%). For B: ESI MS [M+H]$^+$ for $C_{15}H_{20}ClFN_5O_3$, calcd 372.1, found 372.2.

Step b: The phosphonylation step was carried out in similar fashion to Example 1 using product B from Step a: $^1$H NMR (400 MHz, DMSO-$d_6$) δ 8.76 (d, J=7.2 Hz, 1H), 8.29 (s, 1H), 6.52 (d, J=6.5 Hz, 1H), 5.50-5.29 (m, 1H), 4.75 (dt, J=18.7, 7.5 Hz, 1H), 4.43 (h, J=6.9 Hz, 1H), 4.31-4.22 (m, 1H), 4.18-4.05 (m, 1H), 4.04-3.92 (m, 1H), 2.20 (t, J=20.5 Hz, 2H), 2.05-1.93 (m, 2H), 1.80-1.46 (m, 6H). ESI MS [M+H]$^+$ for $C_{16}H_{24}ClFN_5O_8P_2$, calcd 530.1, found 530.2.

Example 109

Synthesis of [({[(2R,3R,4S,5R)-5-(6-chloro-4-{[(1S)-1-phenylethyl]amino}-1H-pyrazolo[3,4-d]pyrimidin-1-yl)-4-fluoro-3-hydroxyoxolan-2-yl]methoxy}(hydroxy)phosphoryl)-methyl]phosphonic acid

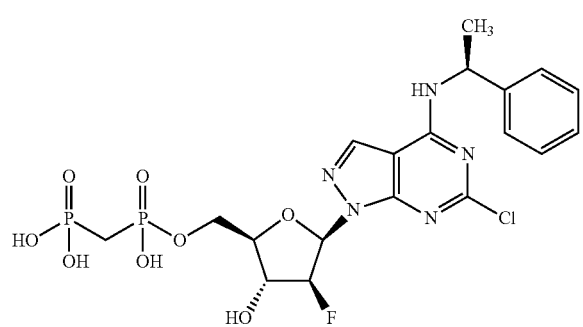 [SMILES: C[C@H](Nc1nc(Cl)nc2c1cnn2[C@@H]1O[C@H](COP(=O)(O)CP(=O)(O)O)[C@@H](O)[C@@H]1F)c1ccccc1]

The title compound was synthesized in similar fashion to Example 108. $^1$H NMR (400 MHz, DMSO-$d_6$) δ 9.19 (d, J=8.1 Hz, 1H), 8.33 (s, 1H), 7.40 (d, J=7.9 Hz, 2H), 7.33 (t, J=7.5 Hz, 2H), 7.23 (t, J=7.4 Hz, 1H),) 6.34 (dd, J=14.3, 4.6 Hz, 1H), 5.39 (bs, 1H), 5.31-5.12 (m, 1H), 5.14 (bs, 1H), 4.48 (dt, J=18.5, 4.5 Hz, 1H), 4.17 (s, 3H), 4.01 (d, J=5.2 Hz, 2H), 2.24 (t, J=20.4 Hz, 3H), 1.51 (d, J=7.0 Hz, 3H). ESI MS [M+H]$^+$ for $C_{19}H_{24}ClFN_5O_8P_2$, calcd 566.1, found 566.1.

Example 110

Synthesis of [({[(2R,3R,4S,5R)-5-(6-chloro-4-{[(1R)-1-phenylethyl]amino}-1H-pyrazolo[3,4-d]pyrimidin-1-yl)-4-fluoro-3-hydroxyoxolan-2-yl]methoxy}(hydroxy)phosphoryl)-methyl]phosphonic acid

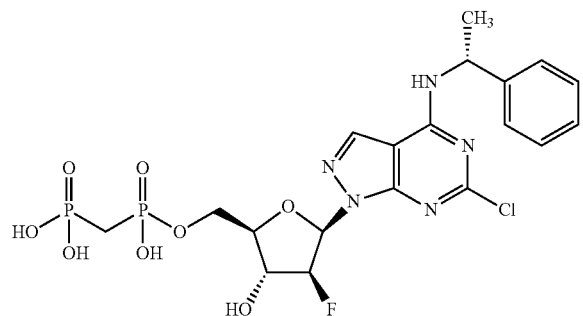 [SMILES: C[C@@H](Nc1nc(Cl)nc2c1cnn2[C@@H]1O[C@H](COP(=O)(O)CP(=O)(O)O)[C@@H](O)[C@@H]1F)c1ccccc1]

The title compound was synthesized in similar fashion to Example 108. $^1$H NMR (400 MHz, DMSO-$d_6$) δ 9.18 (d, J=8.0 Hz, 1H), 8.33 (d, J=1.2 Hz, 1H), 7.40 (d, J=7.9 Hz, 2H), 7.33 (t, J=7.3 Hz, 2H), 7.24 (t, J=7.6 Hz, 1H), 6.50 (d, J=6.5 Hz, 1H), 5.51-5.23 (m, 2H), 4.82-4.66 (m, 1H), 4.22 (bs, 1H), 4.13-4.02 (m, 1H), 3.94 (bs, 1H), 2.17 (t, J=20.5 Hz, 2H), 1.53 (d, J=7.1 Hz, 3H). ESI MS [M+H]$^+$ for $C_{19}H_{24}ClFN_5O_8P_2$, calcd 566.1, found 566.2.

Example 111

Synthesis of [({[(2R,3R,4S,5R)-5-(6-chloro-4-{[(1S)-1-(2-fluorophenyl)ethyl]amino}-1H-pyrazolo[3,4-d]pyrimidin-1-yl)-4-fluoro-3-hydroxyoxolan-2-yl]methoxy}(hydroxy)-phosphoryl)methyl]phosphonic acid

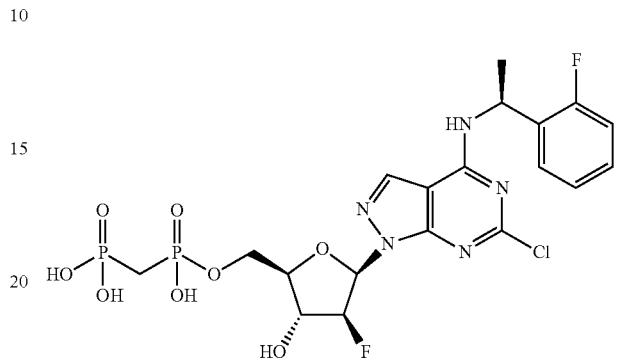

The title compound was synthesized in similar fashion to Example 108. $^1$H NMR (400 MHz, DMSO-$d_6$) δ 9.27 (d, J=7.6 Hz, 1H), 8.36 (s, 1H), 7.48-7.40 (m, 1H), 7.37-7.25 (m, 1H), 7.22-7.13 (m, 2H), 6.51 (d, J=6.6 Hz, 1H), 5.59 (p, J=7.1 Hz, 1H), 5.49-5.26 (m, 1H), 4.74 (dt, J=18.4, 7.6 Hz, 1H), 4.30-4.17 (m, 1H), 4.15-4.02 (m, 1H), 3.99-3.90 (m, 1H), 2.17 (t, J=20.5 Hz, 2H), 1.54 (d, J=7.0 Hz, 3H). ESI MS [M+H]$^+$ for $C_{19}H_{23}ClF_2N_5O_8P_2$, calcd 584.1, found 584.2.

Example 112

Synthesis of [({[(2R,3R,4S,5R)-5-(6-chloro-4-{[(1R)-1-(2-fluorophenyl)ethyl]amino}-1H-pyrazolo[3,4-d]pyrimidin-1-yl)-4-fluoro-3-hydroxyoxolan-2-yl]methoxy}(hydroxy)-phosphoryl)methyl]phosphonic acid

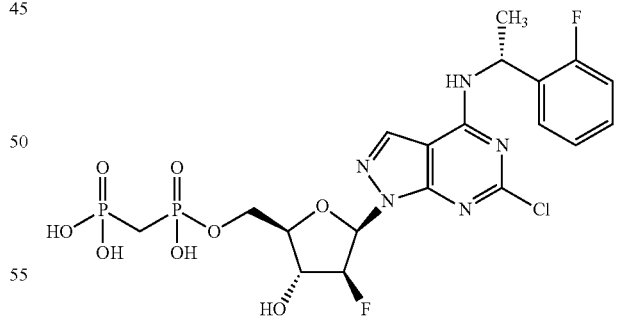

The title compound was synthesized in similar fashion to Example 108. $^1$H NMR (400 MHz, DMSO-$d_6$) δ 9.37-9.16 (m, 1H), 8.36 (d, J=3.4 Hz, 1H), 7.44 (d, J=8.4 Hz, 1H), 7.29 (t, J=7.0 Hz, 1H), 7.18 (dt, J=10.6, 5.6 Hz, 2H), 6.51 (t, J=4.8 Hz, 1H), 5.60 (t, J=6.8 Hz, 1H), 5.53-5.22 (m, 1H), 4.84-4.64 (m, 1H), 4.31-4.16 (m, 1H), 4.16-4.00 (m, 1H), 3.94 (p, J=3.7 Hz, 1H), 2.18 (t, J=20.4 Hz, 2H), 1.54 (d, J=7.2 Hz, 3H). ESI MS [M+H]$^+$ for $C_{19}H_{23}ClF_2N_5O_8P_2$, calcd 584.1, found 584.2.

Example 113

Synthesis of [({[(2R,3R,4S,5R)-5-(6-chloro-4-{[(1S)-1-(3-fluorophenyl)ethyl]amino}-1H-pyrazolo[3,4-d]pyrimidin-1-yl)-4-fluoro-3-hydroxyoxolan-2-yl]methoxy}(hydroxy)-phosphoryl)methyl]phosphonic acid

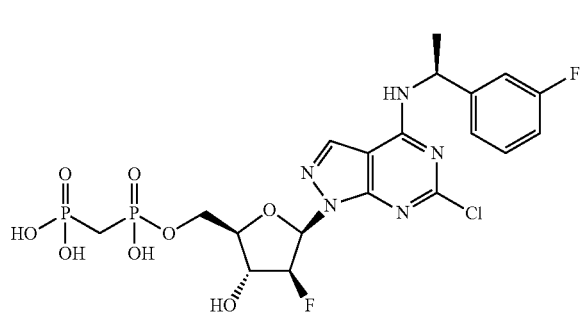 [SMILES: C[C@H](Nc1nc(Cl)nc2c1cnn2[C@@H]1O[C@H](COP(=O)(O)CP(=O)(O)O)[C@@H](O)[C@@H]1F)c1cccc(F)c1]

The title compound was synthesized in similar fashion to Example 108. $^1$H NMR (400 MHz, DMSO-$d_6$) δ 9.21 (d, J=7.8 Hz, 1H), 8.33 (s, 1H), 7.46-7.30 (m, 1H), 7.27-7.16 (m, 2H), 7.12-7.00 (m, 1H), 6.51 (d, J=6.5 Hz, 1H), 5.49-5.26 (m, 2H), 4.74 (dt, J=18.4, 7.6 Hz, 1H), 4.29-4.18 (m, 1H), 4.14-4.02 (m, 11H), 4.00-3.89 (m, 1H), 2.17 (t, J=20.5 Hz, 2H), 1.54 (d, J=7.0 Hz, 3H). ESI MS [M+H]$^+$ for $C_{19}H_{23}ClF_2N_5O_8P_2$, calcd 584.1, found 584.2.

Example 114

Synthesis of [({[(2R,3R,4S,5R)-5-(6-chloro-4-{[(1R)-1-(2-fluorophenyl)ethyl]amino}-1H-pyrazolo[3,4-d]pyrimidin-1-yl)-4-fluoro-3-hydroxyoxolan-2-yl]methoxy}(hydroxy)-phosphoryl)methyl]phosphonic acid

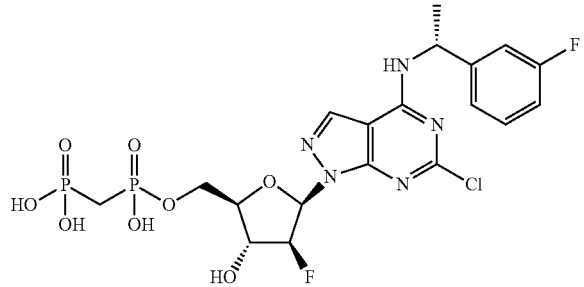 [SMILES: C[C@@H](Nc1nc(Cl)nc2c1cnn2[C@@H]1O[C@H](COP(=O)(O)CP(=O)(O)O)[C@@H](O)[C@@H]1F)c1cccc(F)c1]

The title compound was synthesized in similar fashion to Example 108. $^1$H NMR (400 MHz, DMSO-$d_6$) δ 9.21 (d, J=8.0 Hz, 1H), 8.34 (s, 1H), 7.42-7.32 (m, 1H), 7.27-7.20 (m, 2H), 7.12-7.03 (m, 1H), 6.51 (d, J=6.5 Hz, 1H), 5.49-5.29 (m, 2H), 4.74 (dt, J=18.8, 7.8 Hz, 1H), 4.29-4.18 (m, 1H), 4.15-4.03 (m, 1H), 3.99-3.90 (m, 1H), 2.17 (t, J=20.5 Hz, 2H), 1.54 (d, J=7.0 Hz, 3H). ESI MS [M+H]$^+$ for $C_{19}H_{23}ClF_2N_5O_8P_2$, calcd 584.1, found 584.2.

Example 115

Synthesis of [({[(2R,3R,4S,5R)-5-(6-chloro-4-{[(1S)-1-(4-fluorophenyl)ethyl]amino}-1H-pyrazolo[3,4-d]pyrimidin-1-yl)-4-fluoro-3-hydroxyoxolan-2-yl]methoxy}(hydroxy)-phosphoryl)methyl]phosphonic acid

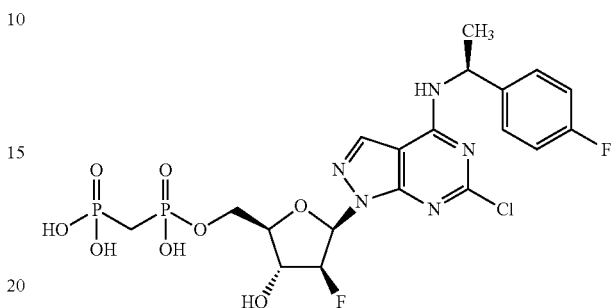

The title compound was synthesized in similar fashion to Example 108. $^1$H NMR (400 MHz, DMSO-$d_6$) δ 9.22 (d, J=7.9 Hz, 1H), 8.34 (s, 1H), 7.45 (dd, J=8.7, 5.6 Hz, 2H), 7.17 (t, J=8.9 Hz, 2H), 6.52 (d, J=6.5 Hz, 1H), 5.53-5.27 (m, 2H), 4.75 (dt, J=18.7, 7.6 Hz, 1H), 4.31-4.20 (m, 1H), 4.17-4.04 (m, 1H), 3.97 (dd, J=7.5, 3.9 Hz, 1H), 2.19 (t, J=20.5 Hz, 2H), 1.54 (d, J=7.0 Hz, 3H). ESI MS [M+H]$^+$ for $C_{19}H_{23}ClF_2N_5O_8P_2$, calcd 584.1, found 584.2.

Example 116

Synthesis of [({[(2R,3R,4S,5R)-5-(6-chloro-4-{[(1R)-1-(4-fluorophenyl)ethyl]amino}-1H-pyrazolo[3,4-d]pyrimidin-1-yl)-4-fluoro-3-hydroxyoxolan-2-yl]methoxy}(hydroxy)phosphoryl)methyl]phosphonic acid

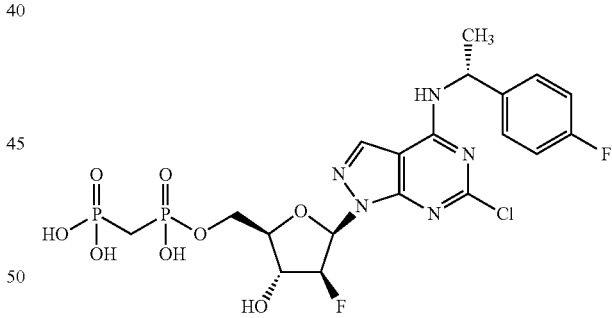

The title compound was synthesized in similar fashion to Example 108. $^1$H NMR (400 MHz, DMSO-$d_6$) δ 9.21 (d, J=7.9 Hz, 1H), 8.34 (s, 1H), 7.54-7.37 (m, 2H), 7.17 (t, J=8.8 Hz, 2H), 6.52 (d, J=6.6 Hz, 1H), 5.60-5.23 (m, 2H), 4.76 (dt, J=18.7, 7.6 Hz, 1H), 4.24 (dt, J=7.4, 4.8 Hz, 1H), 4.09 (dt, J=10.9, 7.4 Hz, 1H), 3.96 (dt, J=10.7, 5.3 Hz, 1H), 2.19 (t, J=20.5 Hz, 2H), 1.54 (d, J=7.1 Hz, 3H). ESI MS [M+H]$^+$ for $C_{19}H_{23}ClF_2N_5O_8P_2$, calcd 584.1, found 584.2.

Example 117

Synthesis of [({[(2R,3S,4R,5R)-5-[5-chloro-7-(cyclopentylamino)-3H-imidazo[4,5-b]pyridin-3-yl]-3,4-dihydroxyoxolan-2-yl]methoxy}(hydroxy)phosphoryl)methyl]phosphonic acid

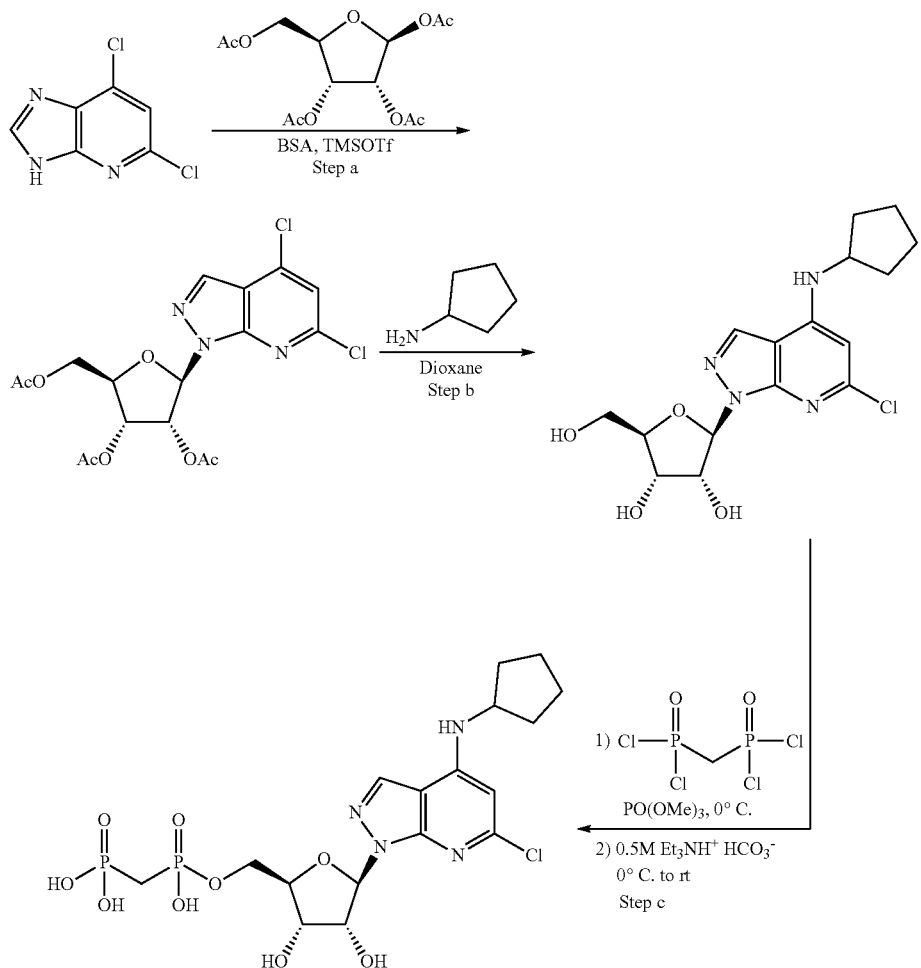

Step a: To a solution of 5,7-Dichloroimidazo[4,5-b]pyridine (376 mg, 2 mmol) in MeCN (14 mL) at r.t. was added N,O-Bis(trimethylsilyl)acetamide (0.523 mL, 2.14 mmol) dropwise and the reaction mixture heated to 85° C. for 1 hour. The mixture was cooled to r.t. and a solution of beta-D-Ribofuranose 1,2,3,5-tetraacetate (726 mg, 2.28 mmol) in MeCN (7 mL) and trimethylsilyl trifluoromethanesulfonate (0.471 mL, 2.60 mmol) were added sequentially dropwise. The reaction mixture was heated to 85° C. for 4 hours. The mixture was cooled and aqueous saturated sodium bicarbonate (50 mL) was added, subsequently extracted three times with EtOAc (100 mL), dried over sodium sulfate and concentrated.

Step b: To the residue was added dioxane (2 mL) and cyclopentylamine (0.987 mL, 10 mmol). The mixture was heated to 100° C. for 16 hours. The reaction mixture was loaded onto silica gel and purified by silica gel chromatography (0-10% MeOH in DCM) to afford the desired product as a brown solid (298 mg, 40%).

Step c: The title compound was synthesized as a white solid (10 mg; 6%) in similar fashion to Example 1. $^1$H NMR (400 MHz, DMSO-$d_6$) δ 8.40 (s, 1H), 7.12 (d, J=7.3 Hz, 1H), 6.40 (s, 1H), 5.91 (d, J=5.8 Hz, 1H), 4.53 (t, J=5.4 Hz, 1H), 4.23-4.18 (m, 1H), 4.18-4.05 (m, 3H), 2.26 (t, J=20.5 Hz, 2H), 2.04-1.91 (m, 2H), 1.76-1.64 (m, 2H), 1.64-1.48 (m, 4H). ESI MS [M–H]$^-$ for $C_{17}H_{24}ClN_4O_9P_2$, calcd 525.1, found 525.2.

Example 118

Synthesis of [({[(2R,3R,4S,5R)-5-[5-chloro-7-(cyclopentylamino)-3H-imidazo[4,5-b]pyridin-3-yl]-4-fluoro-3-hydroxyoxolan-2-yl]methoxy}(hydroxy)phosphoryl)-methyl]phosphonic acid

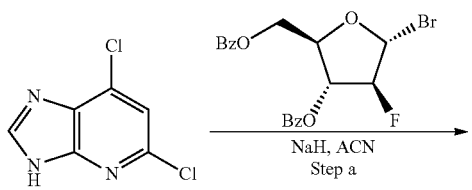

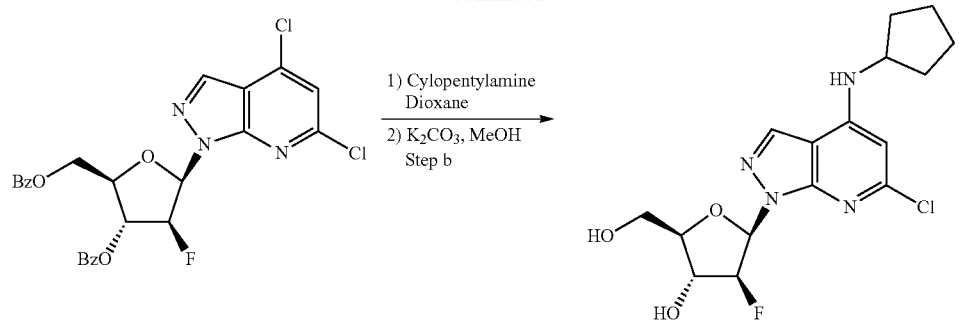

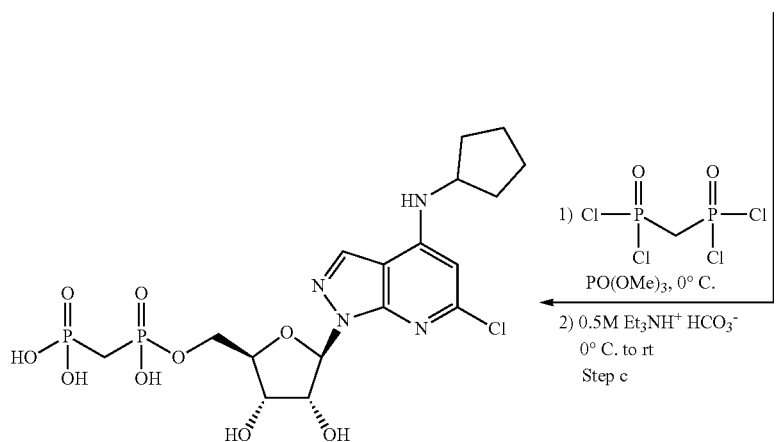

Step a: To a solution of 5,7-Dichloroimidazo[4,5-b]pyridine (564 mg, 3 mmol) in MeCN (18 mL) at r.t. was added sodium hydride (130 mg, 3.24 mmol, 60% suspension in oil). The reaction mixture was stirred at r.t. for 30 minutes. A solution of 2,3,5-Tri-O-benzoyl-D-ribofuranosyl bromide in MeCN (4 mL) was added at r.t. and the reaction mixture stirred at r.t. for 14 hours. The reaction mixture was quenched by addition of methanol (5 mL) and sodium bicarbonate (5 g), filtered through celite, and concentrated.

Step b: 1) To the residue was added dioxane (5 mL) and cyclopentylamine (1.48 mL, 15 mmol). The mixture was heated to 100° C. for 20 hours. The reaction mixture was cooled to r.t.

2) Potassium carbonate (4 g) and methanol (20 mL) were added at r.t. and the reaction mixture was stirred at r.t. for 1 hour. Excess solvent was removed in vacuo and the crude residue was purified by silica gel chromatography (0-15% MeOH in DCM) to afford the desired product as a brown solid (499 mg, 45%).

Step c: The title compound was synthesized as a white solid (26 mg; 10%) in similar fashion to Example 1. $^1$H NMR (400 MHz, DMSO-$d_6$) δ 8.24 (d, J=2.3 Hz, 1H), 7.19 (br s, 1H), 6.42 (dd, J=15.4, 4.4 Hz, 1H), 6.42 (s, 1H), 5.23 (dt, J=52.4, 4.1 Hz, 1H), 4.58-4.44 (m, 1H), 4.19 (t, J=6.1 Hz, 2H), 4.08-3.99 (m, 1H), 2.27 (t, J=20.5 Hz, 2H), 2.04-1.90 (m, 2H), 1.78-1.64 (m, 2H), 1.64-1.47 (m, 4H). ESI MS [M−H]$^-$ for $C_{17}H_{23}ClFN_4O_8P_2$, calcd 527.1, found 527.2.

Example 119

Synthesis of [({[(2R,3S,4R,5R)-5-[6-chloro-4-(cyclopentylamino)-1H-pyrazolo[3,4-b]pyridin-1-yl]-3,4-dihydroxyoxolan-2-yl]methoxy}(hydroxy)phosphoryl)methyl]-phosphonic acid

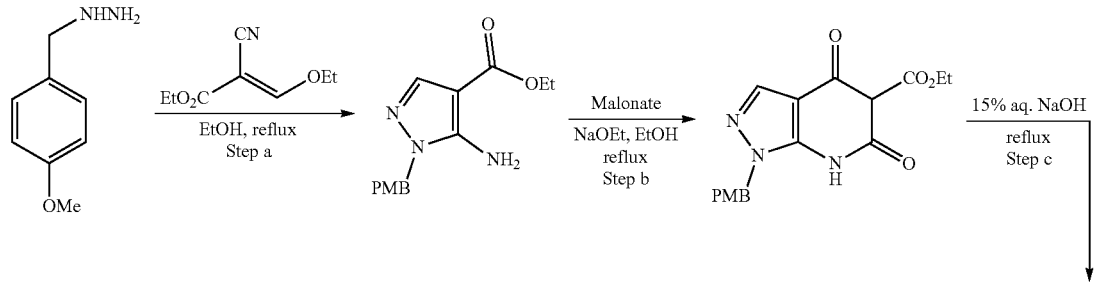

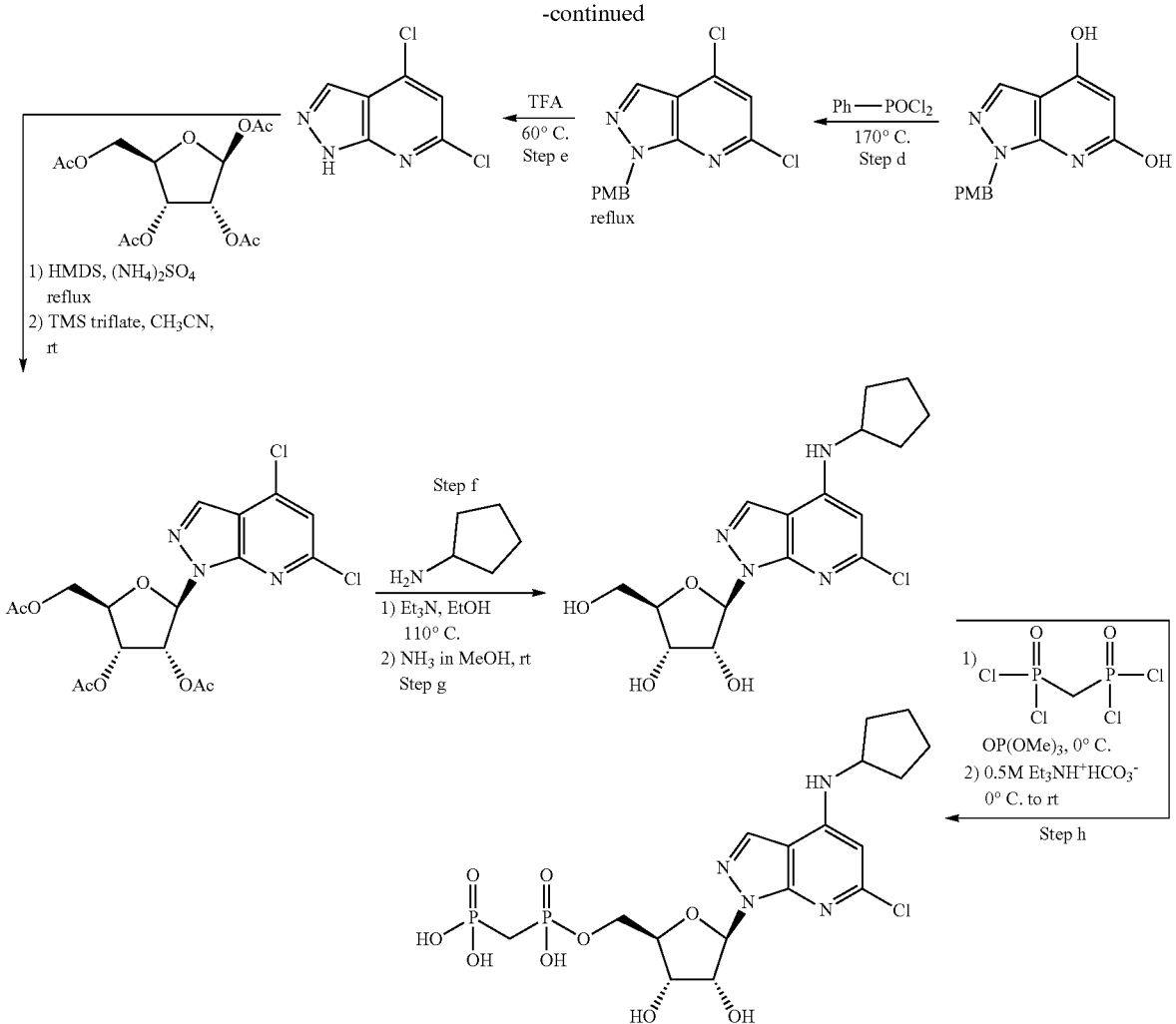

Step a: Ethyl (ethoxymethylene)cyanoacetate (50.5 g, 299.0 mmol) was dissolved in anhydrous EtOH (350 mL) then product hydrazine (50 g, 328.9 mmol, 1.1 equiv.) was added. Reaction mixture was stirred under reflux for overnight, then evaporated. Solid residue was washed with MTBE to give white solid (55.5 g, 63%). ESI MS [M+H]$^+$ for $C_{14}H_{18}N_3O_3$, calcd 276.1, found 276.2.

Step b: Diethyl malonate (90 mL, 0.59 mole, 4 equiv.) was dissolved in anhydrous EtOH (300 mL) and cooled to 0° C. (ice bath). 21% solution of NaOEt in EtOH (220 mL, 0.59 mole, 4 equiv.) was added dropwise (within 10 min.) then the cooling bath was removed and reaction was stirred at room temperature for 15 min. Solid product from Step a (40.4 g, 147 mmol) was added in portions (within 2 min.) and the reaction mixture was stirred under reflux for 5 days, then evaporated. The residue was diluted with $H_2O$ (1.2 L) and neutralized to pH~5 using AcOH. The product was filtered off, washed with $H_2O$ (200 mL) and dried under vacuum (48.4 g, 96%). ESI MS [M+H]$^+$ for $C_{17}H_{18}N_3O_5$, calcd 344.1, found 344.2.

Step c: Product from Step b (48.4 g, 141.1 mmol) was dissolved in 15% aqueous NaOH (500 mL) and stirred under reflux for 5 h. Cooled to 0° C. and carefully neutralized with AcOH until pH~5. White solid was filtered off, washed with $H_2O$ (100 mL) and dried under vacuum (38 g, quant.). ESI MS [M+H]$^+$ for $C_{14}H_{14}N_3O_3$, calcd 272.1, found 272.2.

Step d: The mixture of product from Step c (38 g, 140.2 mmol) and phenylphosphonic dichloride (79.5 mL, 560.8 mmol, 4 equiv.) was stirred at 170° C. for 7 h then cooled to ~80° C. and poured into vigorously stirred ice. Brown, sticky material precipitated that upon extensive stirring turned into solid. Iced cold mixture was neutralized with concentrated aqueous $NH_3$ until pH~7 and the product was extracted using $CH_2Cl_2$ (2×400 mL). Combined organics were dried over $MgSO_4$, filtered and evaporated to give product that was used without further purification (24 g, 55%). ESI MS [M+H]$^+$ for $C_{14}H_{12}Cl_2N_3O$, calcd 308.0, found 308.1.

Step e: Product from Step d (22 g, 71.4 mmol) was dissolved in TFA (75 mL) and stirred at 60° C. for 12 h, then cooled down and poured into $H_2O$ (600 mL). Gray solid was filtered off, washed with saturated $NaHCO_3$, then with $H_2O$ and dried under vacuum. ESI MS [M+H]$^+$ for $C_6H_4Cl_2N_3$, calcd 188.0, found 188.1.

Step f: Step f product was synthesized in similar fashion to Example 87. $^1$H NMR (400 MHz, DMSO-d$_6$) δ 8.55 (s, 1H), 7.72 (s, 1H), 6.48 (d, J=3.0 Hz, 1H), 5.90-5.83 (m, 1H), 5.67-5.61 (m, 1H), 4.46-4.38 (m, 1H), 4.33 (ddd, J=12.1, 3.5, 1.2 Hz, 1H), 4.05 (ddd, J=12.2, 5.1, 1.2 Hz, 1H), 2.09 (s, 3H), 2.06 (s, 3H), 1.96 (s, 3H). ESI MS [M+H]$^+$ for $C_{17}H_{18}Cl_2N_3O_7$, calcd 446.0, found 446.1.

Step g: Step g product was synthesized in similar fashion to Example 87. ESI MS [M+H]⁺ for $C_{16}H_{22}ClN_4O_4$, calcd 369.1, found 369.2.

Step h: The title compound was synthesized in similar fashion to Example 87. ¹H NMR (400 MHz, DMSO-d₆) δ 8.27 (s, 1H), 7.66 (d, J=6.7 Hz, 1H), 6.22 (s, 1H), 6.08 (d, J=4.2 Hz, 1H), 4.51 (t, J=4.7 Hz, 1H), 4.26 (t, J=5.1 Hz, 1H), 4.17-3.83 (m, 4H), 2.17 (t, J=20.5 Hz, 2H), 2.06-1.92 (m, 2H), 1.77-1.45 (m, 6H). ESI MS [M+H]⁺ for $C_{17}H_{26}ClN_4O_9P_2$, calcd 527.1, found 527.2.

Example 120

Synthesis of [({[(2R,3S,4R,5R)-5-(6-chloro-4-{[(1S)-1-phenylethyl]amino}-1H-pyrazolo[3,4-b]pyridin-1-yl)-3,4-dihydroxyoxolan-2-yl]methoxy}(hydroxy)phosphoryl)methyl]-phosphonic acid

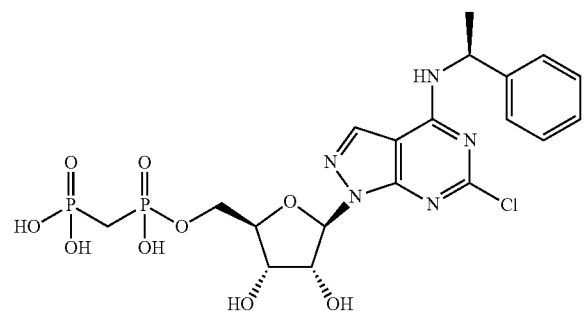 [SMILES: C[C@H](Nc1nc(Cl)nc2c1cnn2[C@@H]1O[C@H](COP(=O)(O)CP(=O)(O)O)[C@@H](O)[C@H]1O)c1ccccc1]

The title compound was synthesized in similar fashion to Example 119. ¹H NMR (400 MHz, DMSO-d₆) δ 8.38 (s, 1H), 8.20 (d, J=7.2 Hz, 1H), 7.42-7.36 (m, 2H), 7.35-7.27 (m, 2H), 7.24-7.18 (m, 1H), 6.08-5.97 (m, 2H), 4.85 (s, 1H), 4.50 (t, J=4.5 Hz, 1H), 4.25 (t, J=4.8 Hz, 1H), 4.14-3.97 (m, 2H), 3.93-3.81 (m, 1H), 2.17 (t, J=20.5 Hz, 2H), 1.52 (d, J=6.2 Hz, 3H). ESI MS [M+H]⁺ for $C_{20}H_{26}ClN_4O_9P_2$, calcd 563.1, found 563.2.

Example 121

Synthesis of [({[(2R,3S,4R,5R)-5-(6-chloro-4-{[(1R)-1-phenylethyl]amino}-1H-pyrazolo[3,4-b]pyridin-1-yl)-3,4-dihydroxyoxolan-2-yl]methoxy}(hydroxy)phosphoryl)methyl]-phosphonic acid

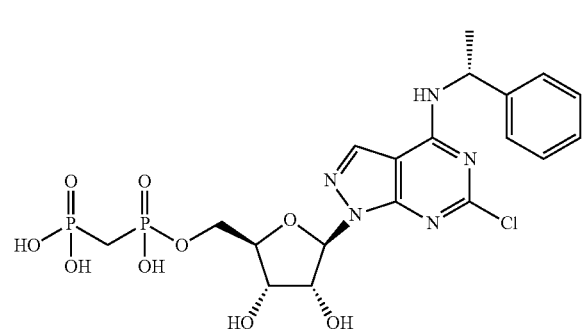 [SMILES: C[C@@H](Nc1nc(Cl)nc2c1cnn2[C@@H]1O[C@H](COP(=O)(O)CP(=O)(O)O)[C@@H](O)[C@H]1O)c1ccccc1]

The title compound was synthesized in similar fashion to Example 119. ¹H NMR (400 MHz, DMSO-d₆) δ 8.38 (s, 1H), 8.20 (d, J=7.2 Hz, 1H), 7.44-7.35 (m, 2H), 7.35-7.28 (m, 2H), 7.25-7.17 (m, 1H), 6.12-5.93 (m, 2H), 4.85 (s, 1H), 4.57-4.48 (m, 1H), 4.25 (t, J=4.9 Hz, 1H), 4.12-3.95 (m, 2H), 3.91-3.79 (m, 1H), 2.17 (t, J=20.5 Hz, 2H), 1.51 (d, J=6.6 Hz, 3H). ESI MS [M+H]⁺ for $C_{20}H_{26}ClN_4O_9P_2$, calcd 563.1, found 563.2.

Example 122

Synthesis of [({[(2R,3S,4R,5R)-5-(6-chloro-4-{[(1S)-1-(2-fluorophenyl)ethyl]amino}-1H-pyrazolo[3,4-b]pyridin-1-yl)-3,4-dihydroxyoxolan-2-yl]methoxy}(hydroxy)phosphoryl)-methyl]phosphonic acid

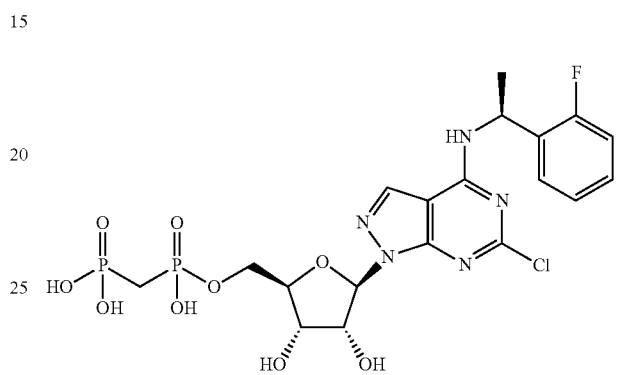

The title compound was synthesized in similar fashion to Example 119. ¹H NMR (400 MHz, DMSO-d₆) δ 8.38 (s, 1H), 8.23 (d, J=6.9 Hz, 1H), 7.42-7.34 (m, 1H), 7.33-7.09 (m, 3H), 6.06 (d, J=4.3 Hz, 1H), 5.97 (s, 1H), 5.04 (s, 1H), 4.53-4.47 (m, 1H), 4.25 (t, J=4.7 Hz, 1H), 4.13-3.97 (m, 2H), 3.92-3.82 (m, 1H), 2.16 (d, J=20.5 Hz, 2H), 1.56 (d, J=6.4 Hz, 3H). ESI MS [M+H]⁺ for $C_{20}H_{25}ClFN_4O_9P_2$, calcd 581.1, found 581.2.

Example 123

Synthesis of [({[(2R,3S,4R,5R)-5-(6-chloro-4-{[(1S)-1-(4-fluorophenyl)ethyl]amino}-1H-pyrazolo[3,4-b]pyridin-1-yl)-3,4-dihydroxyoxolan-2-yl]methoxy}(hydroxy)phosphoryl)-methyl]phosphonic acid

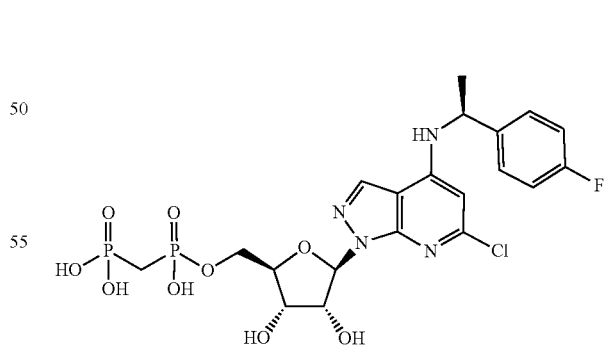

The title compound was synthesized in similar fashion to Example 119. ¹H NMR (400 MHz, DMSO-d₆) δ 8.36 (s, 1H), 8.18 (d, J=7.2 Hz, 1H), 7.46-7.39 (m, 2H), 7.19-7.10 (m, 2H), 6.13-5.99 (m, 2H), 4.89 (s, 1H), 4.53-4.46 (m, 1H), 4.25 (t, J=4.8 Hz, 1H), 4.12-3.97 (m, 2H), 3.92-3.81 (m, 1H), 2.18 (t, J=20.5 Hz, 2H), 1.50 (d, J=7.3 Hz, 3H). ESI MS [M+H]⁺ for $C_{20}H_{25}ClFN_4O_9P_2$, calcd 581.1, found 581.2.

Example 124

Synthesis of [({[(2R,3R,4S,5R)-5-[6-chloro-4-(cyclopentylamino)-1H-pyrazolo[3,4-b]pyridin-1-yl]-4-fluoro-3-hydroxyoxolan-2-yl]methoxy}(hydroxy)phosphoryl)-methyl]phosphonic acid

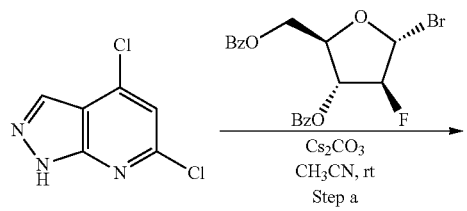

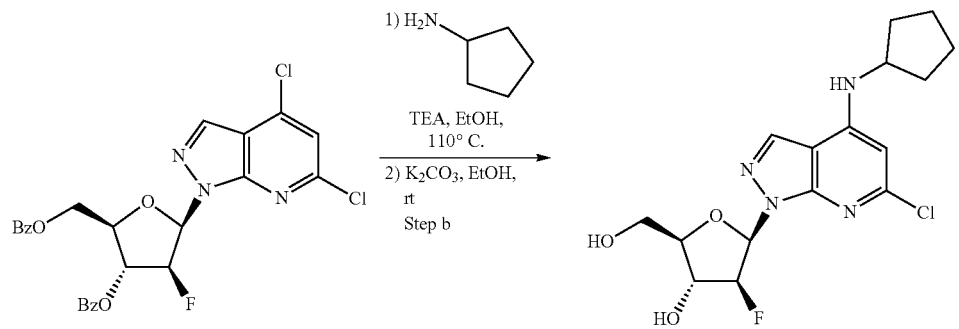

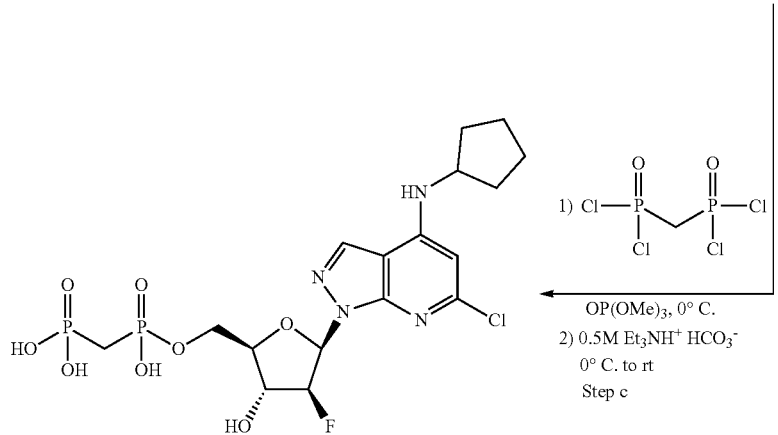

Step a: To the mixture of 4,6-dichloro-1H-pyrazolo[3,4-b]pyridine (2.1 g, 11.1 mmol) and the bromide (4.7 g, 11.1 mmol) in anhydrous $CH_3CN$ (50 mL), $Cs_2CO_3$ (4.3 g, 13.3 mmol, 1.2 equiv.) was added and reaction mixture was stirred at room temperature for overnight. Evaporated with silica gel and purified by column chromatography ($SiO_2$, Hex→Hex:EtOAc, 2:8) to give white solid (2.5 g, 42%). $^1$H NMR (400 MHz, DMSO-$d_6$) δ 8.53 (s, 1H), 8.05 (d, J=8.4 Hz, 2H), 7.91 (d, J=8.4 Hz, 2H), 7.75-7.65 (m, 2H), 7.65-7.51 (m, 3H), 7.49-7.41 (m, 2H), 6.96 (d, J=6.6 Hz, 1H), 6.45 (dt, J=15.8, 7.2 Hz, 1H), 6.19-5.97 (m, 1H), 4.78-4.53 (m, 3H). ESI MS [M+H]$^+$ for $C_{25}H_{19}Cl_2FN_3O_5$, calcd 530.1, found 530.2.

Step b: The mixture of the product from Step a (500 mg, 0.94 mmol), cyclopentylamine (84 mg, 0.99 mmol, 1.05 equiv.), TEA (138 μL, 0.99 mmol, 1.05 equiv.) in anhydrous EtOH (5 mL) was placed in pressure vial and heated to 110° C. for 2 days. Cooled to room temperature and $K_2CO_3$ (262 mg, 1.9 mmol, 2 equiv.) was added and reaction mixture was stirred for overnight. Evaporated with silica gel and purified by column chromatography ($SiO_2$, Hex→100% EtOAc) to give white solid (170 mg, 49%). $^1$H NMR (400 MHz, DMSO-$d_6$) δ 8.28 (s, 1H), 7.66 (d, J=6.9 Hz, 1H), 6.53 (d, J=6.6 Hz, 1H), 6.23 (s, 1H), 5.80 (d, J=5.7 Hz, 1H), 5.45-5.23 (m, 1H), 4.82-4.61 (m, 2H), 3.98 (s, 1H), 3.80-3.50 (m, 3H), 2.09-1.89 (m, 2H), 1.76-1.46 (m, 6H). ESI MS [M+H]$^+$ for $C_{16}H_{21}ClFN_4O_3$, calcd 371.1, found 371.3.

Step c: The title compound was synthesized in similar fashion to Example 1. $^1$H NMR (400 MHz, DMSO-$d_6$) δ 8.30 (s, 1H), 7.69 (d, J=6.7 Hz, 1H), 6.55 (d, J=6.6 Hz, 1H), 6.23 (s, 1H), 5.48-5.25 (m, 1H), 4.77 (dt, J=18.1, 7.6 Hz, 1H), 4.28-4.18 (m, 1H), 4.13-3.88 (m, 3H), 2.17 (t, J=20.5 Hz, 2H), 2.07-1.93 (m, 2H), 1.77-1.44 (m, 6H). ESI MS [M+H]$^+$ for $C_{17}H_{25}ClFN_4O_8P_2$, calcd 529.1, found 529.1.

Example 125

Synthesis of [({[(2R,3R,4S,5R)-5-(6-chloro-4-{[(1S)-1-phenylethyl]amino}-1H-pyrazolo[3,4-b]pyridin-1-yl)-4-fluoro-3-hydroxyoxolan-2-yl]methoxy}(hydroxy)phosphoryl)-methyl]phosphonic acid

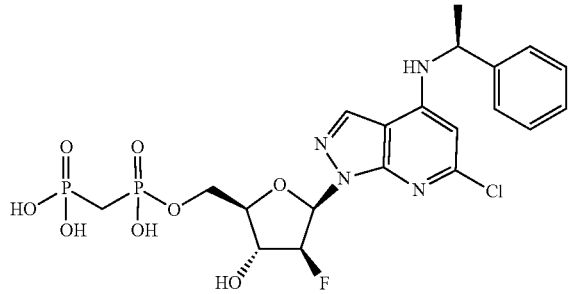 [SMILES: C[C@H](Nc1cc(Cl)nc2c1cnn2[C@@H]1O[C@H](COP(=O)(O)CP(=O)(O)O)[C@@H](O)[C@@H]1F)c1ccccc1]

The title compound was synthesized in similar fashion to Example 124. $^1$H NMR (400 MHz, DMSO-d$_6$) δ 8.40 (s, 1H), 8.23 (d, J=7.1 Hz, 1H), 7.44-7.37 (m, 2H), 7.37-7.28 (m, 2H), 7.26-7.16 (m, 1H), 6.54 (d, J=6.5 Hz, 1H), 6.04 (s, 1H), 5.36 (dt, J=53.5, 7.1 Hz, 1H), 4.93-4.67 (m, 2H), 4.27-4.19 (m, 1H), 4.14-4.02 (m, 1H), 3.98-3.85 (m, 1H), 2.17 (t, J=20.5 Hz, 2H), 1.52 (d, J=6.4 Hz, 3H). ESI MS [M+H]$^+$ for C$_{20}$H$_{25}$ClFN$_4$O$_8$P$_2$, calcd 565.1, found 565.2.

Example 126

Synthesis of [({[(2R,3R,4S,5R)-5-(6-chloro-4-{[(1R)-1-phenylethyl]amino}-1H-pyrazolo[3,4-b]pyridin-1-yl)-4-fluoro-3-hydroxyoxolan-2-yl]methoxy}(hydroxy)phosphoryl)-methyl]phosphonic acid

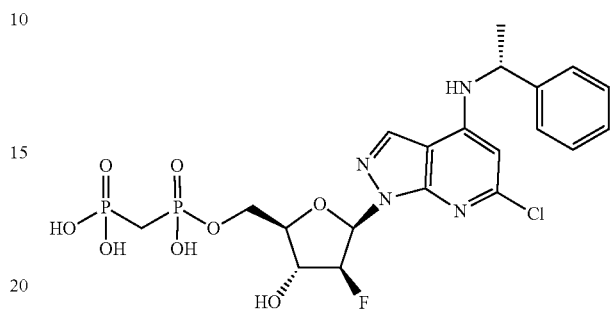

The title compound was synthesized in similar fashion to Example 124. $^1$H NMR (400 MHz, DMSO-d$_6$) δ 8.41 (s, 1H), 8.22 (d, J=7.1 Hz, 1H), 7.43-7.36 (m, 2H), 7.36-7.27 (m, 2H), 7.26-7.17 (m, 1H), 6.54 (d, J=6.5 Hz, 1H), 6.04 (s, 1H), 5.37 (dt, J=53.7, 7.2 Hz, 1H), 4.96-4.67 (m, 2H), 4.27-4.18 (m, 1H), 4.13-4.01 (m, 1H), 3.97-3.87 (m, 1H), 2.18 (t, J=20.5 Hz, 2H), 1.52 (d, J=6.4 Hz, 3H). ESI MS [M+H]$^+$ for C$_{20}$H$_{25}$ClFN$_4$O$_8$P$_2$, calcd 565.1, found 565.2.

Example 127

Synthesis of [({[(2R,3S,4R,5R)-5-(2-chloro-4-{[(1S)-1-(2-fluorophenyl)ethyl]amino}-7H-pyrrolo[2,3-d]pyrimidin-7-yl)-3,4-dihydroxyoxolan-2-yl]methoxy}(hydroxy)phosphoryl)-methyl]phosphonic acid

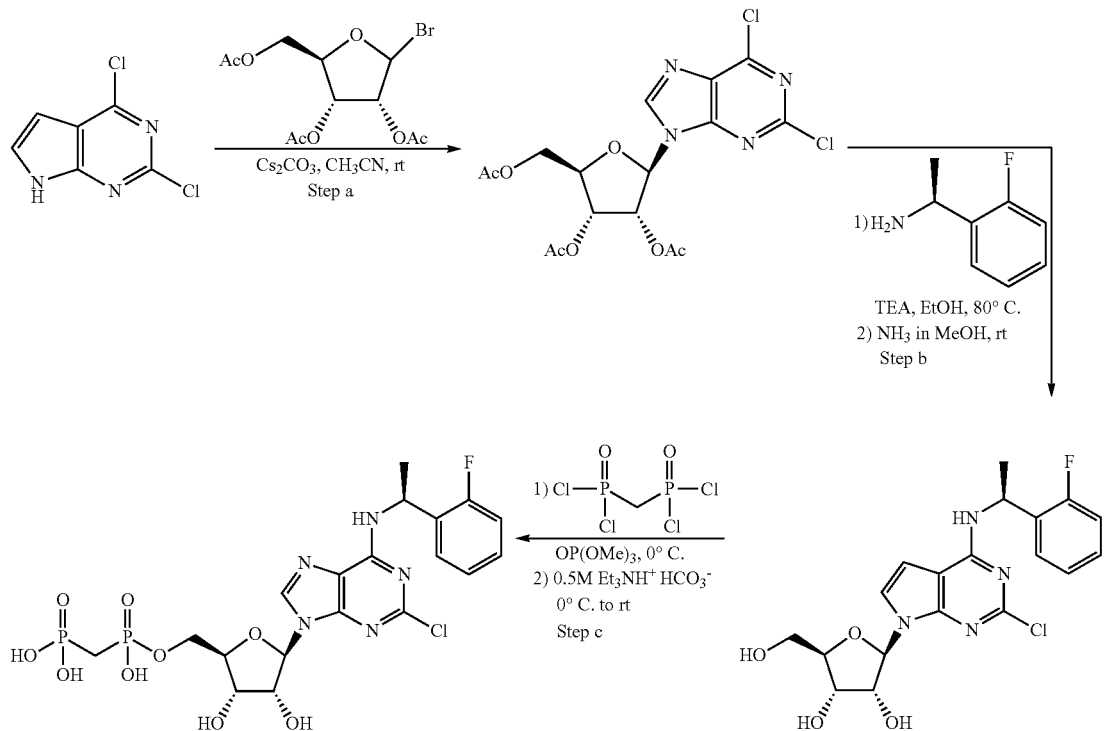

Step a: To the mixture of 2,4-dichloro-7H-pyrrolo[2,3-d]pyrimidine (14.8 g, 78.9 mmol) and the bromide (40 g, 118.3 mmol, 1.5 equiv.) in anhydrous $CH_3CN$ (600 mL), $Cs_2CO_3$ (38.6 g, 118.3 mmol, 1.5 equiv.) was added and the reaction mixture was stirred at room temperature for overnight. Evaporated with silica gel and purified by column chromatography ($SiO_2$, Hex→Hex:EtOAc, 2:8) to give white solid (13.8 g, 39%). ESI MS [M+H]$^+$ for $C_{17}H_{18}C_{12}N_3O_7$, calcd 446.0, found 446.1.

Step b and Step c were performed in similar fashion to Example 1. $^1$H NMR (400 MHz, DMSO-$d_6$) δ 8.38 (d, J=7.9 Hz, 1H), 7.47-7.36 (m, 2H), 7.32-7.23 (m, 1H), 7.20-7.09 (m, 2H), 6.81 (s, 1H), 5.96 (d, J=6.0 Hz, 1H), 5.58 (t, J=7.3 Hz, 1H), 4.29 (t, J=5.7 Hz, 1H), 4.14-3.96 (m, 4H), 2.24 (t, J=20.5 Hz, 2H), 1.51 (d, J=6.9 Hz, 3H). ESI MS [M+H]$^+$ for $C_{20}H_{25}ClFN_4O_9P_2$, calcd 581.1, found 581.2.

Example 128

Synthesis of [({[(2R,3S,4R,5R)-5-(2-chloro-4-{[(1S)-1-(3-fluorophenyl)ethyl]amino}-7H-pyrrolo[2,3-d]pyrimidin-7-yl)-3,4-dihydroxyoxolan-2-yl]methoxy}(hydroxy)phosphoryl)-methyl]phosphonic acid

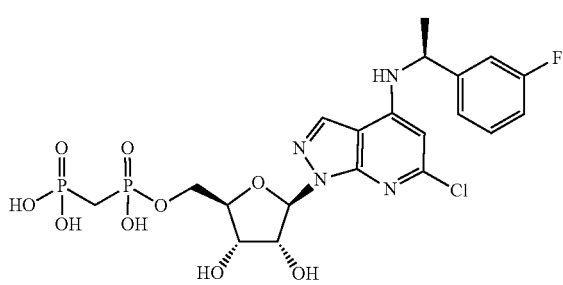 [SMILES: C[C@H](Nc1cc(Cl)nc2c1cnn2[C@@H]1O[C@H](COP(=O)(O)CP(=O)(O)O)[C@@H](O)[C@H]1O)c1cccc(F)c1]

The title compound was synthesized in similar fashion to Example 127: $^1$H NMR (400 MHz, DMSO-$d_6$) δ 8.34 (d, J=8.1 Hz, 1H), 7.42-7.30 (m, 2H), 7.26-7.16 (m, 2H), 7.08-6.98 (m, 1H), 6.77 (s, 1H), 5.97 (d, J=6.0 Hz, 1H), 5.45-5.33 (m, 1H), 4.29 (t, J=5.5 Hz, 1H), 4.14-3.98 (m, 4H), 2.24 (d, J=20.5 Hz, 2H), 1.51 (d, J=6.8 Hz, 3H). ESI MS [M+H]$^+$ for $C_{20}H_{25}ClFN_4O_9P_2$, calcd 581.1, found 581.2.

Example 129

Synthesis of [({[(2R,3S,4R,5R)-5-(2-chloro-4-{[(1S)-1-(4-fluorophenyl)ethyl]amino}-7H-pyrrolo[2,3-d]pyrimidin-7-yl)-3,4-dihydroxyoxolan-2-yl]methoxy}(hydroxy)-phosphoryl)methyl]phosphonic acid

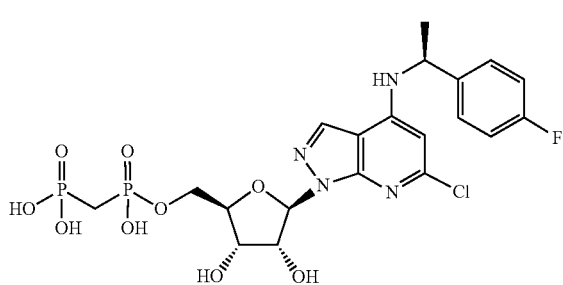 [SMILES: C[C@H](Nc1cc(Cl)nc2c1cnn2[C@@H]1O[C@H](COP(=O)(O)CP(=O)(O)O)[C@@H](O)[C@H]1O)c1ccc(F)cc1]

The title compound was synthesized in similar fashion to Example 127. $^1$H NMR (400 MHz, DMSO-$d_6$) δ 8.32 (d, J=8.0 Hz, 1H), 7.46-7.34 (m, 3H), 7.17-7.08 (m, 2H), 6.76 (s, 1H), 5.97 (d, J=6.3 Hz, 1H), 5.44-5.33 (m, 11H), 4.29 (t, J=5.8 Hz, 11H), 4.14-3.97 (m, 4H), 2.24 (d, J=20.5 Hz, 2H), 1.50 (d, J=6.9 Hz, 3H). ESI MS [M+H]$^+$ for $C_{20}H_{25}ClFN_4O_9P_2$, calcd 581.1, found 581.2.

Example 130

Synthesis of [({[(2R,3R,4S,5R)-5-(2-chloro-4-{[(1R)-1-phenylethyl]amino}-7H-pyrrolo[2,3-d]pyrimidin-7-yl)-4-fluoro-3-hydroxyoxolan-2-yl]methoxy}(hydroxy)phosphoryl)-methyl]phosphonic acid

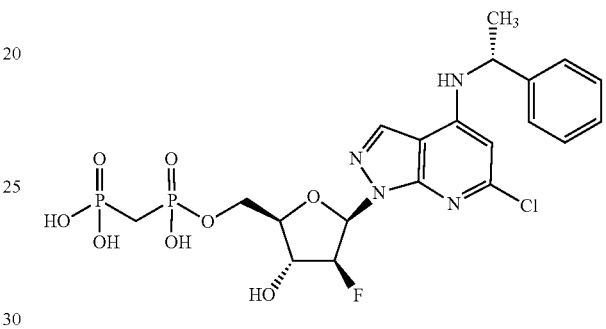

The title compound was synthesized in similar fashion to Example 65. $^1$H NMR (400 MHz, DMSO-$d_6$) δ 8.36 (d, J=8.4 Hz, 1H), 7.39 (d, J=7.6 Hz, 2H), 7.35-7.23 (m, 3H), 7.21 (t, J=7.2 Hz, 1H), 6.78 (s, 1H), 6.44 (dd, J=15.5, 4.6 Hz, 1H), 5.40 (t, J=8.1 Hz, 1H), 4.40 (dt, J=18.8, 4.6 Hz, 1H), 4.13 (d, J=6.7 Hz, 2H), 3.95 (q, J=5.1 Hz, 1H), 2.22 (t, J=20.3 Hz, 2H), 1.51 (d, J=7.0 Hz, 3H). ESI MS [M−H]$^-$ for $C_{209}H_{23}ClFN_4O_8P_2$, calcd 563.1, found 563.2.

Example 131

Synthesis of [({[(2R,3R,4S,5R)-5-(2-chloro-4-{[(1S)-1-phenylethyl]amino}-7H-pyrrolo[2,3-d]pyrimidin-7-yl)-4-fluoro-3-hydroxyoxolan-2-yl]methoxy}(hydroxy)phosphoryl)-methyl]phosphonic acid

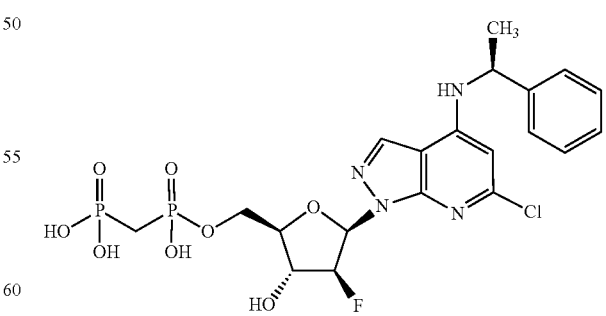

The title compound was synthesized in similar fashion to Example 65. $^1$H NMR (400 MHz, DMSO-$d_6$) δ 8.37 (d, J=8.3 Hz, 1H), 7.39 (d, J=7.7 Hz, 2H), 7.31 (t, J=7.5 Hz, 2H), 7.28-7.16 (m, 2H), 6.79 (s, 1H), 6.44 (dd, J=15.8, 4.5 Hz, 1H), 5.39 (s, 1H), 4.39 (dt, J=18.7, 4.4 Hz, 1H), 4.12 (m, 2H), 3.95 (q, J=5.1 Hz, 1H), 2.23 (t, J=20.5 Hz, 2H), 1.51 (d, J=7.0 Hz, 3H). ESI MS [M+H]+ for C₂H₂₅ClFN₄O₈P₂, calcd 565.1, found 565.2.

Example 132

Synthesis of [({[(2R,3R,4S,5R)-5-(2-chloro-4-{[(1S)-1-(3-fluorophenyl)ethyl]amino}-7H-pyrrolo[2,3-d]pyrimidin-7-yl)-4-fluoro-3-hydroxyoxolan-2-yl]methoxy}(hydroxy)-phosphoryl)methyl]phosphonic acid

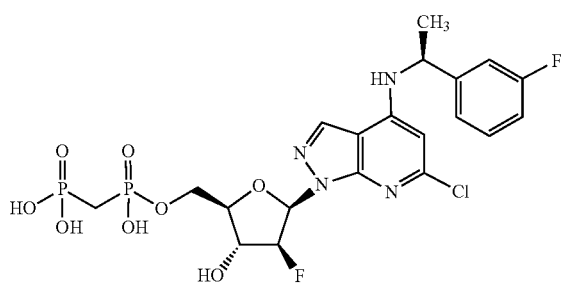 [SMILES: C[C@H](Nc1cc(Cl)nc2c1cnn2[C@@H]1O[C@H](COP(=O)(O)CP(=O)(O)O)[C@@H](O)[C@@H]1F)c1cccc(F)c1]

The title compound was synthesized in similar fashion to Example 65. ¹H NMR (400 MHz, DMSO-d₆) δ 8.40 (d, J=8.0 Hz, 1H), 7.40-7.16 (m, 4H), 7.03 (td, J=8.7, 2.6 Hz, 1H), 6.78 (d, J=3.9 Hz, 1H), 6.45 (dd, J=15.7, 4.4 Hz, 1H), 5.43-5.34 (m, 1H), 5.11 (dt, J=52.7, 4.0 Hz, 1H), 4.38 (dq, J=18.7, 4.5 Hz, 1H), 4.18-4.06 (m, 1H), 3.96 (q, J=5.0 Hz, 1H), 2.25 (t, J=20.5 Hz, 2H), 1.51 (d, J=6.9 Hz, 3H). ESI MS [M−H]⁻ for C₂₀H₂₂ClF₂N₄O₈P₂, calcd 581.1, found 581.2.

Example 133

Synthesis of [({[(2R,3R,4S,5R)-5-(2-chloro-4-{[(1R)-1-(4-fluorophenyl)ethyl]amino}-7H-pyrrolo[2,3-d]pyrimidin-7-yl)-4-fluoro-3-hydroxyoxolan-2-yl]methoxy}(hydroxy)-phosphoryl)methyl]phosphonic acid

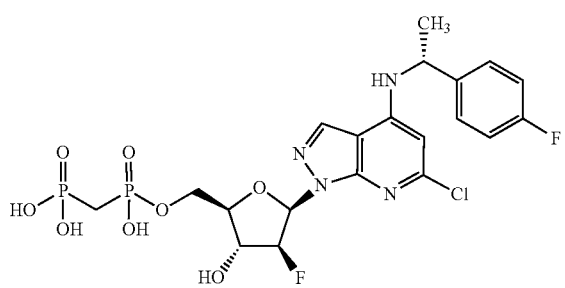 [SMILES: C[C@@H](Nc1cc(Cl)nc2c1cnn2[C@@H]1O[C@H](COP(=O)(O)CP(=O)(O)O)[C@@H](O)[C@@H]1F)c1ccc(F)cc1]

The title compound was synthesized in similar fashion to Example 65. ¹H NMR (400 MHz, DMSO-d₆) δ 8.37 (d, J=8.1 Hz, 1H), 7.42 (dd, J=8.4, 5.5 Hz, 2H), 7.26 (t, J=3.1 Hz, 1H), 7.22-7.09 (m, 2H), 6.77 (d, J=3.6 Hz, 1H), 6.44 (dd, J=15.5, 4.5 Hz, 1H), 5.43-5.34 (m, 1H), 5.14 (dt, J=52.7, 4.0 Hz, 1H), 4.40 (dt, J=18.7, 4.3 Hz, 1H), 4.20-4.02 (m, 2H), 3.95 (q, J=5.1 Hz, 1H), 2.24 (t, J=20.5 Hz, 2H), 1.50 (d, J=7.0 Hz, 3H). ESI MS [M−H]⁻ for C₂₀H₂₂ClF₂N₄O₈P₂, calcd 581.1, found 581.2.

Example 134

Synthesis of [({[(2R,3R,4S,5R)-5-(2-chloro-4-{[(1S)-1-(4-fluorophenyl)ethyl]amino}-7H-pyrrolo[2,3-d]pyrimidin-7-yl)-4-fluoro-3-hydroxyoxolan-2-yl]methoxy}(hydroxy)-phosphoryl)methyl]phosphonic acid

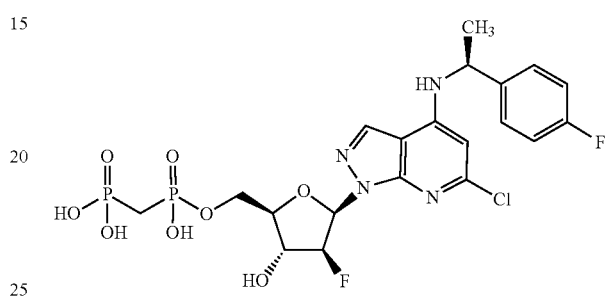

The title compound was synthesized in similar fashion to Example 65. ¹H NMR (400 MHz, DMSO-d₆) δ 8.38 (d, J=7.7 Hz, 1H), 7.41 (dd, J=8.6, 5.5 Hz, 2H), 7.26 (s, 1H), 7.18-7.08 (m, 2H), 6.77 (s, 1H), 6.44 (dd, J=15.6, 4.3 Hz, 1H), 5.38 (s, 1H), 5.24-4.96 (m, 1H), 4.45-4.34 (m, 1H), 4.13 (s, 2H), 3.95 (d, J=5.2 Hz, 1H), 2.23 (t, J=20.4 Hz, 2H), 1.50 (d, J=7.1 Hz, 3H). ESI MS [M+H]+ for C₂₀H₂₄ClF₂N₄O₈P₂, calcd 583.1, found 583.2.

Example 135

Synthesis of [({[(2R,3R,4S,5R)-5-(2-chloro-4-{[(1S)-1-(2-fluorophenyl)ethyl]amino}-7H-pyrrolo[2,3-d]pyrimidin-7-yl)-4-fluoro-3-hydroxyoxolan-2-yl]methoxy}(hydroxy)-phosphoryl)methyl]phosphonic acid

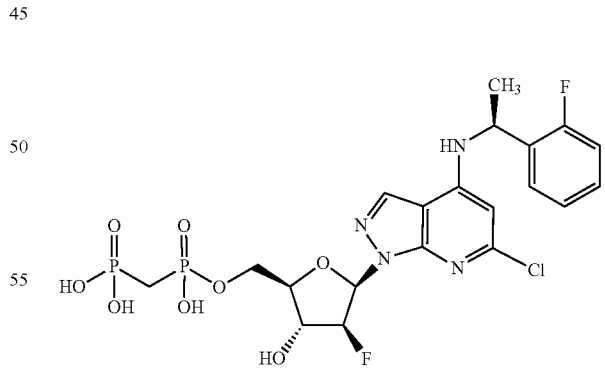

The title compound was synthesized in similar fashion to Example 65. ¹H NMR (400 MHz, DMSO-d₆) δ 8.46 (d, J=7.8 Hz, 1H), 7.44 (t, J=7.8 Hz, 1H), 7.28 (dt, J=11.3, 4.5 Hz, 2H), 7.17 (q, J=8.1, 7.4 Hz, 2H), 6.83 (d, J=3.9 Hz, 1H), 6.47 (dd, J=15.7, 4.5 Hz, 1H), 5.60 (t, J=7.4 Hz, 1H), 5.13 (dt, J=52.5, 4.2 Hz, 1H), 4.41 (dt, J=18.8, 4.4 Hz, 1H), 4.14 (td, J=12.0, 10.7, 5.7 Hz, 2H), 3.97 (q, J=5.0 Hz, 1H), 2.27

(t, J=20.5 Hz, 2H), 1.53 (d, J=7.0 Hz, 3H). ESI MS [M+H]+ for $C_{20}H_{24}ClF_2N_4O_8P_2$, calcd 583.1, found 583.2.

Example 136

Synthesis of [({[(2R,3R,4S,5R)-5-(2-chloro-4-{[(1R)-1-(2-fluorophenyl)ethyl]amino}-7H-pyrrolo[2,3-d]pyrimidin-7-yl)-4-fluoro-3-hydroxyoxolan-2-yl]methoxy}(hydroxy)-phosphoryl)methyl]phosphonic acid

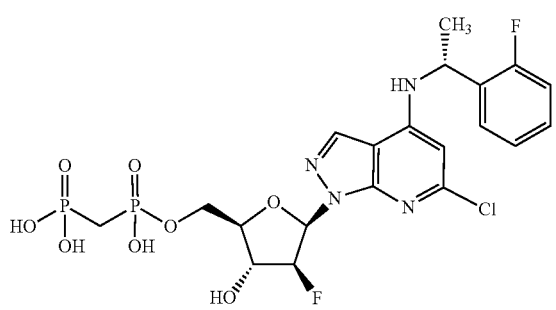 [SMILES: C[C@@H](Nc1cc(Cl)nc2c1cnn2[C@@H]1O[C@H](COP(=O)(O)CP(=O)(O)O)[C@@H](O)[C@@H]1F)c1ccccc1F]

The title compound was synthesized in similar fashion to Example 65. ¹H NMR (400 MHz, DMSO-d₆) δ 8.44 (s, 1H), 7.43 (t, J=7.8 Hz, 1H), 7.28 (s, 2H), 7.21-7.09 (m, 2H), 6.44 (dd, J=15.8, 4.7 Hz, 1H), 5.59 (s, 1H), 5.14 (d, J=52.8 Hz, 1H), 4.40 (d, J=18.9 Hz, 1H), 4.13 (s, 2H), 3.95 (d, J=5.7 Hz, 1H), 2.24 (t, J=20.7 Hz, 2H), 1.51 (d, J=6.9 Hz, 3H). ESI MS [M+H]+ for $C_{20}H_{24}ClF_2N_4O_8P_2$, calcd 583.1, found 583.2.

Example 137

Synthesis of [({[(2R,3R,4S,5R)-5-(2-chloro-4-{[(1R)-1-(3-fluorophenyl)ethyl]amino}-7H-pyrrolo[2,3-d]pyrimidin-7-yl)-4-fluoro-3-hydroxyoxolan-2-yl]methoxy}(hydroxy)-phosphoryl)methyl]phosphonic acid

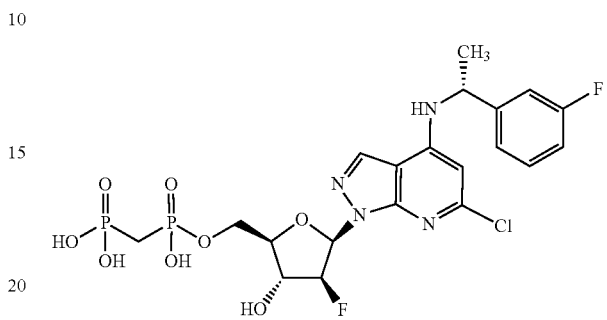

The title compound was synthesized in similar fashion to Example 65. ¹H NMR (400 MHz, DMSO-d₆) δ 8.39 (d, J=8.1 Hz, 1H), 7.35 (td, J=8.0, 7.5, 6.0 Hz, 1H), 7.31-7.17 (m, 3H), 7.04 (td, J=8.6, 2.5 Hz, 1H), 6.81-6.75 (m, 1H), 6.45 (dd, J=15.6, 4.4 Hz, 1H), 5.44-5.35 (m, 1H), 5.14 (dt, J=52.8, 4.1 Hz, 1H), 4.40 (dt, J=18.8, 4.4 Hz, 1H), 4.19-4.09 (m, 1H), 3.95 (q, J=5.0 Hz, 1H), 2.24 (t, J=20.5 Hz, 2H), 1.50 (d, J=6.9 Hz, 3H). ESI MS [M−H]− for $C_{20}H_{22}ClF_2N_4O_8P_2$, calcd 581.1, found 581.2.

Example 138

Synthesis of [({[(2R,3S,4R,5R)-5-[6-chloro-4-(cyclopentylamino)-1H-imidazo[4,5-c]pyridin-1-yl]-3,4-dihydroxyoxolan-2-yl]methoxy}(hydroxy)phosphoryl)methyl]phosphonic acid

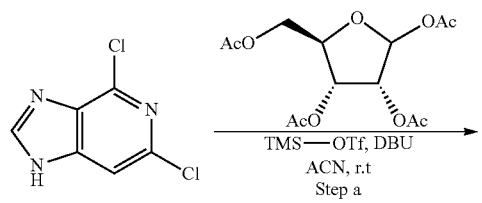

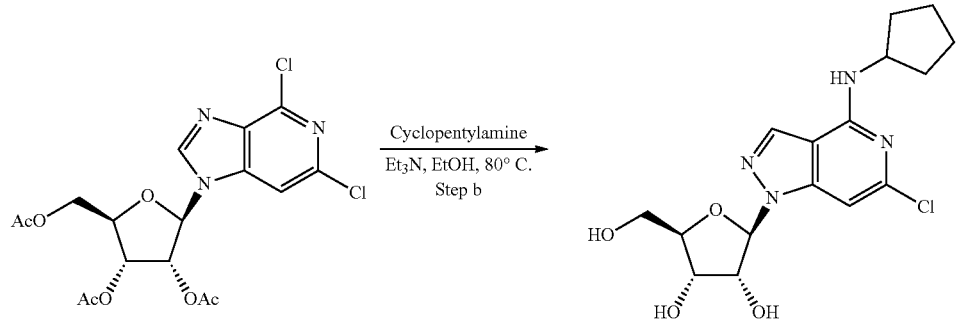

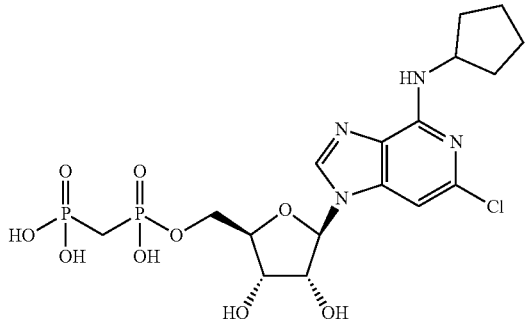

Step a: To a solution of β-D-Ribofuranose-1,2,3,5-tetraacetate (4.07 g, 12.8 mmol) and 4,6-Dichloro-1H-imidazo[4,5-c]pyridine (2.0 g, 10.6 mmol) in ACN (64 mL) was added TMSOTf (4.6 mL, 25.6 mmol) via syringe. Subsequently DBU (1.9 mL, 12.8 mmol) was added dropwise and the reaction was stirred at room temperature for 2 hours. The reaction was cooled to 0° C. and poured in a cold saturated solution of NaHCO$_3$. This mixture was transferred to a separatory funnel and extracted with DCM (3×). The combined organics were dried over MgSO$_4$ and concentrated to dryness. The crude material (1.4 g) was used without further purification. ESI MS [M+H]$^+$ for $C_{17}H_{17}Cl_2N_3O_7$, calcd 446.0, found 446.1.

Step b: To a screw-top flask containing the crude dichloride (1.4 g) was added cyclopentylamine (7 mL). The vial was sealed and heated to 80° C. overnight. The reaction was cooled to room temperature and concentrated to dryness under reduced pressure. The crude product was reconstituted in DCM and purified by column chromatography (SiO$_2$, 0 to 15% MeOH/DCM) to obtain the desired product (352 mg). ESI MS [M+H]$^+$ for $C_{16}H_{21}ClN_4O_4$, calcd 368.1, found 369.2.

Step C: The title compound was synthesized in similar fashion to Example 1. $^1$H NMR (400 MHz, DMSO-d$_6$) δ 8.33 (s, 1H), 7.05 (s, 1H), 6.88 (s, 1H), 5.77 (d, J=5.9 Hz, 1H), 4.43 (br. s, 1H), 4.28 (dd, J=5.9, 5.0 Hz, 1H), 4.21-4.04 (m, 5H), 2.28 (t, J=20.5 Hz, 2H), 2.05-1.77 (m, 2H), 1.79-1.45 (m, 7H). ESI MS [M–H]$^-$ for $C_{17}H_{25}ClN_4O_9P_2$, calcd 525.1, found 525.2.

Example 139

Synthesis of [({[(2R,3R,4S,5R)-5-[6-chloro-4-(cyclopentylamino)-1H-imidazo[4,5-c]pyridin-1-yl]-4-fluoro-3-hydroxyoxolan-2-yl]methoxy}(hydroxy)phosphoryl)methyl]phosphonic acid

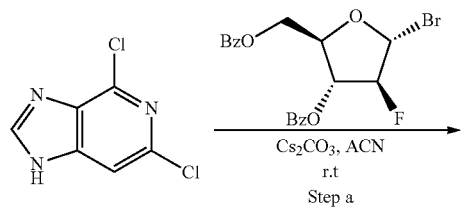

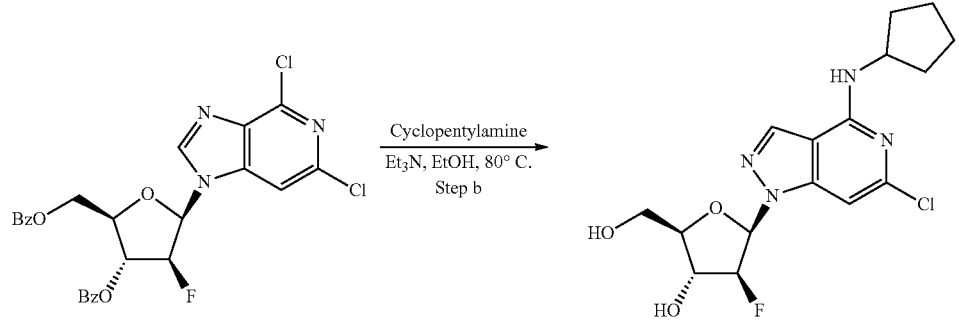

-continued

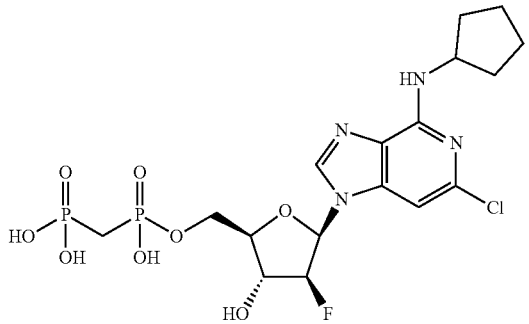
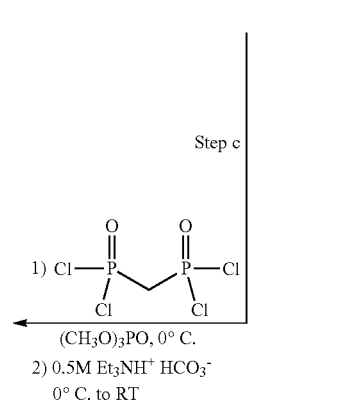

(CH₃O)₃PO, 0° C.
2) 0.5M Et₃NH⁺ HCO₃⁻
0° C. to RT

Step a: A solution of 4,6-Dichloro-1H-imidazo[4,5-c]pyridine (2.0 g, 10.6 mmol) and 2-Deoxy-2-fluoro-D-arabinofuranosyl Bromide 3,5-Dibenzoate (4.95 g, 11.7 mmol; CAS: 97614-44-3) in 50 mL of acetonitrile was treated with Cs₂CO₃ (4.16 g, 12.8 mmol). The mixture was allowed to stir for 3 hours at room temperature then diluted with ethyl acetate and washed with water and brine. The organics were dried over MgSO₄ and concentrated under reduced pressure. The crude product obtained was used without further purification. ESI MS [M+H]⁺ for C₂₅H₁₈C₁₂FN₃O₅, calcd 530.1, found 530.2.

Step b: To a screw-top flask containing the crude dichloride (3.5 g, 6.6 mmol) was added cyclopentylamine (18 mL). The vial was sealed and heated to 80° C. overnight. The reaction was cooled to room temperature and concentrated to dryness under reduced pressure. The crude product was reconstituted in DCM and purified by column chromatography (SiO₂, 0 to 15% MeOH/DCM) to obtain the desired product. ESI MS [M+H]⁺ for C₁₆H₂₀ClFN₄O₃, calcd 371.1, found 371.2.

Step c: The title compound was synthesized in similar fashion to example 1: ¹H NMR (400 MHz, DMSO-d₆) δ 8.22 (d, J=1.8 Hz, 1H), 7.06 (s, 2H), 6.98-6.82 (m, 1H), 6.37 (dd, J=15.9, 4.4 Hz, 1H), 5.21 (dt, J=52.4, 3.8 Hz, 1H), 4.53-4.33 (m, 2H), 4.21 (t, J=5.8 Hz, 2H), 4.00 (q, J=4.9 Hz, 1H), 2.28 (t, J=20.4 Hz, 2H), 1.93 (s, 2H), 1.74-1.47 (m, 7H). ESI MS [M−H]⁻ for C₁₇H₂₄ClFN₄O₈P₂, calcd 527.1, found 527.2.

Example 140

Synthesis of [({[(2R,3R,4S,5R)-5-{6-chloro-4-[cyclopentyl(methyl)amino]-1H-imidazo[4,5-c]pyridin-1-yl}-4-fluoro-3-hydroxyoxolan-2-yl]methoxy}(hydroxy)phosphoryl)-methyl]phosphonic acid

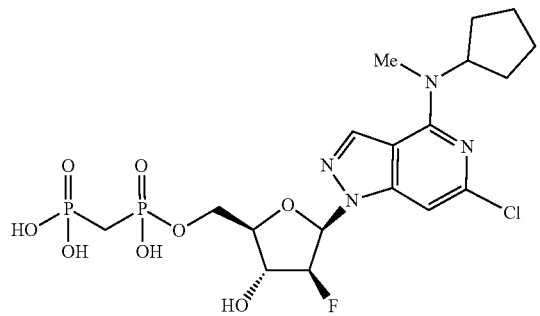 [SMILES: CN(c1nc(Cl)cc2c1cnn2[C@@H]1O[C@H](COP(=O)(O)CP(=O)(O)O)[C@@H](O)[C@@H]1F)C1CCCC1]

The title compound was synthesized in similar fashion to Example 139. ¹H NMR (400 MHz, DMSO-d₆) δ 8.24 (d, J=1.8 Hz, 1H), 6.98 (d, J=0.7 Hz, 1H), 6.39 (dd, J=15.4, 4.4 Hz, 1H), 5.80 (p, J=7.7 Hz, 1H), 5.41-5.03 (m, 1H), 4.43 (ddd, J=19.9, 5.4, 3.5 Hz, 1H), 4.31-4.14 (m, 2H), 4.01 (q, J=4.9 Hz, 1H), 3.15 (s, 4H), 2.29 (t, J=20.5 Hz, 2H), 1.94-1.47 (m, 9H). ESI MS [M−H]⁻ for C₁₈H₂₆ClFN₄O₈P₂, calcd 541.1, found 541.2.

TABLE 1

Specific Examples (Potency: CD73 IC₅₀: + means >1 μM, ++ means 100 nM to 1 μM, +++ means <100 nM).

| | Potency |
|---|---|
| (structure) | +++ |

TABLE 1-continued

Specific Examples (Potency: CD73 IC$_{50}$: + means >1 μM, ++ means 100 nM to 1 μM, +++ means <100 nM).

| Structure | Potency |
|---|---|
| (phosphonate-CH₂-phosphonate-O-ribose; 2-Cl, N6-(4-tert-butylbenzyl)amino adenine) | +++ |
| (phosphonate-CH₂-phosphonate-O-ribose; 2-Cl, N6-isopropylamino adenine) | +++ |
| (phosphonate-CH₂-phosphonate-O-ribose with 2'-F; 2-Cl, N6-cyclopropylamino adenine) | +++ |
| (phosphonate-CH₂-phosphonate-O-ribose; 2-Cl, N6-neopentylamino adenine) | +++ |
| (phosphonate-CH₂-phosphonate-O-ribose; 2-Cl, N6-methyl-N6-isopropylamino adenine) | +++ |

TABLE 1-continued
Specific Examples (Potency: CD73 IC$_{50}$: + means >1 µM, ++ means 100 nM to 1 µM, +++ means <100 nM).
| | Potency |
|---|---|
| 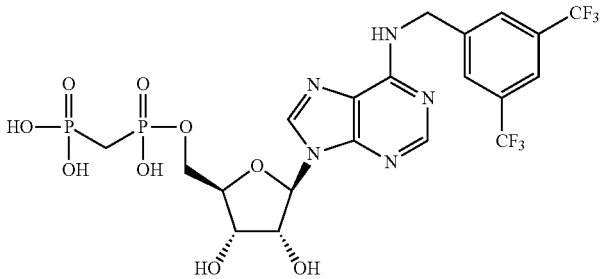 [SMILES: O=P(O)(O)CP(=O)(O)OC[C@H]1O[C@@H](n2cnc3c(NCc4cc(C(F)(F)F)cc(C(F)(F)F)c4)ncnc32)[C@H](O)[C@@H]1O] | +++ |
| 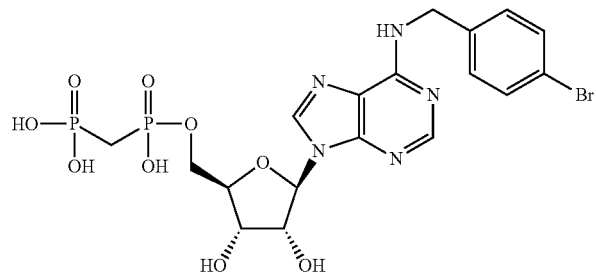 | +++ |
| 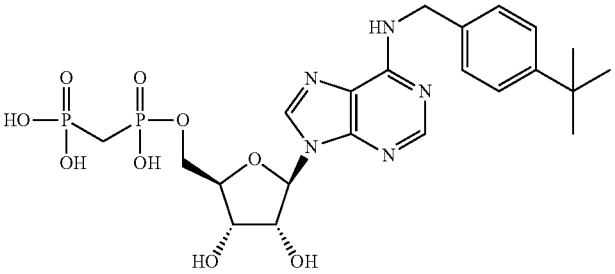 [SMILES: CC(C)(C)c1ccc(CNc2ncnc3c2ncn3[C@@H]2O[C@H](COP(=O)(O)CP(=O)(O)O)[C@@H](O)[C@H]2O)cc1] | +++ |
| 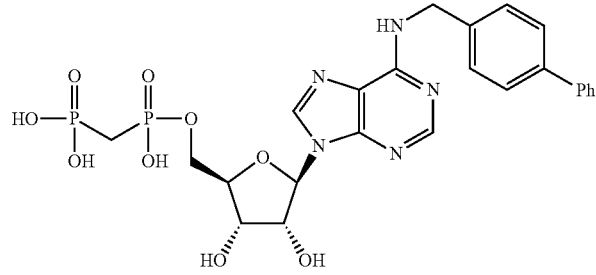 [SMILES: O=P(O)(O)CP(=O)(O)OC[C@H]1O[C@@H](n2cnc3c(NCc4ccc(-c5ccccc5)cc4)ncnc32)[C@H](O)[C@@H]1O] | +++ |
| 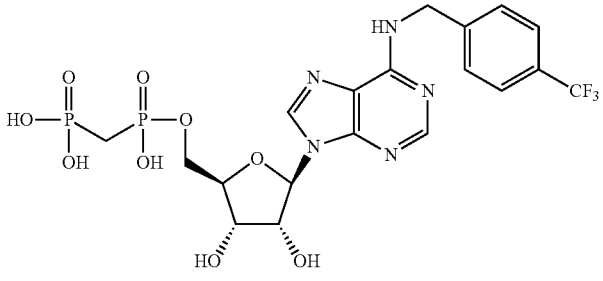 [SMILES: O=P(O)(O)CP(=O)(O)OC[C@H]1O[C@@H](n2cnc3c(NCc4ccc(C(F)(F)F)cc4)ncnc32)[C@H](O)[C@@H]1O] | +++ |

TABLE 1-continued
Specific Examples (Potency: CD73 IC$_{50}$: + means >1 μM, ++ means 100 nM to 1 μM, +++ means <100 nM).
| | Potency |
|---|---|
| 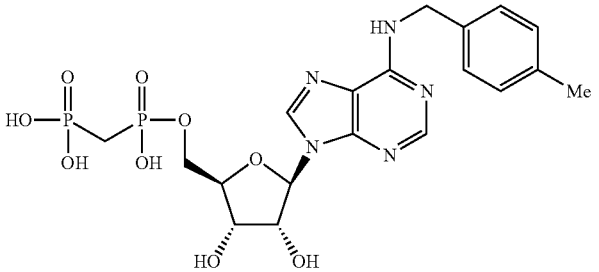 [SMILES: Cc1ccc(CNc2ncnc3c2ncn3[C@@H]2O[C@H](COP(=O)(O)CP(=O)(O)O)[C@@H](O)[C@H]2O)cc1] | +++ |
| 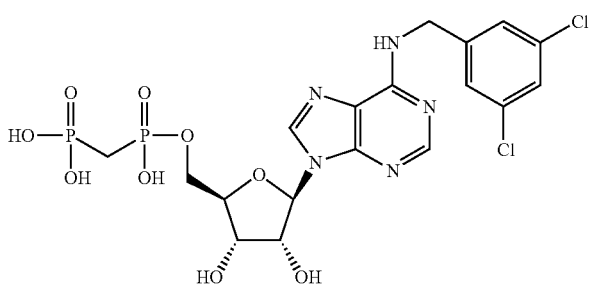 [SMILES: O=P(O)(O)CP(=O)(O)OC[C@H]1O[C@@H](n2cnc3c(NCc4cc(Cl)cc(Cl)c4)ncnc32)[C@H](O)[C@@H]1O] | +++ |
| 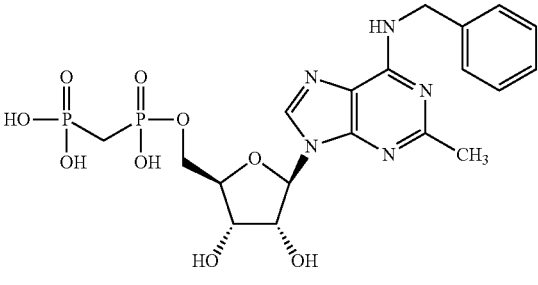 | +++ |
| 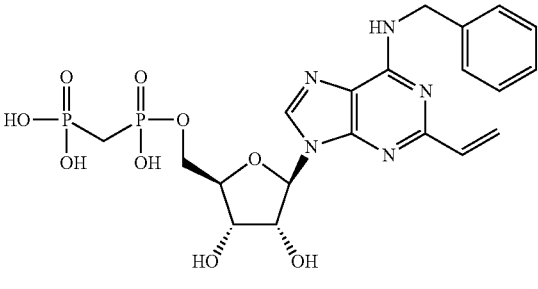 [SMILES: C=Cc1nc(NCc2ccccc2)c2ncn([C@@H]3O[C@H](COP(=O)(O)CP(=O)(O)O)[C@@H](O)[C@H]3O)c2n1] | +++ |
| 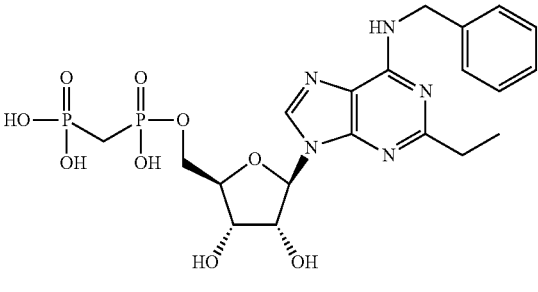 [SMILES: CCc1nc(NCc2ccccc2)c2ncn([C@@H]3O[C@H](COP(=O)(O)CP(=O)(O)O)[C@@H](O)[C@H]3O)c2n1] | +++ |

TABLE 1-continued
Specific Examples (Potency: CD73 IC$_{50}$: + means >1 μM, ++ means 100 nM to 1 μM, +++ means <100 nM).
| | Potency |
|---|---|
| 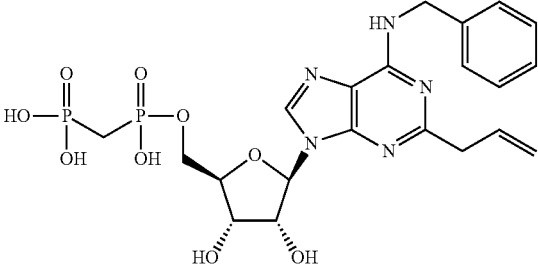 [SMILES: C=CCc1nc(NCc2ccccc2)c2ncn([C@@H]3O[C@H](COP(=O)(O)CP(=O)(O)O)[C@@H](O)[C@H]3O)c2n1] | +++ |
| 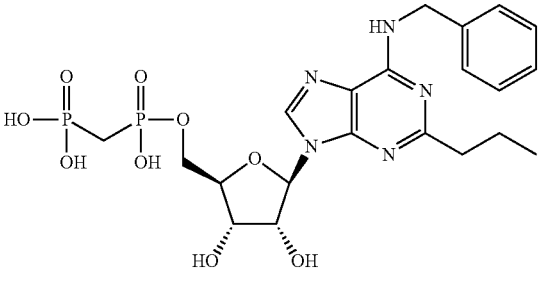 [SMILES: CCCc1nc(NCc2ccccc2)c2ncn([C@@H]3O[C@H](COP(=O)(O)CP(=O)(O)O)[C@@H](O)[C@H]3O)c2n1] | +++ |
| 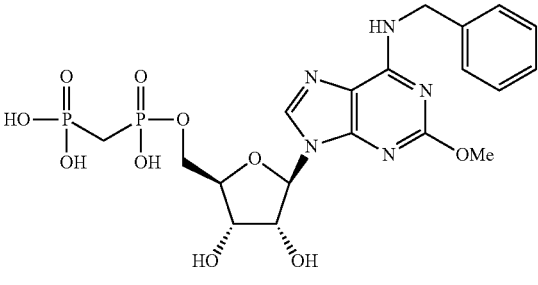 [SMILES: COc1nc(NCc2ccccc2)c2ncn([C@@H]3O[C@H](COP(=O)(O)CP(=O)(O)O)[C@@H](O)[C@H]3O)c2n1] | +++ |
| 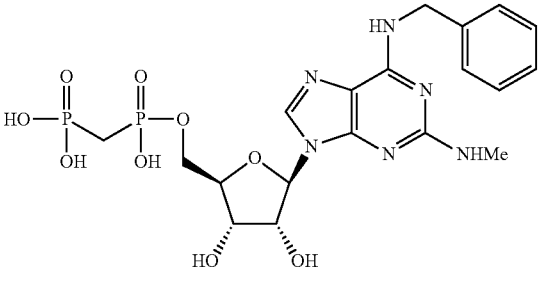 [SMILES: CNc1nc(NCc2ccccc2)c2ncn([C@@H]3O[C@H](COP(=O)(O)CP(=O)(O)O)[C@@H](O)[C@H]3O)c2n1] | +++ |
| 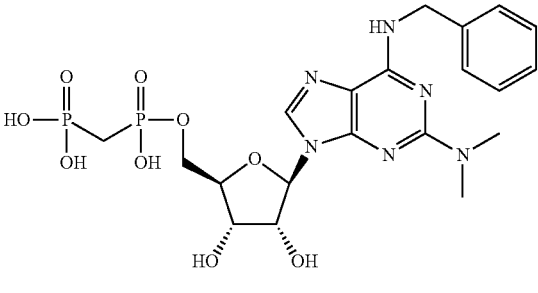 | +++ |

TABLE 1-continued
Specific Examples (Potency: CD73 $IC_{50}$: + means >1 µM, ++ means 100 nM to 1 µM, +++ means <100 nM).
| | Potency |
|---|---|
| 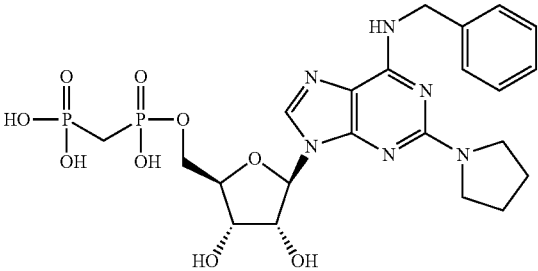 [SMILES: O=P(O)(O)CP(=O)(O)OC[C@H]1O[C@@H](n2cnc3c(NCc4ccccc4)nc(N4CCCC4)nc32)[C@H](O)[C@@H]1O] | +++ |
| 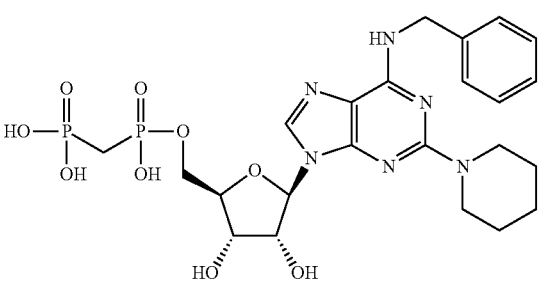 [SMILES: O=P(O)(O)CP(=O)(O)OC[C@H]1O[C@@H](n2cnc3c(NCc4ccccc4)nc(N4CCCCC4)nc32)[C@H](O)[C@@H]1O] | +++ |
| 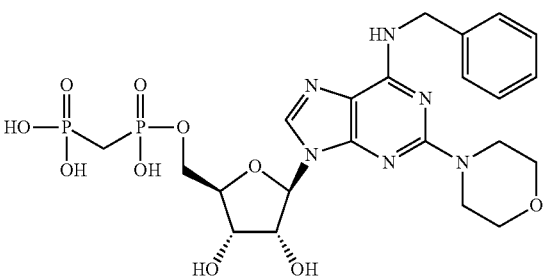 [SMILES: O=P(O)(O)CP(=O)(O)OC[C@H]1O[C@@H](n2cnc3c(NCc4ccccc4)nc(N4CCOCC4)nc32)[C@H](O)[C@@H]1O] | +++ |
| 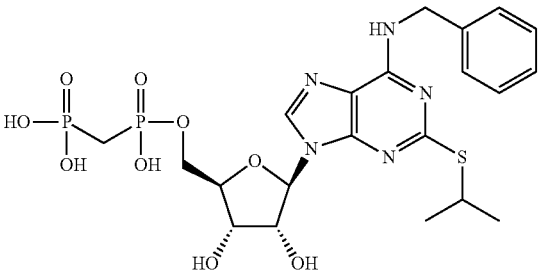 [SMILES: CC(C)Sc1nc(NCc2ccccc2)c2ncn([C@@H]3O[C@H](COP(=O)(O)CP(=O)(O)O)[C@@H](O)[C@H]3O)c2n1] | +++ |
| 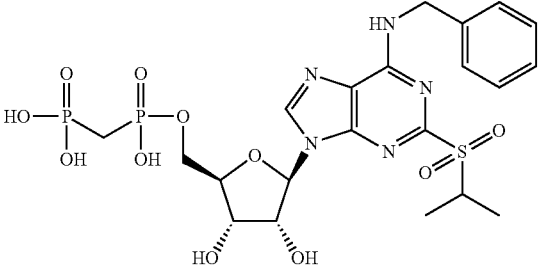 [SMILES: CC(C)S(=O)(=O)c1nc(NCc2ccccc2)c2ncn([C@@H]3O[C@H](COP(=O)(O)CP(=O)(O)O)[C@@H](O)[C@H]3O)c2n1] | ++ |

TABLE 1-continued
Specific Examples (Potency: CD73 IC$_{50}$: + means >1 μM, ++ means 100 nM to 1 μM, +++ means <100 nM).
| | Potency |
|---|---|
| 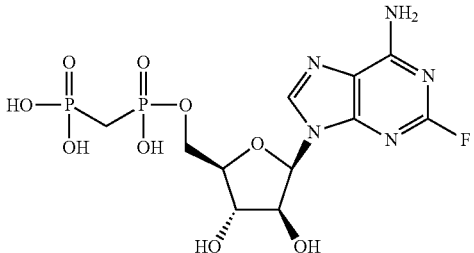 [SMILES: Nc1nc(F)nc2c1ncn2[C@@H]1O[C@H](COP(=O)(O)CP(=O)(O)O)[C@@H](O)[C@@H]1O] | ++ |
| 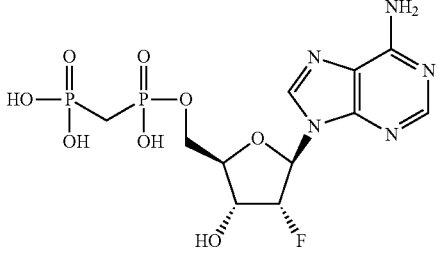 [SMILES: Nc1ncnc2c1ncn2[C@@H]1O[C@H](COP(=O)(O)CP(=O)(O)O)[C@@H](O)[C@H]1F] | + |
| 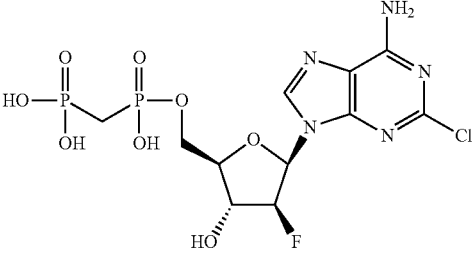 [SMILES: Nc1nc(Cl)nc2c1ncn2[C@@H]1O[C@H](COP(=O)(O)CP(=O)(O)O)[C@@H](O)[C@@H]1F] | +++ |
| 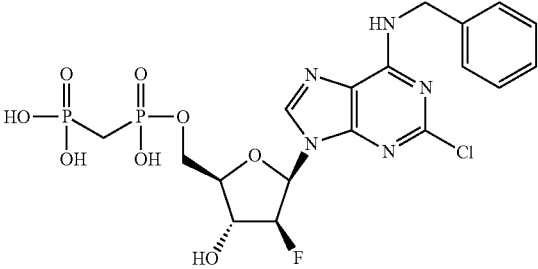 [SMILES: O=P(O)(O)CP(=O)(O)OC[C@H]1O[C@@H](n2cnc3c(NCc4ccccc4)nc(Cl)nc32)[C@@H](F)[C@@H]1O] | +++ |
| 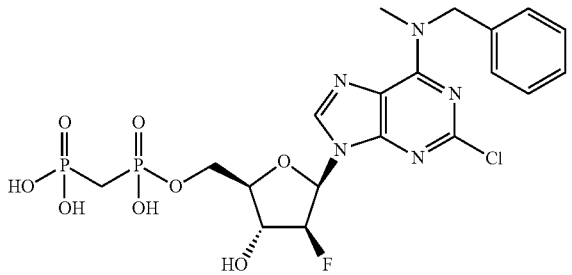 [SMILES: CN(Cc1ccccc1)c1nc(Cl)nc2c1ncn2[C@@H]1O[C@H](COP(=O)(O)CP(=O)(O)O)[C@@H](O)[C@@H]1F] | +++ |

TABLE 1-continued
Specific Examples (Potency: CD73 IC$_{50}$: + means >1 μM, ++ means 100 nM to 1 μM, +++ means <100 nM).
| | Potency |
|---|---|
| 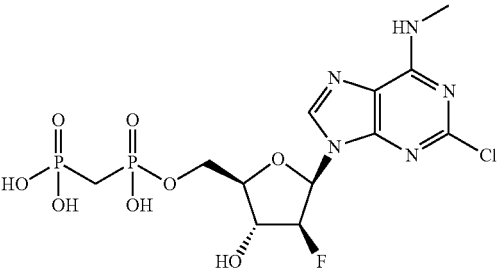 [SMILES: CNc1nc(Cl)nc2c1ncn2[C@@H]1O[C@H](COP(=O)(O)CP(=O)(O)O)[C@@H](O)[C@@H]1F] | +++ |
| 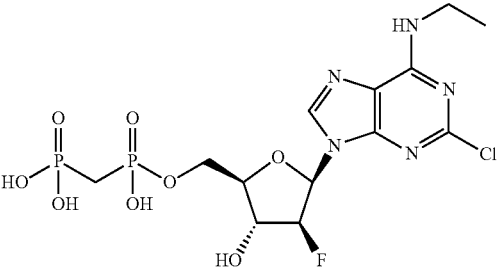 [SMILES: CCNc1nc(Cl)nc2c1ncn2[C@@H]1O[C@H](COP(=O)(O)CP(=O)(O)O)[C@@H](O)[C@@H]1F] | +++ |
| 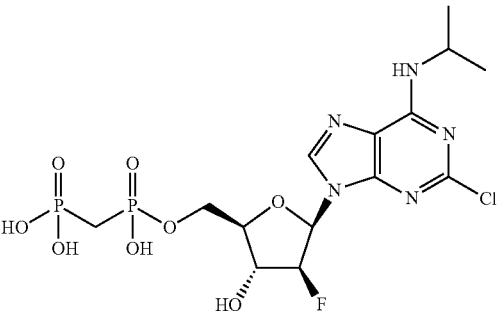 [SMILES: CC(C)Nc1nc(Cl)nc2c1ncn2[C@@H]1O[C@H](COP(=O)(O)CP(=O)(O)O)[C@@H](O)[C@@H]1F] | +++ |
| 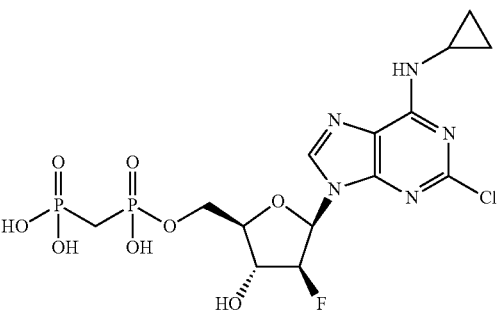 [SMILES: O=P(O)(O)CP(=O)(O)OC[C@H]1O[C@@H](n2cnc3c(NC4CC4)nc(Cl)nc32)[C@@H](F)[C@@H]1O] | +++ |
| 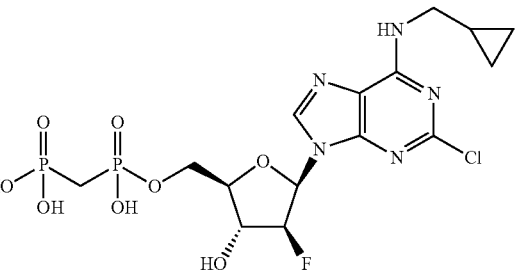 | +++ |

TABLE 1-continued
Specific Examples (Potency: CD73 IC$_{50}$: + means >1 μM, ++ means 100 nM to 1 μM, +++ means <100 nM).
| | Potency |
|---|---|
| 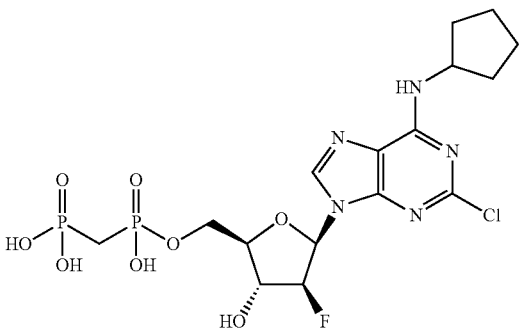 | +++ |
| 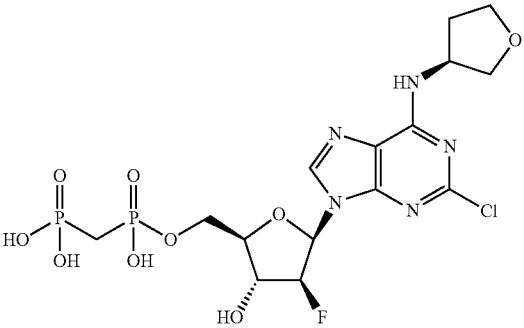 [SMILES: O=P(O)(O)CP(=O)(O)OC[C@H]1O[C@@H](n2cnc3c(N[C@H]4CCOC4)nc(Cl)nc32)[C@@H](F)[C@@H]1O] | +++ |
| 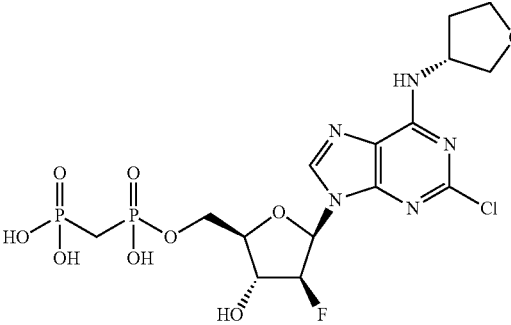 | +++ |
| 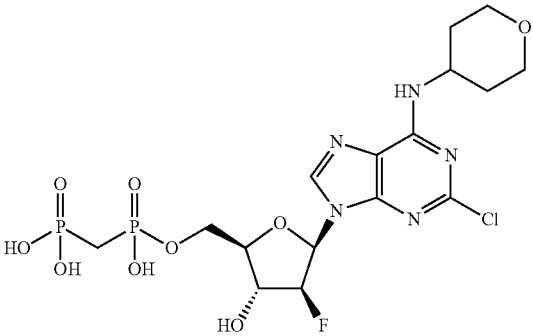 [SMILES: O=P(O)(O)CP(=O)(O)OC[C@H]1O[C@@H](n2cnc3c(NC4CCOCC4)nc(Cl)nc32)[C@@H](F)[C@@H]1O] | +++ |

TABLE 1-continued
Specific Examples (Potency: CD73 IC$_{50}$: + means >1 μM, ++ means 100 nM to 1 μM, +++ means <100 nM).
| Structure | Potency |
|---|---|
| 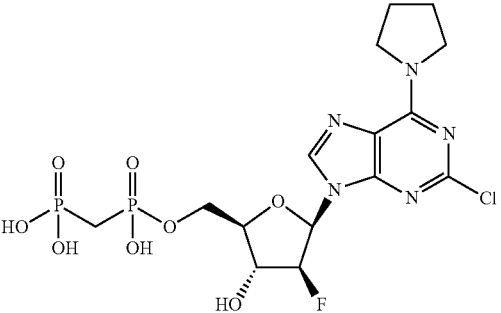 [SMILES: O=P(O)(O)CP(=O)(O)OC[C@H]1O[C@@H](n2cnc3c(N4CCCC4)nc(Cl)nc32)[C@@H](F)[C@@H]1O] | +++ |
| 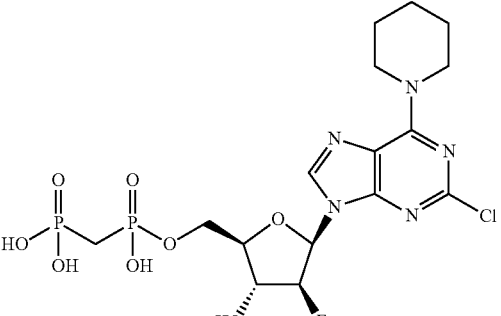 | +++ |
| 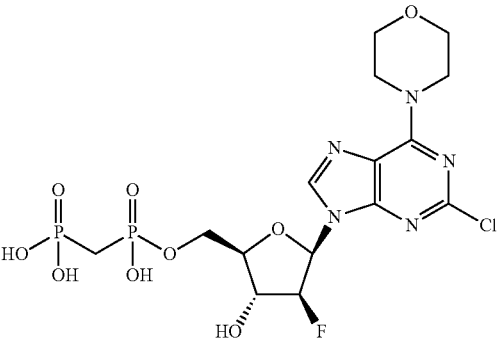 [SMILES: O=P(O)(O)CP(=O)(O)OC[C@H]1O[C@@H](n2cnc3c(N4CCOCC4)nc(Cl)nc32)[C@@H](F)[C@@H]1O] | +++ |
| 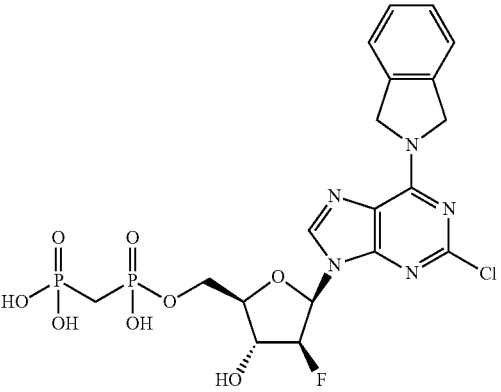 [SMILES: O=P(O)(O)CP(=O)(O)OC[C@H]1O[C@@H](n2cnc3c(N4Cc5ccccc5C4)nc(Cl)nc32)[C@@H](F)[C@@H]1O] | +++ |

TABLE 1-continued
Specific Examples (Potency: CD73 $IC_{50}$: + means >1 µM, ++ means 100 nM to 1 µM, +++ means <100 nM).
| | Potency |
|---|---|
| 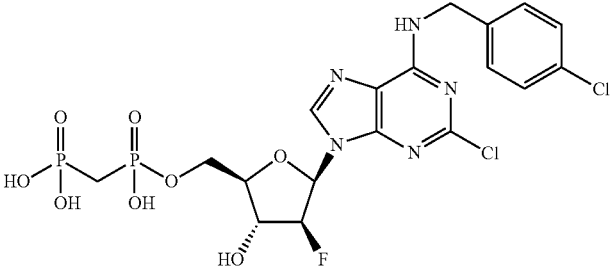 [SMILES: O=P(O)(O)CP(=O)(O)OC[C@H]1O[C@@H](n2cnc3c(NCc4ccc(Cl)cc4)nc(Cl)nc32)[C@@H](F)[C@@H]1O] | +++ |
| 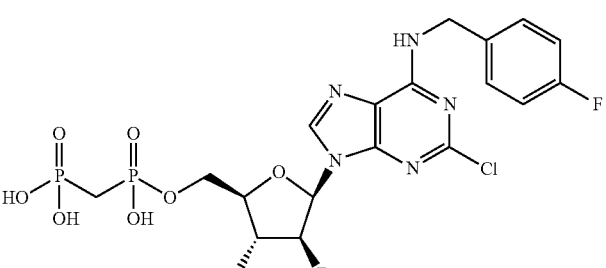 | +++ |
| 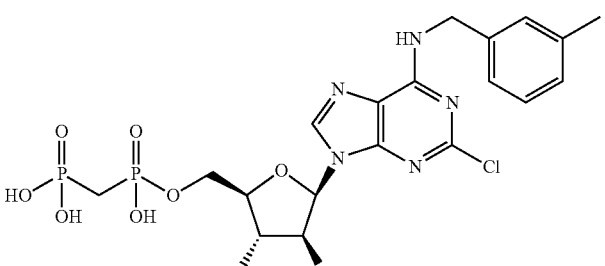 | +++ |
| 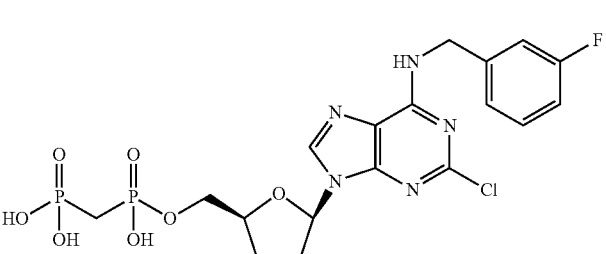 | +++ |
| 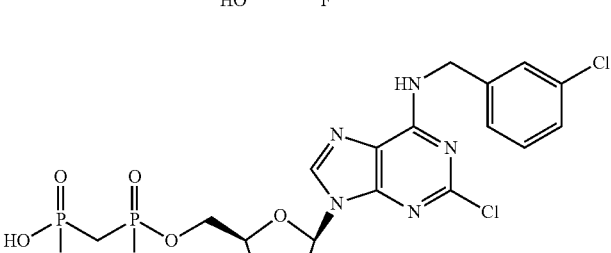 | +++ |

TABLE 1-continued
Specific Examples (Potency: CD73 IC$_{50}$: + means >1 µM, ++ means 100 nM to 1 µM, +++ means <100 nM).
| | Potency |
|---|---|
| 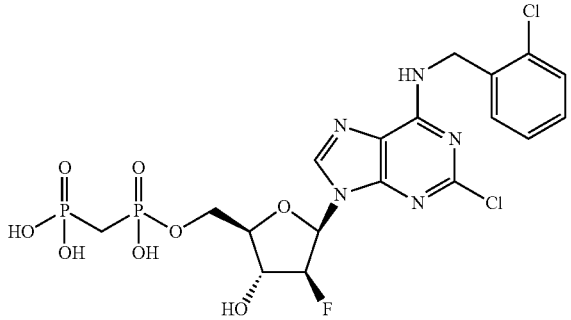 [SMILES: O=P(O)(O)CP(=O)(O)OC[C@H]1O[C@@H](n2cnc3c(NCc4ccccc4Cl)nc(Cl)nc32)[C@@H](F)[C@@H]1O] | +++ |
| 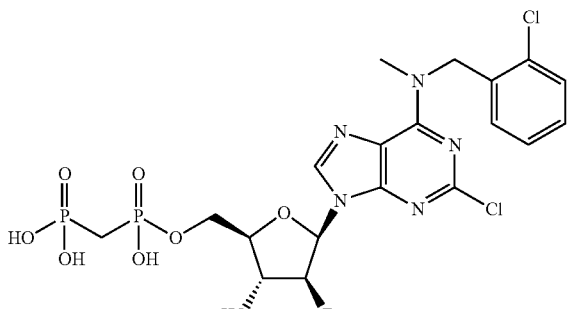 | +++ |
| 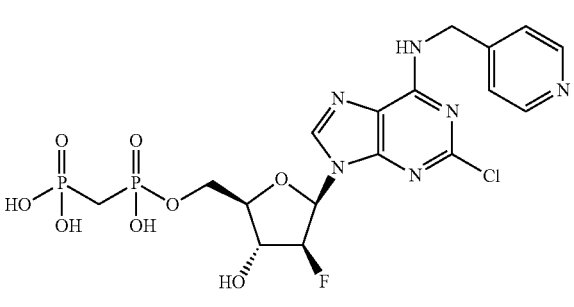 [SMILES: O=P(O)(O)CP(=O)(O)OC[C@H]1O[C@@H](n2cnc3c(NCc4ccncc4)nc(Cl)nc32)[C@@H](F)[C@@H]1O] | +++ |
| 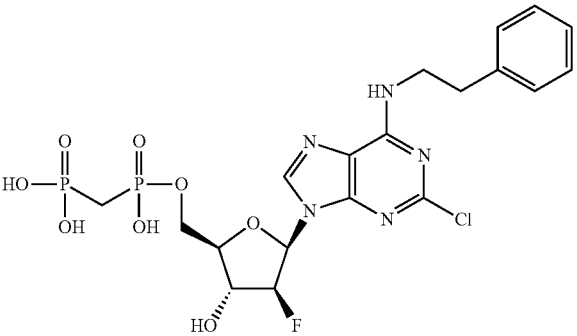 [SMILES: O=P(O)(O)CP(=O)(O)OC[C@H]1O[C@@H](n2cnc3c(NCCc4ccccc4)nc(Cl)nc32)[C@@H](F)[C@@H]1O] | +++ |
| 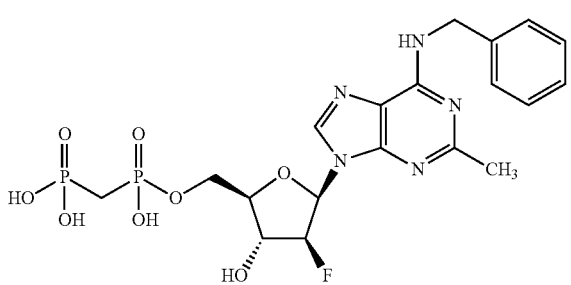 [SMILES: Cc1nc(NCc2ccccc2)c2ncn([C@@H]3O[C@H](COP(=O)(O)CP(=O)(O)O)[C@@H](O)[C@@H]3F)c2n1] | +++ |

TABLE 1-continued

Specific Examples (Potency: CD73 IC$_{50}$: + means >1 µM, ++ means 100 nM to 1 µM, +++ means <100 nM).

| | Potency |
|---|---|
| (structure: cyclopentylamino, 2-methyl purine, 2'-fluoro ribose, methylenebisphosphonate) | +++ |
| (structure: N-benzyl, 2-CF₃ purine, 2'-fluoro ribose, methylenebisphosphonate) | +++ |
| (structure: cyclopentylamino, 2-CF₃ purine, 2'-fluoro ribose, methylenebisphosphonate) | +++ |
| (structure: N-benzyl, 2-Ph purine, 2'-fluoro ribose, methylenebisphosphonate) | +++ |
| (structure: N-benzyl, 2-CH₂Ph purine, 2'-fluoro ribose, methylenebisphosphonate) | +++ |

TABLE 1-continued

Specific Examples (Potency: CD73 IC$_{50}$: + means >1 μM, ++ means 100 nM to 1 μM, +++ means <100 nM).

| | Potency |
|---|---|
| (structure: bisphosphonate-linked ribose with 2'-F, 3'-OH, N6-cyclopentyl-2-methyl adenine) | +++ |
| (structure: bisphosphonate-linked ribose with 2'-F, 3'-OH, N6-cyclopentyl-2-(piperidin-1-ylmethyl) adenine) | ++ |
| (structure: bisphosphonate-linked ribose with 2'-F, 3'-OH, N6-cyclopentyl-2-(methoxymethyl) adenine) | +++ |
| (structure: bisphosphonate-linked ribose with 2'-F, 3'-OH, N6-benzyl-2-(hydroxy(phenyl)methyl) adenine) | +++ |

TABLE 1-continued
Specific Examples (Potency: CD73 IC$_{50}$: + means >1 μM, ++ means 100 nM to 1 μM, +++ means <100 nM).
| | Potency |
|---|---|
| 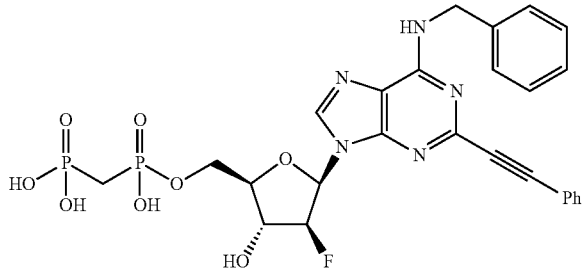 [SMILES: O=P(O)(O)CP(=O)(O)OC[C@H]1O[C@@H](n2cnc3c(NCc4ccccc4)nc(C#Cc4ccccc4)nc32)[C@@H](F)[C@@H]1O] | +++ |
| 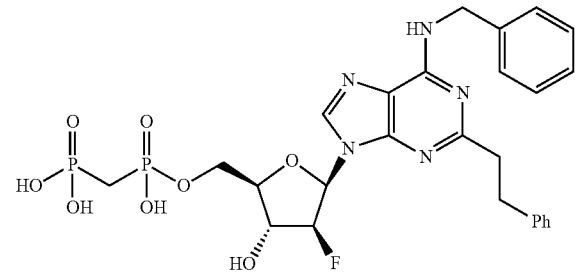 [SMILES: O=P(O)(O)CP(=O)(O)OC[C@H]1O[C@@H](n2cnc3c(NCc4ccccc4)nc(CCc4ccccc4)nc32)[C@@H](F)[C@@H]1O] | +++ |
| 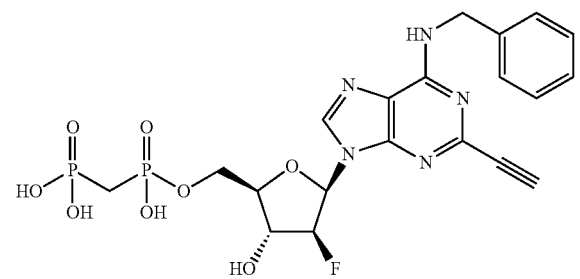 [SMILES: C#Cc1nc(NCc2ccccc2)c2ncn([C@@H]3O[C@H](COP(=O)(O)CP(=O)(O)O)[C@@H](O)[C@@H]3F)c2n1] | +++ |
| 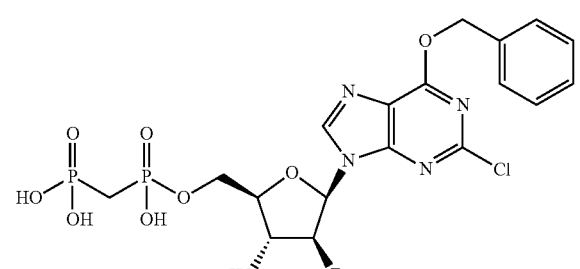 | +++ |
| 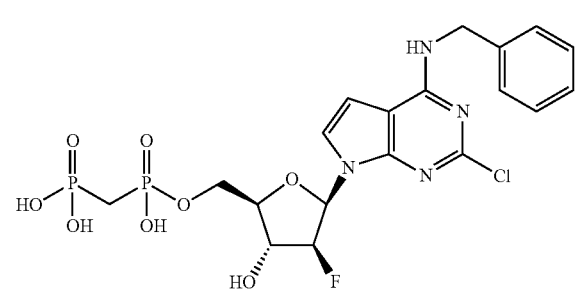 [SMILES: O=P(O)(O)CP(=O)(O)OC[C@H]1O[C@@H](n2ccc3c(NCc4ccccc4)nc(Cl)nc32)[C@@H](F)[C@@H]1O] | +++ |

TABLE 1-continued
Specific Examples (Potency: CD73 $IC_{50}$: + means >1 μM, ++ means 100 nM to 1 μM, +++ means <100 nM).
| | Potency |
|---|---|
| 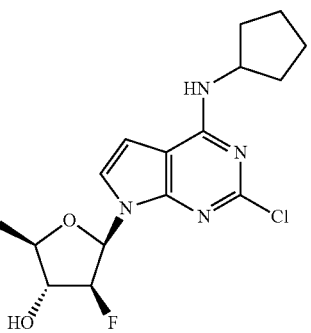 | +++ |
| 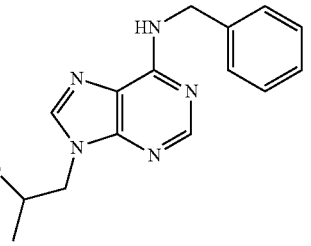 | + |
| 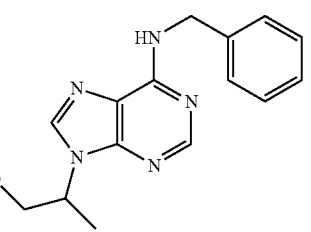 | + |
| 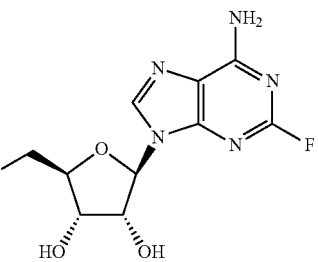 | +++ |
| 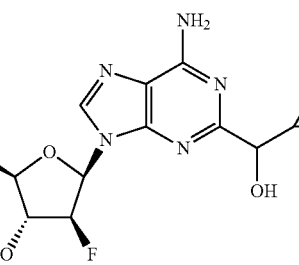 | +++ |

TABLE 1-continued
Specific Examples (Potency: CD73 $IC_{50}$: + means >1 μM, ++ means 100 nM to 1 μM, +++ means <100 nM).
Potency
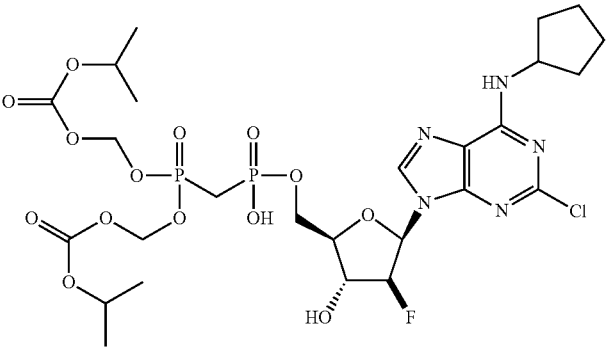 [SMILES: CC(C)OC(=O)OCOP(=O)(CP(=O)(O)OC[C@H]1O[C@@H](n2cnc3c(NC4CCCC4)nc(Cl)nc32)[C@@H](F)[C@@H]1O)OCOC(=O)OC(C)C]
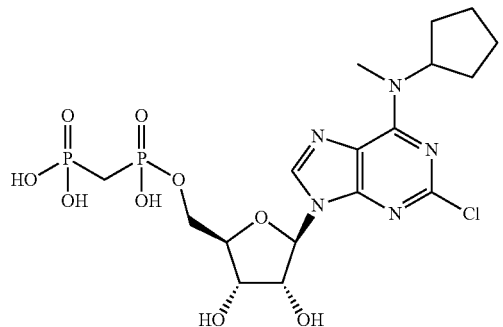 [SMILES: CN(c1nc(Cl)nc2c1ncn2[C@@H]1O[C@H](COP(=O)(O)CP(=O)(O)O)[C@@H](O)[C@H]1O)C1CCCC1]
+++
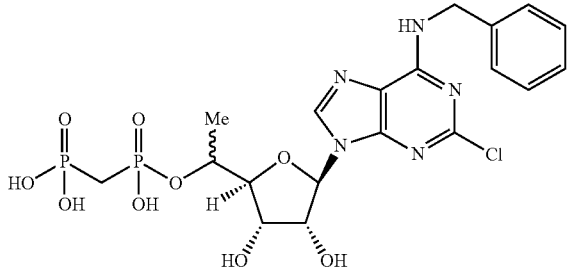 [SMILES: CC(OP(=O)(O)CP(=O)(O)O)[C@H]1O[C@@H](n2cnc3c(NCc4ccccc4)nc(Cl)nc32)[C@H](O)[C@@H]1O]
+++
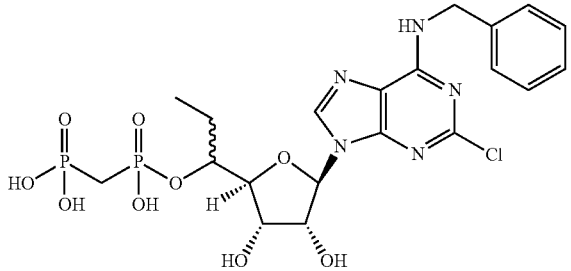 [SMILES: CCC(OP(=O)(O)CP(=O)(O)O)[C@H]1O[C@@H](n2cnc3c(NCc4ccccc4)nc(Cl)nc32)[C@H](O)[C@@H]1O]
+++

TABLE 1-continued

Specific Examples (Potency: CD73 IC$_{50}$: + means >1 μM, ++ means 100 nM to 1 μM, +++ means <100 nM).

| | Potency |
|---|---|
| [structure: N6-cyclopentyl-2-chloro adenine with 2'-methyl ribose, 5'-methylenebisphosphonate (HO)₂P(O)-CH₂-P(O)(OH)-O-] | +++ |
| [structure: N6-methyl-N6-cyclopentyl-2-chloro adenine with 2'-methyl ribose, 5'-methylenebisphosphonate] | +++ |
| [structure: N6-cyclopentyl-2-chloro adenine riboside, 5'-methylenebisphosphonate with one OMe on terminal P] | ++ |
| [structure: N6-methyl-N6-cyclopentyl-2-chloro adenine riboside, 5'-methylenebisphosphonate tri-phenyl ester (PhO, OPh, OPh)] | + |

TABLE 1-continued
Specific Examples (Potency: CD73 IC$_{50}$: + means >1 μM, ++ means 100 nM to 1 μM, +++ means <100 nM).
| | Potency |
|---|---|
| 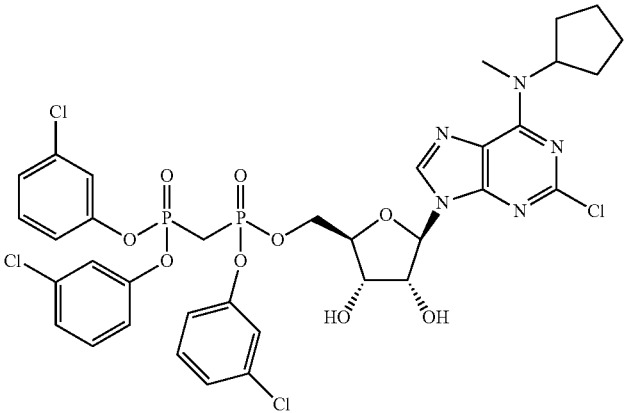 [SMILES: CN(c1nc(Cl)nc2c1ncn2[C@@H]1O[C@H](COP(=O)(CP(=O)(Oc2cccc(Cl)c2)Oc2cccc(Cl)c2)Oc2cccc(Cl)c2)[C@@H](O)[C@H]1O)C1CCCC1] | + |
| 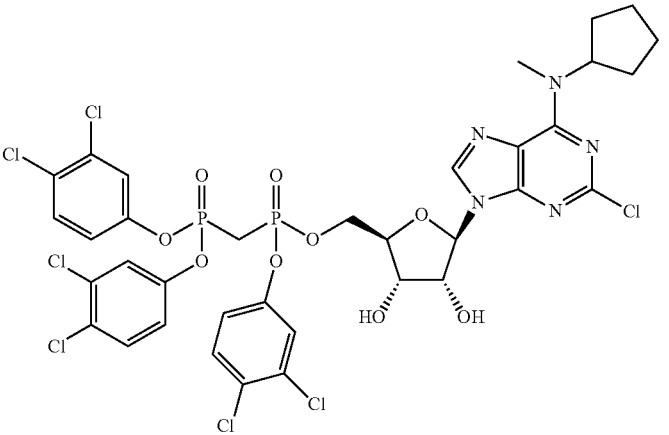 [SMILES: CN(c1nc(Cl)nc2c1ncn2[C@@H]1O[C@H](COP(=O)(CP(=O)(Oc2ccc(Cl)c(Cl)c2)Oc2ccc(Cl)c(Cl)c2)Oc2ccc(Cl)c(Cl)c2)[C@@H](O)[C@H]1O)C1CCCC1] | + |
| 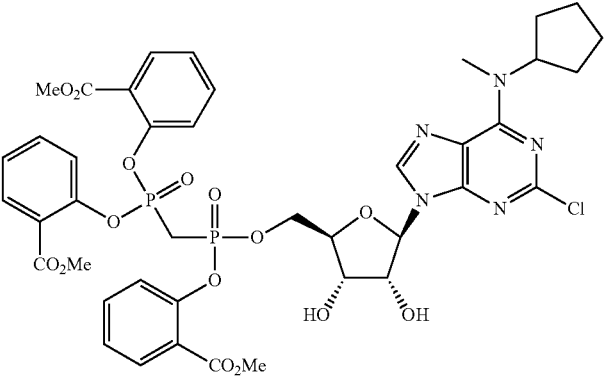 [SMILES: COC(=O)c1ccccc1OP(=O)(CP(=O)(Oc1ccccc1C(=O)OC)Oc1ccccc1C(=O)OC)OC[C@H]1O[C@@H](n2cnc3c(N(C)C4CCCC4)nc(Cl)nc32)[C@H](O)[C@@H]1O] | + |

TABLE 1-continued
Specific Examples (Potency: CD73 $IC_{50}$: + means >1 μM, ++ means 100 nM to 1 μM, +++ means <100 nM).
| | Potency |
|---|---|
| 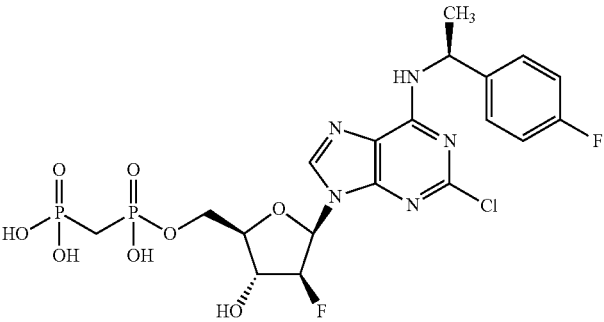 [SMILES: C[C@H](Nc1nc(Cl)nc2c1ncn2[C@@H]1O[C@H](COP(=O)(O)CP(=O)(O)O)[C@@H](O)[C@@H]1F)c1ccc(F)cc1] | +++ |
| 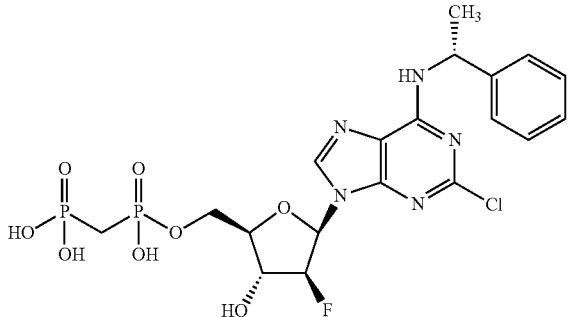 [SMILES: C[C@@H](Nc1nc(Cl)nc2c1ncn2[C@@H]1O[C@H](COP(=O)(O)CP(=O)(O)O)[C@@H](O)[C@@H]1F)c1ccccc1] | +++ |
| 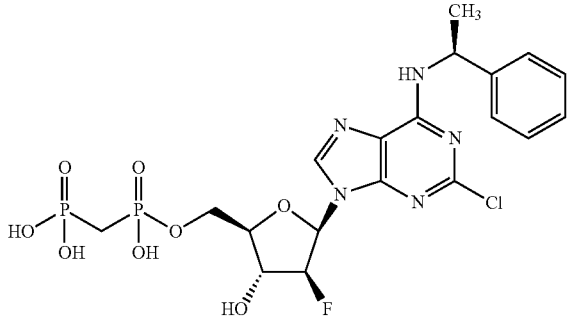 | +++ |
| 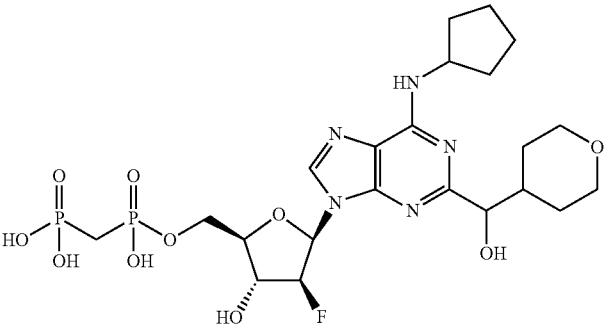 [SMILES: O=P(O)(O)CP(=O)(O)OC[C@H]1O[C@@H](n2cnc3c(NC4CCCC4)nc(C(O)C4CCOCC4)nc32)[C@@H](F)[C@@H]1O] | ++ |

TABLE 1-continued
Specific Examples (Potency: CD73 IC$_{50}$: + means >1 μM, ++ means 100 nM to 1 μM, +++ means <100 nM).
| | Potency |
|---|---|
| 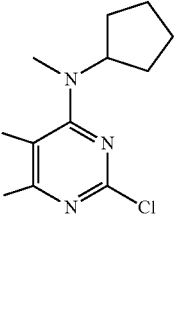 | +++ |
| 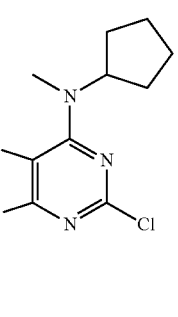 | ++ |
| 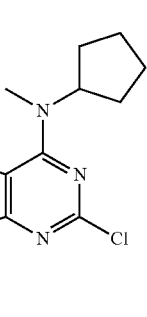 | + |
| 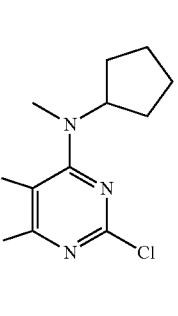 | + |

TABLE 1-continued
Specific Examples (Potency: CD73 IC$_{50}$: + means >1 μM, ++ means 100 nM to 1 μM, +++ means <100 nM).
| | Potency |
|---|---|
| 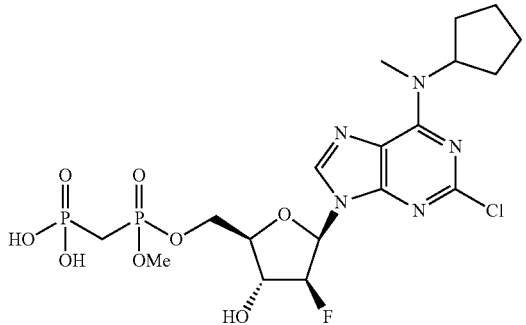 [SMILES: COP(=O)(CP(=O)(O)O)OC[C@H]1O[C@@H](n2cnc3c(N(C)C4CCCC4)nc(Cl)nc32)[C@@H](F)[C@@H]1O] | +++ |
| 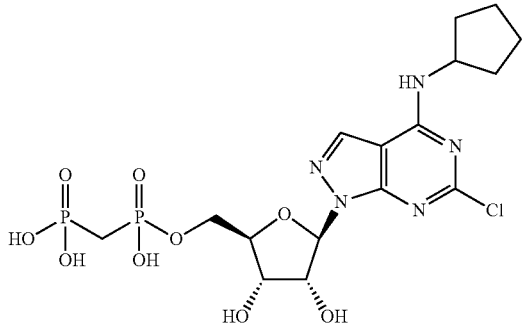 | +++ |
| 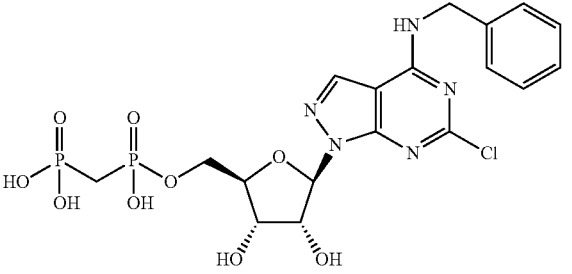 [SMILES: O=P(O)(O)CP(=O)(O)OC[C@H]1O[C@@H](n2ncc3c(NCc4ccccc4)nc(Cl)nc32)[C@H](O)[C@@H]1O] | +++ |
| 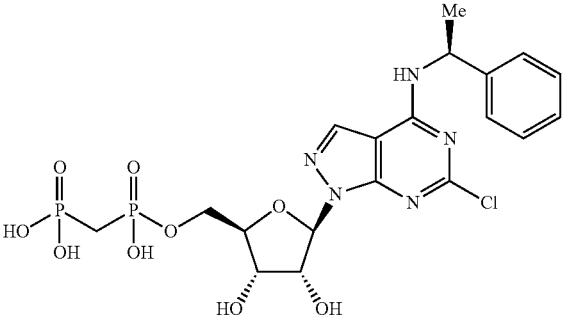 [SMILES: C[C@H](Nc1nc(Cl)nc2c1cnn2[C@@H]1O[C@H](COP(=O)(O)CP(=O)(O)O)[C@@H](O)[C@H]1O)c1ccccc1] | +++ |

TABLE 1-continued
Specific Examples (Potency: CD73 $IC_{50}$: + means >1 µM, ++ means 100 nM to 1 µM, +++ means <100 nM).
| | Potency |
|---|---|
| 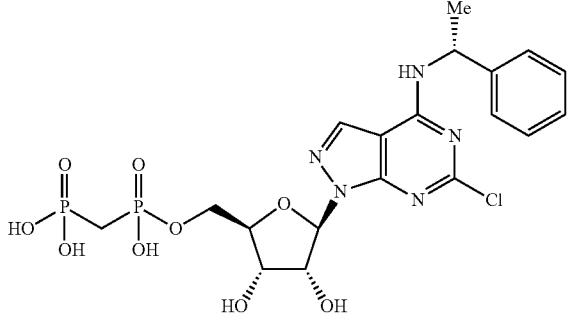 [SMILES: C[C@@H](Nc1nc(Cl)nc2c1cnn2[C@@H]1O[C@H](COP(=O)(O)CP(=O)(O)O)[C@@H](O)[C@H]1O)c1ccccc1] | +++ |
| 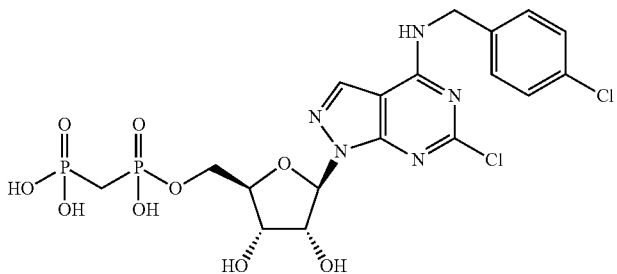 [SMILES: O=P(O)(O)CP(=O)(O)OC[C@H]1O[C@@H](n2ncc3c(NCc4ccc(Cl)cc4)nc(Cl)nc32)[C@H](O)[C@@H]1O] | +++ |
| 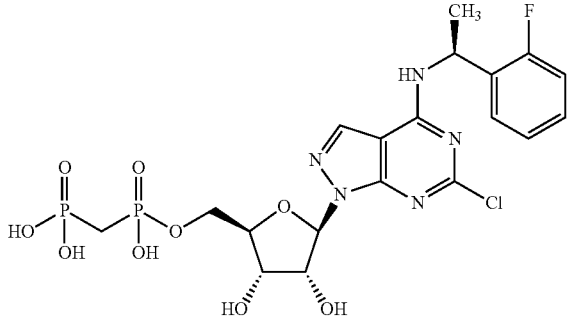 [SMILES: C[C@H](Nc1nc(Cl)nc2c1cnn2[C@@H]1O[C@H](COP(=O)(O)CP(=O)(O)O)[C@@H](O)[C@H]1O)c1ccccc1F] | +++ |
| 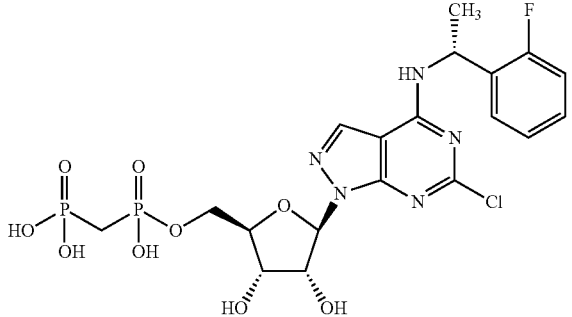 [SMILES: C[C@@H](Nc1nc(Cl)nc2c1cnn2[C@@H]1O[C@H](COP(=O)(O)CP(=O)(O)O)[C@@H](O)[C@H]1O)c1ccccc1F] | +++ |

TABLE 1-continued
Specific Examples (Potency: CD73 IC$_{50}$: + means >1 µM, ++ means 100 nM to 1 µM, +++ means <100 nM).
| | Potency |
|---|---|
| 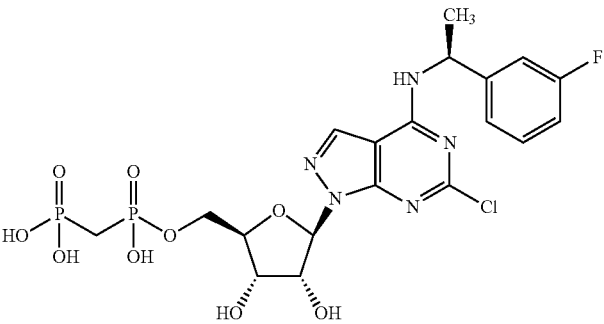 [SMILES: C[C@H](Nc1nc(Cl)nc2c1cnn2[C@@H]1O[C@H](COP(=O)(O)CP(=O)(O)O)[C@@H](O)[C@H]1O)c1cccc(F)c1] | +++ |
| 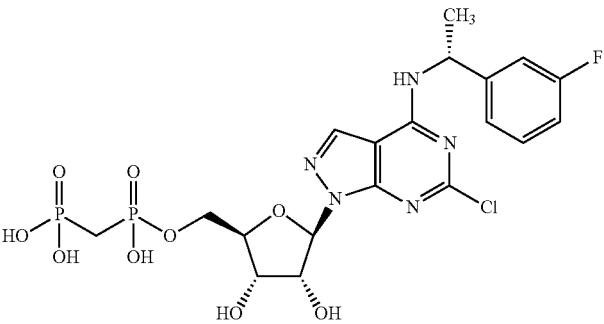 [SMILES: C[C@@H](Nc1nc(Cl)nc2c1cnn2[C@@H]1O[C@H](COP(=O)(O)CP(=O)(O)O)[C@@H](O)[C@H]1O)c1cccc(F)c1] | +++ |
| 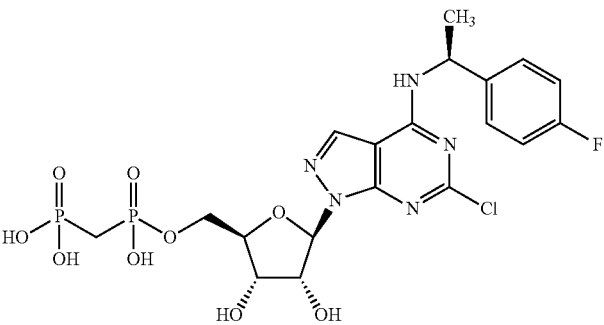 [SMILES: C[C@H](Nc1nc(Cl)nc2c1cnn2[C@@H]1O[C@H](COP(=O)(O)CP(=O)(O)O)[C@@H](O)[C@H]1O)c1ccc(F)cc1] | +++ |
| 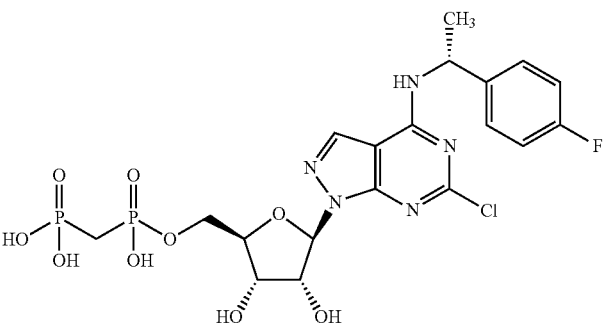 [SMILES: C[C@@H](Nc1nc(Cl)nc2c1cnn2[C@@H]1O[C@H](COP(=O)(O)CP(=O)(O)O)[C@@H](O)[C@H]1O)c1ccc(F)cc1] | +++ |

TABLE 1-continued
Specific Examples (Potency: CD73 IC$_{50}$: + means >1 μM, ++ means 100 nM to 1 μM, +++ means <100 nM).
| | Potency |
|---|---|
| 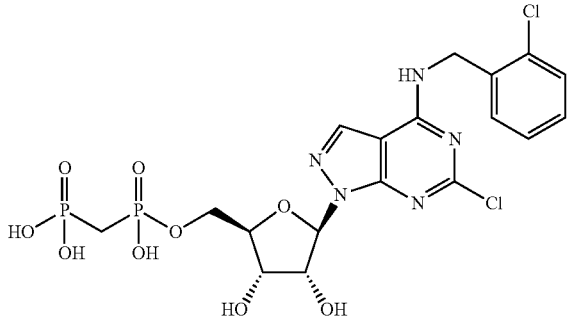 [SMILES: O=P(O)(O)CP(=O)(O)OC[C@H]1O[C@@H](n2ncc3c(NCc4ccccc4Cl)nc(Cl)nc32)[C@H](O)[C@@H]1O] | +++ |
| 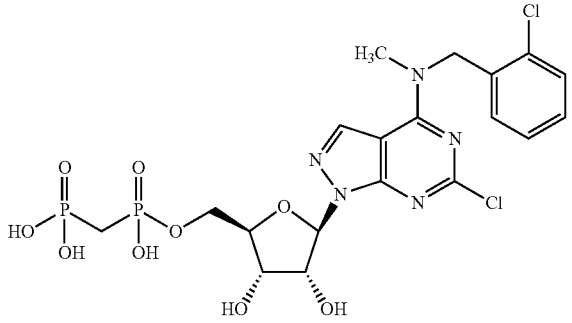 [SMILES: CN(Cc1ccccc1Cl)c1nc(Cl)nc2c1cnn2[C@@H]1O[C@H](COP(=O)(O)CP(=O)(O)O)[C@@H](O)[C@H]1O] | +++ |
| 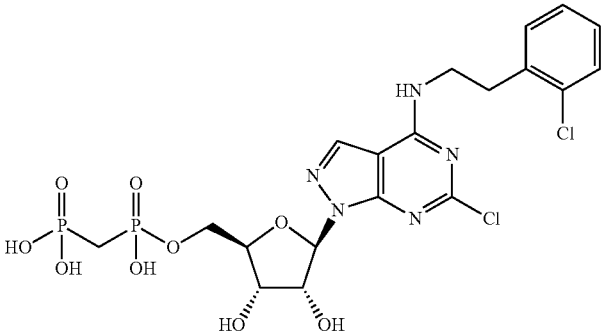 [SMILES: O=P(O)(O)CP(=O)(O)OC[C@H]1O[C@@H](n2ncc3c(NCCc4ccccc4Cl)nc(Cl)nc32)[C@H](O)[C@@H]1O] | +++ |
| 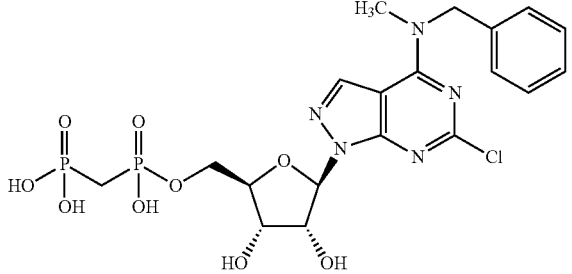 [SMILES: CN(Cc1ccccc1)c1nc(Cl)nc2c1cnn2[C@@H]1O[C@H](COP(=O)(O)CP(=O)(O)O)[C@@H](O)[C@H]1O] | +++ |

TABLE 1-continued
Specific Examples (Potency: CD73 IC$_{50}$: + means >1 μM, ++ means 100 nM to 1 μM, +++ means <100 nM).
| | Potency |
|---|---|
| 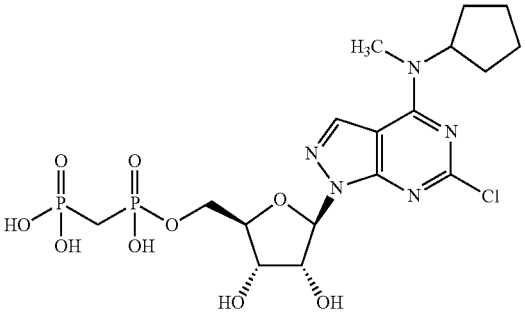 [SMILES: CN(c1nc(Cl)nc2c1cnn2[C@@H]1O[C@H](COP(=O)(O)CP(=O)(O)O)[C@@H](O)[C@H]1O)C1CCCC1] | +++ |
| 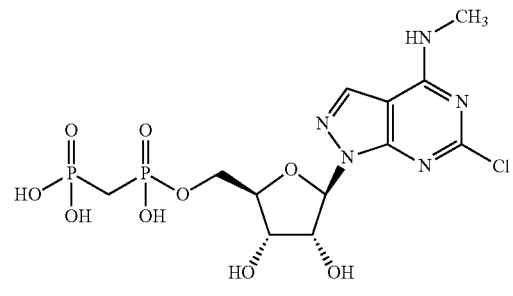 [SMILES: CNc1nc(Cl)nc2c1cnn2[C@@H]1O[C@H](COP(=O)(O)CP(=O)(O)O)[C@@H](O)[C@H]1O] | +++ |
| 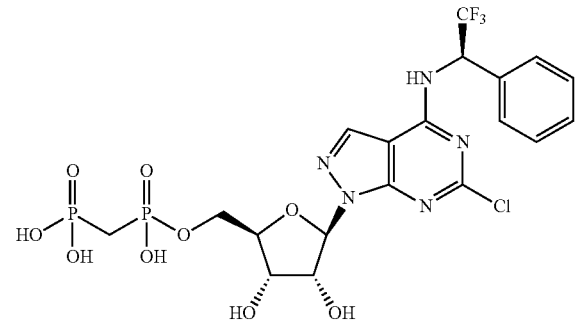 [SMILES: O=P(O)(O)CP(=O)(O)OC[C@H]1O[C@@H](n2ncc3c(N[C@H](c4ccccc4)C(F)(F)F)nc(Cl)nc32)[C@H](O)[C@@H]1O] | +++ |
| 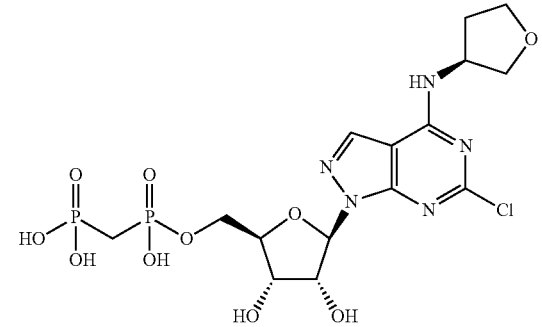 [SMILES: O=P(O)(O)CP(=O)(O)OC[C@H]1O[C@@H](n2ncc3c(N[C@H]4CCOC4)nc(Cl)nc32)[C@H](O)[C@@H]1O] | +++ |

TABLE 1-continued

Specific Examples (Potency: CD73 IC$_{50}$: + means >1 μM, ++ means 100 nM to 1 μM, +++ means <100 nM).

| | Potency |
|---|---|
| (structure) | + |
| (structure) | + |
| (structure) | +++ |
| (structure) | +++ |

TABLE 1-continued
Specific Examples (Potency: CD73 IC$_{50}$: + means >1 μM, ++ means 100 nM to 1 μM, +++ means <100 nM).
| | Potency |
|---|---|
| 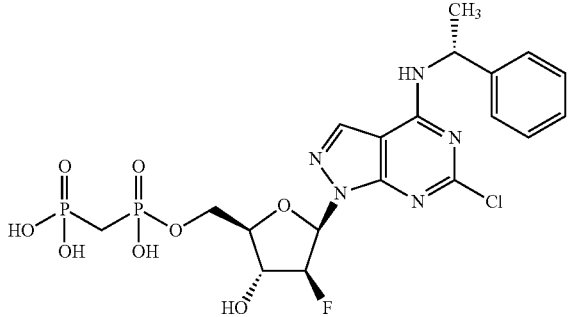 [SMILES: C[C@@H](Nc1nc(Cl)nc2c1cnn2[C@@H]1O[C@H](COP(=O)(O)CP(=O)(O)O)[C@@H](O)[C@@H]1F)c1ccccc1] | +++ |
| 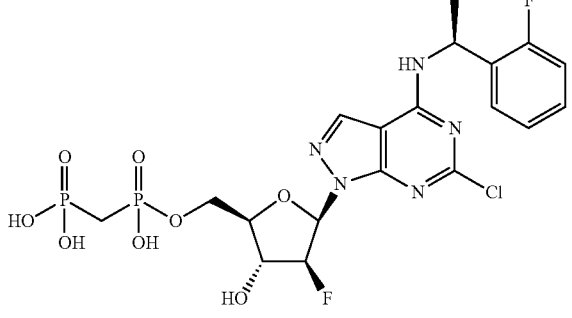 | +++ |
| 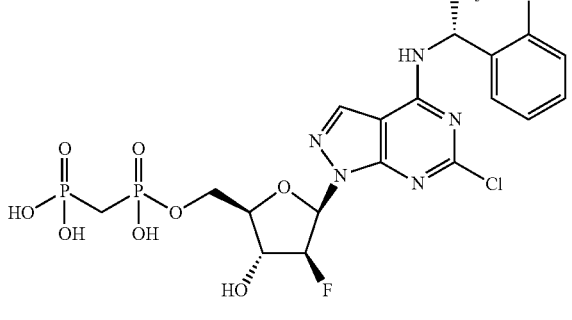 | +++ |
| 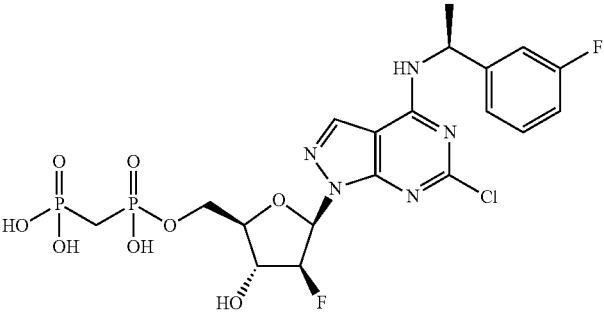 [SMILES: C[C@H](Nc1nc(Cl)nc2c1cnn2[C@@H]1O[C@H](COP(=O)(O)CP(=O)(O)O)[C@@H](O)[C@@H]1F)c1cccc(F)c1] | +++ |

TABLE 1-continued
Specific Examples (Potency: CD73 IC$_{50}$: + means >1 µM, ++ means 100 nM to 1 µM, +++ means <100 nM).
| | Potency |
|---|---|
| 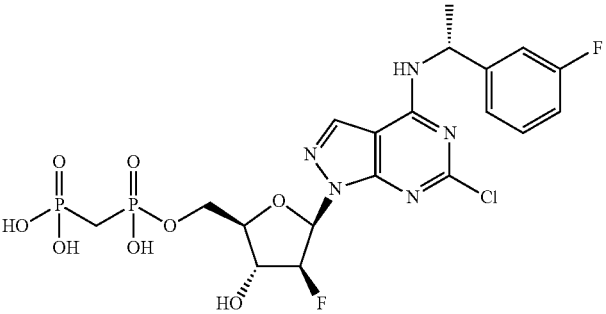 [SMILES: C[C@@H](Nc1nc(Cl)nc2c1cnn2[C@@H]1O[C@H](COP(=O)(O)CP(=O)(O)O)[C@@H](O)[C@@H]1F)c1cccc(F)c1] | +++ |
| 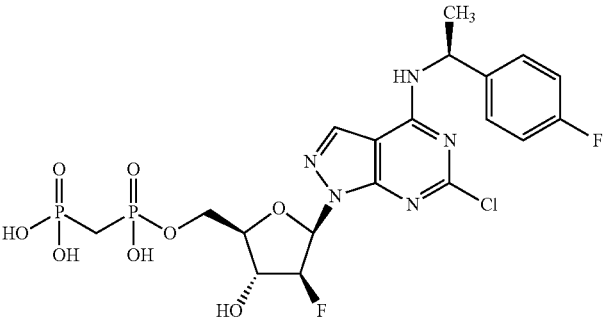 [SMILES: C[C@H](Nc1nc(Cl)nc2c1cnn2[C@@H]1O[C@H](COP(=O)(O)CP(=O)(O)O)[C@@H](O)[C@@H]1F)c1ccc(F)cc1] | +++ |
| 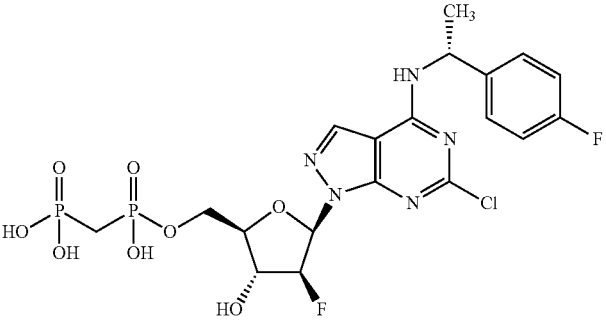 [SMILES: C[C@@H](Nc1nc(Cl)nc2c1cnn2[C@@H]1O[C@H](COP(=O)(O)CP(=O)(O)O)[C@@H](O)[C@@H]1F)c1ccc(F)cc1] | +++ |
| 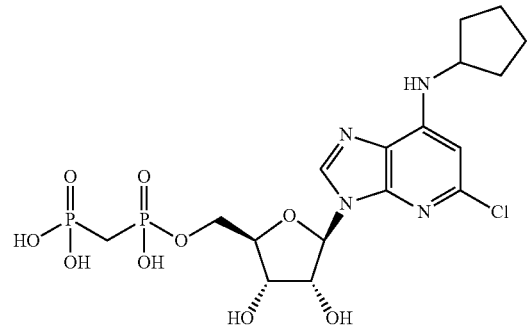 [SMILES: O=P(O)(O)CP(=O)(O)OC[C@H]1O[C@@H](n2cnc3c(NC4CCCC4)cc(Cl)nc32)[C@H](O)[C@@H]1O] | +++ |

TABLE 1-continued

Specific Examples (Potency: CD73 IC$_{50}$: + means >1 μM, ++ means 100 nM to 1 μM, +++ means <100 nM).

| | Potency |
|---|---|
| [Structure: methylene bisphosphonate linked via O to ribose (3'-OH, 2'-F) attached to N of imidazo[4,5-b]pyridine bearing 7-NH-cyclopentyl and 5-Cl] | +++ |
| [Structure: methylene bisphosphonate linked via O to ribose (2',3'-diOH) attached to N of pyrazolo[3,4-b]pyridine bearing 4-NH-cyclopentyl and 6-Cl] | +++ |
| [Structure: methylene bisphosphonate linked via O to ribose (2',3'-diOH) attached to N of pyrazolo[3,4-b]pyridine bearing 4-NH-((S)-1-phenylethyl) and 6-Cl] | +++ |
| [Structure: methylene bisphosphonate linked via O to ribose (2',3'-diOH) attached to N of pyrazolo[3,4-b]pyridine bearing 4-NH-((R)-1-phenylethyl) and 6-Cl] | +++ |

TABLE 1-continued
Specific Examples (Potency: CD73 IC$_{50}$: + means >1 μM, ++ means 100 nM to 1 μM, +++ means <100 nM).
| | Potency |
|---|---|
| 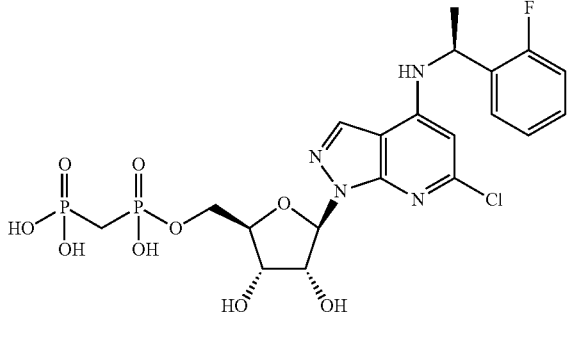 [SMILES: C[C@H](Nc1cc(Cl)nc2c1cnn2[C@@H]1O[C@H](COP(=O)(O)CP(=O)(O)O)[C@@H](O)[C@H]1O)c1ccccc1F] | +++ |
| 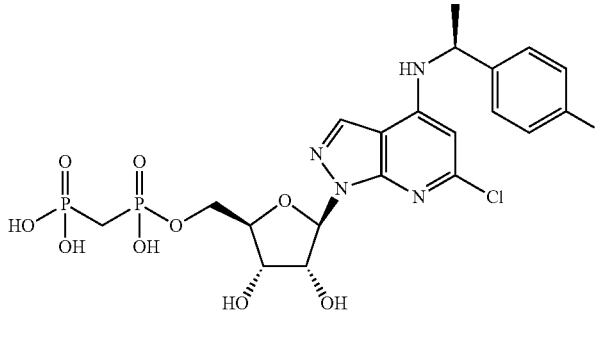 | +++ |
| 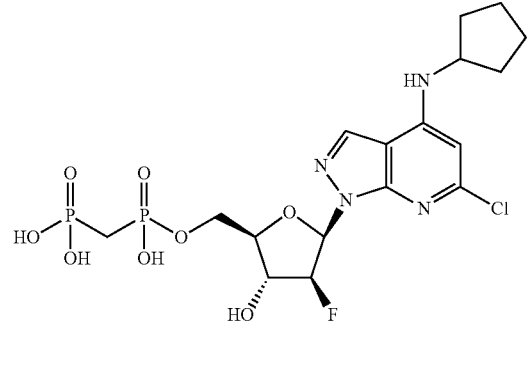 [SMILES: O=P(O)(O)CP(=O)(O)OC[C@H]1O[C@@H](n2ncc3c(NC4CCCC4)cc(Cl)nc32)[C@@H](F)[C@@H]1O] | +++ |
| 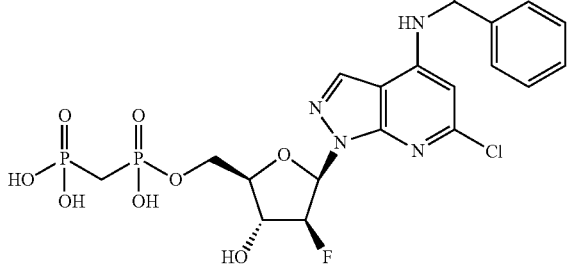 | +++ |

TABLE 1-continued
Specific Examples (Potency: CD73 IC$_{50}$: + means >1 μM, ++ means 100 nM to 1 μM, +++ means <100 nM).
| | Potency |
|---|---|
| 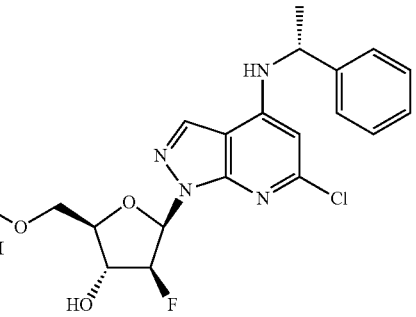 | +++ |
| 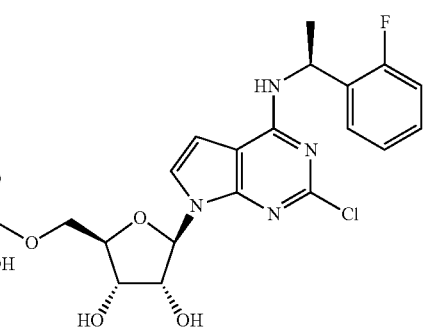 | +++ |
| 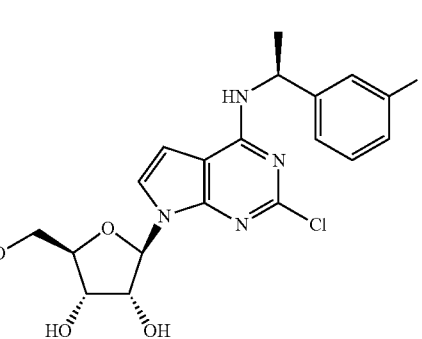 | +++ |
| 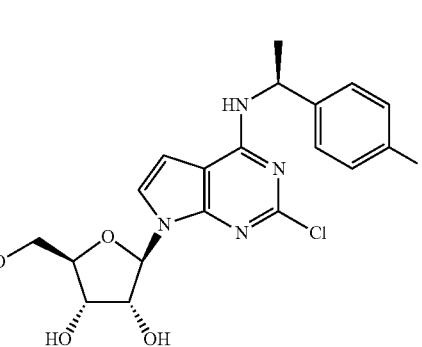 | +++ |

TABLE 1-continued
Specific Examples (Potency: CD73 IC$_{50}$: + means >1 µM, ++ means 100 nM to 1 µM, +++ means <100 nM).
| | Potency |
|---|---|
| 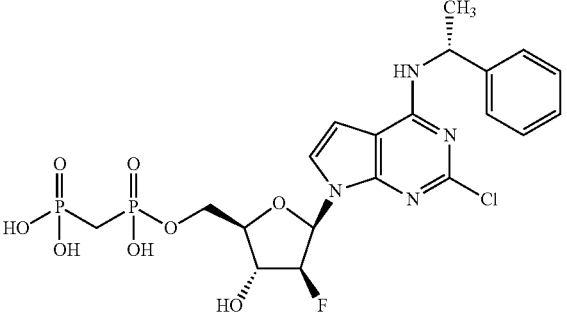 [SMILES: C[C@@H](Nc1nc(Cl)nc2c1ccn2[C@@H]1O[C@H](COP(=O)(O)CP(=O)(O)O)[C@@H](O)[C@@H]1F)c1ccccc1] | +++ |
| 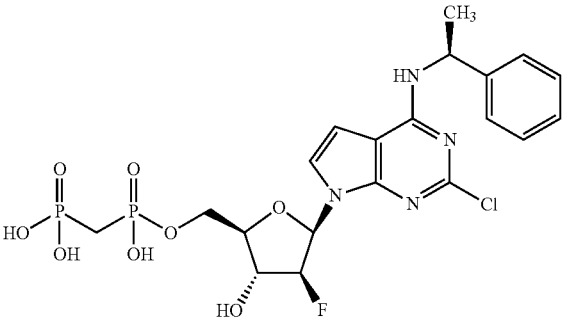 [SMILES: C[C@H](Nc1nc(Cl)nc2c1ccn2[C@@H]1O[C@H](COP(=O)(O)CP(=O)(O)O)[C@@H](O)[C@@H]1F)c1ccccc1] | +++ |
| 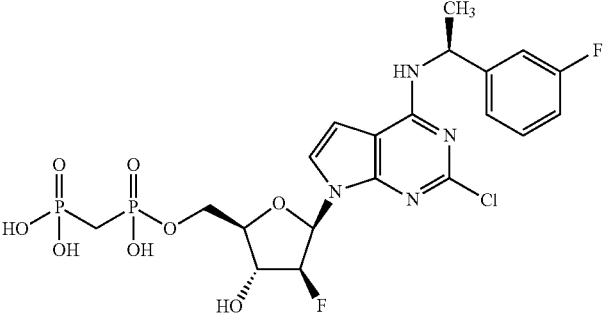 [SMILES: C[C@H](Nc1nc(Cl)nc2c1ccn2[C@@H]1O[C@H](COP(=O)(O)CP(=O)(O)O)[C@@H](O)[C@@H]1F)c1cccc(F)c1] | +++ |
| 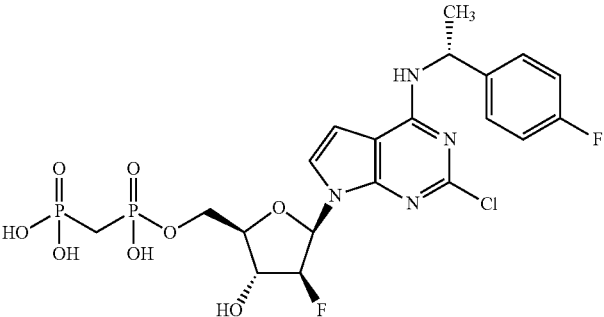 [SMILES: C[C@@H](Nc1nc(Cl)nc2c1ccn2[C@@H]1O[C@H](COP(=O)(O)CP(=O)(O)O)[C@@H](O)[C@@H]1F)c1ccc(F)cc1] | +++ |

TABLE 1-continued

Specific Examples (Potency: CD73 IC$_{50}$: + means >1 μM, ++ means 100 nM to 1 μM, +++ means <100 nM).

| | Potency |
|---|---|
| *[structure: methylenebisphosphonate linked to fluoro-ribose-pyrrolopyrimidine with 2-Cl and 4-NH-CH(CH$_3$)-(4-fluorophenyl)]* | +++ |
| *[structure: methylenebisphosphonate linked to fluoro-ribose-pyrrolopyrimidine with 2-Cl and 4-NH-CH(CH$_3$)-(2-fluorophenyl)]* | +++ |
| *[structure: methylenebisphosphonate linked to fluoro-ribose-pyrrolopyrimidine with 2-Cl and 4-NH-CH(CH$_3$)-(2-fluorophenyl), alternate stereochemistry]* | +++ |
| *[structure: methylenebisphosphonate linked to fluoro-ribose-pyrrolopyrimidine with 2-Cl and 4-NH-CH(CH$_3$)-(3-fluorophenyl)]* | +++ |

TABLE 1-continued
Specific Examples (Potency: CD73 IC$_{50}$: + means >1 μM, ++ means 100 nM to 1 μM, +++ means <100 nM).
| | Potency |
|---|---|
| 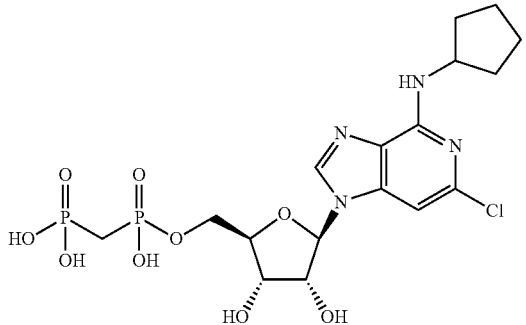 [SMILES: O=P(O)(O)CP(=O)(O)OC[C@H]1O[C@@H](n2cnc3c(NC4CCCC4)nc(Cl)cc32)[C@H](O)[C@@H]1O] | +++ |
| 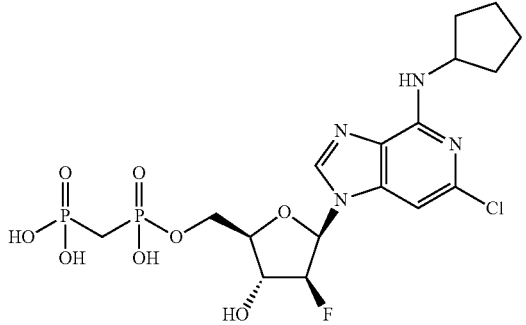 [SMILES: O=P(O)(O)CP(=O)(O)OC[C@H]1O[C@@H](n2cnc3c(NC4CCCC4)nc(Cl)cc32)[C@@H](F)[C@@H]1O] | +++ |
| 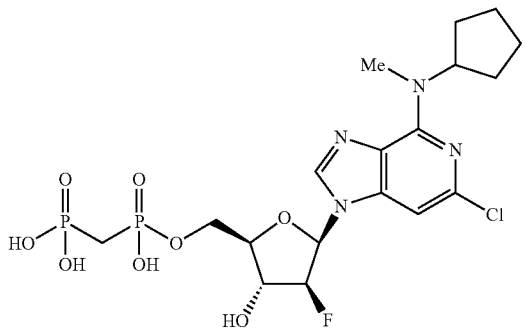 [SMILES: CN(c1nc(Cl)cc2c1ncn2[C@@H]1O[C@H](COP(=O)(O)CP(=O)(O)O)[C@@H](O)[C@@H]1F)C1CCCC1] | +++ |
| 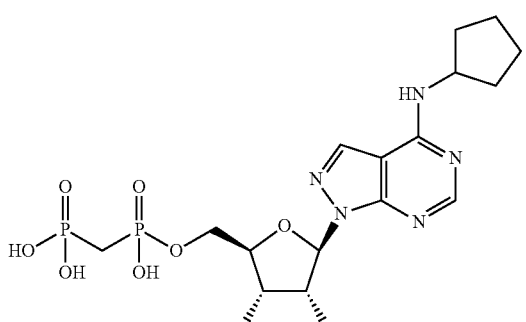 | +++ |

BIOLOGICAL EXAMPLES

Materials and Methods

The following general materials and methods were used, where indicated, or may be used in the Examples below:

Standard methods in molecular biology are described in the scientific literature (see, e.g., Sambrook and Russell (2001) Molecular Cloning, 3$^{rd}$ ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Software packages and databases for determining, e.g., antigenic fragments, leader sequences, protein folding, functional domains, glycosylation sites, and sequence alignments, are available (see, e.g., GCG Wisconsin Package (Accelrys, Inc., San Diego, Calif.); and DeCypher™ (TimeLogic Corp., Crystal Bay, Nev.).

The literature is replete with assays and other experimental techniques that can serve as a basis for evaluation of the compounds described herein.

Inhibition of Ecto-5'-nucleotidase Activity. Compounds were evaluated to determine their ecto-5'-nucleotidase (CD73) inhibitory activity. Briefly, CHO-K1 cells stably transfected with human CD73 were generated by LakePharma (Belmont, Calif.) using molecular cloning of human CD73 (http://www.uniprot.org/uniprot/P21589) and mammalian transient expression vector (P21589.1). After antibiotic selection in CD OptiCHO cell media (Invitrogen, Catalog #12681-011) containing 5 µg/mL Puromycin and 200 µg/mL Hygromycin B, a suspension pool of CHO-CD73 cells was collected and frozen in 7.5% DMSO in cell media without antibiotics.

On the day of the experiment, one vial of CHO-CD73 cells was thawed and suspended in assay media which consisted of 20 mM HEPES, pH 7.4, 137 mM NaCl, 5.4 mM KCl, 1.3 mM $CaCl_2$, 4.2 mM $NaHCO_3$ and 0.1% glucose. To test the ability of compounds to inhibit CD73 enzymatic activity, 2 µL of 500 µM of compounds dissolved in DMSO (50×) were added to a 96-well polystyrene plate containing 58 µL of assay buffer. Next, 20 µL of CHO-CD73 cells in assay buffer were added to assay plate followed by 20 µL of 125 µM AMP (Adenosine 5'-monophosphate monohydrate) in assay buffer. Final assay conditions consisted of 2500 cells per well in 2% DMSO and 25 µM of AMP substrate. After 50 minutes of incubation (37° C. and 5% $CO_2$) and centrifugation at 225×g for 5 mins, 80 µL of supernatant were transferred to a 96-well Spectra Plate (PerkinElmer, cat #6005640) which was pre-dispensed with 20 µL of PiColorLock Gold colorimetric assay reagents (Thermo, cat #30 300 30). The amount of inorganic phosphate was determined by reading the absorbance at 620 nm on an EnVision Multilabel Plate Reader (PerkinElmer). Enzymatic activity of CD73 was based on the amount of phosphate generated. Percentage of activity was calculated based on DMSO and no cells control wells. $IC_{50}$ values of compounds were determined by four parameter non-linear regression fitting of percentage of activity in GraphPad Prism software.

Pharmacodynamic and Pharmacokinetic Evaluation. A pharmacodynamic assay can be based on measuring CD73 mediated serum levels of adenosine. Adenosine levels can be determined by HPLC analysis, and serum compound levels can optionally also be determined in the same HPLC run.

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A compound having the structure

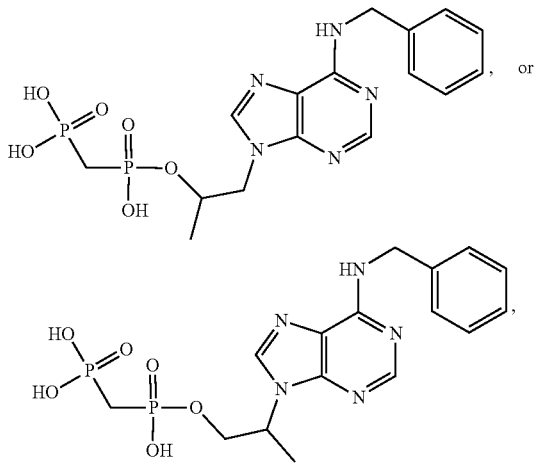

or a pharmaceutically acceptable salt thereof.

2. A compound selected from the group consisting of

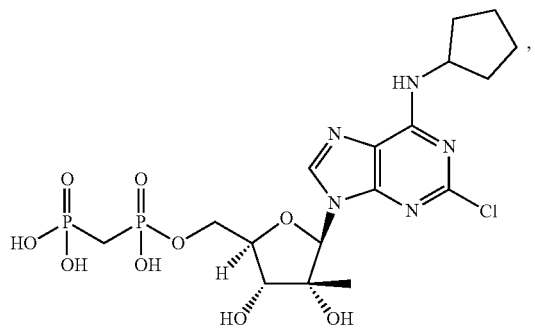

225
-continued

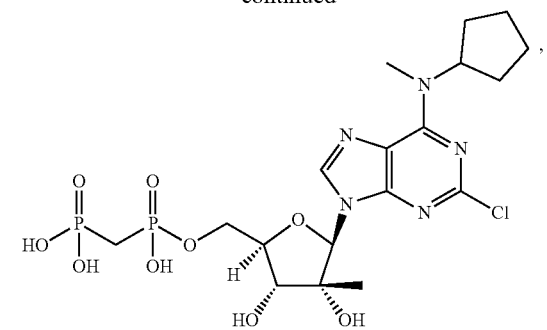

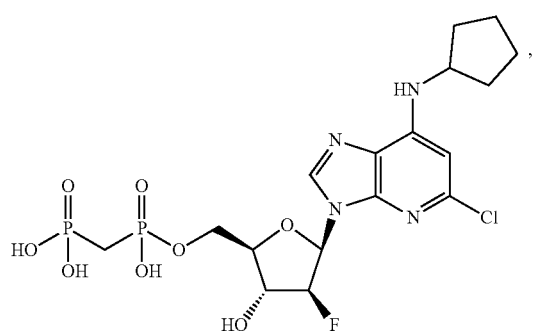

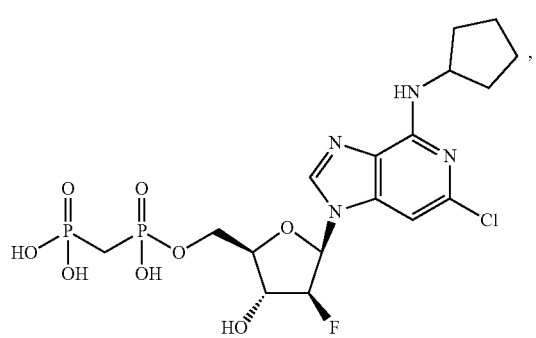

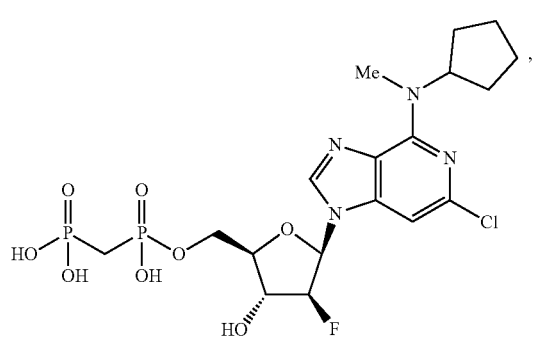

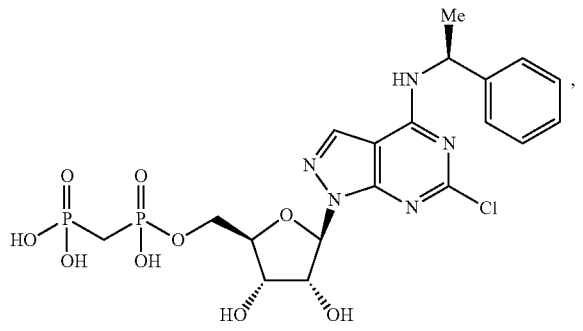

226
-continued

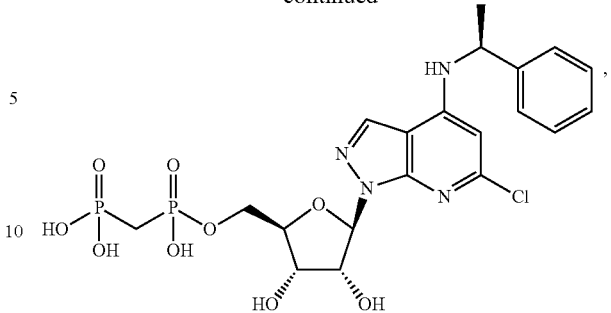

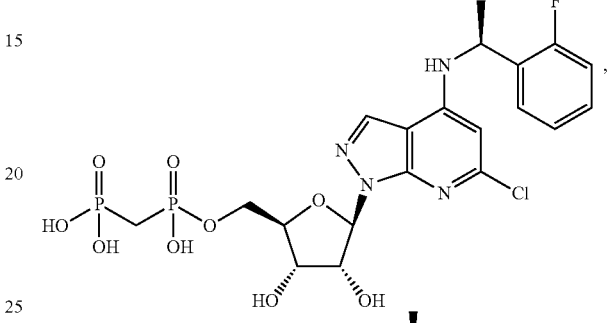

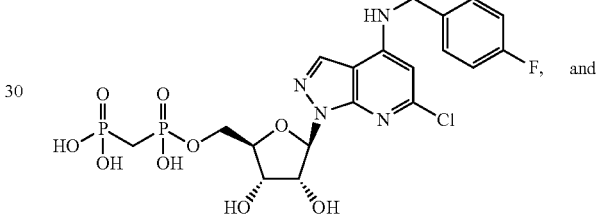

, and

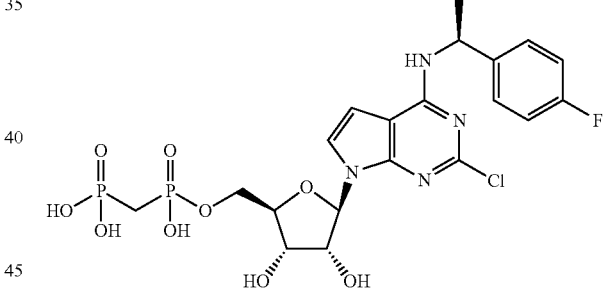

or a pharmaceutically acceptable salt thereof.

3. A method of treating a disease, disorder, or condition, mediated at least in part by CD73, said method comprising administering to a subject an effective amount of a compound of claim 2, or a pharmaceutically acceptable salt thereof.

4. The method of claim 3, wherein said disease, disorder, or condition is cancer.

5. The method of claim 4, wherein said cancer is a cancer of the prostate, colon, rectum, pancreas, cervix, stomach, endometrium, brain, liver, bladder, ovary, testis, head, neck, skin, mesothelial lining, white blood cell, esophagus, breast, muscle, connective tissue, lung, adrenal gland, thyroid, kidney, or bone; or is glioblastoma, mesothelioma, renal cell carcinoma, gastric carcinoma, sarcoma, choriocarcinoma, cutaneous basocellular carcinoma, or testicular seminoma.

6. The method of claim 5, wherein the cancer is selected from the group consisting of melanoma, colon cancer, pancreatic cancer, breast cancer, prostate cancer, small-cell lung carcinoma, non-small-cell carcinoma, leukemia, a brain tumor, lymphoma, ovarian cancer, and Kaposi's sarcoma.

7. The method of claim 3, wherein said disease, disorder, or condition is an immune-related disease, disorder, or condition selected from the group consisting of rheumatoid arthritis, kidney failure, lupus, asthma, psoriasis, colitis, pancreatitis, allergies, fibrosis, anemia fibromyalgia, Alzheimer's disease, congestive heart failure, stroke, aortic valve stenosis, arteriosclerosis, osteoporosis, Parkinson's disease, infections, Crohn's disease, ulcerative colitis, allergic contact dermatitis and other eczemas, systemic sclerosis, and multiple sclerosis.

8. A method of treating cancer in a subject, said method comprising administering to said subject an effective amount of a compound of claim 2, or a pharmaceutically acceptable salt thereof and an immune checkpoint inhibitor.

9. The method of claim 8, wherein the immune checkpoint inhibitor inhibits PD-1, PD-L1, $A_{2a}R$, BTLA, CTLA-4, TIM-3, or LAG-3.

* * * * *